US011447526B2

(12) United States Patent
Milder et al.

(10) Patent No.: US 11,447,526 B2

(45) Date of Patent: Sep. 20, 2022

(54) INFLUENZA VIRUS VACCINES AND USES THEREOF

(71) Applicant: JANSSEN VACCINES & PREVENTION B.V., CN Leiden (NL)

(72) Inventors: Ferdinand Jacobus Milder, Zwolle (NL); Tina Ritschel, Oegstgeest (NL); Boerries Brandenburg, Utrecht (NL); Mandy Antonia Catharina Jongeneelen, Leiden (NL); Daphné Truan, Cambridge (GB); Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 215 days.

(21) Appl. No.: 16/964,089

(22) PCT Filed: Jan. 22, 2019

(86) PCT No.: PCT/EP2019/051532

§ 371 (c)(1),
(2) Date: Jul. 22, 2020

(87) PCT Pub. No.: WO2019/145310

PCT Pub. Date: Aug. 1, 2019

(65) Prior Publication Data

US 2020/0377555 A1 Dec. 3, 2020

(30) Foreign Application Priority Data

Jan. 23, 2018 (EP) .................................... 18152991

(51) Int. Cl.

| | |
|---|---|
| ***A61K 39/00*** | (2006.01) |
| ***C07K 16/10*** | (2006.01) |
| ***A61K 39/145*** | (2006.01) |
| ***A61K 39/42*** | (2006.01) |
| ***C07K 14/005*** | (2006.01) |
| ***A61P 31/16*** | (2006.01) |
| ***C12N 7/00*** | (2006.01) |

(52) U.S. Cl.
CPC .......... *C07K 14/005* (2013.01); *A61K 39/145* (2013.01); *A61P 31/16* (2018.01); *C12N 7/00* (2013.01); *C12N 2760/16122* (2013.01); *C12N 2760/16134* (2013.01)

(58) Field of Classification Search
CPC ..... A61K 2300/00; A61K 39/42; A61P 31/16; C07K 16/1018; C07K 2317/76
See application file for complete search history.

(56) References Cited

U.S. PATENT DOCUMENTS

| | | | |
|---|---|---|---|
| 5,057,540 | A | 10/1991 | Kensil |
| 2010/0297174 | A1 | 11/2010 | Garcia-Sastre |
| 2013/0129761 | A1 | 5/2013 | Garcia-Sastre |
| 2014/0357845 | A1 | 12/2014 | Meijberg |

FOREIGN PATENT DOCUMENTS

| | | | |
|---|---|---|---|
| EP | 20110173953 | | 7/2011 |
| WO | 9003184 | A1 | 4/1990 |
| WO | 9014837 | A1 | 12/1990 |
| WO | 9611711 | A1 | 4/1996 |
| WO | 2004004762 | A1 | 1/2004 |
| WO | 2005002620 | A1 | 1/2005 |
| WO | 2008028946 | | 3/2008 |
| WO | 2010117786 | | 10/2010 |
| WO | 2010130636 | | 11/2010 |
| WO | 2011123495 | | 10/2011 |
| WO | 2013007770 | A1 | 1/2013 |
| WO | 2013079473 | A1 | 6/2013 |
| WO | WO2013079473 | * | 6/2013 |
| WO | 2014191435 | | 12/2014 |
| WO | 2016005480 | | 1/2016 |
| WO | 2016005482 | | 1/2016 |

OTHER PUBLICATIONS

Alberini et al., "Pseudoparticle Neutralization is a Reliable Assay to Measure Immunity and Cross-Reactivity to H5N1 Influenza Viruses", Vaccine, vol. 27, pp. 5998-6003 (2009).
Atsmon et al., "Safety and Immunogenicity of Multimeric-001—a Novel Universal Influenza Vaccine", Journ. Clin Immunol., vol. 32, pp. 595-603 (2012).
Bianchi et al., Universal influenza B vaccine based on the maturational cleavage site of the hemagglutinin precursor, Journal of Virology, The American Society for Microbiology, pp. 7380-7388, vol. 79, No. 12, 2005.
Cheng et al., "Development of a Robust Reporter-based ADCC Assay with Frozen, Thaw-and-use Cells to Measure Fc Effector Function of Therapeutic Antibodies", Journ. Immunol. Methods, vol. 414, pp. 69-81 (2014).
Coffman et al., "Vaccine Adjuvants" Putting Innate Immunity to Work, Immunity, vol. 33, pp. 492-503(Oct. 2010).
Degorce et al., "HTRF: A technology tailored for drug discovery—a review of theoretical aspects and recent applications," Curr. Chem. Genomics 3:22-32 (2009).
Devereux et al., "A Comprehensive Set of Sequence Analysis Programs for the VAX", Nucl. Acids Res., vol. 12, No. 1, pp. 387-395 (1984).
DiLillo et al., "Broadly Neutralizing Hemagglutinin Stalk-Specific Antibodies Require FcyR Interactions for Protection Against Influenza Virus in Vivo", Nat. Med., vol. 20, No. 2, pp. 143-153 (Feb. 2014).

(Continued)

*Primary Examiner* — Barry A Chestnut
(74) *Attorney, Agent, or Firm* — Ice Miller LLP

(57) ABSTRACT

Provided herein are influenza hemagglutinin stem polypeptides, nucleic acids encoding said polypeptides, vectors comprising said nucleic acid and pharmaceutical compositions comprising the same, as well as methods of their use, in particular in the prevention and/or treatment of influenza virus infections.

34 Claims, 21 Drawing Sheets

Specification includes a Sequence Listing.

(56) References Cited

OTHER PUBLICATIONS

Dopheide et al., "The Location of the Bromelain Cleavage Site in a Hong Kond Influenza Virus Haemagglutinin", Journ. Gen. Virol., vol. 52, pp. 367-370 (1981).
Eckert et al., Stalking influenza, Proceedings of the National Academy of Sciences of the United States of America, , pp. 13563-13564, vol. 107, No. 31, Aug. 3, 2010.
Ferguson et al., "Ecological and Immunological Determinants of Influenza Evolution", Nature, vol. 422, pp. 428-443 (Mar. 2003).
Gayathri Bommakanti et al, "Supporting Information. Bommakanti et al. 10.1073/pnas.1007465107", vol. 107, No. 31, doi:10.1073/PNAS.1007465107, ISSN 0027-8424, (Aug. 3, 2010), pp. 1-6, Proceedings of the National Academy of Sciences, National Academy of Sciences, URL: http://www.pnas.org/content/107/31/13701, (Jul. 6, 2010), XP002675046.
Ichihashi et al., "Cross-Protective Peptide Vaccine against Influenza A Viruses developed in HLA-A *2402 Human Immunity Model", PLoS One, vol. 6, Issue 9, pp. 1-9, Sep. 2011.
Int'l Search Report and Written Opinion dated Mar. 5, 2013 in Int'l Application No. PCT/EP2012/073706. (13 pages).
Int'l Search Report and Written Opinion dated Sep. 16, 2014 in Int'l Application No. PCT/EP2014/060997. (12 pages).
Int'l Search Report and Written Opinion dated Sep. 18, 2015 in Int'l Application No. PCT/EP2015/065661. (12 pages).
Int'l Search Report and Written Opinion dated Sep. 30, 2015 in Int'l Application No. PCT/EP2015/065663. (10 pages).
Kang et al., Novel vaccines against influenza viruses, Virus Research, pp. 31-38, vol. 162, No. 1., Oct. 1, 2011.
Kodihalli et al., "Strategies for inducing protection against avian influenza A virus subtypes with DNA vaccines", Vaccine, 18(23)2592-2599, 2000.
Parekh et al., "Development and Validation of an Antibody-Dependent Cell-Mediated Cytotoxicity-Reporter Gene Assay", mAbs, vol. 4, No. 3, pp. 310-318 (2012).
Safronetz et al., "Pandemic Swine-Origin H1N1 Influenza A Virus Isolates Show Heterogeneous Virulence in Macaques", Journ. of Virol., vol. 85, No. 3, pp. 1214-1223 (Feb. 2011).
Sagawa H et al, "The immunological activity of a deletion mutant of influenza virus haemagglutinin lacking the globular region", Journal of General Virology, (Jan. 1, 1996), vol. 77, No. 7, ISSN 0022-1317, pp. 1483-1487, XP002675043.
Schnueriger et al., "Development of a Quantitative, Cell-Line Based Assay to Measure ADCC Activity Mediated by Therapeutic Antibodies", Molec. Immun., vol. 48, pp. 1512-1517 (2011).
Steel et al., Live Attenuated Influenza Viruses Containing NS1 Truncations as Vaccine Candidates against H5N1 Highly Pathogenic Avian influenza, Journal of Virology, pp. 1742-1753, vol. 83, No. 4, Feb. 2009.
Stevens et al., "Structure and Receptor Specificity of the Hemagglutinin from an H5N1 Influenza Virus", Science, vol. 312, pp. 404-410 (Apr. 2006).
Stevens et al., "Structure of the Uncleaved Human H1 Hemagglutinin from the Extinct 1918 Influenza Virus", Science, vol. 303, pp. 1866-1870 (Mar. 2004).
Sun et al., "Modifications to the hemagglutinin cleavage site control the virulence of a neurotropic HIN1 influenza virus," Journ. of Virol., vol. 84, No. 17, pp. 8683-8690 (Sep. 2010).
Temperton et al., "A Sensitive Retroviral Pseudotype Assay for Influenza H5N1-Neutralizing Antibodies", Viruses, vol. 1, No. 3,, pp. 105-112 (2007).
Wang et al., Vaccination with a synthetic peptide from the influenza virus hemagglutinin provides protection against distinct viral subtypes, Proceedings of the National Academy of Sciences of the United States of America, pp. 18979-18984, vol. 107, No. 44., Nov. 2010.
Wilson et al., "Structure of the Haemagglutinin Membrane Glycoprotein of Influenza Virus at 3 A Resolution", Nature, vol. 289, pp. 366-373 (Jan. 1981).
Zhirnov et al., "Cleavage of Influenza A Virus Hemagglutinin in Human Respiratory Epithelium is Cell Associated and Sensitive to Exogenous Antiproteases", Journal of Virology, vol. 76, No. 17, pp. 8682-8689, Sep. 2002.
G. Bommakanti et al., "Design of *Escherichia coli*-Expressed Stalk Doman Immunogens of H1N1 Hemagglutinin That Protect Mice from Lethal Challenge," Journal of Virology, vol. 86, No. 24, Sep. 26, 2012.
Y. Lu et al., "Production and stabilization of the trimeric influenza hemagglutinin stem domain for potentially broadly protective influenza vaccines," Proceedings of the National Academy of Sciences, Dec. 16, 2013.
Peter S. Lee et al., "Design and Structure of an Engineered Disulfide-Stabilized Influenza Virus Hemagglutinin Trimer," Journal of Virology, vol. 89, No. 14, Apr. 29, 2015.
John Steel et al., "Influenza Virus Vaccine Based on the Conserved Hemagglutinin Stalk Domain," MBIO, American Society for Microbiology, vol. 1, No. 1, May 18, 2010.
Sophie A. Valkenburg et al., "Stalking influenza by vaccination with pre-fusion headless HA mini-stem," Scientific Reports, vol. 6, No. 1, Mar. 7, 2016.
International Search Report dated Mar. 20, 2019 in International Application No. PCT/EP2019/051532.
Written Opinion dated Mar. 20, 2019 in International Application No. PCT/EP2019/051532.
Damian C. Ekiert et al., "A Highly Conserved Neutralizing Epitope on Group 2 Influenza A Viruses," Science, Aug. 12, 2011.
Bommakanti et al., "Design of an HA2-based *Escherichia coli* expressed influenza immunogen that protects mice from pathogentic challenge" PNAS, vol. 107, No. 31, Aug. 3, 2010.
B. Ciani et al., "Molecular basis of coiled-coil oligomerization-state specificity," PNAS, vol. 107, No. 46, Nov. 16, 2010.
G. Das et al., "SV 40 Promoters and Their Regulation," Progress in Nucleic Acid Research and Molecular Biology, vol. 32, 1985.
D. Ekiert et al., "Antibody Recognition of a Highly Conserved Influenza Virus Epitope," Science, vol. 324, Apr. 10, 2009.
Dr. Gill et al., "Increased persistence of lung gene expression using plasmids containing the ubiquitin C or elongation Factor 1 promoter," Gene Therapy, vol. 8, pp. 1539-1546 (2001).
S. Guthe et al., "Very Fast Folding and Association of a Trimerization Domain from Bacteriophase T4 Fibritin," J. Molecular Biology, vol. 337, pp. 905-915 (2004).
R. Kaufman, "Overview of Vector Design for Mammalian Gene Expression," Molecular Biotechnology, vol. 16, (2000).
A.V. Letarov et al., "The Carboxy-Terminal Domain Initiates Trimerization of Bacteriophage T4 Fibritin," Biochemistry (Moscow), vol. 64, No. 7, pp. 817-823 (1999).
J.L. Lorieau et al., "The complete influenza hemagglutinin fusion domain adopts a tight helical hairpin arrangement at the lipid:water interface," PNAS, vol. 107, No. 25, Jun. 22, 2010.
V.V.A. Mallajosyula et al., "Influenza Hemagglutinin stem-fragment immunogen elicits broadly neutralizing antibodies and confers heterologous protection," PNAS, Jun. 9, 2014.
M. Throsby et al., "Heterosubtypic Neutralizing Monoclonal Antibodies Cross-Protective against H5N1 and H1N1 Recovered from Human IgM+ Memor B Cells," Plos One, vol. 3, Issue 12, Dec. 2008.
G. Winter et al., "Nucleotid sequence of the haemagglutinin gene of a human influenza virus H1 subtype," Nature, vol. 292, Jul. 2, 1981.
Y. Lu et al., "Production and stabilization of the trimeric influenza hemagglutinin stem domain for potentially broadly protective influenza vaccines," PNAS, vol. 111, No. 1, Jan. 7, 2014.

* cited by examiner

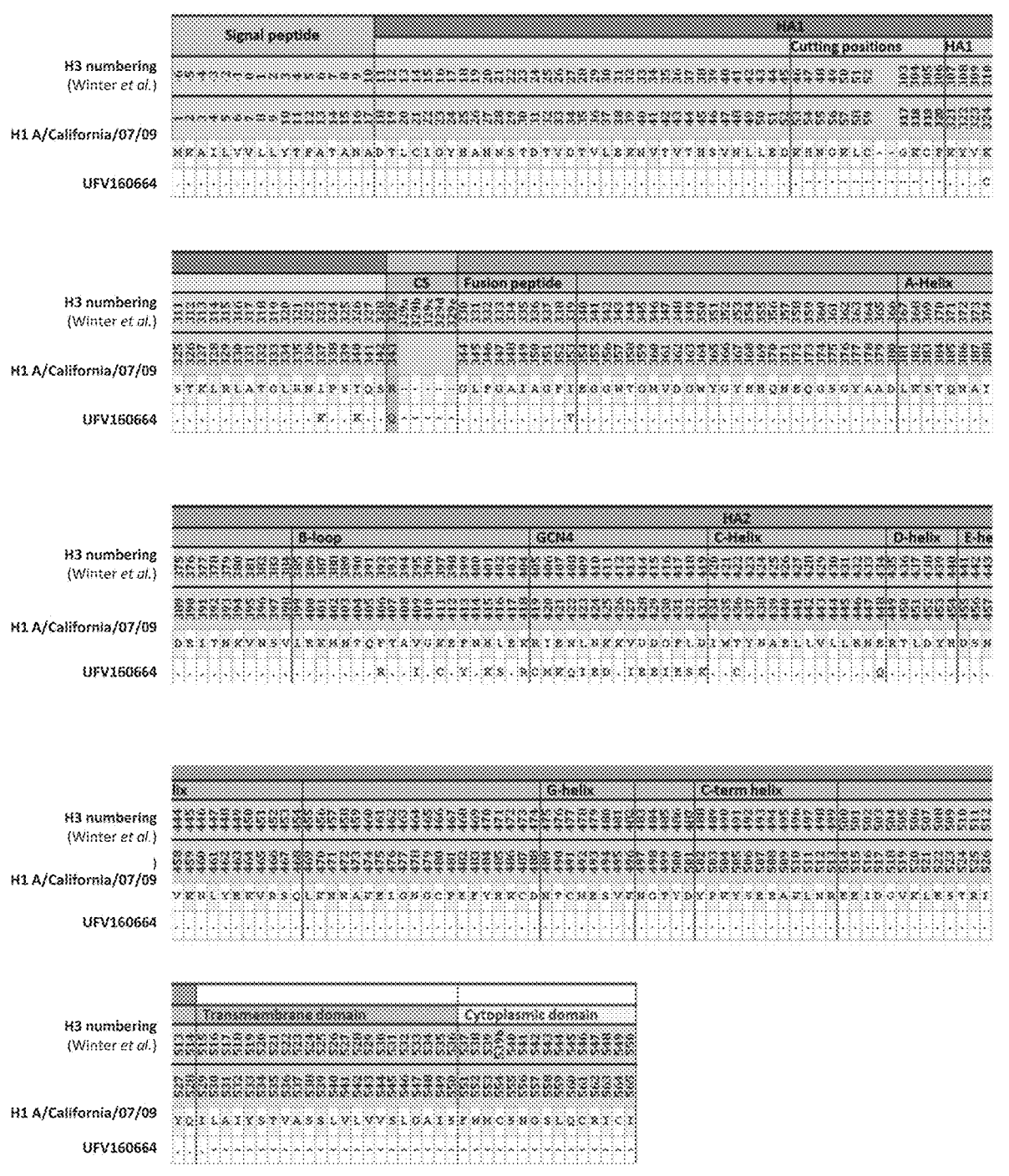

| | Signal peptide | HA1 | Cutting positions | HA1 |
|---|---|---|---|---|
| H3 numbering (Winter *et al.*) | [illegible] | [illegible] | [illegible] | [illegible] |
| H1 A/California/07/09 | [illegible] | [illegible] | [illegible] | [illegible] |
| | MKAILVVLLYTFATANA | DTLCIGYHANNSTDTVDTVLEKNVTVTHSVNLLED | KHNGKLC--GKCP | KYVK |
| UFV160664 | ................. | ................................... | .------------ | ...C |

| | | CS | Fusion peptide | | A-Helix |
|---|---|---|---|---|---|
| H3 numbering (Winter *et al.*) | [illegible] | [illegible] | [illegible] | [illegible] | [illegible] |
| H1 A/California/07/09 | [illegible] | | [illegible] | [illegible] | [illegible] |
| | STKLRLATGLRNIPSIQS | R---- | GLFGAIAGFI | EGGWTGMVDGWYGYHHQNEQGSGYAAD | LKSTQNAI |
| UFV160664 | ............K..K.. | Q---- | .........T | ........................... | ........ |

| | HA2 | | | | | |
|---|---|---|---|---|---|---|
| | | B-loop | GCN4 | C-Helix | D-helix | E-he |
| H3 numbering (Winter *et al.*) | [illegible] | [illegible] | [illegible] | [illegible] | [illegible] | [illegible] |
| H1 A/California/07/09 | [illegible] | [illegible] | [illegible] | [illegible] | [illegible] | [illegible] |
| | DSITHKVNSV | IEKMNTQFTAVGKEFNKLEK | RIENLNKKVDDGFLD | IWTYNAELLVLLENE | RTLDYH | DSN |
| UFV160664 | .......... | .......R..I.C.Y.KS. | RCNKQIED.IEEIESK | ..C............ | Q..... | ... |

| | lix | | G-helix | | C-term helix | |
|---|---|---|---|---|---|---|
| H3 numbering (Winter *et al.*) | [illegible] | [illegible] | [illegible] | [illegible] | [illegible] | [illegible] |
| ) H1 A/California/07/09 | [illegible] | [illegible] | [illegible] | [illegible] | [illegible] | [illegible] |
| | VKNLYEKVRSQ | LKNNAKEIGNGCFEFYHKCD | NTCMESVK | NGTYD | YPKYSEEAKLNR | EEIDGVKLESTRI |
| UFV160664 | ........... | .................... | ........ | ..... | ............ | ............. |

| | | | |
|---|---|---|---|
| | | Transmembrane domain | Cytoplasmic domain |
| H3 numbering (Winter *et al.*) | [illegible] | [illegible] | [illegible] |
| H1 A/California/07/09 | [illegible] | [illegible] | [illegible] |
| | YQ | ILAIYSTVASSLVLVVSLGAISF | WMCSNGSLQCRICI |
| UFV160664 | .. | ----------------------- | -------------- |

FIG. 14

FIG. 15
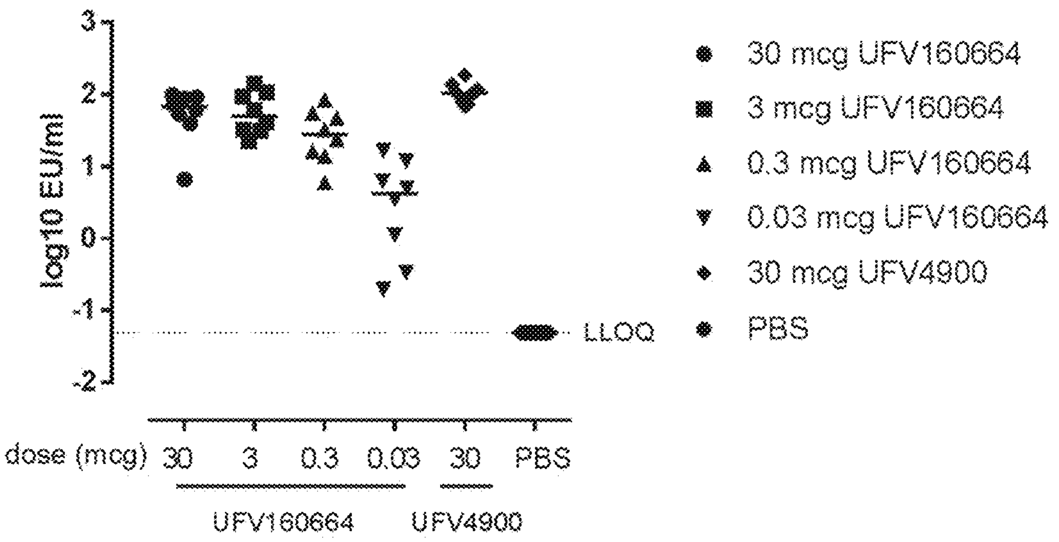
FIG. 16
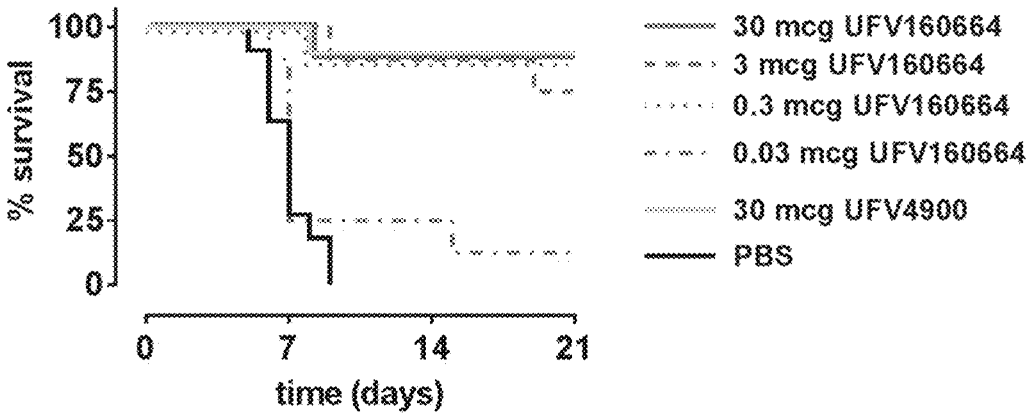
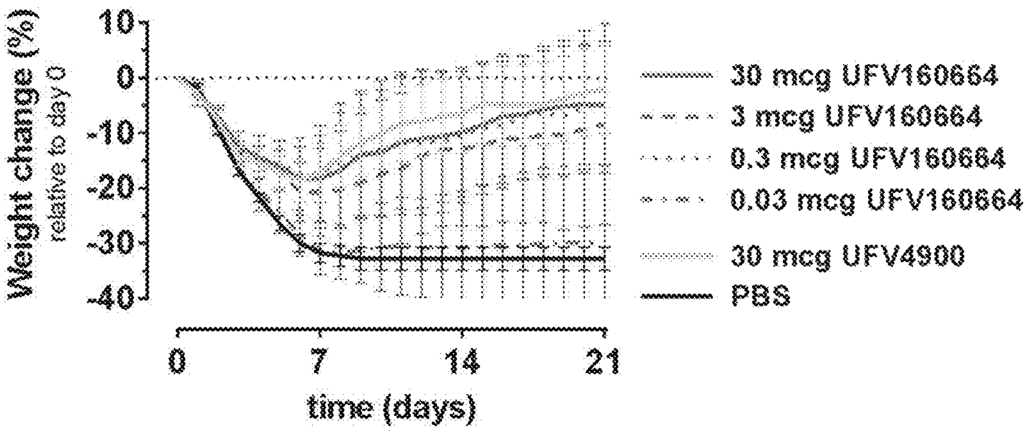

A

| ID. | Strain | Expression |
|---|---|---|
| UFV180496 | H1 A/California/07/09 | 375 mg/L |
| UFV180497 | H1 A/Michigan/45/2015 | 367 mg/L |
| UFV180498 | H1 A/Puerto Rico/8/1934 | 244 mg/L |
| UFV180499 | H5 A/Hong Kong/156/97 | 133 mg/L |
| UFV180500 | H5 A/Vietnam/1203/04 | 42 mg/L |
| UFV180501 | H2 A/Singapore/1/57 | 229 mg/L |

B

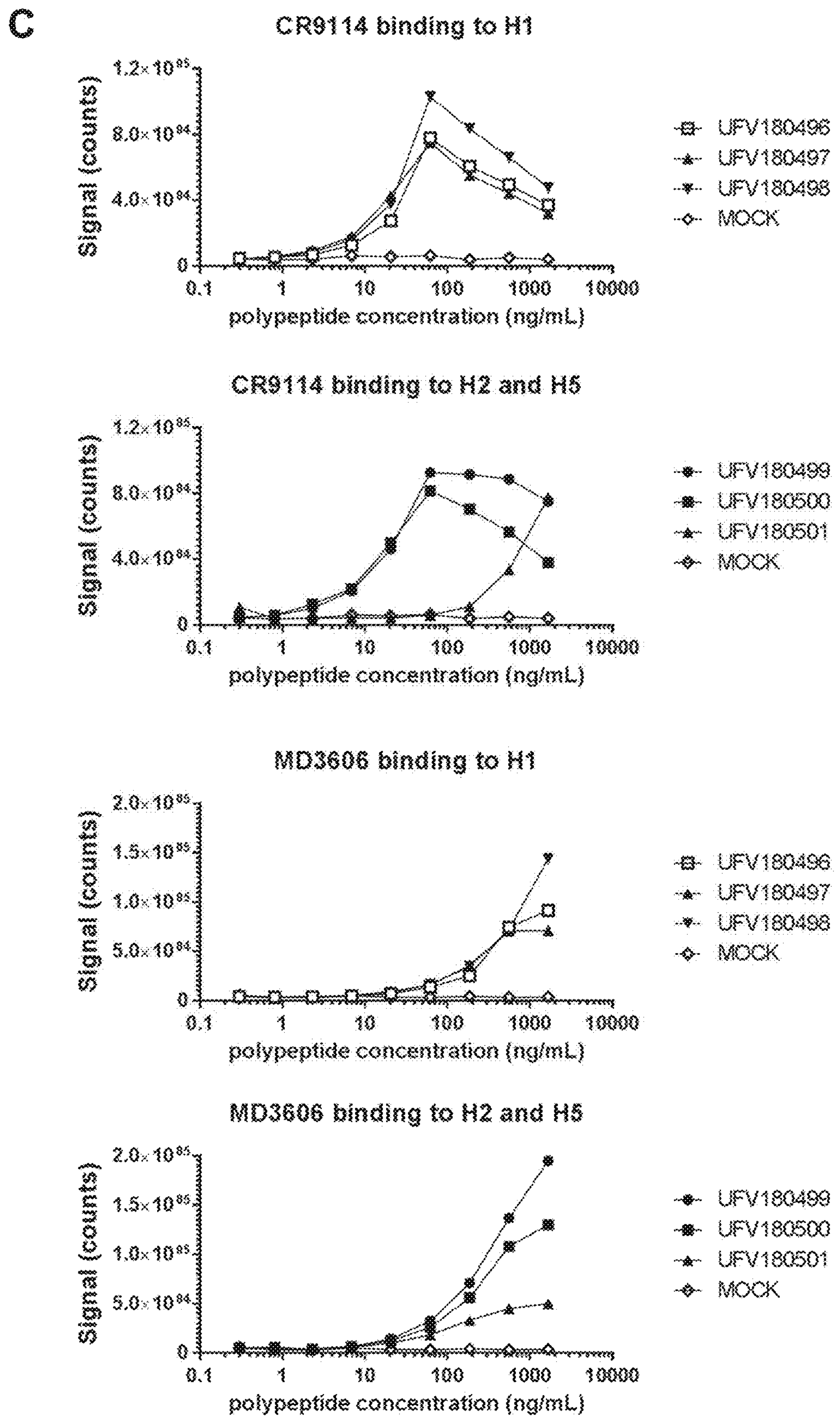
FIG. 28 - continued

SEQUENCE LISTING

<160> NUMBER OF SEQ ID NOS: 154

<210> SEQ ID NO 1
<211> LENGTH: 565
<212> TYPE: PRT
<213> ORGANISM: Artificial Sequence
<220> FEATURE:
<223> OTHER INFORMATION: H1 Full length (A/Brisbane/59/2007)

<400> SEQUENCE: 1

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 2
<211> LENGTH: 566
<212> TYPE: PRT
<213> ORGANISM: Artificial Sequence
<220> FEATURE:
<223> OTHER INFORMATION: H1 Full length (A/California/07/2009)

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240
```

-continued

```
Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 3
<211> LENGTH: 565
<212> TYPE: PRT
<213> ORGANISM: Artificial Sequence
<220> FEATURE:
<223> OTHER INFORMATION: A/Texas/UR06-0526/2007(H1N1)

<400> SEQUENCE: 3

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Thr
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
        275                 280                 285

Gly Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
```

```
    450                 455                 460

Val Lys Asn Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Ile
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 4
<211> LENGTH: 566
<212> TYPE: PRT
<213> ORGANISM: Artificial Sequence
<220> FEATURE:
<223> OTHER INFORMATION: A/NewYork/629/1995 (H1N1)

<400> SEQUENCE: 4

Met Lys Val Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Thr
    50                  55                  60

Ala Pro Leu Gln Leu Gly Asn Cys Ser Val Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
```

-continued

```
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Ser Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 5
<211> LENGTH: 566
<212> TYPE: PRT
<213> ORGANISM: Artificial Sequence
<220> FEATURE:
<223> OTHER INFORMATION: A/AA_Marton/1943 (H1N1)

<400> SEQUENCE: 5

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

-continued

```
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Ser Lys Glu Ser Ser Trp Pro Lys His Asn
    130                 135                 140

Thr Thr Arg Gly Val Thr Ala Ala Cys Ser His Ala Gly Lys Ser Ser
145                 150                 155                 160

Phe Tyr Arg Asn Leu Leu Trp Leu Thr Glu Lys Asp Gly Ser Tyr Pro
                165                 170                 175

Asn Leu Asn Asn Ser Tyr Val Asn Lys Lys Gly Lys Glu Val Leu Val
            180                 185                 190

Leu Trp Gly Val His His Pro Ser Asn Ile Lys Asp Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Lys Pro Gly Asp Thr
                245                 250                 255

Ile Met Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460
```

```
Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 6
<211> LENGTH: 562
<212> TYPE: PRT
<213> ORGANISM: Artificial Sequence
<220> FEATURE:
<223> OTHER INFORMATION: A/Adachi/2/57 (H2N2)

<400> SEQUENCE: 6

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asn Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Gln Ala Cys Ala Val Ser Gly Asn Pro Ser Phe Phe Arg Asn
145                 150                 155                 160

Met Val Trp Leu Thr Lys Lys Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255
```

```
Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Gly Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile
```

<210> SEQ ID NO 7
<211> LENGTH: 562
<212> TYPE: PRT
<213> ORGANISM: Artificial Sequence
<220> FEATURE:
<223> OTHER INFORMATION: A/Singapore/1/57 (H2N2)

<400> SEQUENCE: 7

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45
```

-continued

```
Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Glu Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Lys Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Ile Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
```

-continued 465 470 475 480

Tyr His Lys Cys Asp Asp Glu Cys Met Asn Ser Val Lys Asn Gly Thr
485 490 495

Tyr Asp Tyr Pro Lys Tyr Glu Glu Glu Ser Lys Leu Asn Arg Asn Glu
500 505 510

Ile Lys Gly Val Lys Leu Ser Ser Met Gly Val Tyr Gln Ile Leu Ala
515 520 525

Ile Tyr Ala Thr Val Ala Gly Ser Leu Ser Leu Ala Ile Met Met Ala
530 535 540

Gly Ile Ser Phe Trp Met Cys Ser Asn Gly Ser Leu Gln Cys Arg Ile
545 550 555 560

Cys Ile

<210> SEQ ID NO 8
<211> LENGTH: 568
<212> TYPE: PRT
<213> ORGANISM: Artificial Sequence
<220> FEATURE:
<223> OTHER INFORMATION: A/Viet Nam/1203/2004 H5N1)

<400> SEQUENCE: 8

Met Glu Lys Ile Val Leu Leu Phe Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Lys His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Asn Pro Val Asn Asp Leu Cys Tyr Pro Gly Asp Phe Asn
100 105 110

Asp Tyr Glu Glu Leu Lys His Leu Leu Ser Arg Ile Asn His Phe Glu
115 120 125

Lys Ile Gln Ile Ile Pro Lys Ser Ser Trp Ser Ser His Glu Ala Ser
130 135 140

Leu Gly Val Ser Ser Ala Cys Pro Tyr Gln Gly Lys Ser Ser Phe Phe
145 150 155 160

Arg Asn Val Val Trp Leu Ile Lys Lys Asn Ser Thr Tyr Pro Thr Ile
165 170 175

Lys Arg Ser Tyr Asn Asn Thr Asn Gln Glu Asp Leu Leu Val Leu Trp
180 185 190

Gly Ile His His Pro Asn Asp Ala Ala Glu Gln Thr Lys Leu Tyr Gln
195 200 205

Asn Pro Thr Thr Tyr Ile Ser Val Gly Thr Ser Thr Leu Asn Gln Arg
210 215 220

Leu Val Pro Arg Ile Ala Thr Arg Ser Lys Val Asn Gly Gln Ser Gly
225 230 235 240

Arg Met Glu Phe Phe Trp Thr Ile Leu Lys Pro Asn Asp Ala Ile Asn
245 250 255

Phe Glu Ser Asn Gly Asn Phe Ile Ala Pro Glu Tyr Ala Tyr Lys Ile
260 265 270

Val Lys Lys Gly Asp Ser Thr Ile Met Lys Ser Glu Leu Glu Tyr Gly
275 280 285

Asn Cys Asn Thr Lys Cys Gln Thr Pro Met Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Ser
325 330 335

Pro Gln Arg Glu Arg Arg Arg Lys Lys Arg Gly Leu Phe Gly Ala Ile
340 345 350

Ala Gly Phe Ile Glu Gly Gly Trp Gln Gly Met Val Asp Gly Trp Tyr
355 360 365

Gly Tyr His His Ser Asn Glu Gln Gly Ser Gly Tyr Ala Ala Asp Lys
370 375 380

Glu Ser Thr Gln Lys Ala Ile Asp Gly Val Thr Asn Lys Val Asn Ser
385 390 395 400

Ile Ile Asp Lys Met Asn Thr Gln Phe Glu Ala Val Gly Arg Glu Phe
405 410 415

Asn Asn Leu Glu Arg Arg Ile Glu Asn Leu Asn Lys Lys Met Glu Asp
420 425 430

Gly Phe Leu Asp Val Trp Thr Tyr Asn Ala Glu Leu Leu Val Leu Met
435 440 445

Glu Asn Glu Arg Thr Leu Asp Phe His Asp Ser Asn Val Lys Asn Leu
450 455 460

Tyr Asp Lys Val Arg Leu Gln Leu Arg Asp Asn Ala Lys Glu Leu Gly
465 470 475 480

Asn Gly Cys Phe Glu Phe Tyr His Lys Cys Asp Asn Glu Cys Met Glu
485 490 495

Ser Val Arg Asn Gly Thr Tyr Asp Tyr Pro Gln Tyr Ser Glu Glu Ala
500 505 510

Arg Leu Lys Arg Glu Glu Ile Ser Gly Val Lys Leu Glu Ser Ile Gly
515 520 525

Ile Tyr Gln Ile Leu Ser Ile Tyr Ser Thr Val Ala Ser Ser Leu Ala
530 535 540

Leu Ala Ile Met Val Ala Gly Leu Ser Leu Trp Met Cys Ser Asn Gly
545 550 555 560

Ser Leu Gln Cys Arg Ile Cys Ile
565

<210> SEQ ID NO 9
<211> LENGTH: 121
<212> TYPE: PRT
<213> ORGANISM: Artificial Sequence
<220> FEATURE:
<223> OTHER INFORMATION: CR9114 VH PROTEIN

<400> SEQUENCE: 9

Gln Val Gln Leu Val Gln Ser Gly Ala Glu Val Lys Lys Pro Gly Ser
1 5 10 15

Ser Val Lys Val Ser Cys Lys Ser Ser Gly Gly Thr Ser Asn Asn Tyr
20 25 30

Ala Ile Ser Trp Val Arg Gln Ala Pro Gly Gln Gly Leu Asp Trp Met
35 40 45

Gly Gly Ile Ser Pro Ile Phe Gly Ser Thr Ala Tyr Ala Gln Lys Phe
50 55 60

```
Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Val Trp Gly
            100                 105                 110

Gln Gly Thr Thr Val Thr Val Ser Ser
        115                 120


<210> SEQ ID NO 10
<211> LENGTH: 110
<212> TYPE: PRT
<213> ORGANISM: Artificial Sequence
<220> FEATURE:
<223> OTHER INFORMATION: CR9114 VL PROTEIN

<400> SEQUENCE: 10

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110


<210> SEQ ID NO 11
<211> LENGTH: 121
<212> TYPE: PRT
<213> ORGANISM: Artificial Sequence
<220> FEATURE:
<223> OTHER INFORMATION: CR6261 VH PROTEIN

<400> SEQUENCE: 11

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120
```

<210> SEQ ID NO 12
<211> LENGTH: 112
<212> TYPE: PRT
<213> ORGANISM: Artificial Sequence
<220> FEATURE:
<223> OTHER INFORMATION: CR6261 VL PROTEIN

<400> SEQUENCE: 12

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
            100                 105                 110
```

<210> SEQ ID NO 13
<211> LENGTH: 153
<212> TYPE: PRT
<213> ORGANISM: Artificial Sequence
<220> FEATURE:
<223> OTHER INFORMATION: SD15016

<400> SEQUENCE: 13

```
Glu Val Gln Leu Val Glu Ser Gly Gly Gly Leu Val Gln Ala Gly Gly
1               5                   10                  15

Ser Leu Arg Leu Ser Cys Val Ala Ser Gly Met Phe Phe Gly Ile Ala
            20                  25                  30

Ala Met Gly Trp Tyr Arg Gln Ala Pro Gly Lys Gln Arg Glu Leu Val
        35                  40                  45

Ala Asn Ile Thr Ser Asp Phe Ser Thr Asn Tyr Ala Asp Ser Val Lys
    50                  55                  60

Asp Arg Phe Thr Ile Ser Arg Asp Asn Ala Glu Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Ser Leu Gly Thr Gly Trp Arg His Tyr Tyr Tyr Trp Gly Gln
            100                 105                 110

Gly Thr Gln Val Thr Val Ser Ser Ala Ala Ala Trp Ser His Pro Gln
        115                 120                 125

Phe Glu Lys Gly Ala Ala Trp Ser His Pro Gln Phe Glu Lys Gly Ala
    130                 135                 140

Ala Trp Ser His Pro Gln Phe Glu Lys
145                 150
```

<210> SEQ ID NO 14
<211> LENGTH: 157
<212> TYPE: PRT
<213> ORGANISM: Artificial Sequence
<220> FEATURE:
<223> OTHER INFORMATION: SD15004

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Val Ser Ile Ser Ile Phe Asp Ile Tyr
            20                  25                  30

Ala Met Asp Trp Tyr Arg Gln Ala Pro Gly Lys Gln Arg Asp Leu Val
        35                  40                  45

Ala Thr Ser Phe Arg Asp Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Leu Cys His
                85                  90                  95

Val Ser Leu Tyr Arg Asp Pro Leu Gly Val Ala Gly Gly Met Gly Val
            100                 105                 110

Tyr Trp Gly Lys Gly Ala Leu Val Thr Val Ser Ser Ala Ala Ala Trp
        115                 120                 125

Ser His Pro Gln Phe Glu Lys Gly Ala Ala Trp Ser His Pro Gln Phe
    130                 135                 140

Glu Lys Gly Ala Ala Trp Ser His Pro Gln Phe Glu Lys
145                 150                 155
```

<210> SEQ ID NO 15
<211> LENGTH: 550
<212> TYPE: PRT
<213> ORGANISM: Artificial Sequence
<220> FEATURE:
<223> OTHER INFORMATION: CAA24269.1 haemagglutinin (Influenza A virus (A/Aichi/2/1968(H3N2) (excluding signal sequence)

<400> SEQUENCE: 15

```
Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
```

-continued

```
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
                325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
    370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Arg Arg Gln Leu Arg Glu Asn Ala Glu Glu Met Gly Asn
    450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Val Leu Leu Gly Phe Ile Met Trp Ala Cys Gln Arg Gly Asn Ile
    530                 535                 540

Arg Cys Asn Ile Cys Ile
545                 550


<210> SEQ ID NO 16
<211> LENGTH: 248
<212> TYPE: PRT
<213> ORGANISM: Artificial Sequence
<220> FEATURE:
<223> OTHER INFORMATION: UFV5367

<400> SEQUENCE: 16

Asp Thr Ile Cys Ile Gly Tyr His Ala Asn Asn Ser Thr Asp Thr Val
```

```
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile
                245


<210> SEQ ID NO 17
<211> LENGTH: 248
<212> TYPE: PRT
<213> ORGANISM: Artificial Sequence
<220> FEATURE:
<223> OTHER INFORMATION: UFV5369

<400> SEQUENCE: 17

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
```

```
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 18
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 18

Arg Met Lys Gln Ile Glu Asp Lys Ile Glu Glu Ile Glu Ser Lys
1               5                   10                  15


<210> SEQ ID NO 19
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 19

Arg Ile Lys Gln Ile Glu Asp Lys Ile Glu Glu Ile Glu Ser Lys
1               5                   10                  15


<210> SEQ ID NO 20
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 20

Arg Met Glu Ala Leu Glu Lys Lys Val Asp Asp Ile Glu Lys Lys
1               5                   10                  15


<210> SEQ ID NO 21
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 21

Arg Ile Glu Ala Leu Glu Lys Lys Val Asp Asp Ile Glu Lys Lys
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 22

Arg Met Glu Asn Leu Glu Lys Lys Val Asp Asp Ile Glu Glu Lys
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 23

Arg Ile Glu Asn Leu Glu Lys Lys Val Asp Asp Ile Glu Glu Lys
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 24

Cys Met Lys Gln Ile Glu Asp Lys Ile Glu Glu Ile Glu Ser Lys
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 25

Cys Ile Lys Gln Ile Glu Asp Lys Ile Glu Glu Ile Glu Ser Lys
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 26

Cys Met Glu Ala Leu Glu Lys Lys Val Asp Asp Ile Glu Lys Lys
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 27

Cys Ile Glu Ala Leu Glu Lys Lys Val Asp Asp Ile Glu Lys Lys
1 5 10 15

<210> SEQ ID NO 28

<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 28

Arg Met Glu Cys Leu Glu Lys Lys Val Asp Asp Ile Glu Lys Lys
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: heterologous trimerization sequence

<400> SEQUENCE: 29

Arg Ile Glu Cys Leu Glu Lys Lys Val Asp Asp Ile Glu Lys Lys
1 5 10 15

<210> SEQ ID NO 30
<211> LENGTH: 248
<212> TYPE: PRT
<213> ORGANISM: Artificial Sequence
<220> FEATURE:
<223> OTHER INFORMATION: UFV150558

<400> SEQUENCE: 30

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Pro Thr Ala Ile
115 120 125

Gly Cys Glu Tyr Asn Lys Ser Glu Gln Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ala Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 31
<211> LENGTH: 248
<212> TYPE: PRT
<213> ORGANISM: Artificial Sequence
<220> FEATURE:
<223> OTHER INFORMATION: UFV150559

<400> SEQUENCE: 31

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Arg Thr Ala Ile
115 120 125

Gly Cys Glu Phe Asn Lys Ser Glu Gln Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ser Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 32
<211> LENGTH: 252
<212> TYPE: PRT
<213> ORGANISM: Artificial Sequence
<220> FEATURE:
<223> OTHER INFORMATION: UFV150565

<400> SEQUENCE: 32

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

```
Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Leu Ala Ile Tyr
                245                 250


<210> SEQ ID NO 33
<211> LENGTH: 250
<212> TYPE: PRT
<213> ORGANISM: Artificial Sequence
<220> FEATURE:
<223> OTHER INFORMATION: UFV150566

<400> SEQUENCE: 33

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160
```

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Leu Ala
245 250

<210> SEQ ID NO 34
<211> LENGTH: 246
<212> TYPE: PRT
<213> ORGANISM: Artificial Sequence
<220> FEATURE:
<223> OTHER INFORMATION: UFV150567

<400> SEQUENCE: 34

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr
245

<210> SEQ ID NO 35

<211> LENGTH: 244
<212> TYPE: PRT
<213> ORGANISM: Artificial Sequence
<220> FEATURE:
<223> OTHER INFORMATION: UFV150568

<400> SEQUENCE: 35

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly

<210> SEQ ID NO 36
<211> LENGTH: 242
<212> TYPE: PRT
<213> ORGANISM: Artificial Sequence
<220> FEATURE:
<223> OTHER INFORMATION: UFV150569

<400> SEQUENCE: 36

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

```
Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser


<210> SEQ ID NO 37
<211> LENGTH: 240
<212> TYPE: PRT
<213> ORGANISM: Artificial Sequence
<220> FEATURE:
<223> OTHER INFORMATION: UFV150570

<400> SEQUENCE: 37

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190
```

```
Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240


<210> SEQ ID NO 38
<211> LENGTH: 238
<212> TYPE: PRT
<213> ORGANISM: Artificial Sequence
<220> FEATURE:
<223> OTHER INFORMATION: UFV150571

<400> SEQUENCE: 38

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val
225                 230                 235


<210> SEQ ID NO 39
<211> LENGTH: 236
<212> TYPE: PRT
<213> ORGANISM: Artificial Sequence
<220> FEATURE:
<223> OTHER INFORMATION: UFV150572

<400> SEQUENCE: 39

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30
```

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp
225 230 235

<210> SEQ ID NO 40
<211> LENGTH: 234
<212> TYPE: PRT
<213> ORGANISM: Artificial Sequence
<220> FEATURE:
<223> OTHER INFORMATION: UFV150573

<400> SEQUENCE: 40

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

-continued

```
Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys
225                 230


<210> SEQ ID NO 41
<211> LENGTH: 232
<212> TYPE: PRT
<213> ORGANISM: Artificial Sequence
<220> FEATURE:
<223> OTHER INFORMATION: UFV150574

<400> SEQUENCE: 41

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg
225                 230


<210> SEQ ID NO 42
<211> LENGTH: 252
<212> TYPE: PRT
<213> ORGANISM: Artificial Sequence
<220> FEATURE:
<223> OTHER INFORMATION: UFV150575
```

<400> SEQUENCE: 42

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile Leu Ala Ile Tyr
                245                 250
```

<210> SEQ ID NO 43
<211> LENGTH: 250
<212> TYPE: PRT
<213> ORGANISM: Artificial Sequence
<220> FEATURE:
<223> OTHER INFORMATION: UFV150576

<400> SEQUENCE: 43

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
```

-continued

```
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile Leu Ala
                245                 250


<210> SEQ ID NO 44
<211> LENGTH: 246
<212> TYPE: PRT
<213> ORGANISM: Artificial Sequence
<220> FEATURE:
<223> OTHER INFORMATION: UFV150577

<400> SEQUENCE: 44

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
```

```
    210                 215                 220

Ser Glu Glu Ala Lys Leu Asn Arg Glu Glu Ile Asp Gly Val Lys Leu
225                 230                 235                 240

Glu Ser Thr Arg Ile Tyr
                245
```

<210> SEQ ID NO 45
<211> LENGTH: 244
<212> TYPE: PRT
<213> ORGANISM: Artificial Sequence
<220> FEATURE:
<223> OTHER INFORMATION: UFV150578

<400> SEQUENCE: 45

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg
```

<210> SEQ ID NO 46
<211> LENGTH: 242
<212> TYPE: PRT
<213> ORGANISM: Artificial Sequence
<220> FEATURE:
<223> OTHER INFORMATION: UFV150579

<400> SEQUENCE: 46

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
```

```
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser


<210> SEQ ID NO 47
<211> LENGTH: 240
<212> TYPE: PRT
<213> ORGANISM: Artificial Sequence
<220> FEATURE:
<223> OTHER INFORMATION: UFV150580

<400> SEQUENCE: 47

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140
```

```
Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240


<210> SEQ ID NO 48
<211> LENGTH: 238
<212> TYPE: PRT
<213> ORGANISM: Artificial Sequence
<220> FEATURE:
<223> OTHER INFORMATION: UFV150581

<400> SEQUENCE: 48

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val
225                 230                 235


<210> SEQ ID NO 49
<211> LENGTH: 236
<212> TYPE: PRT
<213> ORGANISM: Artificial Sequence
```

<220> FEATURE:
<223> OTHER INFORMATION: UFV150582

<400> SEQUENCE: 49

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Tyr Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Tyr His Asp Ser Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp
225 230 235

<210> SEQ ID NO 50
<211> LENGTH: 234
<212> TYPE: PRT
<213> ORGANISM: Artificial Sequence
<220> FEATURE:
<223> OTHER INFORMATION: UFV150583

<400> SEQUENCE: 50

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn

-continued

```
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu
225                 230


<210> SEQ ID NO 51
<211> LENGTH: 232
<212> TYPE: PRT
<213> ORGANISM: Artificial Sequence
<220> FEATURE:
<223> OTHER INFORMATION: UFV150584

<400> SEQUENCE: 51

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg
```

```
225                 230

<210> SEQ ID NO 52
<211> LENGTH: 248
<212> TYPE: PRT
<213> ORGANISM: Artificial Sequence
<220> FEATURE:
<223> OTHER INFORMATION: UFV150849

<400> SEQUENCE: 52

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Arg Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Glu Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile
                245

<210> SEQ ID NO 53
<211> LENGTH: 248
<212> TYPE: PRT
<213> ORGANISM: Artificial Sequence
<220> FEATURE:
<223> OTHER INFORMATION: UFV150850

<400> SEQUENCE: 53

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45
```

```
Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Arg Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Glu Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 54
<211> LENGTH: 248
<212> TYPE: PRT
<213> ORGANISM: Artificial Sequence
<220> FEATURE:
<223> OTHER INFORMATION: UFV150552

<400> SEQUENCE: 54

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160
```

-continued

```
Leu Val Leu Leu Glu Asn Gln Arg Thr Leu Asp Phe His Asp Ala Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile
                245
```

```
<210> SEQ ID NO 55
<211> LENGTH: 248
<212> TYPE: PRT
<213> ORGANISM: Artificial Sequence
<220> FEATURE:
<223> OTHER INFORMATION: UFV160088

<400> SEQUENCE: 55

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Arg Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Arg Thr Ala Ile
        115                 120                 125

Cys Lys Glu Tyr Pro Lys Ser Glu Gln Arg Met Glu Cys Leu Glu Lys
    130                 135                 140

Lys Val Asp Asp Ile Glu Lys Lys Ile Trp Cys Tyr Asn Ala Glu Leu
145                 150                 155                 160

Leu Val Leu Leu Glu Asn Gln Arg Thr Leu Glu Phe His Asp Ile Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile
                245


<210> SEQ ID NO 56
<211> LENGTH: 248
```

-continued

<212> TYPE: PRT
<213> ORGANISM: Artificial Sequence
<220> FEATURE:
<223> OTHER INFORMATION: UFV160090

<400> SEQUENCE: 56

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Arg Thr Ala Ile
        115                 120                 125

Gly Cys Glu Tyr Asn Lys Ser Glu Arg Cys Ile Glu Ala Leu Glu Lys
    130                 135                 140

Lys Val Asp Asp Ile Glu Lys Lys Ile Trp Cys Tyr Asn Ala Glu Leu
145                 150                 155                 160

Leu Val Leu Leu Glu Asn Gln Arg Thr Leu Glu Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 57
<211> LENGTH: 248
<212> TYPE: PRT
<213> ORGANISM: Artificial Sequence
<220> FEATURE:
<223> OTHER INFORMATION: UFV160093

<400> SEQUENCE: 57

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80
```

-continued

```
Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Arg Thr Ala Ile
        115                 120                 125

Gly Lys Glu Cys Asn Lys Ser Glu Arg Cys Ile Glu Ala Leu Glu Lys
    130                 135                 140

Lys Val Asp Asp Ile Glu Lys Lys Ile Trp Cys Tyr Asn Ala Glu Leu
145                 150                 155                 160

Leu Val Leu Leu Glu Asn Gln Arg Thr Leu Glu Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 58
<211> LENGTH: 248
<212> TYPE: PRT
<213> ORGANISM: Artificial Sequence
<220> FEATURE:
<223> OTHER INFORMATION: UFV160097

<400> SEQUENCE: 58

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Arg Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Glu Tyr His Asp Ser Asn
                165                 170                 175

Val Lys Asn Leu Tyr Glu Lys Val Arg Ser Gln Leu Lys Asn Asn Ala
            180                 185                 190
```

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 59
<211> LENGTH: 251
<212> TYPE: PRT
<213> ORGANISM: Artificial Sequence
<220> FEATURE:
<223> OTHER INFORMATION: UFV160301

<400> SEQUENCE: 59

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Arg Arg Arg Lys
50 55 60

Lys Gly Leu Phe Gly Ala Ile Ala Gly Phe Thr Glu Gly Gly Trp Thr
65 70 75 80

Gly Met Val Asp Gly Trp Tyr Gly Tyr His His Gln Asn Glu Gln Gly
85 90 95

Ser Gly Tyr Ala Ala Asp Leu Lys Ser Thr Gln Asn Ala Ile Asp Glu
100 105 110

Ile Thr Asn Lys Val Asn Ser Val Ile Glu Lys Met Asn Thr Gln Arg
115 120 125

Thr Ala Ile Gly Cys Glu Tyr Asn Lys Ser Glu Arg Cys Met Lys Gln
130 135 140

Ile Glu Asp Lys Ile Glu Glu Ile Glu Ser Lys Ile Trp Cys Tyr Asn
145 150 155 160

Ala Glu Leu Leu Val Leu Leu Glu Asn Gln Arg Thr Leu Glu Tyr His
165 170 175

Asp Ser Asn Val Lys Asn Leu Tyr Glu Lys Val Arg Ser Gln Leu Lys
180 185 190

Asn Asn Ala Lys Glu Ile Gly Asn Gly Cys Phe Glu Phe Tyr His Lys
195 200 205

Cys Asp Asn Thr Cys Met Glu Ser Val Lys Asn Gly Thr Tyr Asp Tyr
210 215 220

Pro Lys Tyr Ser Glu Glu Ala Lys Leu Asn Arg Glu Glu Ile Asp Gly
225 230 235 240

Val Lys Leu Glu Ser Thr Arg Ile Tyr Gln Ile
245 250

<210> SEQ ID NO 60
<211> LENGTH: 248
<212> TYPE: PRT
<213> ORGANISM: Artificial Sequence
<220> FEATURE:
<223> OTHER INFORMATION: UFV160302

<400> SEQUENCE: 60

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Arg Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Arg Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Glu Tyr His Asp Ser Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 61
<211> LENGTH: 248
<212> TYPE: PRT
<213> ORGANISM: Artificial Sequence
<220> FEATURE:
<223> OTHER INFORMATION: UFV160303

<400> SEQUENCE: 61

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Arg Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn

```
            100                 105                 110

Lys Val Asn Ser Val Ile Glu Lys Met Asn Thr Gln Arg Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 62
<211> LENGTH: 248
<212> TYPE: PRT
<213> ORGANISM: Artificial Sequence
<220> FEATURE:
<223> OTHER INFORMATION: UFV160304

<400> SEQUENCE: 62

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Arg Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Tyr Thr Ala Ile
        115                 120                 125

Gly Cys Glu Tyr Asn Lys Ser Glu Arg Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Glu Tyr His Asp Ser Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
```

```
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 63
<211> LENGTH: 248
<212> TYPE: PRT
<213> ORGANISM: Artificial Sequence
<220> FEATURE:
<223> OTHER INFORMATION: UFV160360

<400> SEQUENCE: 63

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 64
<211> LENGTH: 244
<212> TYPE: PRT
<213> ORGANISM: Artificial Sequence
<220> FEATURE:
<223> OTHER INFORMATION: UFV160361

<400> SEQUENCE: 64

Asp Thr Leu Cys Ile Gly Tyr His Ala Asn Asn Ser Thr Asp Thr Val
1               5                   10                  15
```

```
Asp Thr Val Leu Glu Lys Asn Val Thr Val Thr His Ser Val Asn Leu
            20                  25                  30

Leu Glu Asp Lys Tyr Val Cys Ser Thr Lys Leu Arg Leu Ala Thr Gly
        35                  40                  45

Leu Arg Asn Lys Pro Ser Lys Gln Ser Gln Gly Leu Phe Gly Ala Ile
    50                  55                  60

Ala Gly Phe Thr Glu Gly Gly Trp Thr Gly Met Val Asp Gly Trp Tyr
65                  70                  75                  80

Gly Tyr His His Gln Asn Glu Gln Gly Ser Gly Tyr Ala Ala Asp Leu
                85                  90                  95

Lys Ser Thr Gln Asn Ala Ile Asp Glu Ile Thr Asn Lys Val Asn Ser
            100                 105                 110

Val Ile Glu Lys Met Asn Thr Gln Pro Thr Ala Ile Gly Cys Glu Tyr
        115                 120                 125

Asn Lys Ser Glu Gln Cys Met Lys Gln Ile Glu Asp Lys Ile Glu Glu
    130                 135                 140

Ile Glu Ser Lys Ile Trp Cys Tyr Asn Ala Glu Leu Leu Val Leu Leu
145                 150                 155                 160

Glu Asn Gln Arg Thr Leu Asp Tyr His Asp Ala Asn Val Lys Asn Leu
                165                 170                 175

Tyr Glu Lys Val Arg Ser Gln Leu Lys Asn Asn Ala Lys Glu Ile Gly
            180                 185                 190

Asn Gly Cys Phe Glu Phe Tyr His Lys Cys Asp Asn Thr Cys Met Glu
        195                 200                 205

Ser Val Lys Asn Gly Thr Tyr Asp Tyr Pro Lys Tyr Ser Glu Glu Ala
    210                 215                 220

Lys Leu Asn Arg Glu Glu Ile Asp Gly Val Lys Leu Glu Ser Thr Arg
225                 230                 235                 240

Ile Tyr Gln Ile
```

<210> SEQ ID NO 65
<211> LENGTH: 245
<212> TYPE: PRT
<213> ORGANISM: Artificial Sequence
<220> FEATURE:
<223> OTHER INFORMATION: UFV160362

<400> SEQUENCE: 65

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys Lys Tyr Val Cys Ser Thr Lys Leu Arg Leu Ala Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Leu Lys Ser Thr Gln Asn Ala Ile Asp Glu Ile Thr Asn Lys Val Asn
            100                 105                 110

Ser Val Ile Glu Lys Met Asn Thr Gln Pro Thr Ala Ile Gly Cys Glu
        115                 120                 125

Tyr Asn Lys Ser Glu Gln Cys Met Lys Gln Ile Glu Asp Lys Ile Glu
```

```
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Asp Tyr His Asp Ala Asn Val Lys Asn
                165                 170                 175

Leu Tyr Glu Lys Val Arg Ser Gln Leu Lys Asn Asn Ala Lys Glu Ile
            180                 185                 190

Gly Asn Gly Cys Phe Glu Phe Tyr His Lys Cys Asp Asn Thr Cys Met
        195                 200                 205

Glu Ser Val Lys Asn Gly Thr Tyr Asp Tyr Pro Lys Tyr Ser Glu Glu
    210                 215                 220

Ala Lys Leu Asn Arg Glu Glu Ile Asp Gly Val Lys Leu Glu Ser Thr
225                 230                 235                 240

Arg Ile Tyr Gln Ile
                245


<210> SEQ ID NO 66
<211> LENGTH: 246
<212> TYPE: PRT
<213> ORGANISM: Artificial Sequence
<220> FEATURE:
<223> OTHER INFORMATION: UFV160363

<400> SEQUENCE: 66

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Lys Tyr Val Cys Ser Thr Lys Leu Arg Leu Ala
        35                  40                  45

Thr Gly Leu Arg Asn Lys Pro Ser Lys Gln Ser Gln Gly Leu Phe Gly
    50                  55                  60

Ala Ile Ala Gly Phe Thr Glu Gly Gly Trp Thr Gly Met Val Asp Gly
65                  70                  75                  80

Trp Tyr Gly Tyr His His Gln Asn Glu Gln Gly Ser Gly Tyr Ala Ala
                85                  90                  95

Asp Leu Lys Ser Thr Gln Asn Ala Ile Asp Glu Ile Thr Asn Lys Val
            100                 105                 110

Asn Ser Val Ile Glu Lys Met Asn Thr Gln Pro Thr Ala Ile Gly Cys
        115                 120                 125

Glu Tyr Asn Lys Ser Glu Gln Cys Met Lys Gln Ile Glu Asp Lys Ile
    130                 135                 140

Glu Glu Ile Glu Ser Lys Ile Trp Cys Tyr Asn Ala Glu Leu Leu Val
145                 150                 155                 160

Leu Leu Glu Asn Gln Arg Thr Leu Asp Tyr His Asp Ala Asn Val Lys
                165                 170                 175

Asn Leu Tyr Glu Lys Val Arg Ser Gln Leu Lys Asn Asn Ala Lys Glu
            180                 185                 190

Ile Gly Asn Gly Cys Phe Glu Phe Tyr His Lys Cys Asp Asn Thr Cys
        195                 200                 205

Met Glu Ser Val Lys Asn Gly Thr Tyr Asp Tyr Pro Lys Tyr Ser Glu
    210                 215                 220

Glu Ala Lys Leu Asn Arg Glu Glu Ile Asp Gly Val Lys Leu Glu Ser
225                 230                 235                 240

Thr Arg Ile Tyr Gln Ile
```

245

<210> SEQ ID NO 67
<211> LENGTH: 247
<212> TYPE: PRT
<213> ORGANISM: Artificial Sequence
<220> FEATURE:
<223> OTHER INFORMATION: UFV160364

<400> SEQUENCE: 67

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Lys Tyr Val Cys Ser Thr Lys Leu Arg Leu
        35                  40                  45

Ala Thr Gly Leu Arg Asn Lys Pro Ser Lys Gln Ser Gln Gly Leu Phe
    50                  55                  60

Gly Ala Ile Ala Gly Phe Thr Glu Gly Gly Trp Thr Gly Met Val Asp
65                  70                  75                  80

Gly Trp Tyr Gly Tyr His His Gln Asn Glu Gln Gly Ser Gly Tyr Ala
                85                  90                  95

Ala Asp Leu Lys Ser Thr Gln Asn Ala Ile Asp Glu Ile Thr Asn Lys
            100                 105                 110

Val Asn Ser Val Ile Glu Lys Met Asn Thr Gln Pro Thr Ala Ile Gly
        115                 120                 125

Cys Glu Tyr Asn Lys Ser Glu Gln Cys Met Lys Gln Ile Glu Asp Lys
    130                 135                 140

Ile Glu Glu Ile Glu Ser Lys Ile Trp Cys Tyr Asn Ala Glu Leu Leu
145                 150                 155                 160

Val Leu Leu Glu Asn Gln Arg Thr Leu Asp Tyr His Asp Ala Asn Val
                165                 170                 175

Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245
```

<210> SEQ ID NO 68
<211> LENGTH: 248
<212> TYPE: PRT
<213> ORGANISM: Artificial Sequence
<220> FEATURE:
<223> OTHER INFORMATION: UFV160365

<400> SEQUENCE: 68

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Tyr Val Cys Ser Thr Lys Leu Arg
        35                  40                  45
```

```
Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 69
<211> LENGTH: 249
<212> TYPE: PRT
<213> ORGANISM: Artificial Sequence
<220> FEATURE:
<223> OTHER INFORMATION: UFV160366

<400> SEQUENCE: 69

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Lys Tyr Val Cys Ser Thr Lys Leu
        35                  40                  45

Arg Leu Ala Thr Gly Leu Arg Asn Lys Pro Ser Lys Gln Ser Gln Gly
    50                  55                  60

Leu Phe Gly Ala Ile Ala Gly Phe Thr Glu Gly Gly Trp Thr Gly Met
65                  70                  75                  80

Val Asp Gly Trp Tyr Gly Tyr His His Gln Asn Glu Gln Gly Ser Gly
                85                  90                  95

Tyr Ala Ala Asp Leu Lys Ser Thr Gln Asn Ala Ile Asp Glu Ile Thr
            100                 105                 110

Asn Lys Val Asn Ser Val Ile Glu Lys Met Asn Thr Gln Pro Thr Ala
        115                 120                 125

Ile Gly Cys Glu Tyr Asn Lys Ser Glu Gln Cys Met Lys Gln Ile Glu
    130                 135                 140

Asp Lys Ile Glu Glu Ile Glu Ser Lys Ile Trp Cys Tyr Asn Ala Glu
145                 150                 155                 160
```

```
Leu Leu Val Leu Leu Glu Asn Gln Arg Thr Leu Asp Tyr His Asp Ala
                165                 170                 175

Asn Val Lys Asn Leu Tyr Glu Lys Val Arg Ser Gln Leu Lys Asn Asn
            180                 185                 190

Ala Lys Glu Ile Gly Asn Gly Cys Phe Glu Phe Tyr His Lys Cys Asp
        195                 200                 205

Asn Thr Cys Met Glu Ser Val Lys Asn Gly Thr Tyr Asp Tyr Pro Lys
    210                 215                 220

Tyr Ser Glu Glu Ala Lys Leu Asn Arg Glu Glu Ile Asp Gly Val Lys
225                 230                 235                 240

Leu Glu Ser Thr Arg Ile Tyr Gln Ile
                245
```

<210> SEQ ID NO 70
<211> LENGTH: 250
<212> TYPE: PRT
<213> ORGANISM: Artificial Sequence
<220> FEATURE:
<223> OTHER INFORMATION: UFV160367

<400> SEQUENCE: 70

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Lys Tyr Val Cys Ser Thr Lys
        35                  40                  45

Leu Arg Leu Ala Thr Gly Leu Arg Asn Lys Pro Ser Lys Gln Ser Gln
    50                  55                  60

Gly Leu Phe Gly Ala Ile Ala Gly Phe Thr Glu Gly Gly Trp Thr Gly
65                  70                  75                  80

Met Val Asp Gly Trp Tyr Gly Tyr His His Gln Asn Glu Gln Gly Ser
                85                  90                  95

Gly Tyr Ala Ala Asp Leu Lys Ser Thr Gln Asn Ala Ile Asp Glu Ile
            100                 105                 110

Thr Asn Lys Val Asn Ser Val Ile Glu Lys Met Asn Thr Gln Pro Thr
        115                 120                 125

Ala Ile Gly Cys Glu Tyr Asn Lys Ser Glu Gln Cys Met Lys Gln Ile
    130                 135                 140

Glu Asp Lys Ile Glu Glu Ile Glu Ser Lys Ile Trp Cys Tyr Asn Ala
145                 150                 155                 160

Glu Leu Leu Val Leu Leu Glu Asn Gln Arg Thr Leu Asp Tyr His Asp
                165                 170                 175

Ala Asn Val Lys Asn Leu Tyr Glu Lys Val Arg Ser Gln Leu Lys Asn
            180                 185                 190

Asn Ala Lys Glu Ile Gly Asn Gly Cys Phe Glu Phe Tyr His Lys Cys
        195                 200                 205

Asp Asn Thr Cys Met Glu Ser Val Lys Asn Gly Thr Tyr Asp Tyr Pro
    210                 215                 220

Lys Tyr Ser Glu Glu Ala Lys Leu Asn Arg Glu Glu Ile Asp Gly Val
225                 230                 235                 240

Lys Leu Glu Ser Thr Arg Ile Tyr Gln Ile
                245                 250
```

<210> SEQ ID NO 71
<211> LENGTH: 251

```
<212> TYPE: PRT
<213> ORGANISM: Artificial Sequence
<220> FEATURE:
<223> OTHER INFORMATION: UFV160368

<400> SEQUENCE: 71

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Lys Tyr Val Cys Ser Thr
        35                  40                  45

Lys Leu Arg Leu Ala Thr Gly Leu Arg Asn Lys Pro Ser Lys Gln Ser
    50                  55                  60

Gln Gly Leu Phe Gly Ala Ile Ala Gly Phe Thr Glu Gly Gly Trp Thr
65                  70                  75                  80

Gly Met Val Asp Gly Trp Tyr Gly Tyr His His Gln Asn Glu Gln Gly
                85                  90                  95

Ser Gly Tyr Ala Ala Asp Leu Lys Ser Thr Gln Asn Ala Ile Asp Glu
            100                 105                 110

Ile Thr Asn Lys Val Asn Ser Val Ile Glu Lys Met Asn Thr Gln Pro
        115                 120                 125

Thr Ala Ile Gly Cys Glu Tyr Asn Lys Ser Glu Gln Cys Met Lys Gln
    130                 135                 140

Ile Glu Asp Lys Ile Glu Glu Ile Glu Ser Lys Ile Trp Cys Tyr Asn
145                 150                 155                 160

Ala Glu Leu Leu Val Leu Leu Glu Asn Gln Arg Thr Leu Asp Tyr His
                165                 170                 175

Asp Ala Asn Val Lys Asn Leu Tyr Glu Lys Val Arg Ser Gln Leu Lys
            180                 185                 190

Asn Asn Ala Lys Glu Ile Gly Asn Gly Cys Phe Glu Phe Tyr His Lys
        195                 200                 205

Cys Asp Asn Thr Cys Met Glu Ser Val Lys Asn Gly Thr Tyr Asp Tyr
    210                 215                 220

Pro Lys Tyr Ser Glu Glu Ala Lys Leu Asn Arg Glu Glu Ile Asp Gly
225                 230                 235                 240

Val Lys Leu Glu Ser Thr Arg Ile Tyr Gln Ile
                245                 250


<210> SEQ ID NO 72
<211> LENGTH: 252
<212> TYPE: PRT
<213> ORGANISM: Artificial Sequence
<220> FEATURE:
<223> OTHER INFORMATION: UFV160369

<400> SEQUENCE: 72

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Pro Lys Tyr Val Cys Ser
        35                  40                  45

Thr Lys Leu Arg Leu Ala Thr Gly Leu Arg Asn Lys Pro Ser Lys Gln
    50                  55                  60

Ser Gln Gly Leu Phe Gly Ala Ile Ala Gly Phe Thr Glu Gly Gly Trp
65                  70                  75                  80
```

Thr Gly Met Val Asp Gly Trp Tyr Gly Tyr His His Gln Asn Glu Gln
85 90 95

Gly Ser Gly Tyr Ala Ala Asp Leu Lys Ser Thr Gln Asn Ala Ile Asp
100 105 110

Glu Ile Thr Asn Lys Val Asn Ser Val Ile Glu Lys Met Asn Thr Gln
115 120 125

Pro Thr Ala Ile Gly Cys Glu Tyr Asn Lys Ser Glu Gln Cys Met Lys
130 135 140

Gln Ile Glu Asp Lys Ile Glu Glu Ile Glu Ser Lys Ile Trp Cys Tyr
145 150 155 160

Asn Ala Glu Leu Leu Val Leu Leu Glu Asn Gln Arg Thr Leu Asp Tyr
165 170 175

His Asp Ala Asn Val Lys Asn Leu Tyr Glu Lys Val Arg Ser Gln Leu
180 185 190

Lys Asn Asn Ala Lys Glu Ile Gly Asn Gly Cys Phe Glu Phe Tyr His
195 200 205

Lys Cys Asp Asn Thr Cys Met Glu Ser Val Lys Asn Gly Thr Tyr Asp
210 215 220

Tyr Pro Lys Tyr Ser Glu Glu Ala Lys Leu Asn Arg Glu Glu Ile Asp
225 230 235 240

Gly Val Lys Leu Glu Ser Thr Arg Ile Tyr Gln Ile
245 250

<210> SEQ ID NO 73
<211> LENGTH: 248
<212> TYPE: PRT
<213> ORGANISM: Artificial Sequence
<220> FEATURE:
<223> OTHER INFORMATION: UFV160370

<400> SEQUENCE: 73

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Lys His Gly Pro Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Pro Thr Ala Ile
115 120 125

Gly Cys Glu Tyr Asn Lys Ser Glu Gln Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ala Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 74
<211> LENGTH: 248
<212> TYPE: PRT
<213> ORGANISM: Artificial Sequence
<220> FEATURE:
<223> OTHER INFORMATION: UFV160371

<400> SEQUENCE: 74

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Glu Gly Pro Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Pro Thr Ala Ile
115 120 125

Gly Cys Glu Tyr Asn Lys Ser Glu Gln Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ala Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 75
<211> LENGTH: 242
<212> TYPE: PRT
<213> ORGANISM: Artificial Sequence
<220> FEATURE:
<223> OTHER INFORMATION: UFV160372

<400> SEQUENCE: 75

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Val Cys Ser Thr Lys Leu Arg Leu Ala Thr Gly Leu Arg
        35                  40                  45

Asn Lys Pro Ser Lys Gln Ser Gln Gly Leu Phe Gly Ala Ile Ala Gly
    50                  55                  60

Phe Thr Glu Gly Gly Trp Thr Gly Met Val Asp Gly Trp Tyr Gly Tyr
65                  70                  75                  80

His His Gln Asn Glu Gln Gly Ser Gly Tyr Ala Ala Asp Leu Lys Ser
                85                  90                  95

Thr Gln Asn Ala Ile Asp Glu Ile Thr Asn Lys Val Asn Ser Val Ile
            100                 105                 110

Glu Lys Met Asn Thr Gln Pro Thr Ala Ile Gly Cys Glu Tyr Asn Lys
        115                 120                 125

Ser Glu Gln Cys Met Lys Gln Ile Glu Asp Lys Ile Glu Glu Ile Glu
    130                 135                 140

Ser Lys Ile Trp Cys Tyr Asn Ala Glu Leu Leu Val Leu Leu Glu Asn
145                 150                 155                 160

Gln Arg Thr Leu Asp Tyr His Asp Ala Asn Val Lys Asn Leu Tyr Glu
                165                 170                 175

Lys Val Arg Ser Gln Leu Lys Asn Asn Ala Lys Glu Ile Gly Asn Gly
            180                 185                 190

Cys Phe Glu Phe Tyr His Lys Cys Asp Asn Thr Cys Met Glu Ser Val
        195                 200                 205

Lys Asn Gly Thr Tyr Asp Tyr Pro Lys Tyr Ser Glu Glu Ala Lys Leu
    210                 215                 220

Asn Arg Glu Glu Ile Asp Gly Val Lys Leu Glu Ser Thr Arg Ile Tyr
225                 230                 235                 240

Gln Ile
```

<210> SEQ ID NO 76
<211> LENGTH: 243
<212> TYPE: PRT
<213> ORGANISM: Artificial Sequence
<220> FEATURE:
<223> OTHER INFORMATION: UFV160373

<400> SEQUENCE: 76

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys Val Cys Ser Thr Lys Leu Arg Leu Ala Thr Gly Leu
        35                  40                  45

Arg Asn Lys Pro Ser Lys Gln Ser Gln Gly Leu Phe Gly Ala Ile Ala
    50                  55                  60

Gly Phe Thr Glu Gly Gly Trp Thr Gly Met Val Asp Gly Trp Tyr Gly
65                  70                  75                  80

Tyr His His Gln Asn Glu Gln Gly Ser Gly Tyr Ala Ala Asp Leu Lys
                85                  90                  95

Ser Thr Gln Asn Ala Ile Asp Glu Ile Thr Asn Lys Val Asn Ser Val
            100                 105                 110
```

```
Ile Glu Lys Met Asn Thr Gln Pro Thr Ala Ile Gly Cys Glu Tyr Asn
        115                 120                 125

Lys Ser Glu Gln Cys Met Lys Gln Ile Glu Asp Lys Ile Glu Glu Ile
    130                 135                 140

Glu Ser Lys Ile Trp Cys Tyr Asn Ala Glu Leu Leu Val Leu Leu Glu
145                 150                 155                 160

Asn Gln Arg Thr Leu Asp Tyr His Asp Ala Asn Val Lys Asn Leu Tyr
                165                 170                 175

Glu Lys Val Arg Ser Gln Leu Lys Asn Asn Ala Lys Glu Ile Gly Asn
            180                 185                 190

Gly Cys Phe Glu Phe Tyr His Lys Cys Asp Asn Thr Cys Met Glu Ser
        195                 200                 205

Val Lys Asn Gly Thr Tyr Asp Tyr Pro Lys Tyr Ser Glu Glu Ala Lys
    210                 215                 220

Leu Asn Arg Glu Glu Ile Asp Gly Val Lys Leu Glu Ser Thr Arg Ile
225                 230                 235                 240

Tyr Gln Ile


<210> SEQ ID NO 77
<211> LENGTH: 244
<212> TYPE: PRT
<213> ORGANISM: Artificial Sequence
<220> FEATURE:
<223> OTHER INFORMATION: UFV160374

<400> SEQUENCE: 77

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Val Cys Ser Thr Lys Leu Arg Leu Ala Thr Gly
        35                  40                  45

Leu Arg Asn Lys Pro Ser Lys Gln Ser Gln Gly Leu Phe Gly Ala Ile
    50                  55                  60

Ala Gly Phe Thr Glu Gly Gly Trp Thr Gly Met Val Asp Gly Trp Tyr
65                  70                  75                  80

Gly Tyr His His Gln Asn Glu Gln Gly Ser Gly Tyr Ala Ala Asp Leu
                85                  90                  95

Lys Ser Thr Gln Asn Ala Ile Asp Glu Ile Thr Asn Lys Val Asn Ser
            100                 105                 110

Val Ile Glu Lys Met Asn Thr Gln Pro Thr Ala Ile Gly Cys Glu Tyr
        115                 120                 125

Asn Lys Ser Glu Gln Cys Met Lys Gln Ile Glu Asp Lys Ile Glu Glu
    130                 135                 140

Ile Glu Ser Lys Ile Trp Cys Tyr Asn Ala Glu Leu Leu Val Leu Leu
145                 150                 155                 160

Glu Asn Gln Arg Thr Leu Asp Tyr His Asp Ala Asn Val Lys Asn Leu
                165                 170                 175

Tyr Glu Lys Val Arg Ser Gln Leu Lys Asn Asn Ala Lys Glu Ile Gly
            180                 185                 190

Asn Gly Cys Phe Glu Phe Tyr His Lys Cys Asp Asn Thr Cys Met Glu
        195                 200                 205

Ser Val Lys Asn Gly Thr Tyr Asp Tyr Pro Lys Tyr Ser Glu Glu Ala
    210                 215                 220
```

Lys Leu Asn Arg Glu Glu Ile Asp Gly Val Lys Leu Glu Ser Thr Arg
225 230 235 240

Ile Tyr Gln Ile

<210> SEQ ID NO 78
<211> LENGTH: 245
<212> TYPE: PRT
<213> ORGANISM: Artificial Sequence
<220> FEATURE:
<223> OTHER INFORMATION: UFV160375

<400> SEQUENCE: 78

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Lys His Asn Val Cys Ser Thr Lys Leu Arg Leu Ala Thr
35 40 45

Gly Leu Arg Asn Lys Pro Ser Lys Gln Ser Gln Gly Leu Phe Gly Ala
50 55 60

Ile Ala Gly Phe Thr Glu Gly Gly Trp Thr Gly Met Val Asp Gly Trp
65 70 75 80

Tyr Gly Tyr His His Gln Asn Glu Gln Gly Ser Gly Tyr Ala Ala Asp
85 90 95

Leu Lys Ser Thr Gln Asn Ala Ile Asp Glu Ile Thr Asn Lys Val Asn
100 105 110

Ser Val Ile Glu Lys Met Asn Thr Gln Pro Thr Ala Ile Gly Cys Glu
115 120 125

Tyr Asn Lys Ser Glu Gln Cys Met Lys Gln Ile Glu Asp Lys Ile Glu
130 135 140

Glu Ile Glu Ser Lys Ile Trp Cys Tyr Asn Ala Glu Leu Leu Val Leu
145 150 155 160

Leu Glu Asn Gln Arg Thr Leu Asp Tyr His Asp Ala Asn Val Lys Asn
165 170 175

Leu Tyr Glu Lys Val Arg Ser Gln Leu Lys Asn Asn Ala Lys Glu Ile
180 185 190

Gly Asn Gly Cys Phe Glu Phe Tyr His Lys Cys Asp Asn Thr Cys Met
195 200 205

Glu Ser Val Lys Asn Gly Thr Tyr Asp Tyr Pro Lys Tyr Ser Glu Glu
210 215 220

Ala Lys Leu Asn Arg Glu Glu Ile Asp Gly Val Lys Leu Glu Ser Thr
225 230 235 240

Arg Ile Tyr Gln Ile
245

<210> SEQ ID NO 79
<211> LENGTH: 246
<212> TYPE: PRT
<213> ORGANISM: Artificial Sequence
<220> FEATURE:
<223> OTHER INFORMATION: UFV160376

<400> SEQUENCE: 79

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

```
Leu Glu Asp Lys His Asn Gly Val Cys Ser Thr Lys Leu Arg Leu Ala
        35                  40                  45

Thr Gly Leu Arg Asn Lys Pro Ser Lys Gln Ser Gln Gly Leu Phe Gly
    50                  55                  60

Ala Ile Ala Gly Phe Thr Glu Gly Gly Trp Thr Gly Met Val Asp Gly
65                  70                  75                  80

Trp Tyr Gly Tyr His His Gln Asn Glu Gln Gly Ser Gly Tyr Ala Ala
                85                  90                  95

Asp Leu Lys Ser Thr Gln Asn Ala Ile Asp Glu Ile Thr Asn Lys Val
            100                 105                 110

Asn Ser Val Ile Glu Lys Met Asn Thr Gln Pro Thr Ala Ile Gly Cys
        115                 120                 125

Glu Tyr Asn Lys Ser Glu Gln Cys Met Lys Gln Ile Glu Asp Lys Ile
    130                 135                 140

Glu Glu Ile Glu Ser Lys Ile Trp Cys Tyr Asn Ala Glu Leu Leu Val
145                 150                 155                 160

Leu Leu Glu Asn Gln Arg Thr Leu Asp Tyr His Asp Ala Asn Val Lys
                165                 170                 175

Asn Leu Tyr Glu Lys Val Arg Ser Gln Leu Lys Asn Asn Ala Lys Glu
            180                 185                 190

Ile Gly Asn Gly Cys Phe Glu Phe Tyr His Lys Cys Asp Asn Thr Cys
        195                 200                 205

Met Glu Ser Val Lys Asn Gly Thr Tyr Asp Tyr Pro Lys Tyr Ser Glu
    210                 215                 220

Glu Ala Lys Leu Asn Arg Glu Glu Ile Asp Gly Val Lys Leu Glu Ser
225                 230                 235                 240

Thr Arg Ile Tyr Gln Ile
                245


<210> SEQ ID NO 80
<211> LENGTH: 247
<212> TYPE: PRT
<213> ORGANISM: Artificial Sequence
<220> FEATURE:
<223> OTHER INFORMATION: UFV160377

<400> SEQUENCE: 80

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Val Cys Ser Thr Lys Leu Arg Leu
        35                  40                  45

Ala Thr Gly Leu Arg Asn Lys Pro Ser Lys Gln Ser Gln Gly Leu Phe
    50                  55                  60

Gly Ala Ile Ala Gly Phe Thr Glu Gly Gly Trp Thr Gly Met Val Asp
65                  70                  75                  80

Gly Trp Tyr Gly Tyr His His Gln Asn Glu Gln Gly Ser Gly Tyr Ala
                85                  90                  95

Ala Asp Leu Lys Ser Thr Gln Asn Ala Ile Asp Glu Ile Thr Asn Lys
            100                 105                 110

Val Asn Ser Val Ile Glu Lys Met Asn Thr Gln Pro Thr Ala Ile Gly
        115                 120                 125

Cys Glu Tyr Asn Lys Ser Glu Gln Cys Met Lys Gln Ile Glu Asp Lys
    130                 135                 140
```

```
Ile Glu Glu Ile Glu Ser Lys Ile Trp Cys Tyr Asn Ala Glu Leu Leu
145                 150                 155                 160

Val Leu Leu Glu Asn Gln Arg Thr Leu Asp Tyr His Asp Ala Asn Val
                165                 170                 175

Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245


<210> SEQ ID NO 81
<211> LENGTH: 248
<212> TYPE: PRT
<213> ORGANISM: Artificial Sequence
<220> FEATURE:
<223> OTHER INFORMATION: UFV160378

<400> SEQUENCE: 81

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 82
<211> LENGTH: 249
<212> TYPE: PRT
<213> ORGANISM: Artificial Sequence
<220> FEATURE:
<223> OTHER INFORMATION: UFV160379

<400> SEQUENCE: 82

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Val Cys Ser Thr Lys Leu
        35                  40                  45

Arg Leu Ala Thr Gly Leu Arg Asn Lys Pro Ser Lys Gln Ser Gln Gly
    50                  55                  60

Leu Phe Gly Ala Ile Ala Gly Phe Thr Glu Gly Gly Trp Thr Gly Met
65                  70                  75                  80

Val Asp Gly Trp Tyr Gly Tyr His His Gln Asn Glu Gln Gly Ser Gly
                85                  90                  95

Tyr Ala Ala Asp Leu Lys Ser Thr Gln Asn Ala Ile Asp Glu Ile Thr
            100                 105                 110

Asn Lys Val Asn Ser Val Ile Glu Lys Met Asn Thr Gln Pro Thr Ala
        115                 120                 125

Ile Gly Cys Glu Tyr Asn Lys Ser Glu Gln Cys Met Lys Gln Ile Glu
    130                 135                 140

Asp Lys Ile Glu Glu Ile Glu Ser Lys Ile Trp Cys Tyr Asn Ala Glu
145                 150                 155                 160

Leu Leu Val Leu Leu Glu Asn Gln Arg Thr Leu Asp Tyr His Asp Ala
                165                 170                 175

Asn Val Lys Asn Leu Tyr Glu Lys Val Arg Ser Gln Leu Lys Asn Asn
            180                 185                 190

Ala Lys Glu Ile Gly Asn Gly Cys Phe Glu Phe Tyr His Lys Cys Asp
        195                 200                 205

Asn Thr Cys Met Glu Ser Val Lys Asn Gly Thr Tyr Asp Tyr Pro Lys
    210                 215                 220

Tyr Ser Glu Glu Ala Lys Leu Asn Arg Glu Glu Ile Asp Gly Val Lys
225                 230                 235                 240

Leu Glu Ser Thr Arg Ile Tyr Gln Ile
                245

<210> SEQ ID NO 83
<211> LENGTH: 248
<212> TYPE: PRT
<213> ORGANISM: Artificial Sequence
<220> FEATURE:
<223> OTHER INFORMATION: UFV160380

<400> SEQUENCE: 83

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ala Gly Ser Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

-continued

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Pro Thr Ala Ile
115 120 125

Gly Cys Glu Tyr Asn Lys Ser Glu Gln Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ala Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 84
<211> LENGTH: 247
<212> TYPE: PRT
<213> ORGANISM: Artificial Sequence
<220> FEATURE:
<223> OTHER INFORMATION: UFV160381

<400> SEQUENCE: 84

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ala Gly Ser Lys Tyr Val Cys Ser Thr Lys Leu Arg Leu
35 40 45

Ala Thr Gly Leu Arg Asn Lys Pro Ser Lys Gln Ser Gln Gly Leu Phe
50 55 60

Gly Ala Ile Ala Gly Phe Thr Glu Gly Gly Trp Thr Gly Met Val Asp
65 70 75 80

Gly Trp Tyr Gly Tyr His His Gln Asn Glu Gln Gly Ser Gly Tyr Ala
85 90 95

Ala Asp Leu Lys Ser Thr Gln Asn Ala Ile Asp Glu Ile Thr Asn Lys
100 105 110

Val Asn Ser Val Ile Glu Lys Met Asn Thr Gln Pro Thr Ala Ile Gly
115 120 125

Cys Glu Tyr Asn Lys Ser Glu Gln Cys Met Lys Gln Ile Glu Asp Lys
130 135 140

Ile Glu Glu Ile Glu Ser Lys Ile Trp Cys Tyr Asn Ala Glu Leu Leu
145 150 155 160

Val Leu Leu Glu Asn Gln Arg Thr Leu Asp Tyr His Asp Ala Asn Val
165 170 175

```
Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245


<210> SEQ ID NO 85
<211> LENGTH: 249
<212> TYPE: PRT
<213> ORGANISM: Artificial Sequence
<220> FEATURE:
<223> OTHER INFORMATION: UFV160382

<400> SEQUENCE: 85

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ala Gly Ser Gly Ile Lys Tyr Val Cys Ser Thr Lys Leu
        35                  40                  45

Arg Leu Ala Thr Gly Leu Arg Asn Lys Pro Ser Lys Gln Ser Gln Gly
    50                  55                  60

Leu Phe Gly Ala Ile Ala Gly Phe Thr Glu Gly Gly Trp Thr Gly Met
65                  70                  75                  80

Val Asp Gly Trp Tyr Gly Tyr His His Gln Asn Glu Gln Gly Ser Gly
                85                  90                  95

Tyr Ala Ala Asp Leu Lys Ser Thr Gln Asn Ala Ile Asp Glu Ile Thr
            100                 105                 110

Asn Lys Val Asn Ser Val Ile Glu Lys Met Asn Thr Gln Pro Thr Ala
        115                 120                 125

Ile Gly Cys Glu Tyr Asn Lys Ser Glu Gln Cys Met Lys Gln Ile Glu
    130                 135                 140

Asp Lys Ile Glu Glu Ile Glu Ser Lys Ile Trp Cys Tyr Asn Ala Glu
145                 150                 155                 160

Leu Leu Val Leu Leu Glu Asn Gln Arg Thr Leu Asp Tyr His Asp Ala
                165                 170                 175

Asn Val Lys Asn Leu Tyr Glu Lys Val Arg Ser Gln Leu Lys Asn Asn
            180                 185                 190

Ala Lys Glu Ile Gly Asn Gly Cys Phe Glu Phe Tyr His Lys Cys Asp
        195                 200                 205

Asn Thr Cys Met Glu Ser Val Lys Asn Gly Thr Tyr Asp Tyr Pro Lys
    210                 215                 220

Tyr Ser Glu Glu Ala Lys Leu Asn Arg Glu Glu Ile Asp Gly Val Lys
225                 230                 235                 240

Leu Glu Ser Thr Arg Ile Tyr Gln Ile
                245


<210> SEQ ID NO 86
<211> LENGTH: 247
<212> TYPE: PRT
<213> ORGANISM: Artificial Sequence
```

<220> FEATURE:
<223> OTHER INFORMATION: UFV160383

<400> SEQUENCE: 86

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Ala Gly Ser Gly Ile Val Cys Ser Thr Lys Leu Arg Leu
35 40 45

Ala Thr Gly Leu Arg Asn Lys Pro Ser Lys Gln Ser Gln Gly Leu Phe
50 55 60

Gly Ala Ile Ala Gly Phe Thr Glu Gly Gly Trp Thr Gly Met Val Asp
65 70 75 80

Gly Trp Tyr Gly Tyr His His Gln Asn Glu Gln Gly Ser Gly Tyr Ala
85 90 95

Ala Asp Leu Lys Ser Thr Gln Asn Ala Ile Asp Glu Ile Thr Asn Lys
100 105 110

Val Asn Ser Val Ile Glu Lys Met Asn Thr Gln Pro Thr Ala Ile Gly
115 120 125

Cys Glu Tyr Asn Lys Ser Glu Gln Cys Met Lys Gln Ile Glu Asp Lys
130 135 140

Ile Glu Glu Ile Glu Ser Lys Ile Trp Cys Tyr Asn Ala Glu Leu Leu
145 150 155 160

Val Leu Leu Glu Asn Gln Arg Thr Leu Asp Tyr His Asp Ala Asn Val
165 170 175

Lys Asn Leu Tyr Glu Lys Val Arg Ser Gln Leu Lys Asn Asn Ala Lys
180 185 190

Glu Ile Gly Asn Gly Cys Phe Glu Phe Tyr His Lys Cys Asp Asn Thr
195 200 205

Cys Met Glu Ser Val Lys Asn Gly Thr Tyr Asp Tyr Pro Lys Tyr Ser
210 215 220

Glu Glu Ala Lys Leu Asn Arg Glu Glu Ile Asp Gly Val Lys Leu Glu
225 230 235 240

Ser Thr Arg Ile Tyr Gln Ile
245

<210> SEQ ID NO 87
<211> LENGTH: 248
<212> TYPE: PRT
<213> ORGANISM: Artificial Sequence
<220> FEATURE:
<223> OTHER INFORMATION: UFV160384

<400> SEQUENCE: 87

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Ser Gly Ile Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr

```
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 88
<211> LENGTH: 247
<212> TYPE: PRT
<213> ORGANISM: Artificial Sequence
<220> FEATURE:
<223> OTHER INFORMATION: UFV160385

<400> SEQUENCE: 88

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Ser Gly Lys Tyr Val Cys Ser Thr Lys Leu Arg Leu
        35                  40                  45

Ala Thr Gly Leu Arg Asn Lys Pro Ser Lys Gln Ser Gln Gly Leu Phe
    50                  55                  60

Gly Ala Ile Ala Gly Phe Thr Glu Gly Gly Trp Thr Gly Met Val Asp
65                  70                  75                  80

Gly Trp Tyr Gly Tyr His His Gln Asn Glu Gln Gly Ser Gly Tyr Ala
                85                  90                  95

Ala Asp Leu Lys Ser Thr Gln Asn Ala Ile Asp Glu Ile Thr Asn Lys
            100                 105                 110

Val Asn Ser Val Ile Glu Lys Met Asn Thr Gln Pro Thr Ala Ile Gly
        115                 120                 125

Cys Glu Tyr Asn Lys Ser Glu Gln Cys Met Lys Gln Ile Glu Asp Lys
    130                 135                 140

Ile Glu Glu Ile Glu Ser Lys Ile Trp Cys Tyr Asn Ala Glu Leu Leu
145                 150                 155                 160

Val Leu Leu Glu Asn Gln Arg Thr Leu Asp Tyr His Asp Ala Asn Val
                165                 170                 175

Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
```

```
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245


<210> SEQ ID NO 89
<211> LENGTH: 248
<212> TYPE: PRT
<213> ORGANISM: Artificial Sequence
<220> FEATURE:
<223> OTHER INFORMATION: UFV160386

<400> SEQUENCE: 89

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp His Ala Gly Ala Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 90
<211> LENGTH: 248
<212> TYPE: PRT
<213> ORGANISM: Artificial Sequence
<220> FEATURE:
<223> OTHER INFORMATION: UFV160387

<400> SEQUENCE: 90
```

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Asp Gln Glu Gly Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 91
<211> LENGTH: 248
<212> TYPE: PRT
<213> ORGANISM: Artificial Sequence
<220> FEATURE:
<223> OTHER INFORMATION: UFV160388

<400> SEQUENCE: 91

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Asp Thr Pro Val Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110
```

```
Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 92
<211> LENGTH: 248
<212> TYPE: PRT
<213> ORGANISM: Artificial Sequence
<220> FEATURE:
<223> OTHER INFORMATION: UFV160389

<400> SEQUENCE: 92

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Phe Pro Lys Thr Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220
```

-continued

```
Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 93
<211> LENGTH: 248
<212> TYPE: PRT
<213> ORGANISM: Artificial Sequence
<220> FEATURE:
<223> OTHER INFORMATION: UFV160390

<400> SEQUENCE: 93

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Glu Pro Gly Asp Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 94
<211> LENGTH: 247
<212> TYPE: PRT
<213> ORGANISM: Artificial Sequence
<220> FEATURE:
<223> OTHER INFORMATION: UFV160391

<400> SEQUENCE: 94

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30
```

```
Leu Glu Asp Glu Pro Gly Lys Tyr Val Cys Ser Thr Lys Leu Arg Leu
        35                  40                  45

Ala Thr Gly Leu Arg Asn Lys Pro Ser Lys Gln Ser Gln Gly Leu Phe
    50                  55                  60

Gly Ala Ile Ala Gly Phe Thr Glu Gly Gly Trp Thr Gly Met Val Asp
65                  70                  75                  80

Gly Trp Tyr Gly Tyr His His Gln Asn Glu Gln Gly Ser Gly Tyr Ala
                85                  90                  95

Ala Asp Leu Lys Ser Thr Gln Asn Ala Ile Asp Glu Ile Thr Asn Lys
            100                 105                 110

Val Asn Ser Val Ile Glu Lys Met Asn Thr Gln Pro Thr Ala Ile Gly
        115                 120                 125

Cys Glu Tyr Asn Lys Ser Glu Gln Cys Met Lys Gln Ile Glu Asp Lys
    130                 135                 140

Ile Glu Glu Ile Glu Ser Lys Ile Trp Cys Tyr Asn Ala Glu Leu Leu
145                 150                 155                 160

Val Leu Leu Glu Asn Gln Arg Thr Leu Asp Tyr His Asp Ala Asn Val
                165                 170                 175

Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245


<210> SEQ ID NO 95
<211> LENGTH: 248
<212> TYPE: PRT
<213> ORGANISM: Artificial Sequence
<220> FEATURE:
<223> OTHER INFORMATION: UFV160392

<400> SEQUENCE: 95

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Thr Gly Asn Leu Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140
```

```
Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 96
<211> LENGTH: 248
<212> TYPE: PRT
<213> ORGANISM: Artificial Sequence
<220> FEATURE:
<223> OTHER INFORMATION: UFV160393

<400> SEQUENCE: 96

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Thr Pro Ser Ser Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245
```

<210> SEQ ID NO 97
<211> LENGTH: 247
<212> TYPE: PRT
<213> ORGANISM: Artificial Sequence
<220> FEATURE:
<223> OTHER INFORMATION: UFV160394

<400> SEQUENCE: 97

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Thr Pro Ser Lys Tyr Val Cys Ser Thr Lys Leu Arg Leu
        35                  40                  45

Ala Thr Gly Leu Arg Asn Lys Pro Ser Lys Gln Ser Gln Gly Leu Phe
    50                  55                  60

Gly Ala Ile Ala Gly Phe Thr Glu Gly Gly Trp Thr Gly Met Val Asp
65                  70                  75                  80

Gly Trp Tyr Gly Tyr His His Gln Asn Glu Gln Gly Ser Gly Tyr Ala
                85                  90                  95

Ala Asp Leu Lys Ser Thr Gln Asn Ala Ile Asp Glu Ile Thr Asn Lys
            100                 105                 110

Val Asn Ser Val Ile Glu Lys Met Asn Thr Gln Pro Thr Ala Ile Gly
        115                 120                 125

Cys Glu Tyr Asn Lys Ser Glu Gln Cys Met Lys Gln Ile Glu Asp Lys
    130                 135                 140

Ile Glu Glu Ile Glu Ser Lys Ile Trp Cys Tyr Asn Ala Glu Leu Leu
145                 150                 155                 160

Val Leu Leu Glu Asn Gln Arg Thr Leu Asp Tyr His Asp Ala Asn Val
                165                 170                 175

Lys Asn Leu Tyr Glu Lys Val Arg Ser Gln Leu Lys Asn Asn Ala Lys
            180                 185                 190

Glu Ile Gly Asn Gly Cys Phe Glu Phe Tyr His Lys Cys Asp Asn Thr
        195                 200                 205

Cys Met Glu Ser Val Lys Asn Gly Thr Tyr Asp Tyr Pro Lys Tyr Ser
    210                 215                 220

Glu Glu Ala Lys Leu Asn Arg Glu Glu Ile Asp Gly Val Lys Leu Glu
225                 230                 235                 240

Ser Thr Arg Ile Tyr Gln Ile
                245
```

<210> SEQ ID NO 98
<211> LENGTH: 248
<212> TYPE: PRT
<213> ORGANISM: Artificial Sequence
<220> FEATURE:
<223> OTHER INFORMATION: UFV160395

<400> SEQUENCE: 98

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ala Thr Gly Asn Lys Tyr Val Cys Ser Thr Lys Leu Arg
        35                  40                  45

Leu Ala Thr Gly Leu Arg Asn Lys Pro Ser Lys Gln Ser Gln Gly Leu
```

```
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 99
<211> LENGTH: 248
<212> TYPE: PRT
<213> ORGANISM: Artificial Sequence
<220> FEATURE:
<223> OTHER INFORMATION: UFV160396

<400> SEQUENCE: 99

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Tyr Pro Gly Asp Lys Tyr Val Cys Ser Thr Lys Leu Arg
        35                  40                  45

Leu Ala Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Leu Lys Ser Thr Gln Asn Ala Ile Asp Glu Ile Thr Asn
            100                 105                 110

Lys Val Asn Ser Val Ile Glu Lys Met Asn Thr Gln Pro Thr Ala Ile
        115                 120                 125

Gly Cys Glu Tyr Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Tyr His Asp Ala Asn
```

```
                165                 170                 175

Val Lys Asn Leu Tyr Glu Lys Val Arg Ser Gln Leu Lys Asn Asn Ala
            180                 185                 190

Lys Glu Ile Gly Asn Gly Cys Phe Glu Phe Tyr His Lys Cys Asp Asn
        195                 200                 205

Thr Cys Met Glu Ser Val Lys Asn Gly Thr Tyr Asp Tyr Pro Lys Tyr
    210                 215                 220

Ser Glu Glu Ala Lys Leu Asn Arg Glu Glu Ile Asp Gly Val Lys Leu
225                 230                 235                 240

Glu Ser Thr Arg Ile Tyr Gln Ile
                245


<210> SEQ ID NO 100
<211> LENGTH: 246
<212> TYPE: PRT
<213> ORGANISM: Artificial Sequence
<220> FEATURE:
<223> OTHER INFORMATION: UFV160397

<400> SEQUENCE: 100

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Tyr Pro Gly Asp Val Cys Ser Thr Lys Leu Arg Leu Ala
        35                  40                  45

Thr Gly Leu Arg Asn Lys Pro Ser Lys Gln Ser Gln Gly Leu Phe Gly
    50                  55                  60

Ala Ile Ala Gly Phe Thr Glu Gly Gly Trp Thr Gly Met Val Asp Gly
65                  70                  75                  80

Trp Tyr Gly Tyr His His Gln Asn Glu Gln Gly Ser Gly Tyr Ala Ala
                85                  90                  95

Asp Leu Lys Ser Thr Gln Asn Ala Ile Asp Glu Ile Thr Asn Lys Val
            100                 105                 110

Asn Ser Val Ile Glu Lys Met Asn Thr Gln Pro Thr Ala Ile Gly Cys
        115                 120                 125

Glu Tyr Asn Lys Ser Glu Gln Cys Met Lys Gln Ile Glu Asp Lys Ile
    130                 135                 140

Glu Glu Ile Glu Ser Lys Ile Trp Cys Tyr Asn Ala Glu Leu Leu Val
145                 150                 155                 160

Leu Leu Glu Asn Gln Arg Thr Leu Asp Tyr His Asp Ala Asn Val Lys
                165                 170                 175

Asn Leu Tyr Glu Lys Val Arg Ser Gln Leu Lys Asn Asn Ala Lys Glu
            180                 185                 190

Ile Gly Asn Gly Cys Phe Glu Phe Tyr His Lys Cys Asp Asn Thr Cys
        195                 200                 205

Met Glu Ser Val Lys Asn Gly Thr Tyr Asp Tyr Pro Lys Tyr Ser Glu
    210                 215                 220

Glu Ala Lys Leu Asn Arg Glu Glu Ile Asp Gly Val Lys Leu Glu Ser
225                 230                 235                 240

Thr Arg Ile Tyr Gln Ile
                245


<210> SEQ ID NO 101
<211> LENGTH: 251
<212> TYPE: PRT
```

<213> ORGANISM: Artificial Sequence
<220> FEATURE:
<223> OTHER INFORMATION: UFV160503

<400> SEQUENCE: 101

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Ser Lys Gln Ser Arg Lys Arg
    50                  55                  60

Arg Gly Leu Phe Gly Ala Ile Ala Gly Phe Thr Glu Gly Gly Trp Thr
65                  70                  75                  80

Gly Met Val Asp Gly Trp Tyr Gly Tyr His His Gln Asn Glu Gln Gly
                85                  90                  95

Ser Gly Tyr Ala Ala Asp Leu Lys Ser Thr Gln Asn Ala Ile Asp Glu
            100                 105                 110

Ile Thr Asn Lys Val Asn Ser Val Ile Glu Lys Met Asn Thr Gln Arg
        115                 120                 125

Thr Ala Ile Gly Cys Glu Tyr Asn Lys Ser Glu Arg Cys Met Lys Gln
    130                 135                 140

Ile Glu Asp Lys Ile Glu Glu Ile Glu Ser Lys Ile Trp Cys Tyr Asn
145                 150                 155                 160

Ala Glu Leu Leu Val Leu Leu Glu Asn Gln Arg Thr Leu Glu Tyr His
                165                 170                 175

Asp Ser Asn Val Lys Asn Leu Tyr Glu Lys Val Arg Ser Gln Leu Lys
            180                 185                 190

Asn Asn Ala Lys Glu Ile Gly Asn Gly Cys Phe Glu Phe Tyr His Lys
        195                 200                 205

Cys Asp Asn Thr Cys Met Glu Ser Val Lys Asn Gly Thr Tyr Asp Tyr
    210                 215                 220

Pro Lys Tyr Ser Glu Glu Ala Lys Leu Asn Arg Glu Glu Ile Asp Gly
225                 230                 235                 240

Val Lys Leu Glu Ser Thr Arg Ile Tyr Gln Ile
                245                 250
```

<210> SEQ ID NO 102
<211> LENGTH: 252
<212> TYPE: PRT
<213> ORGANISM: Artificial Sequence
<220> FEATURE:
<223> OTHER INFORMATION: UFV160504

<400> SEQUENCE: 102

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Gly Gly Gly Gly Lys Tyr Val Cys Ser Thr Lys Leu Arg
        35                  40                  45

Leu Ala Thr Gly Leu Arg Asn Lys Pro Gln Arg Glu Arg Arg Arg Lys
    50                  55                  60

Lys Arg Gly Leu Phe Gly Ala Ile Ala Gly Phe Thr Glu Gly Gly Trp
65                  70                  75                  80
```

```
Thr Gly Met Val Asp Gly Trp Tyr Gly Tyr His His Gln Asn Glu Gln
                85                  90                  95

Gly Ser Gly Tyr Ala Ala Asp Leu Lys Ser Thr Gln Asn Ala Ile Asp
            100                 105                 110

Glu Ile Thr Asn Lys Val Asn Ser Val Ile Glu Lys Met Asn Thr Gln
        115                 120                 125

Arg Thr Ala Ile Gly Cys Glu Tyr Asn Lys Ser Glu Arg Cys Met Lys
    130                 135                 140

Gln Ile Glu Asp Lys Ile Glu Glu Ile Glu Ser Lys Ile Trp Cys Tyr
145                 150                 155                 160

Asn Ala Glu Leu Leu Val Leu Leu Glu Asn Gln Arg Thr Leu Glu Tyr
                165                 170                 175

His Asp Ser Asn Val Lys Asn Leu Tyr Glu Lys Val Arg Ser Gln Leu
            180                 185                 190

Lys Asn Asn Ala Lys Glu Ile Gly Asn Gly Cys Phe Glu Phe Tyr His
        195                 200                 205

Lys Cys Asp Asn Thr Cys Met Glu Ser Val Lys Asn Gly Thr Tyr Asp
    210                 215                 220

Tyr Pro Lys Tyr Ser Glu Glu Ala Lys Leu Asn Arg Glu Glu Ile Asp
225                 230                 235                 240

Gly Val Lys Leu Glu Ser Thr Arg Ile Tyr Gln Ile
                245                 250


<210> SEQ ID NO 103
<211> LENGTH: 245
<212> TYPE: PRT
<213> ORGANISM: Artificial Sequence
<220> FEATURE:
<223> OTHER INFORMATION: UFV160655

<400> SEQUENCE: 103

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser Lys Tyr Val Cys Ser Ala Lys Leu Arg Met Val Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Gln Lys Ser Thr Gln Asn Ala Ile Asn Gly Ile Thr Asn Lys Val Asn
            100                 105                 110

Ser Val Ile Glu Lys Met Asn Thr Gln Pro Thr Ala Ile Gly Cys Glu
        115                 120                 125

Tyr Asn Lys Ser Glu Gln Cys Met Lys Gln Ile Glu Asp Lys Ile Glu
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Asp Phe His Asp Ala Asn Val Lys Asn
                165                 170                 175

Leu Tyr Glu Lys Val Lys Ser Gln Leu Lys Asn Asn Ala Lys Glu Ile
            180                 185                 190
```

```
Gly Asn Gly Cys Phe Glu Phe Tyr His Lys Cys Asn Asp Glu Cys Met
        195                 200                 205

Glu Ser Val Lys Asn Gly Thr Tyr Asp Tyr Pro Lys Tyr Ser Glu Glu
    210                 215                 220

Ser Lys Leu Asn Arg Glu Lys Ile Asp Gly Val Lys Leu Glu Ser Met
225                 230                 235                 240

Gly Val Tyr Gln Ile
                245


<210> SEQ ID NO 104
<211> LENGTH: 245
<212> TYPE: PRT
<213> ORGANISM: Artificial Sequence
<220> FEATURE:
<223> OTHER INFORMATION: UFV160656

<400> SEQUENCE: 104

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys Lys Tyr Val Cys Ser Thr Lys Leu Arg Leu Ala Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Leu Lys Ser Thr Gln Asn Ala Ile Asp Glu Ile Thr Asn Lys Val Asn
            100                 105                 110

Ser Val Ile Glu Lys Met Asn Thr Gln Pro Thr Ala Ile Gly Cys Glu
        115                 120                 125

Tyr Asn Lys Ser Glu Gln Cys Met Lys Gln Ile Glu Asp Lys Ile Glu
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Asp Tyr His Asp Ala Asn Val Lys Asn
                165                 170                 175

Leu Tyr Glu Lys Val Arg Ser Gln Leu Lys Asn Asn Ala Lys Glu Ile
            180                 185                 190

Gly Asn Gly Cys Phe Glu Phe Tyr His Lys Cys Asp Asn Thr Cys Met
        195                 200                 205

Glu Ser Val Lys Asn Gly Thr Tyr Asp Tyr Pro Lys Tyr Ser Glu Glu
    210                 215                 220

Ala Lys Leu Asn Arg Glu Glu Ile Asp Gly Val Lys Leu Glu Ser Thr
225                 230                 235                 240

Arg Ile Tyr Gln Ile
                245


<210> SEQ ID NO 105
<211> LENGTH: 251
<212> TYPE: PRT
<213> ORGANISM: Artificial Sequence
<220> FEATURE:
<223> OTHER INFORMATION: UFV160657

<400> SEQUENCE: 105
```

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Lys Tyr Val Cys Ser Thr
        35                  40                  45

Lys Leu Arg Leu Ala Thr Gly Leu Arg Asn Lys Pro Ser Lys Gln Ser
    50                  55                  60

Gln Gly Leu Phe Gly Ala Ile Ala Gly Phe Thr Glu Gly Gly Trp Thr
65                  70                  75                  80

Gly Met Val Asp Gly Trp Tyr Gly Tyr His His Gln Asn Glu Gln Gly
                85                  90                  95

Ser Gly Tyr Ala Ala Asp Leu Lys Ser Thr Gln Asn Ala Ile Asp Glu
            100                 105                 110

Ile Thr Asn Lys Val Asn Ser Val Ile Glu Lys Met Asn Thr Gln Pro
        115                 120                 125

Thr Ala Ile Gly Cys Glu Tyr Asn Lys Ser Glu Gln Cys Met Lys Gln
    130                 135                 140

Ile Glu Asp Lys Ile Glu Glu Ile Glu Ser Lys Ile Trp Cys Tyr Asn
145                 150                 155                 160

Ala Glu Leu Leu Val Leu Leu Glu Asn Gln Arg Thr Leu Asp Tyr His
                165                 170                 175

Asp Ala Asn Val Lys Asn Leu Tyr Glu Lys Val Arg Ser Gln Leu Lys
            180                 185                 190

Asn Asn Ala Lys Glu Ile Gly Asn Gly Cys Phe Glu Phe Tyr His Lys
        195                 200                 205

Cys Asp Asn Thr Cys Met Glu Ser Val Lys Asn Gly Thr Tyr Asp Tyr
    210                 215                 220

Pro Lys Tyr Ser Glu Glu Ala Lys Leu Asn Arg Glu Glu Ile Asp Gly
225                 230                 235                 240

Val Lys Leu Glu Ser Thr Arg Ile Tyr Gln Ile
                245                 250
```

<210> SEQ ID NO 106
<211> LENGTH: 245
<212> TYPE: PRT
<213> ORGANISM: Artificial Sequence
<220> FEATURE:
<223> OTHER INFORMATION: UFV160658

<400> SEQUENCE: 106

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys Lys Tyr Val Cys Ser Thr Lys Leu Arg Leu Ala Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Leu Lys Ser Thr Gln Asn Ala Ile Asp Glu Ile Thr Asn Lys Val Asn
            100                 105                 110
```

```
Ser Val Ile Glu Lys Met Asn Thr Gln Arg Thr Ala Ile Gly Cys Glu
        115                 120                 125

Tyr Asn Lys Ser Glu Arg Cys Met Lys Gln Ile Glu Asp Lys Ile Glu
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Glu Tyr His Asp Ser Asn Val Lys Asn
                165                 170                 175

Leu Tyr Glu Lys Val Arg Ser Gln Leu Lys Asn Asn Ala Lys Glu Ile
            180                 185                 190

Gly Asn Gly Cys Phe Glu Phe Tyr His Lys Cys Asp Asn Thr Cys Met
        195                 200                 205

Glu Ser Val Lys Asn Gly Thr Tyr Asp Tyr Pro Lys Tyr Ser Glu Glu
    210                 215                 220

Ala Lys Leu Asn Arg Glu Glu Ile Asp Gly Val Lys Leu Glu Ser Thr
225                 230                 235                 240

Arg Ile Tyr Gln Ile
                245


<210> SEQ ID NO 107
<211> LENGTH: 251
<212> TYPE: PRT
<213> ORGANISM: Artificial Sequence
<220> FEATURE:
<223> OTHER INFORMATION: UFV160659

<400> SEQUENCE: 107

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Lys Tyr Val Cys Ser Thr
        35                  40                  45

Lys Leu Arg Leu Ala Thr Gly Leu Arg Asn Lys Pro Ser Lys Gln Ser
    50                  55                  60

Gln Gly Leu Phe Gly Ala Ile Ala Gly Phe Thr Glu Gly Gly Trp Thr
65                  70                  75                  80

Gly Met Val Asp Gly Trp Tyr Gly Tyr His His Gln Asn Glu Gln Gly
                85                  90                  95

Ser Gly Tyr Ala Ala Asp Leu Lys Ser Thr Gln Asn Ala Ile Asp Glu
            100                 105                 110

Ile Thr Asn Lys Val Asn Ser Val Ile Glu Lys Met Asn Thr Gln Arg
        115                 120                 125

Thr Ala Ile Gly Cys Glu Tyr Asn Lys Ser Glu Arg Cys Met Lys Gln
    130                 135                 140

Ile Glu Asp Lys Ile Glu Glu Ile Glu Ser Lys Ile Trp Cys Tyr Asn
145                 150                 155                 160

Ala Glu Leu Leu Val Leu Leu Glu Asn Gln Arg Thr Leu Glu Tyr His
                165                 170                 175

Asp Ser Asn Val Lys Asn Leu Tyr Glu Lys Val Arg Ser Gln Leu Lys
            180                 185                 190

Asn Asn Ala Lys Glu Ile Gly Asn Gly Cys Phe Glu Phe Tyr His Lys
        195                 200                 205

Cys Asp Asn Thr Cys Met Glu Ser Val Lys Asn Gly Thr Tyr Asp Tyr
    210                 215                 220
```

Pro Lys Tyr Ser Glu Glu Ala Lys Leu Asn Arg Glu Glu Ile Asp Gly
225 230 235 240

Val Lys Leu Glu Ser Thr Arg Ile Tyr Gln Ile
245 250

<210> SEQ ID NO 108
<211> LENGTH: 248
<212> TYPE: PRT
<213> ORGANISM: Artificial Sequence
<220> FEATURE:
<223> OTHER INFORMATION: UFV160663

<400> SEQUENCE: 108

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Gly Gly Gly Gly Lys Tyr Val Cys Ser Thr Lys Leu Arg
35 40 45

Leu Ala Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Leu Lys Ser Thr Gln Asn Ala Ile Asp Glu Ile Thr Asn
100 105 110

Lys Val Asn Ser Val Ile Glu Lys Met Asn Thr Gln Arg Thr Ala Ile
115 120 125

Gly Cys Glu Tyr Asn Lys Ser Glu Arg Cys Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Gln Arg Thr Leu Asp Tyr His Asp Ser Asn
165 170 175

Val Lys Asn Leu Tyr Glu Lys Val Arg Ser Gln Leu Lys Asn Asn Ala
180 185 190

Lys Glu Ile Gly Asn Gly Cys Phe Glu Phe Tyr His Lys Cys Asp Asn
195 200 205

Thr Cys Met Glu Ser Val Lys Asn Gly Thr Tyr Asp Tyr Pro Lys Tyr
210 215 220

Ser Glu Glu Ala Lys Leu Asn Arg Glu Glu Ile Asp Gly Val Lys Leu
225 230 235 240

Glu Ser Thr Arg Ile Tyr Gln Ile
245

<210> SEQ ID NO 109
<211> LENGTH: 245
<212> TYPE: PRT
<213> ORGANISM: Artificial Sequence
<220> FEATURE:
<223> OTHER INFORMATION: UFV160664

<400> SEQUENCE: 109

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu

```
            20                  25                  30

Leu Glu Asp Lys Lys Tyr Val Cys Ser Thr Lys Leu Arg Leu Ala Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Leu Lys Ser Thr Gln Asn Ala Ile Asp Glu Ile Thr Asn Lys Val Asn
            100                 105                 110

Ser Val Ile Glu Lys Met Asn Thr Gln Arg Thr Ala Ile Gly Cys Glu
        115                 120                 125

Tyr Asn Lys Ser Glu Arg Cys Met Lys Gln Ile Glu Asp Lys Ile Glu
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Asp Tyr His Asp Ser Asn Val Lys Asn
                165                 170                 175

Leu Tyr Glu Lys Val Arg Ser Gln Leu Lys Asn Asn Ala Lys Glu Ile
            180                 185                 190

Gly Asn Gly Cys Phe Glu Phe Tyr His Lys Cys Asp Asn Thr Cys Met
        195                 200                 205

Glu Ser Val Lys Asn Gly Thr Tyr Asp Tyr Pro Lys Tyr Ser Glu Glu
    210                 215                 220

Ala Lys Leu Asn Arg Glu Glu Ile Asp Gly Val Lys Leu Glu Ser Thr
225                 230                 235                 240

Arg Ile Tyr Gln Ile
                245


<210> SEQ ID NO 110
<211> LENGTH: 245
<212> TYPE: PRT
<213> ORGANISM: Artificial Sequence
<220> FEATURE:
<223> OTHER INFORMATION: UFV160665

<400> SEQUENCE: 110

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys Lys Tyr Val Cys Ser Thr Lys Leu Arg Leu Ala Thr
        35                  40                  45

Gly Leu Arg Asn Lys Pro Ser Lys Gln Ser Gln Gly Leu Phe Gly Ala
    50                  55                  60

Ile Ala Gly Phe Thr Glu Gly Gly Trp Thr Gly Met Val Asp Gly Trp
65                  70                  75                  80

Tyr Gly Tyr His His Gln Asn Glu Gln Gly Ser Gly Tyr Ala Ala Asp
                85                  90                  95

Leu Lys Ser Thr Gln Asn Ala Ile Asp Glu Ile Thr Asn Lys Val Asn
            100                 105                 110

Ser Val Ile Glu Lys Met Asn Thr Gln Pro Thr Ala Ile Gly Cys Glu
        115                 120                 125

Tyr Asn Lys Ser Glu Arg Cys Met Lys Gln Ile Glu Asp Lys Ile Glu
```

```
    130                 135                 140

Glu Ile Glu Ser Lys Ile Trp Cys Tyr Asn Ala Glu Leu Leu Val Leu
145                 150                 155                 160

Leu Glu Asn Gln Arg Thr Leu Asp Tyr His Asp Ser Asn Val Lys Asn
                165                 170                 175

Leu Tyr Glu Lys Val Arg Ser Gln Leu Lys Asn Asn Ala Lys Glu Ile
            180                 185                 190

Gly Asn Gly Cys Phe Glu Phe Tyr His Lys Cys Asp Asn Thr Cys Met
        195                 200                 205

Glu Ser Val Lys Asn Gly Thr Tyr Asp Tyr Pro Lys Tyr Ser Glu Glu
    210                 215                 220

Ala Lys Leu Asn Arg Glu Glu Ile Asp Gly Val Lys Leu Glu Ser Thr
225                 230                 235                 240

Arg Ile Tyr Gln Ile
                245


<210> SEQ ID NO 111
<211> LENGTH: 251
<212> TYPE: PRT
<213> ORGANISM: Artificial Sequence
<220> FEATURE:
<223> OTHER INFORMATION: UFV160666

<400> SEQUENCE: 111

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Gly Lys Tyr Val Cys Ser Thr
        35                  40                  45

Lys Leu Arg Leu Ala Thr Gly Leu Arg Asn Lys Pro Ser Lys Gln Ser
    50                  55                  60

Gln Gly Leu Phe Gly Ala Ile Ala Gly Phe Thr Glu Gly Gly Trp Thr
65                  70                  75                  80

Gly Met Val Asp Gly Trp Tyr Gly Tyr His His Gln Asn Glu Gln Gly
                85                  90                  95

Ser Gly Tyr Ala Ala Asp Leu Lys Ser Thr Gln Asn Ala Ile Asp Glu
            100                 105                 110

Ile Thr Asn Lys Val Asn Ser Val Ile Glu Lys Met Asn Thr Gln Arg
        115                 120                 125

Thr Ala Ile Gly Cys Glu Tyr Asn Lys Ser Glu Arg Cys Met Lys Gln
    130                 135                 140

Ile Glu Asp Lys Ile Glu Glu Ile Glu Ser Lys Ile Trp Cys Tyr Asn
145                 150                 155                 160

Ala Glu Leu Leu Val Leu Leu Glu Asn Gln Arg Thr Leu Asp Tyr His
                165                 170                 175

Asp Ser Asn Val Lys Asn Leu Tyr Glu Lys Val Arg Ser Gln Leu Lys
            180                 185                 190

Asn Asn Ala Lys Glu Ile Gly Asn Gly Cys Phe Glu Phe Tyr His Lys
        195                 200                 205

Cys Asp Asn Thr Cys Met Glu Ser Val Lys Asn Gly Thr Tyr Asp Tyr
    210                 215                 220

Pro Lys Tyr Ser Glu Glu Ala Lys Leu Asn Arg Glu Glu Ile Asp Gly
225                 230                 235                 240

Val Lys Leu Glu Ser Thr Arg Ile Tyr Gln Ile
```

245 250

<210> SEQ ID NO 112
<211> LENGTH: 251
<212> TYPE: PRT
<213> ORGANISM: Artificial Sequence
<220> FEATURE:
<223> OTHER INFORMATION: UFV160667

<400> SEQUENCE: 112

Asp Thr Leu Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asp Lys His Asn Gly Lys Leu Gly Lys Tyr Val Cys Ser Thr
35 40 45

Lys Leu Arg Leu Ala Thr Gly Leu Arg Asn Lys Pro Ser Lys Gln Ser
50 55 60

Gln Gly Leu Phe Gly Ala Ile Ala Gly Phe Thr Glu Gly Gly Trp Thr
65 70 75 80

Gly Met Val Asp Gly Trp Tyr Gly Tyr His His Gln Asn Glu Gln Gly
85 90 95

Ser Gly Tyr Ala Ala Asp Leu Lys Ser Thr Gln Asn Ala Ile Asp Glu
100 105 110

Ile Thr Asn Lys Val Asn Ser Val Ile Glu Lys Met Asn Thr Gln Pro
115 120 125

Thr Ala Ile Gly Cys Glu Tyr Asn Lys Ser Glu Arg Cys Met Lys Gln
130 135 140

Ile Glu Asp Lys Ile Glu Glu Ile Glu Ser Lys Ile Trp Cys Tyr Asn
145 150 155 160

Ala Glu Leu Leu Val Leu Leu Glu Asn Gln Arg Thr Leu Asp Tyr His
165 170 175

Asp Ser Asn Val Lys Asn Leu Tyr Glu Lys Val Arg Ser Gln Leu Lys
180 185 190

Asn Asn Ala Lys Glu Ile Gly Asn Gly Cys Phe Glu Phe Tyr His Lys
195 200 205

Cys Asp Asn Thr Cys Met Glu Ser Val Lys Asn Gly Thr Tyr Asp Tyr
210 215 220

Pro Lys Tyr Ser Glu Glu Ala Lys Leu Asn Arg Glu Glu Ile Asp Gly
225 230 235 240

Val Lys Leu Glu Ser Thr Arg Ile Tyr Gln Ile
245 250

<210> SEQ ID NO 113
<211> LENGTH: 6
<212> TYPE: PRT
<213> ORGANISM: Artificial Sequence
<220> FEATURE:
<223> OTHER INFORMATION: His-tag

<400> SEQUENCE: 113

His His His His His His
1 5

<210> SEQ ID NO 114
<211> LENGTH: 7
<212> TYPE: PRT
<213> ORGANISM: Artificial Sequence
<220> FEATURE:

<223> OTHER INFORMATION: His-tag

<400> SEQUENCE: 114

His His His His His His His
1 5

<210> SEQ ID NO 115
<211> LENGTH: 8
<212> TYPE: PRT
<213> ORGANISM: Artificial Sequence
<220> FEATURE:
<223> OTHER INFORMATION: FLAG tag

<400> SEQUENCE: 115

Asp Tyr Lys Asp Asp Asp Asp Lys
1 5

<210> SEQ ID NO 116
<211> LENGTH: 4
<212> TYPE: PRT
<213> ORGANISM: Artificial Sequence
<220> FEATURE:
<223> OTHER INFORMATION: proteolytic cleavage site

<400> SEQUENCE: 116

Ile Glu Gly Arg
1

<210> SEQ ID NO 117
<211> LENGTH: 6
<212> TYPE: PRT
<213> ORGANISM: Artificial Sequence
<220> FEATURE:
<223> OTHER INFORMATION: proteolytic cleavage site

<400> SEQUENCE: 117

Leu Val Pro Arg Gly Ser
1 5

<210> SEQ ID NO 118
<211> LENGTH: 27
<212> TYPE: PRT
<213> ORGANISM: Artificial Sequence
<220> FEATURE:
<223> OTHER INFORMATION: foldon

<400> SEQUENCE: 118

Gly Tyr Ile Pro Glu Ala Pro Arg Asp Gly Gln Ala Tyr Val Arg Lys
1 5 10 15

Asp Gly Glu Trp Val Leu Leu Ser Thr Phe Leu
20 25

<210> SEQ ID NO 119
<211> LENGTH: 54
<212> TYPE: PRT
<213> ORGANISM: Artificial Sequence
<220> FEATURE:
<223> OTHER INFORMATION: Flag - Foldon - His tag

<400> SEQUENCE: 119

Ser Gly Arg Asp Tyr Lys Asp Asp Asp Asp Lys Leu Val Pro Arg Gly
1 5 10 15

Ser Pro Gly Ser Gly Tyr Ile Pro Glu Ala Pro Arg Asp Gly Gln Ala
20 25 30

Tyr Val Arg Lys Asp Gly Glu Trp Val Leu Leu Ser Thr Phe Leu Gly

```
        35                  40                  45

His His His His His His
    50


<210> SEQ ID NO 120
<211> LENGTH: 53
<212> TYPE: PRT
<213> ORGANISM: Artificial Sequence
<220> FEATURE:
<223> OTHER INFORMATION: FLAG- GS linker - His tag

<400> SEQUENCE: 120

Ser Gly Arg Asp Tyr Lys Asp Asp Asp Asp Lys Pro Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser His
        35                  40                  45

His His His His His
    50


<210> SEQ ID NO 121
<211> LENGTH: 218
<212> TYPE: PRT
<213> ORGANISM: Artificial Sequence
<220> FEATURE:
<223> OTHER INFORMATION: Nanoluc - Strep tag

<400> SEQUENCE: 121

Glu Gly Arg Ala Ala Ala Gly Gly Ser Gly Gly Gly Gly Ser Met Val
1               5                   10                  15

Phe Thr Leu Glu Asp Phe Val Gly Asp Trp Arg Gln Thr Ala Gly Tyr
            20                  25                  30

Asn Leu Asp Gln Val Leu Glu Gln Gly Gly Val Ser Ser Leu Phe Gln
        35                  40                  45

Asn Leu Gly Val Ser Val Thr Pro Ile Gln Arg Ile Val Leu Ser Gly
    50                  55                  60

Glu Asn Gly Leu Lys Ile Asp Ile His Val Ile Ile Pro Tyr Glu Gly
65                  70                  75                  80

Leu Ser Gly Asp Gln Met Gly Gln Ile Glu Lys Ile Phe Lys Val Val
                85                  90                  95

Tyr Pro Val Asp Asp His His Phe Lys Val Ile Leu His Tyr Gly Thr
            100                 105                 110

Leu Val Ile Asp Gly Val Thr Pro Asn Met Ile Asp Tyr Phe Gly Arg
        115                 120                 125

Pro Tyr Glu Gly Ile Ala Val Phe Asp Gly Lys Lys Ile Thr Val Thr
    130                 135                 140

Gly Thr Leu Trp Asn Gly Asn Lys Ile Ile Asp Glu Arg Leu Ile Asn
145                 150                 155                 160

Pro Asp Gly Ser Leu Leu Phe Arg Val Thr Ile Asn Gly Val Thr Gly
                165                 170                 175

Trp Arg Leu Cys Glu Arg Ile Leu Ala Ala Ala Ala Trp Ser His Pro
            180                 185                 190

Gln Phe Glu Lys Gly Ala Ala Trp Ser His Pro Gln Phe Glu Lys Gly
        195                 200                 205

Ala Ala Trp Ser His Pro Gln Phe Glu Lys
    210                 215
```

<210> SEQ ID NO 122
<211> LENGTH: 192
<212> TYPE: PRT
<213> ORGANISM: Artificial Sequence
<220> FEATURE:
<223> OTHER INFORMATION: Nanoluc - C tag

<400> SEQUENCE: 122

```
Glu Gly Arg Ala Ala Ala Gly Gly Ser Gly Gly Gly Gly Ser Met Val
1               5                   10                  15

Phe Thr Leu Glu Asp Phe Val Gly Asp Trp Arg Gln Thr Ala Gly Tyr
            20                  25                  30

Asn Leu Asp Gln Val Leu Glu Gln Gly Gly Val Ser Ser Leu Phe Gln
        35                  40                  45

Asn Leu Gly Val Ser Val Thr Pro Ile Gln Arg Ile Val Leu Ser Gly
    50                  55                  60

Glu Asn Gly Leu Lys Ile Asp Ile His Val Ile Ile Pro Tyr Glu Gly
65                  70                  75                  80

Leu Ser Gly Asp Gln Met Gly Gln Ile Glu Lys Ile Phe Lys Val Val
                85                  90                  95

Tyr Pro Val Asp Asp His His Phe Lys Val Ile Leu His Tyr Gly Thr
            100                 105                 110

Leu Val Ile Asp Gly Val Thr Pro Asn Met Ile Asp Tyr Phe Gly Arg
        115                 120                 125

Pro Tyr Glu Gly Ile Ala Val Phe Asp Gly Lys Lys Ile Thr Val Thr
    130                 135                 140

Gly Thr Leu Trp Asn Gly Asn Lys Ile Ile Asp Glu Arg Leu Ile Asn
145                 150                 155                 160

Pro Asp Gly Ser Leu Leu Phe Arg Val Thr Ile Asn Gly Val Thr Gly
                165                 170                 175

Trp Arg Leu Cys Glu Arg Ile Leu Ala Gly Ala Ala Glu Pro Glu Ala
            180                 185                 190
```

<210> SEQ ID NO 123
<211> LENGTH: 19
<212> TYPE: PRT
<213> ORGANISM: Artificial Sequence
<220> FEATURE:
<223> OTHER INFORMATION: Sortase - C tag

<400> SEQUENCE: 123

```
Glu Gly Arg Ala Ala Ala Leu Pro Glu Thr Gly Gly Gly Ala Ala Glu
1               5                   10                  15

Pro Glu Ala
```

<210> SEQ ID NO 124
<211> LENGTH: 77
<212> TYPE: PRT
<213> ORGANISM: Artificial Sequence
<220> FEATURE:
<223> OTHER INFORMATION: FLAG - GS linker - Strep tag

<400> SEQUENCE: 124

```
Ser Gly Arg Asp Tyr Lys Asp Asp Asp Asp Lys Pro Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Trp
        35                  40                  45
```

```
Ser His Pro Gln Phe Glu Lys Gly Ala Ala Trp Ser His Pro Gln Phe
    50                  55                  60

Glu Lys Gly Ala Ala Trp Ser His Pro Gln Phe Glu Lys
65                  70                  75


<210> SEQ ID NO 125
<211> LENGTH: 81
<212> TYPE: PRT
<213> ORGANISM: Artificial Sequence
<220> FEATURE:
<223> OTHER INFORMATION: Myc tag - GS linker - Strep tag

<400> SEQUENCE: 125

Glu Gly Arg Ala Ala Ala Glu Gln Lys Leu Ile Ser Glu Glu Asp Leu
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser Trp Ser His Pro Gln Phe Glu Lys Gly Ala Ala Trp Ser
    50                  55                  60

His Pro Gln Phe Glu Lys Gly Ala Ala Trp Ser His Pro Gln Phe Glu
65                  70                  75                  80

Lys


<210> SEQ ID NO 126
<211> LENGTH: 20
<212> TYPE: PRT
<213> ORGANISM: Artificial Sequence
<220> FEATURE:
<223> OTHER INFORMATION: B-loop

<400> SEQUENCE: 126

Ile Glu Lys Met Asn Thr Gln Tyr Thr Ala Ile Gly Lys Glu Tyr Asn
1               5                   10                  15

Lys Ser Glu Arg
            20


<210> SEQ ID NO 127
<211> LENGTH: 20
<212> TYPE: PRT
<213> ORGANISM: Artificial Sequence
<220> FEATURE:
<223> OTHER INFORMATION: B-loop

<400> SEQUENCE: 127

Ile Glu Lys Met Asn Thr Gln Tyr Thr Ala Ile Gly Cys Glu Tyr Asn
1               5                   10                  15

Lys Ser Glu Arg
            20


<210> SEQ ID NO 128
<211> LENGTH: 20
<212> TYPE: PRT
<213> ORGANISM: Artificial Sequence
<220> FEATURE:
<223> OTHER INFORMATION: B-loop

<400> SEQUENCE: 128

Ile Glu Lys Met Asn Thr Gln Pro Thr Ala Ile Gly Cys Glu Tyr Asn
1               5                   10                  15
```

Lys Ser Glu Gln
20

<210> SEQ ID NO 129
<211> LENGTH: 20
<212> TYPE: PRT
<213> ORGANISM: Artificial Sequence
<220> FEATURE:
<223> OTHER INFORMATION: B-loop

<400> SEQUENCE: 129

Ile Glu Lys Met Asn Thr Gln Arg Thr Ala Ile Gly Cys Glu Phe Asn
1 5 10 15

Lys Ser Glu Gln
20

<210> SEQ ID NO 130
<211> LENGTH: 20
<212> TYPE: PRT
<213> ORGANISM: Artificial Sequence
<220> FEATURE:
<223> OTHER INFORMATION: B-loop

<400> SEQUENCE: 130

Ile Glu Lys Met Asn Thr Gln Pro Thr Ala Ile Gly Cys Glu Tyr Asn
1 5 10 15

Lys Ser Glu Arg
20

<210> SEQ ID NO 131
<211> LENGTH: 20
<212> TYPE: PRT
<213> ORGANISM: Artificial Sequence
<220> FEATURE:
<223> OTHER INFORMATION: B-loop

<400> SEQUENCE: 131

Ile Glu Lys Met Asn Thr Gln Pro Thr Ala Ile Gly Cys Glu Phe Asn
1 5 10 15

Lys Ser Glu Gln
20

<210> SEQ ID NO 132
<211> LENGTH: 20
<212> TYPE: PRT
<213> ORGANISM: Artificial Sequence
<220> FEATURE:
<223> OTHER INFORMATION: B-loop

<400> SEQUENCE: 132

Ile Glu Lys Met Asn Thr Gln Arg Thr Ala Ile Gly Cys Glu Tyr Asn
1 5 10 15

Lys Ser Glu Arg
20

<210> SEQ ID NO 133
<211> LENGTH: 20
<212> TYPE: PRT
<213> ORGANISM: Artificial Sequence
<220> FEATURE:
<223> OTHER INFORMATION: B-loop

<400> SEQUENCE: 133

Ile Glu Lys Met Asn Thr Gln Arg Thr Ala Ile Cys Lys Glu Tyr Pro
1 5 10 15

```
Lys Ser Glu Gln
            20


<210> SEQ ID NO 134
<211> LENGTH: 20
<212> TYPE: PRT
<213> ORGANISM: Artificial Sequence
<220> FEATURE:
<223> OTHER INFORMATION: B-loop

<400> SEQUENCE: 134

Ile Glu Lys Met Asn Thr Gln Arg Thr Ala Ile Gly Lys Glu Cys Asn
1               5                   10                  15

Lys Ser Glu Arg
            20


<210> SEQ ID NO 135
<211> LENGTH: 248
<212> TYPE: PRT
<213> ORGANISM: Artificial Sequence
<220> FEATURE:
<223> OTHER INFORMATION: UFV150553

<400> SEQUENCE: 135

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Arg Thr Ala Ile
        115                 120                 125

Gly Cys Glu Phe Asn Lys Ser Glu Gln Cys Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Gln Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile
                245
```

<210> SEQ ID NO 136
<211> LENGTH: 19
<212> TYPE: PRT
<213> ORGANISM: Artificial Sequence
<220> FEATURE:
<223> OTHER INFORMATION: signal peptide

<400> SEQUENCE: 136

Met Gly Ser Thr Ala Ile Leu Gly Leu Leu Leu Ala Val Leu Gln Gly
1 5 10 15

Val Cys Ala

<210> SEQ ID NO 137
<211> LENGTH: 21
<212> TYPE: PRT
<213> ORGANISM: Artificial Sequence
<220> FEATURE:
<223> OTHER INFORMATION: signal peptide

<400> SEQUENCE: 137

Met Gly Met Thr Ser Ala Leu Leu Ala Leu Leu Ala Leu Ala Leu Lys
1 5 10 15

Pro Gly Ala Trp Ala
20

<210> SEQ ID NO 138
<211> LENGTH: 792
<212> TYPE: DNA
<213> ORGANISM: Artificial Sequence
<220> FEATURE:
<223> OTHER INFORMATION: UFV160655

<400> SEQUENCE: 138
atgaaagtca aactgctggt cctgctgtgc accttcaccg ccacttacgc cgacaccatc 60
tgtattgggt accacgctaa caactccacc gacacagtgg ataccgtgct ggagaagaac 120
gtgaccgtga cacactctgt gaacctgctg gagaattcca agtacgtctg cagcgccaag 180
ctgaggatgg tgacaggcct gagaaataag cccagcaagc agtcccaggg cctgttcgga 240
gcaatcgcag gctttaccga gggaggatgg acaggaatgg tggacggatg gtacggctat 300
caccaccaga acgagcaggg ctccggctat gccgccgatc agaagtctac ccagaacgcc 360
atcaatggca tcacaaacaa ggtcaatagc gtgatcgaga agatgaacac ccagcctaca 420
gccatcggct gcgagtacaa taagtccgag cagtgcatga agcagatcga ggacaagatc 480
gaggagatcg agtctaagat ctggtgctat aacgccgagc tgctggtgct gctcgagaat 540
cagaggaccc tggacttcca cgatgccaac gtgaagaatc tgtacgagaa ggtgaagtcc 600
cagctgaaga acaatgccaa ggagatcggc aacggctgtt tcgagtttta ccacaagtgc 660
aacgacgagt gtatggagtc cgtgaagaat ggcacatacg attatcctaa gtattctgag 720
gagagcaaac tgaatcggga aaaaatcgat ggcgtgaaac tggaatcaat gggggtgtat 780
cagatctaat aa 792

<210> SEQ ID NO 139
<211> LENGTH: 792
<212> TYPE: DNA
<213> ORGANISM: Artificial Sequence
<220> FEATURE:
<223> OTHER INFORMATION: UFV160656

<400> SEQUENCE: 139
atgaaggcca tcctggtggt gctgctgtac accttcgcca cagccaacgc cgacaccctg 60
tgcatcgggt accacgccaa caattccacc gacacagtgg atacagtgct ggagaagaat 120
gtgaccgtga cacactccgt gaacctgctg gaggataaga agtacgtctg cagcaccaag 180
ctgaggctgg ccacaggcct gagaaacaag ccaagcaagc agtcccaggg cctgttcgga 240
gccatcgccg gctttaccga gggaggatgg acaggaatgg tggacggatg gtacggctat 300
caccaccaga acgagcaggg cagcggatac gccgccgacc tgaagtccac ccagaatgcc 360
atcgacgaga ttaccaacaa ggtcaatagc gtgattgaga agatgaacac ccagcccaca 420
gccatcggct gcgagtacaa taagagcgag cagtgtatga agcagattga ggataagatt 480
gaggagattg agtccaagat ttggtgctat aacgccgagc tgctggtgct gctcgagaat 540
cagaggaccc tggactacca cgatgccaac gtgaagaatc tgtatgagaa ggtgaggagc 600
cagctgaaga acaatgccaa ggagattggc aacggctgtt tcgagtttta ccacaagtgc 660
gacaacacct gtatggagtc tgtgaagaat ggcacatacg attatcccaa gtatagcgag 720
gaggccaagc tgaatcggga ggaaatcgat ggcgtgaagc tggagagcac ccgcatctac 780
cagatctaat aa 792

<210> SEQ ID NO 140
<211> LENGTH: 792
<212> TYPE: DNA
<213> ORGANISM: Artificial Sequence
<220> FEATURE:
<223> OTHER INFORMATION: UFV160664

<400> SEQUENCE: 140
atgaaggcca tcctggtcgt cctgctgtac actttcgcca ccgccaacgc tgataccctg 60
tgcatcgggt accacgctaa caactctacc gacacagtgg ataccgtgct ggagaagaac 120
gtgaccgtga cacactctgt gaatctgctg gaggataaga agtacgtctg cagcaccaag 180
ctgaggctgg ccacaggcct gagaaacaag cccagcaagc agagccaggg cctgtttgga 240
gcaattgcag gctttaccga gggcggctgg acaggcatgg tggatggctg gtacggctat 300
caccaccaga atgagcaggg atctggatat gctgctgacc tgaagtctac ccagaatgcc 360
attgatgaga tcacaaacaa ggtcaatagc gtgatcgaga agatgaacac ccagcggaca 420
gccatcggct gcgagtacaa taagtccgag aggtgcatga agcagatcga ggacaagatc 480
gaggagatcg agtctaagat ctggtgctat aacgccgagc tgctggtgct gctcgagaat 540
cagcggaccc tggactacca cgacagcaac gtgaagaatc tgtatgagaa ggtgcgctcc 600
cagctgaaga acaatgccaa ggagatcggc aacggctgtt tcgagtttta ccacaagtgc 660
gacaacacct gtatggagtc tgtgaagaat ggcacatacg attatcccaa gtatagcgag 720
gaggccaagc tgaataggga ggaaatcgat ggcgtgaagc tggagtctac aagaatctac 780
cagatctaat aa 792

<210> SEQ ID NO 141
<211> LENGTH: 792
<212> TYPE: DNA
<213> ORGANISM: Artificial Sequence
<220> FEATURE:
<223> OTHER INFORMATION: UFV160665

<400> SEQUENCE: 141
atgaaggcca tcctggtcgt cctgctgtac actttcgcca ccgccaacgc tgataccctg 60
tgcatcgggt accacgctaa caactctacc gacacagtgg ataccgtgct ggagaagaac 120
gtgaccgtga cacactctgt gaatctgctg gaggataaga agtacgtctg cagcaccaag 180
ctgaggctgg ccacaggcct gagaaacaag cccagcaagc agagccaggg cctgtttgga 240
gcaattgcag gctttaccga gggcggctgg acaggcatgg tggatggctg gtacggctat 300
caccaccaga atgagcaggg atctggatat gctgctgacc tgaagtctac ccagaatgcc 360
attgatgaga tcacaaacaa ggtcaatagc gtgatcgaga agatgaacac ccagcctaca 420
gccatcggct gcgagtacaa taagtccgag aggtgcatga agcagatcga ggacaagatc 480
gaggagatcg agtctaagat ctggtgctat aacgccgagc tgctggtgct gctcgagaat 540
cagcggaccc tggactacca cgacagcaac gtgaagaatc tgtatgagaa ggtgcgctcc 600
cagctgaaga acaatgccaa ggagatcggc aacggctgtt tcgagtttta ccacaagtgc 660
gacaacacct gtatggagtc tgtgaagaat ggcacatacg attatcccaa gtatagcgag 720
gaggccaagc tgaataggga ggaaatcgat ggcgtgaagc tggagtctac aagaatctac 780
cagatctaat aa 792

<210> SEQ ID NO 142
<211> LENGTH: 900
<212> TYPE: DNA
<213> ORGANISM: Artificial Sequence
<220> FEATURE:
<223> OTHER INFORMATION: UFV171588

<400> SEQUENCE: 142
atgaaggtca aactgctggt cctgctgtgc acttttactg ccacctacgc tgacactatc 60
tgtatcgggt accacgcaaa caactcaacc gacacagtgg ataccgtgct ggagaagaac 120
gtgaccgtga cacactccgt gaacctgctg gagaatagca agtacgtctg cagcgccaag 180
ctgcggatgg tgacaggcct gagaaataag ccctctaagc agagccaggg actgttcgga 240
gcaatcgcag gctttaccga gggaggatgg acaggaatgg tggacggatg gtacggctat 300
caccaccaga acgagcaggg cagcggctat gccgccgatc agaagtccac ccagaacgcc 360
atcaatggca tcacaaacaa ggtgaacagc gtgatcgaga agatgaacac ccagcctaca 420
gccatcggct gcgagtataa taagagcgag cagtgtatga agcagatcga ggacaagatc 480
gaggagatcg agtccaagat ctggtgctac aacgccgagc tgctggtgct gctggagaat 540
cagcgcaccc tggacttcca cgatgccaac gtgaagaatc tgtatgagaa ggtgaagagc 600
cagctgaaga acaatgccaa ggagatcggc aacggctgtt tcgagtttta ccacaagtgc 660
aacgacgagt gtatggagag cgtgaagaat ggcacctacg attatcctaa gtattccgag 720
gagtctaagc tgaatcggga gaaaatcgat ggcgtgaagc tggagtccat gggcgtgtac 780
cagatcctgg ccatctattc tacagtggcc agctccctgg tgctgctggt gagcctgggg 840
gctatttcat tctggatgtg ctctaacggc tctctccagt gtcgcatttg tatctgataa 900

<210> SEQ ID NO 143
<211> LENGTH: 900
<212> TYPE: DNA
<213> ORGANISM: Artificial Sequence
<220> FEATURE:
<223> OTHER INFORMATION: UFV171589

<400> SEQUENCE: 143
atgaaggcca ttctggtcgt gctgctgtac actttcgcca ccgctaacgc tgacaccctg 60
tgcatcgggt accacgccaa taactccacc gacacagtgg ataccgtgct ggagaagaac 120
gtgaccgtga cacactctgt gaatctgctg gaggacaaga agtacgtctg cagcaccaag 180

```
ctgaggctgg ccacaggcct gagaaacaag ccctctaagc agagccaggg cctgttcgga    240

gcaatcgcag gctttaccga gggaggatgg acaggcatgg tggatggctg gtacggctat    300

caccaccaga acgagcaggg atccggatat gccgccgacc tgaagtctac ccagaatgcc    360

atcgacgaga tcacaaacaa ggtcaattct gtgatcgaga agatgaacac ccagcctaca    420

gccatcggct gcgagtacaa taagagcgag cagtgtatga agcagatcga ggacaagatc    480

gaggagatcg agtccaagat ctggtgctat aacgccgagc tgctggtgct gctggagaat    540

cagaggaccc tggactacca cgatgccaac gtgaagaatc tgtatgagaa ggtgcggtcc    600

cagctgaaga acaatgccaa ggagatcggc aacggctgtt tcgagtttta ccacaagtgc    660

gacaacacct gtatggagtc cgtgaagaat ggcacatacg attatcccaa gtattctgag    720

gaggccaagc tgaatcggga ggaaatcgat ggcgtgaagc tggagtctac ccgcatctac    780

cagatcctgg ccatctatag cacagtggcc agctccctgg tgctggtggt gtccctgggg    840

gctatctctt tctggatgtg ctcaaatggg tccctccagt gtcgcatctg tatctgataa    900
```

```
<210> SEQ ID NO 144
<211> LENGTH: 900
<212> TYPE: DNA
<213> ORGANISM: Artificial Sequence
<220> FEATURE:
<223> OTHER INFORMATION: UFV171590

<400> SEQUENCE: 144

atgaaggcca ttctggtcgt gctgctgtac actttcgcca ccgctaacgc tgacaccctg     60

tgcatcgggt accacgccaa taactccacc gacacagtgg ataccgtgct ggagaagaac    120

gtgaccgtga cacactctgt gaatctgctg gaggacaaga agtacgtctg cagcaccaag    180

ctgaggctgg ccacaggcct gagaaacaag ccctctaagc agagccaggg cctgttcgga    240

gcaatcgcag gctttaccga gggaggatgg acaggcatgg tggatggctg gtacggctat    300

caccaccaga acgagcaggg atccggatat gccgccgacc tgaagtctac ccagaatgcc    360

atcgacgaga tcacaaacaa ggtcaattct gtgatcgaga agatgaacac ccagaggaca    420

gccatcggct gcgagtacaa taagagcgag aggtgtatga agcagatcga ggacaagatc    480

gaggagatcg agtccaagat ctggtgctat aacgccgagc tgctggtgct gctggagaat    540

cagaggaccc tggactacca cgatagcaac gtgaagaatc tgtatgagaa ggtgcggtcc    600

cagctgaaga acaatgccaa ggagatcggc aacggctgtt tcgagtttta ccacaagtgc    660

gacaacacct gtatggagtc cgtgaagaat ggcacatacg attatcccaa gtattctgag    720

gaggccaagc tgaatcggga ggaaatcgat ggcgtgaagc tggagtctac ccgcatctac    780

cagatcctgg ccatctatag cacagtggcc agctccctgg tgctggtggt gtccctgggg    840

gctatctctt tctggatgtg ctcaaatggg tccctccagt gtcgcatctg tatctgataa    900
```

```
<210> SEQ ID NO 145
<211> LENGTH: 900
<212> TYPE: DNA
<213> ORGANISM: Artificial Sequence
<220> FEATURE:
<223> OTHER INFORMATION: UFV171591

<400> SEQUENCE: 145

atgaaggcca ttctggtcgt gctgctgtac actttcgcca ccgctaacgc tgacaccctg     60

tgcatcgggt accacgccaa taactccacc gacacagtgg ataccgtgct ggagaagaac    120
```

gtgaccgtga cacactctgt gaatctgctg gaggacaaga agtacgtctg cagcaccaag 180
ctgaggctgg ccacaggcct gagaaacaag ccctctaagc agagccaggg cctgttcgga 240
gcaatcgcag gctttaccga gggaggatgg acaggcatgg tggatggctg gtacggctat 300
caccaccaga acgagcaggg atccggatat gccgccgacc tgaagtctac ccagaatgcc 360
atcgacgaga tcacaaacaa ggtcaattct gtgatcgaga agatgaacac ccagcctaca 420
gccatcggct gcgagtacaa taagagcgag aggtgtatga agcagatcga ggacaagatc 480
gaggagatcg agtccaagat ctggtgctat aacgccgagc tgctggtgct gctggagaat 540
cagaggaccc tggactacca cgatagcaac gtgaagaatc tgtatgagaa ggtgcggtcc 600
cagctgaaga acaatgccaa ggagatcggc aacggctgtt tcgagtttta ccacaagtgc 660
gacaacacct gtatggagtc cgtgaagaat ggcacatacg attatcccaa gtattctgag 720
gaggccaagc tgaatcggga ggaaatcgat ggcgtgaagc tggagtctac ccgcatctac 780
cagatcctgg ccatctatag cacagtggcc agctccctgg tgctggtggt gtccctgggg 840
gctatctctt tctggatgtg ctcaaatggg tccctccagt gtcgcatctg tatctgataa 900

<210> SEQ ID NO 146
<211> LENGTH: 749
<212> TYPE: PRT
<213> ORGANISM: Artificial Sequence
<220> FEATURE:
<223> OTHER INFORMATION: MD3606

<400> SEQUENCE: 146

Glu Val Gln Leu Val Glu Ser Gly Gly Gly Leu Val Gln Pro Gly Gly
1 5 10 15

Ser Leu Arg Leu Ser Cys Ala Val Ser Ile Ser Ile Phe Asp Ile Tyr
20 25 30

Ala Met Asp Trp Tyr Arg Gln Ala Pro Gly Lys Gln Arg Asp Leu Val
35 40 45

Ala Thr Ser Phe Arg Asp Gly Ser Thr Asn Tyr Ala Asp Ser Val Lys
50 55 60

Gly Arg Phe Thr Ile Ser Arg Asp Asn Ala Lys Asn Thr Leu Tyr Leu
65 70 75 80

Gln Met Asn Ser Leu Lys Pro Glu Asp Thr Ala Val Tyr Leu Cys His
85 90 95

Val Ser Leu Tyr Arg Asp Pro Leu Gly Val Ala Gly Gly Met Gly Val
100 105 110

Tyr Trp Gly Lys Gly Ala Leu Val Thr Val Ser Ser Gly Gly Gly Gly
115 120 125

Ser Gly Gly Gly Gly Ser Glu Val Gln Leu Val Glu Ser Gly Gly Gly
130 135 140

Leu Val Gln Ala Gly Gly Ser Leu Lys Leu Ser Cys Ala Ala Ser Gly
145 150 155 160

Arg Thr Tyr Ala Met Gly Trp Phe Arg Gln Ala Pro Gly Lys Glu Arg
165 170 175

Glu Phe Val Ala His Ile Asn Ala Leu Gly Thr Arg Thr Tyr Tyr Ser
180 185 190

Asp Ser Val Lys Gly Arg Phe Thr Ile Ser Arg Asp Asn Ala Lys Asn
195 200 205

Thr Glu Tyr Leu Glu Met Asn Asn Leu Lys Pro Glu Asp Thr Ala Val
210 215 220

Tyr Tyr Cys Thr Ala Gln Gly Gln Trp Arg Ala Ala Pro Val Ala Val

-continued

```
225                 230                 235                 240

Ala Ala Glu Tyr Glu Phe Trp Gly Gln Gly Thr Gln Val Thr Val Ser
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Arg Leu Ser
        275                 280                 285

Cys Ala Ala Thr Gly Phe Thr Leu Glu Asn Lys Ala Ile Gly Trp Phe
    290                 295                 300

Arg Gln Thr Pro Gly Ser Glu Arg Glu Gly Val Leu Cys Ile Ser Lys
305                 310                 315                 320

Ser Gly Ser Trp Thr Tyr Tyr Thr Asp Ser Met Arg Gly Arg Phe Thr
                325                 330                 335

Ile Ser Arg Asp Asn Ala Glu Asn Thr Val Tyr Leu Gln Met Asp Ser
            340                 345                 350

Leu Lys Pro Glu Asp Thr Ala Val Tyr Tyr Cys Ala Thr Thr Thr Ala
        355                 360                 365

Gly Gly Gly Leu Cys Trp Asp Gly Thr Thr Phe Ser Arg Leu Ala Ser
    370                 375                 380

Ser Trp Gly Gln Gly Thr Gln Val Thr Val Ser Ser Gly Gly Gly Gly
385                 390                 395                 400

Ser Gly Gly Gly Gly Ser Glu Val Gln Leu Val Glu Ser Gly Gly Gly
                405                 410                 415

Leu Val Gln Pro Gly Gly Ser Leu Lys Leu Ser Cys Ala Ala Ser Gly
            420                 425                 430

Phe Thr Phe Ser Thr Ser Trp Met Tyr Trp Leu Arg Gln Ala Pro Gly
        435                 440                 445

Lys Gly Leu Glu Trp Val Ser Val Ile Asn Thr Asp Gly Gly Thr Tyr
    450                 455                 460

Tyr Ala Asp Ser Val Lys Asp Arg Phe Thr Ile Ser Arg Asp Asn Ala
465                 470                 475                 480

Lys Asp Thr Leu Tyr Leu Gln Met Ser Ser Leu Lys Ser Glu Asp Thr
                485                 490                 495

Ala Val Tyr Tyr Cys Ala Lys Asp Trp Gly Gly Pro Glu Pro Thr Arg
            500                 505                 510

Gly Gln Gly Thr Gln Val Thr Val Ser Ser Asp Lys Thr His Thr Cys
        515                 520                 525

Pro Pro Cys Pro Ala Pro Glu Leu Leu Gly Gly Pro Ser Val Phe Leu
    530                 535                 540

Phe Pro Pro Lys Pro Lys Asp Thr Leu Met Ile Ser Arg Thr Pro Glu
545                 550                 555                 560

Val Thr Cys Val Val Val Asp Val Ser His Glu Asp Pro Glu Val Lys
                565                 570                 575

Phe Asn Trp Tyr Val Asp Gly Val Glu Val His Asn Ala Lys Thr Lys
            580                 585                 590

Pro Arg Glu Glu Gln Tyr Asn Ser Thr Tyr Arg Val Val Ser Val Leu
        595                 600                 605

Thr Val Leu His Gln Asp Trp Leu Asn Gly Lys Glu Tyr Lys Cys Lys
    610                 615                 620

Val Ser Asn Lys Ala Leu Pro Ala Pro Ile Glu Lys Thr Ile Ser Lys
625                 630                 635                 640

Ala Lys Gly Gln Pro Arg Glu Pro Gln Val Tyr Thr Leu Pro Pro Ser
                645                 650                 655
```

```
Arg Glu Glu Met Thr Lys Asn Gln Val Ser Leu Thr Cys Leu Val Lys
            660                 665                 670

Gly Phe Tyr Pro Ser Asp Ile Ala Val Glu Trp Glu Ser Asn Gly Gln
        675                 680                 685

Pro Glu Asn Asn Tyr Lys Thr Thr Pro Pro Val Leu Asp Ser Asp Gly
    690                 695                 700

Ser Phe Phe Leu Tyr Ser Lys Leu Thr Val Asp Lys Ser Arg Trp Gln
705                 710                 715                 720

Gln Gly Asn Val Phe Ser Cys Ser Val Met His Glu Ala Leu His Asn
                725                 730                 735

His Tyr Thr Gln Lys Ser Leu Ser Leu Ser Pro Gly Lys
            740                 745


<210> SEQ ID NO 147
<211> LENGTH: 268
<212> TYPE: PRT
<213> ORGANISM: Artificial Sequence
<220> FEATURE:
<223> OTHER INFORMATION: UFV180496 H1 A/California/07/09

<400> SEQUENCE: 147

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys Lys Tyr Val Cys Ser Thr Lys Leu Arg Leu Ala
    50                  55                  60

Thr Gly Leu Arg Asn Lys Pro Ser Lys Gln Ser Gln Gly Leu Phe Gly
65                  70                  75                  80

Ala Ile Ala Gly Phe Thr Glu Gly Gly Trp Thr Gly Met Val Asp Gly
                85                  90                  95

Trp Tyr Gly Tyr His His Gln Asn Glu Gln Gly Ser Gly Tyr Ala Ala
            100                 105                 110

Asp Leu Lys Ser Thr Gln Asn Ala Ile Asp Glu Ile Thr Asn Lys Val
        115                 120                 125

Asn Ser Val Ile Glu Lys Met Asn Thr Gln Arg Thr Ala Ile Gly Cys
    130                 135                 140

Glu Tyr Asn Lys Ser Glu Arg Cys Met Lys Gln Ile Glu Asp Lys Ile
145                 150                 155                 160

Glu Glu Ile Glu Ser Lys Ile Trp Cys Tyr Asn Ala Glu Leu Leu Val
                165                 170                 175

Leu Leu Glu Asn Gln Arg Thr Leu Asp Tyr His Asp Ser Asn Val Lys
            180                 185                 190

Asn Leu Tyr Glu Lys Val Arg Ser Gln Leu Lys Asn Asn Ala Lys Glu
        195                 200                 205

Ile Gly Asn Gly Cys Phe Glu Phe Tyr His Lys Cys Asp Asn Thr Cys
    210                 215                 220

Met Glu Ser Val Lys Asn Gly Thr Tyr Asp Tyr Pro Lys Tyr Ser Glu
225                 230                 235                 240

Glu Ala Lys Leu Asn Arg Glu Glu Ile Asp Gly Val Lys Leu Glu Ser
                245                 250                 255

Thr Arg Ile Tyr Gln Ile His His His His His His
            260                 265
```

<210> SEQ ID NO 148
<211> LENGTH: 268
<212> TYPE: PRT
<213> ORGANISM: Artificial Sequence
<220> FEATURE:
<223> OTHER INFORMATION: UFV180497 H1 A/Michigan/45/2015

<400> SEQUENCE: 148

```
Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys Lys Tyr Val Cys Ser Thr Lys Leu Arg Leu Ala
    50                  55                  60

Thr Gly Leu Arg Asn Lys Pro Ser Lys Gln Ser Gln Gly Leu Phe Gly
65                  70                  75                  80

Ala Ile Ala Gly Phe Thr Glu Gly Gly Trp Thr Gly Met Val Asp Gly
                85                  90                  95

Trp Tyr Gly Tyr His His Gln Asn Glu Gln Gly Ser Gly Tyr Ala Ala
            100                 105                 110

Asp Leu Lys Ser Thr Gln Asn Ala Ile Asp Lys Ile Thr Asn Lys Val
        115                 120                 125

Asn Ser Val Ile Glu Lys Met Asn Thr Gln Arg Thr Ala Ile Gly Cys
    130                 135                 140

Glu Tyr Asn Lys Ser Glu Lys Cys Met Lys Gln Ile Glu Asp Lys Ile
145                 150                 155                 160

Glu Glu Ile Glu Ser Lys Ile Trp Cys Tyr Asn Ala Glu Leu Leu Val
                165                 170                 175

Leu Leu Glu Asn Gln Arg Thr Leu Asp Tyr His Asp Ser Asn Val Lys
            180                 185                 190

Asn Leu Tyr Glu Lys Val Arg Asn Gln Leu Lys Asn Asn Ala Lys Glu
        195                 200                 205

Ile Gly Asn Gly Cys Phe Glu Phe Tyr His Lys Cys Asp Asn Thr Cys
    210                 215                 220

Met Glu Ser Val Lys Asn Gly Thr Tyr Asp Tyr Pro Lys Tyr Ser Glu
225                 230                 235                 240

Glu Ala Lys Leu Asn Arg Glu Lys Ile Asp Gly Val Lys Leu Glu Ser
                245                 250                 255

Thr Arg Ile Tyr Gln Ile His His His His His His
            260                 265
```

<210> SEQ ID NO 149
<211> LENGTH: 268
<212> TYPE: PRT
<213> ORGANISM: Artificial Sequence
<220> FEATURE:
<223> OTHER INFORMATION: UFV180498 H1 A/Puerto Rico/8/1934

<400> SEQUENCE: 149

```
Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
        35                  40                  45

Leu Leu Glu Asp Ser Lys Tyr Val Cys Ser Ala Lys Leu Arg Met Val
    50                  55                  60

Thr Gly Leu Arg Asn Lys Pro Ser Lys Gln Ser Gln Gly Leu Phe Gly
65                  70                  75                  80

Ala Ile Ala Gly Phe Thr Glu Gly Gly Trp Thr Gly Met Ile Asp Gly
                85                  90                  95

Trp Tyr Gly Tyr His His Gln Asn Glu Gln Gly Ser Gly Tyr Ala Ala
            100                 105                 110

Asp Gln Lys Ser Thr Gln Asn Ala Ile Asn Gly Ile Thr Asn Lys Val
        115                 120                 125

Asn Ser Val Ile Glu Lys Met Asn Ile Gln Arg Thr Ala Ile Gly Cys
    130                 135                 140

Glu Tyr Asn Lys Ser Glu Lys Cys Met Lys Gln Ile Glu Asp Lys Ile
145                 150                 155                 160

Glu Glu Ile Glu Ser Lys Ile Trp Cys Tyr Asn Ala Glu Leu Leu Val
                165                 170                 175

Leu Leu Glu Asn Gln Arg Thr Leu Asp Phe His Asp Ser Asn Val Lys
            180                 185                 190

Asn Leu Tyr Glu Lys Val Lys Ser Gln Leu Lys Asn Asn Ala Lys Glu
        195                 200                 205

Ile Gly Asn Gly Cys Phe Glu Phe Tyr His Lys Cys Asp Asn Glu Cys
    210                 215                 220

Met Glu Ser Val Arg Asn Gly Thr Tyr Asp Tyr Pro Lys Tyr Ser Glu
225                 230                 235                 240

Glu Ser Lys Leu Asn Arg Glu Lys Val Asp Gly Val Lys Leu Glu Ser
                245                 250                 255

Met Gly Ile Tyr Gln Ile His His His His His His
            260                 265
```

<210> SEQ ID NO 150
<211> LENGTH: 267
<212> TYPE: PRT
<213> ORGANISM: Artificial Sequence
<220> FEATURE:
<223> OTHER INFORMATION: UFV180499 H5 A/Hong Kong/156/97

<400> SEQUENCE: 150

```
Met Glu Lys Thr Val Leu Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr Lys Tyr Val Cys Ser Asn Arg Leu Val Leu Ala Thr
    50                  55                  60

Gly Leu Arg Asn Lys Pro Gln Lys Glu Ser Gln Gly Leu Phe Gly Ala
65                  70                  75                  80

Ile Ala Gly Phe Thr Glu Gly Gly Trp Gln Gly Met Val Asp Gly Trp
                85                  90                  95

Tyr Gly Tyr His His Ser Asn Glu Gln Gly Ser Gly Tyr Ala Ala Asp
            100                 105                 110

Lys Glu Ser Thr Gln Lys Ala Ile Asp Gly Val Thr Asn Lys Val Asn
        115                 120                 125

Ser Ile Ile Asn Lys Met Asn Thr Gln Arg Glu Ala Ile Gly Cys Glu
```

```
    130                 135                 140

Tyr Asn Lys Ser Glu Arg Cys Met Lys Gln Ile Glu Asp Lys Ile Glu
145                 150                 155                 160

Glu Ile Glu Ser Lys Val Trp Cys Tyr Asn Ala Glu Leu Leu Val Leu
                165                 170                 175

Met Glu Asn Gln Arg Thr Leu Asp Phe His Asp Ser Asn Val Lys Asn
            180                 185                 190

Leu Tyr Asp Lys Val Arg Leu Gln Leu Arg Asp Asn Ala Lys Glu Leu
        195                 200                 205

Gly Asn Gly Cys Phe Glu Phe Tyr His Lys Cys Asp Asn Glu Cys Met
    210                 215                 220

Glu Ser Val Lys Asn Gly Thr Tyr Asp Tyr Pro Gln Tyr Ser Glu Glu
225                 230                 235                 240

Ala Arg Leu Asn Arg Glu Glu Ile Ser Gly Val Lys Leu Glu Ser Met
                245                 250                 255

Gly Thr Tyr Gln Ile His His His His His His
            260                 265


<210> SEQ ID NO 151
<211> LENGTH: 267
<212> TYPE: PRT
<213> ORGANISM: Artificial Sequence
<220> FEATURE:
<223> OTHER INFORMATION: UFV180500 H5 A/Vietnam/1203/04

<400> SEQUENCE: 151

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys Lys Tyr Val Cys Ser Asn Arg Leu Val Leu Ala Thr
    50                  55                  60

Gly Leu Arg Asn Lys Pro Gln Lys Glu Ser Gln Gly Leu Phe Gly Ala
65                  70                  75                  80

Ile Ala Gly Phe Thr Glu Gly Gly Trp Gln Gly Met Val Asp Gly Trp
                85                  90                  95

Tyr Gly Tyr His His Ser Asn Glu Gln Gly Ser Gly Tyr Ala Ala Asp
            100                 105                 110

Lys Glu Ser Thr Gln Lys Ala Ile Asp Gly Val Thr Asn Lys Val Asn
        115                 120                 125

Ser Ile Ile Asp Lys Met Asn Thr Gln Arg Glu Ala Ile Gly Cys Glu
    130                 135                 140

Tyr Asn Lys Ser Glu Arg Cys Met Lys Gln Ile Glu Asp Lys Ile Glu
145                 150                 155                 160

Glu Ile Glu Ser Lys Val Trp Cys Tyr Asn Ala Glu Leu Leu Val Leu
                165                 170                 175

Met Glu Asn Gln Arg Thr Leu Asp Phe His Asp Ser Asn Val Lys Asn
            180                 185                 190

Leu Tyr Asp Lys Val Arg Leu Gln Leu Arg Asp Asn Ala Lys Glu Leu
        195                 200                 205

Gly Asn Gly Cys Phe Glu Phe Tyr His Lys Cys Asp Asn Glu Cys Met
    210                 215                 220

Glu Ser Val Arg Asn Gly Thr Tyr Asp Tyr Pro Gln Tyr Ser Glu Glu
```

```
225                 230                 235                 240

Ala Arg Leu Lys Arg Glu Glu Ile Ser Gly Val Lys Leu Glu Ser Ile
                245                 250                 255

Gly Ile Tyr Gln Ile His His His His His His
            260                 265


<210> SEQ ID NO 152
<211> LENGTH: 266
<212> TYPE: PRT
<213> ORGANISM: Artificial Sequence
<220> FEATURE:
<223> OTHER INFORMATION: UFV180501 H2 A/Singapore/1/57

<400> SEQUENCE: 152

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr Lys Tyr Val Cys Ser Glu Lys Leu Val Leu Ala Thr Gly
    50                  55                  60

Leu Arg Asn Lys Pro Gln Lys Glu Ser Gln Gly Leu Phe Gly Ala Ile
65                  70                  75                  80

Ala Gly Phe Thr Glu Gly Gly Trp Gln Gly Met Val Asp Gly Trp Tyr
                85                  90                  95

Gly Tyr His His Ser Asn Asp Gln Gly Ser Gly Tyr Ala Ala Asp Lys
            100                 105                 110

Glu Ser Thr Gln Lys Ala Phe Asp Gly Ile Thr Asn Lys Val Asn Ser
        115                 120                 125

Val Ile Glu Lys Met Asn Thr Gln Arg Glu Ala Ile Gly Cys Glu Tyr
    130                 135                 140

Ser Lys Ser Glu Arg Cys Met Lys Gln Ile Glu Asp Lys Ile Glu Glu
145                 150                 155                 160

Ile Glu Ser Lys Val Trp Cys Tyr Asn Ala Glu Leu Leu Val Leu Met
                165                 170                 175

Glu Asn Gln Arg Thr Leu Asp Phe His Asp Ser Asn Val Lys Asn Leu
            180                 185                 190

Tyr Asp Lys Val Arg Met Gln Leu Arg Asp Asn Val Lys Glu Leu Gly
        195                 200                 205

Asn Gly Cys Phe Glu Phe Tyr His Lys Cys Asp Asp Glu Cys Met Asn
    210                 215                 220

Ser Val Lys Asn Gly Thr Tyr Asp Tyr Pro Lys Tyr Glu Glu Glu Ser
225                 230                 235                 240

Lys Leu Asn Arg Asn Glu Ile Lys Gly Val Lys Leu Ser Ser Met Gly
                245                 250                 255

Val Tyr Gln Ile His His His His His His
            260                 265


<210> SEQ ID NO 153
<211> LENGTH: 298
<212> TYPE: PRT
<213> ORGANISM: Artificial Sequence
<220> FEATURE:
<223> OTHER INFORMATION: UFV171590 (UFV160664+TM)

<400> SEQUENCE: 153
```

-continued

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys Lys Tyr Val Cys Ser Thr Lys Leu Arg Leu Ala
    50                  55                  60

Thr Gly Leu Arg Asn Lys Pro Ser Lys Gln Ser Gln Gly Leu Phe Gly
65                  70                  75                  80

Ala Ile Ala Gly Phe Thr Glu Gly Gly Trp Thr Gly Met Val Asp Gly
                85                  90                  95

Trp Tyr Gly Tyr His His Gln Asn Glu Gln Gly Ser Gly Tyr Ala Ala
            100                 105                 110

Asp Leu Lys Ser Thr Gln Asn Ala Ile Asp Glu Ile Thr Asn Lys Val
        115                 120                 125

Asn Ser Val Ile Glu Lys Met Asn Thr Gln Arg Thr Ala Ile Gly Cys
    130                 135                 140

Glu Tyr Asn Lys Ser Glu Arg Cys Met Lys Gln Ile Glu Asp Lys Ile
145                 150                 155                 160

Glu Glu Ile Glu Ser Lys Ile Trp Cys Tyr Asn Ala Glu Leu Leu Val
                165                 170                 175

Leu Leu Glu Asn Gln Arg Thr Leu Asp Tyr His Asp Ser Asn Val Lys
            180                 185                 190

Asn Leu Tyr Glu Lys Val Arg Ser Gln Leu Lys Asn Asn Ala Lys Glu
        195                 200                 205

Ile Gly Asn Gly Cys Phe Glu Phe Tyr His Lys Cys Asp Asn Thr Cys
    210                 215                 220

Met Glu Ser Val Lys Asn Gly Thr Tyr Asp Tyr Pro Lys Tyr Ser Glu
225                 230                 235                 240

Glu Ala Lys Leu Asn Arg Glu Glu Ile Asp Gly Val Lys Leu Glu Ser
                245                 250                 255

Thr Arg Ile Tyr Gln Ile Leu Ala Ile Tyr Ser Thr Val Ala Ser Ser
            260                 265                 270

Leu Val Leu Val Val Ser Leu Gly Ala Ile Ser Phe Trp Met Cys Ser
        275                 280                 285

Asn Gly Ser Leu Gln Cys Arg Ile Cys Ile
    290                 295


<210> SEQ ID NO 154
<211> LENGTH: 36
<212> TYPE: PRT
<213> ORGANISM: Artificial Sequence
<220> FEATURE:
<223> OTHER INFORMATION: Strep tag

<400> SEQUENCE: 154

Glu Gly Arg Ala Ala Ala Trp Ser His Pro Gln Phe Glu Lys Gly Ala
1               5                   10                  15

Ala Trp Ser His Pro Gln Phe Glu Lys Gly Ala Ala Trp Ser His Pro
            20                  25                  30

Gln Phe Glu Lys
        35
```

INFLUENZA VIRUS VACCINES AND USES THEREOF

CROSS-REFERENCE TO RELATED APPLICATION

This application is a Section 371 of International Application No. PCT/EP2019/051532, filed Jan. 22, 2019, which was published in the English language on Aug. 1, 2019, under International Publication No. WO 2019/145310 A1, which claims priority under 35 U.S.C. § 119(b) to EP Application No. 18152991.8, filed Jan. 23, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing" and a creation date of Jun. 30, 2020 and having a size of 283 kb. The sequence listing submitted via EFS-Web is part of the specification and is herein incorporated by reference in its entirety.

INTRODUCTION

The invention relates to the field of medicine. Provided herein are influenza A hemagglutinin (HA) stem domain polypeptides, nucleic acids encoding said polypeptides, pharmaceutical compositions comprising the same, and methods of their use.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses, and therefore representatives of these are typically included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition, the possibility of a pandemic caused by a highly virulent viral strain originating from animal reservoirs and reassorted to increase human to human spread, still poses a significant and realistic threat to global health.

Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA).

Influenza A viruses are widely distributed in nature and can infect a variety of birds and mammals. The viruses are classified on the basis of differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis of influenza A viruses has demonstrated a subdivision of hemagglutinins into two main, so-called phylogenetic groups: inter alia the H1, H2, H5 and H9 subtypes in phylogenetic group 1 (the group 1 viruses) and inter alia the H3, H4 and H7 subtypes in phylogenetic group 2 (group 2 viruses).

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages. Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored in the viral membrane and has a dual function: it is responsible for binding to the cell surface receptor sialic acid and, after uptake, it mediates the fusion of viral and endosomal membrane leading to the release of viral RNA into the cytosol of the target cell. HA comprises a large head domain and a smaller stem domain. The stem domain is anchored in to the viral membrane via a C-terminal transmembrane domain sequence. The protein is post-translationally cleaved to yield two HA polypeptides, HA1 and HA2 (the full sequence is referred to as HA0) (FIG. 1A). The membrane distal head region is mainly derived from HA1 and the membrane proximal stem region primarily from HA2. Cleavage of the HA precursor molecule HA0 is required to activate virus infectivity, and the distribution of activating proteases in the host is one of the determinants of pathogenicity of the influenza virus. The HAs of mammalian and nonpathogenic avian viruses are cleaved extracellularly, which limits their spread in hosts to tissues where the appropriate proteases are encountered. On the other hand, the HAs of pathogenic viruses are cleaved intracellularly by ubiquitously occurring proteases and therefore have the capacity to infect various cell types and cause systemic infections.

The reason that the seasonal influenza vaccine must be updated every year is the large variability of the virus. In the HA protein this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain explains why infection with a particular strain does not lead to immunity to other strains: the antibodies elicited by the first infection only recognize a limited number of strains closely related to the virus of the primary infection.

Recently, influenza hemagglutinin stem polypeptides, lacking the complete influenza hemagglutinin globular head domain or a substantial part of it, have been described and have been used to generate an immune response to one or more conserved epitopes of the stem domain polypeptide. It is believed that epitopes of the stem polypeptide are less immunogenic than the highly immunogenic regions of a globular head domain, and that the absence of a globular head domain in the stem polypeptide might allow an immune response against one or more epitopes of the stem polypeptide to develop (Steel et al., 2010). Steel et al. thus created an influenza HA stem polypeptide by deleting amino acid residue 53 to 276 from the HA1 domain of the A/Puerto Rico/8/1934 (H1N1) and A/Hong Kong/1968 (H3N2) strains and replacing the deleted sequence by a short flexible linking sequence GGGG. Vaccination of mice with the H3 HK68 construct did not elicit antisera that were cross-reactive with group 1 HAs. In addition, as shown in WO2013/079473, the stem polypeptides were unstable and did not adopt the correct conformation as proven by the lack of binding of antibodies that were shown to bind to conserved epitopes in the stem region.

Bommakanti et al. (2010) described an HA2 based polypeptide comprising amino acid residues 330-501 (HA2), a 7-amino acid linker (GSAGSAG), amino acid residues 16-55 of HA1, a 6-amino acid linker GSAGSA, followed by residues 290-321 of HA1, with the mutations V297T, 1300E, Y302T and C305T in HA1. The design was based on the sequence of H3 HA (A/Hong Kong/1968). The polypeptide did only provide cross-protection against another influenza virus strain within the H3 subtype (A/Phil/2/82 but not against an H1 subtype (A/PR/8/34). In a more recent paper by Bommakanti et al. (2012), a stem polypeptide based on HA from H1N1 A/Puerto Rico/8/1934 (H1HA0HA6) was described. In this polypeptide, the equivalent of amino acid residues 48 to 288 have been deleted and mutations 1297T, V300T, 1302N, C305S, F392D, F395T, and L402D have been made. Both the H3 and H1 based polypeptides were expressed in *E. coli* and therefore lack the glycans that are part of the naturally occurring HA proteins.

More recently, Lu et al. (2014) also described soluble stem polypeptides derived from the HA of H1N1 A/California/05/2009. In the final design, the amino acid residues from 52 to 277 were deleted (the leader sequence is also not present) and two mutations were introduced in the B-loop of the protein, i.e. F392D, and L402D. Furthermore, the polypeptide contained a C-terminal trimerization domain (foldon). In addition, two intermonomer disulfide bridges were introduced, one in the area of the trimeric foldon domain, and one at position 416 and 417 (i.e. G416C and F417C in H3 numbering). The polypeptide was produced in an *E. coli* based cell free system, (and thus lacks the glycans that are part of the naturally occurring HA proteins) and was recovered in a denatured form, which needs to be refolded prior to use. The refolded protein failed to bind the broadly neutralizing antibody (bnAb) CR6261 which is binding to a conserved conformational stem epitope. No immunological or protection data from influenza challenge were shown.

In another paper Mallajosyula et al. (2014) also described an influenza HA stem polypeptide. In this design, based on HA from H1N1 A/Puerto Rico/8/1934, not only a large part of the HA1 sequence was deleted (residue 48 to 289, H3 numbering), but also large part of the N- and C-terminal sequences of HA2 (residues 323 to 369 and 443 to end, respectively). The polypeptide contained a foldon trimerization domain at the C-terminus and was also produced in *E. coli*, so is lacking the naturally occurring glycans on viral HA. The polypeptide was shown to bind the bnAbs CR6261, F10 and FI6v3, and protected mice from a leathal influenza virus challenge (1LD90 of H1N1 A/Puerto Rico/8/1934). Equivalent polypeptides derived from HA of H1N1 A/New Caledonia/20/1999 and H1N1 A/California/04/2009 could also partially protect. A polypeptide derived from H5N1 A/Viet Nam/1203/2004 only gave limited protection in this challenge model. Moreover, the challenge model used was mild with a relatively low dose administered (1-2 LD90).

Lastly, Yassine et al. (2015) also described the development of a stabilized HA stem polypeptide derived from HA of H1N1 A/New Caledonia/20/1999. In this design, a large part of the HA1 sequence (residue 43 to 313, H3 numbering) and HA2 sequence (residue 504 to end) have been deleted. In addition, the design contains two stabilizing mutations (K380M and E432L) in HA2 and is genetically fused to the ferritin subunit of *H. pylori* to create self-assembling nanoparticles displaying the stabilized HA-stem polypeptide. The stabilized HA-stem polypeptide seemed not soluble or functional without being fused to the ferritin subunit. The HA stem-ferritin polypeptide assembled to nanoparticles was tested in a heterosubtypic H5N1 2004 VN influenza virus challenge model (25×$LD_{50}$ and 1,000×$TCID_{50}$ in mouse and ferrets, respectively) and could protect mice from death whereas only partial protection was observed in ferrets. It is unclear how much ferritin response would be induced in humans and which effect that would have for multiple administrations.

There thus still exists a need for a safe and effective "universal" vaccine that stimulates the production of a robust, broadly neutralizing antibody response and that offers protection against a broad set of current and future influenza virus strains (both seasonal and pandemic), in particular a vaccine that provides protection against one or more influenza A virus subtypes within phylogenetic group 1 and/or group 2, for the effective prevention and/or treatment of influenza.

SUMMARY

The present invention provides novel polypeptides derived from influenza hemaggluinin (HA), which polypeptides comprise the influenza HA stem domain and lack the globular head region, herein referred to as influenza hemagglutinin (HA) stem polypeptides. The polypeptides induce an immune response against HA when administered to a subject, in particular a human subject. The polypeptides of the invention present conserved epitopes of the membrane proximal stem of the HA molecule to the immune system in the absence of dominant epitopes that are present in the membrane distal head domain. Thus, part of the primary sequence of the HA0 protein, i.e. the part making up the head domain has been deleted, and the remaining amino acid sequence has been reconnected, either directly or, in some embodiments, by introducing a short flexible linking sequence ('linker') to restore the continuity of the amino acid chain. The resulting amino acid sequence is further modified by introducing specific modifications that stabilize the native 3-dimensional structure of the remaining part of the HA molecule.

In a first aspect, the present invention relates to group 1 influenza A hemagglutinin (HA) stem polypeptides comprising an HA1 and an HA2 domain, said polypeptides comprising an amino acid sequence which comprises, as compared to the amino acid sequence of a full-length HA polypeptide comprising an HAT and an HA2 domain:

(i) a deletion of the head region in the HA1 domain;

(ii) a modification of the trimerization region in the HA2 domain, preferably a modification in the C-helix, (iii) at least 2 cysteine residues (capable of) forming an intramonomeric disulphide bridge;

(iv) at least 2 cysteine residues (capable of) forming an intermonomeric disulphide bridge;

wherein the amino acid corresponding to the amino acid at position 392 is P, R or Y, preferably P or R, and the amino acid corresponding to the amino acid at position 434 is Q, and wherein the numbering of the amino acid positions is based on H3 numbering as used in Winter et al. (1981).

In certain embodiments, the present invention relates to group 1 influenza A hemagglutinin (HA) stem polypeptides comprising an HA1 and an HA2 domain, wherein said HA stem polypeptides comprise an amino acid sequence which comprises, as compared to the amino acid sequence of the full-length HA polypeptide (HA0) comprising an HA1 and an HA2 domain:

(i) a deletion of the head region in the HA1 domain, said deletion comprising at least the amino acid sequence from the amino acid corresponding to the amino acid at position 53 up to and including the amino acid corresponding to the amino acid at position 302;

(ii) a modification of the trimerization region in the HA2 domain, preferably a modification of the trimerization region in the C-helix, said trimerization region comprising the amino acid sequence from the amino acid corresponding to the amino acid at position 405 up to and including the amino acid corresponding to the amino acid at position 419;

(iii) a cysteine at the amino acid position corresponding to position 310 and a cysteine at the position corresponding to position 422 (capable of) forming an intramonomeric disulphide bridge;

(iv) a cysteine at the position corresponding to position 397 in combination with a cysteine at the position corresponding to position 405; or a cysteine at the position corresponding to position 396 in combination with a cysteine at the position corresponding to position 408; or a cysteine at the position corresponding to position 399 in combination with a cysteine at position 405;

wherein the amino acid at the position corresponding to position 392 is P, R or Y, preferably P or R, and wherein the amino acid at the position corresponding to position 434 is Q; and wherein the numbering of the amino acid positions is based on H3 numbering as used in Winter et al. (1981).

According to the present invention it has surprisingly been shown that the novel influenza HA stem polypeptides of the invention can be expressed in high levels, are overwhelmingly trimeric in cell culture supernatant, have an increased melting temperature which leads to greater stability. In addition, the HA stem polypeptides of the invention mimick the stem of the full-length HA by stably presenting the epitope of HA stem binding bnAbs, such as CR9114 and/or CR6261.

In a further aspect, the present invention provides nucleic acid molecules encoding the influenza HA stem polypeptides.

In yet another aspect, the invention provides vectors, in particular recombinant adenoviral vectors, comprising the nucleic acids encoding the influenza HA stem polypeptides.

In a further aspect, the invention provides methods for inducing an immune response against influenza HA in a subject in need thereof, the method comprising administering to the subject an influenza HA stem polypeptide, a nucleic acid molecule, and/or a vector according to the invention.

In another aspect, the invention provides pharmaceutical compositions comprising an influenza HA stem polypeptide, a nucleic acid molecule and/or a vector according to the invention, and a pharmaceutically acceptable carrier.

In a further aspect, the invention provides influenza HA stem polypeptides, nucleic acid molecules encoding said influenza HA stem polypeptides, and/or vectors comprising said nucleic acid molecules for use as a medicament, in particular for use as a vaccine for the prevention and/or treatment of a disease or condition caused by an influenza virus A strain from phylogenetic group 1 and/or 2 and/or an influenza B virus strain.

BRIEF DESCRIPTION OF THE FIGURES

FIG. 14: Numbering of amino acid positions in H1 A/California/07/09 and in UFV160664, according to H3 numbering of Winter et al. (1981).

FIG. 15: H1 A/Brisbane/59/07 FL HA-specific antibody titers after immunization of mice with polypeptides of the invention. The dashed line indicates the LLOQ (Lower Limit of Quantification), the horizontal line per group denotes the group median.

FIG. 16: Upper panel: Survival proportion during the follow-up period after H1N1 A/Brisbane/59/07 challenge of mice immunized with polypeptides of the invention. Bottom panel: Relative bodyweight during the follow-up period after H1N1 A/Brisbane/59/07 challenge of mice immunized with polypeptides of the invention. Relative bodyweight change was expressed relative to Day 0. Cumulative bodyweight loss during the follow-up period was determined by calculating the Area Under the Curve (AUC). Error bars denote 95% confidence interval.

DEFINITIONS

Figure 1:
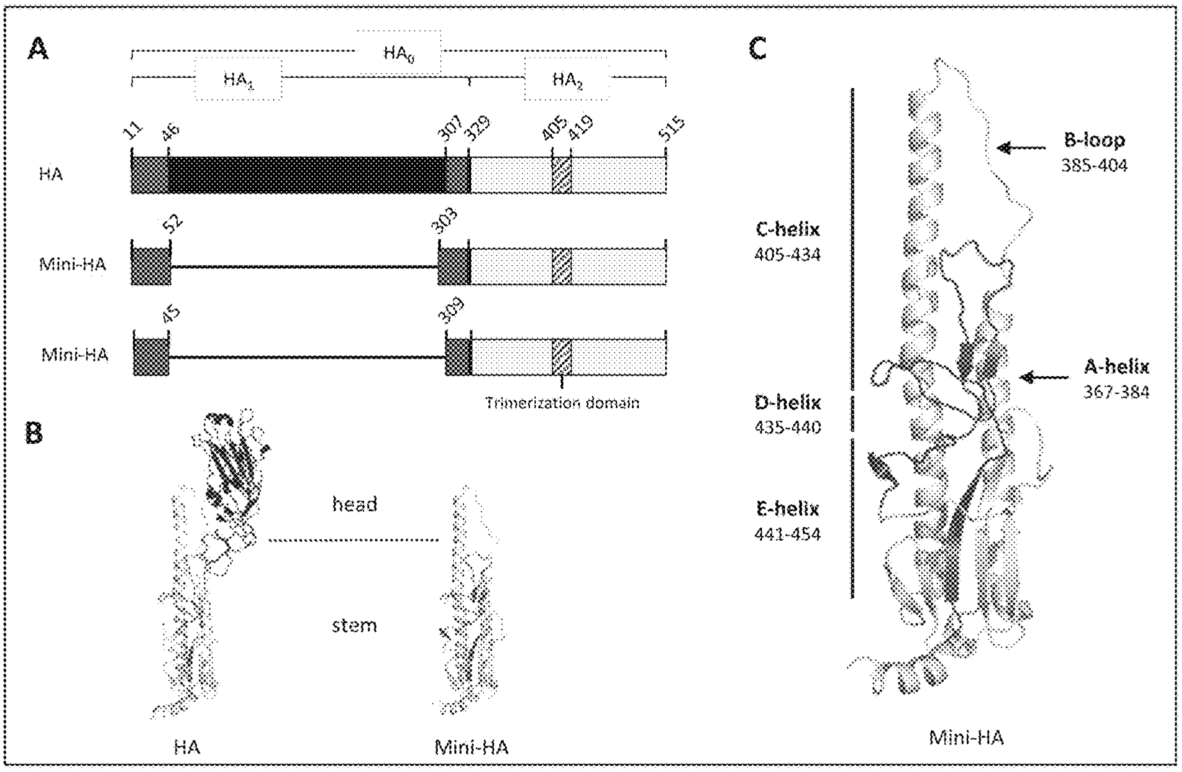
FIG. 1. A. Schematic overview of the polypeptides of the invention; B. Removal of the head region of HA results in the stem polypeptides of the invention (mini-HA); C. Three-dimensional representation of a stem-based polypeptide of the invention.

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 12 shows the abbreviations and properties of the standard amino acids.

The term "included" or "including" as used herein is deemed to be followed by the words "without limitation".

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are typically classified into influenza virus types: genus A, B and C. The term "influenza virus subtype" as used herein refers to influenza A virus variants that are characterized by combinations of the hemagglutinin (H) and neuramidase (N) viral surface proteins. According to the present invention influenza virus subtypes may be referred to by their H number, such as for example "influenza virus comprising HA of the H3 subtype", "influenza virus of the H3 subtype" or "H3 influenza", or by a combination of a H number and an N number, such as for example "influenza virus subtype H3N2" or "H3N2". The term "subtype" specifically includes all individual "strains", within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e. A, B or C, the geographical location of the first isolation, strain number and year of isolation, usually with the antigenic description of HA and NA given in brackets, e.g. A/Moscow/10/00 (H3N2). Non-human strains also include the host of origin in the nomenclature.

The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

As used herein, the term "influenza virus disease" or "influenza" refers to the pathological condition resulting from the presence of an influenza virus, e.g. an influenza A or B virus, in a subject. As used herein, the terms "disease" and "disorder" are used interchangeably. In specific embodiments, the term refers to a respiratory illness caused by the infection of the subject by the influenza virus.

As used herein, the term "nucleic acid" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

Figure 2:
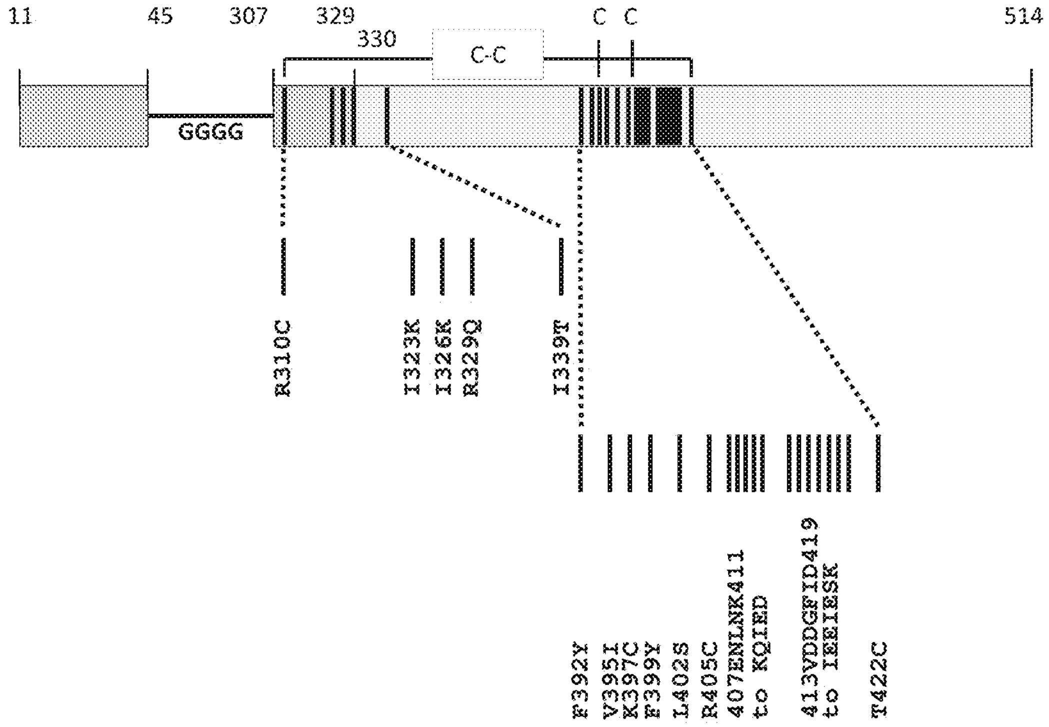
FIG. 2. Schematic drawing of the A/Brisbane based parental construct 5367.

As used herein, the numbering of the amino acids in HA is based on H3 numbering, as described by Winter et al. (1981). The numbering of the amino acid residues or amino acid positions thus refers to the numbering in the full length H3 HA (in particular, the numbering of amino acid positions in A/Aichi/2/68), as described by and shown in FIG. 2 in Winter et al. (1981). The numbering in particular refers to the numbering of the amino acid positions in SEQ ID NO: 15. For example, the wording 'the amino acid at position 392" or "the amino acid corresponding to the amino acid at position 392" (which are used interchangeably throughout this application) refers to the amino acid residue that is at position 392 according to the H3 numbering of Winter et al. (1981). It is noted that, because in the polypeptides of the invention part of the HA1 domain (the head domain) has been deleted, the numbering, as used herein, does not necessarily refer to the actual positions of the amino acids in the HA stem polypeptides of the invention. It will furthermore be understood by the skilled person that equivalent amino acids in other influenza virus strains and/or subtypes, such as in H1 HA, and in the stem polypeptides of the invention, can be determined by sequence alignment (as shown e.g in FIG. 14).

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

"HA stem polypeptide" refers to a HA derived polypeptide which does not comprise the head domain of a naturally-occurring (or wild-type) hemagglutinin (HA). As used herein, the term "wild-type" refers to HA from influenza viruses that are circulating naturally.

DETAILED DESCRIPTION

Influenza viruses have a significant impact on global public health, causing millions of cases of severe illness each year, thousands of deaths, and considerable economic losses. Current trivalent or quidrivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently still impossible.

Hemagglutinin (HA) is the major envelope glycoprotein from influenza viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides (HA1 and HA2) that remain linked by a disulfide bond. The majority of the N-terminal fragment (the HA1 domain, 320-330 amino acids) forms a membrane-distal globular "head domain" that contains the receptor-binding site and most determinants recognized by virus-neutralizing antibodies. The smaller C-terminal portion (HA2 domain, ~180 amino acids) forms a stem-like structure that anchors the globular domain to the cellular or viral membrane. The degree of sequence identity between subtypes is smaller in the HA1 polypeptides (34%-59% identity between subtypes) than in the HA2 polypeptide (51%-80% identity). The most conserved region is the sequence around the protease cleavage site, particularly the HA2 N-terminal 23 amino acids, which is conserved among all influenza A virus subtypes (Lorieau et al., 2010). Part of this region is exposed as a surface loop in the HA precursor molecule (HA0), but becomes inaccessible when HA0 is cleaved into HAT and HA2.

Most neutralizing antibodies bind to the loops that surround the receptor binding site and thereby interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated, such as e.g. CR6261. Functional and structural analysis have revealed that these antibodies interfere with the membrane fusion process and are directed against highly conserved epitopes in the stem domain of group 1 influenza HA protein (Throsby et al., 2008; Ekiert et al. 2009, WO 2008/028946). With the identification of CR9114 (as described in WO2013/007770) which cross-reacts with many group 1 and 2 HA molecules, it has become clear that it is possible for the human immune system to elicit very broad neutralizing antibodies against influenza viruses. However, given the need for a yearly vaccination scheme these antibodies are apparently not elicited, or only to a very low extent, following infection or vaccination with (seasonal) influenza viruses of subtypes H1 and/or H3.

According to the present invention novel HA stem polypeptides are provided that mimic the specific epitopes of the antibody CR6261 (comprising a heavy chain variable region of SEQ ID NO: 11 and a light chain variable region of SEQ ID NO: 12) and/or the antibody CR9114 (comprising a heavy chain variable region of SEQ ID NO: 9 and a light chain variable region of SEQ ID NO: 10). The polypeptides of the invention can be used to elicit influenza virus neutralizing antibodies, preferably cross-neutralizing antibodies when administered in vivo, either alone, or in combination with other prophylactic and/or therapeutic treatments. With "cross-neutralizing antibodies", antibodies are meant that are capable of neutralizing at least two, preferably at least three, four, or five different subtypes of influenza A viruses from phylogenetic group 1, or at least two, preferably at least three, four, or five different subtypes of influenza A viruses from phylogenetic group 2, or at least two different subtypes of influenza B viruses, or antibodies that are capable of neutralizing at least one group 1 influenza virus, and at least one group 2 influenza virus and/or at least on influenza B virus.

Influenza HA stem polypeptides stably presenting the epitopes of these antibodies have previously been described in WO2013/079473. At least some of these HA stem polypeptides were capable of stably presenting the epitope of CR6261 and/or CR9114 and were shown to be immunogenic in mice. Additional HA stem domain polypeptides, capable of stably presenting the epitope of CR6261 and/or CR9114 were described in WO2014/191435, WO2016/005480 and WO2016/005482.

The HA stem polypeptides of the present invention, comprising novel modifications, show an increased level of expression in mammalian cells, an increased propensity to trimerize (e.g. as measured by AlphaLISA) and/or an increased level of thermo-stability (e.g. as measured by, Dynamic Scanning Fluorimetry/Calorimetry (DSF/DSC)), as compared to the previously described HA stem polypeptides. In addition, the affinity of all tested bnAb to the polypeptide of the invention is less than 1 nM (measured by Octet and ELISA), which is similar to the affinity of the antibodies to full-length HA. This clearly shows that the polypeptides mimick the stem of native, full length HA. The novel HA stem polypeptides furthermore do not require any artificial linkers, tags, nor N- or C-terminal trimerization domains.

The present invention thus provides group 1 influenza A hemagglutinin (HA) stem polypeptides comprising an HA1 and an HA2 domain, said polypeptides comprising an amino acid sequence which comprises, as compared to the amino acid sequence of a full-length HA polypeptide (HA0) comprising an HA1 and an HA2 domain:

(i) a deletion of the head region in the HA1 domain;

(ii) a modification of the trimerization region in the HA2 domain, preferably a modification in the C-helix, (iii) at least 2 cysteine residues forming an intramonomeric disulphide bridge;

(iv) at least 2 cysteine residues forming an intermonomeric disulphide bridge;

wherein the amino acid corresponding to the amino acid at position 392 is P, R or Y, preferably P or R, and the amino acid corresponding to the amino acid at position 434 is Q, and wherein the numbering of the amino acid positions is based on H3 numbering according to Winter et al. (1981).

The present invention thus provides HA stem polypeptides (i.e. headless HA polypeptides), comprising:

a modification of the trimerization region in the HA2 domain, preferably a modification in the C-helix, at least 2 cysteine residues forming an intramonomeric disulphide bridge;

at least 2 cysteine residues forming an intermonomeric disulphide bridge;

wherein the amino acid corresponding to the amino acid at position 392 is P, R or Y, preferably P or R, and the amino acid corresponding to the amino acid at position 434 is Q, and wherein the numbering of the amino acid positions is based on H3 numbering as used in Winter et al. (1981).

In certain embodiments, the present invention provides group 1 influenza A hemagglutinin (HA) stem polypeptides comprising an HA1 and an HA2 domain, wherein said HA stem polypeptides comprise an amino acid sequence which comprises, as compared to the amino acid sequence of a full-length HA polypeptide (HA0) comprising an HA1 and an HA2 domain comprising an HA1 and an HA2 domain:

(i) a deletion of the head region in the HA1 domain, said deletion comprising at least the amino acid sequence from the amino acid at position 53 up to and including the amino acid at position 302;

(ii) a modification of the trimerization region in the HA2 domain, preferably a modification in the trimerization region in the C-helix, said region comprising the amino acid sequence from the amino acid corresponding to the amino acid at position at position 405 up to and including the amino acid corresponding to the amino acid at position at position 419;

(iii) a cysteine at position 310 and a cysteine at position 422;

(iv) a cysteine at position 397 in combination with a cysteine at position 405; or a cysteine at position 396 in combination with a cysteine at position 408; or a cysteine at position 399 in combination with a cysteine at position 405;

wherein the amino acid corresponding to the amino acid at position 392 is P, R or Y, preferably P or R, and wherein the amino acid corresponding to the amino acid at position 434 is Q; wherein the numbering of the amino acid positions is based on H3 numbering according to Winter et al. (1981).

In certain embodiments, the present invention provides group 1 influenza A hemagglutinin (HA) stem polypeptides comprising:

(i) a deletion of the head region in the HA1 domain, said deletion comprising at least the amino acid sequence from the amino acid at position 53 up to and including the amino acid at position 302;

(ii) a modification of the trimerization region in the HA2 domain, preferably a modification in the trimerization region in the C-helix, said region comprising the amino acid sequence from the amino acid at position 405 up to and including the amino acid at position 419;

(iii) a mutation of the amino acids at positions 310 and 422 into C;

(iv) a mutation of the amino acid at position 397 into C and a mutation of the amino acid at position 405 into C; or a mutation of the amino acid at position 396 into C and a mutation of the amino acid at position 408 into C; or a mutation of the amino acid at position 399 into C and a mutation of the amino acid at position 405 into C;

wherein the polypeptides further comprise at least one mutation in the B-loop, said B-loop comprising the amino acid sequence from the amino acid at position 385 up to and including the amino acid at position 404, wherein said at least one mutation in the B-loop is a mutation of the amino acid at position 392 into P, R or Y, preferably into P or R; and wherein the polypeptides comprise a mutation of the amino acid at position 434 into Q;

wherein the numbering of the amino acid positions is based on H3 numbering as used in Winter et al. (1981).

According to the present invention, it has surprisingly been found that HA stem polypeptides having the amino acid residue Y, P or R, preferably P or R, at position 392, e.g. by introducing a mutation of the amino acid at position 392 in the B-loop into Y, P or R, preferably into P or R; in combination with the amino acid position Q at position 434, e.g. by introducing a mutation of the amino acid at position 434 into Q, showed increased expression levels, an increased propensity to trimerize and/or an increased stability, compared to the previously described HA stem polypeptides. In addition, the HA stem polypeptides of the invention are capable of inducing an immune response against influenza virus.

As is known to those of skill in the art, a full-length influenza hemagglutinin (HA0) typically comprises an HA1 domain and an HA2 domain. The stem domain is formed by two segments of the HA1 domain and most or all of the HA2 domain. The two segments of the HA1 domain are separated, in the primary sequence, by the globular head domain. As described herein, the HA stem polypeptides of the invention comprise an amino acid sequence which comprises several modifications in the HAT and/or HA2 domain, as compared to the amino acid sequence of the wild-type, full-length HA polypeptide (HA0), in particular the amino acid sequence of a group 1 HA.

Thus, at least part of the highly variable and immunodominant head in the HA domain of the influenza HA polypeptide, said part comprising at least the amino acid sequence starting with the amino acid at position 53 up to and including the amino acid at position 302, has been deleted from the full-length HA (HA0) protein to create a stem polypeptide, also called “mini-HA” (FIG. 1A, second design). The remaining parts of the HAT domain are linked, either directly or through a linker of 1 to 10 amino acids. Thus, for example, when the amino acid sequence from the amino acid at position 53 up to and including the amino acid at position 302 is deleted, the amino acid at position 52 is linked to the amino acid at position 303, either directly, or through replacement of the deleted head region with a linker of 1 to 10 amino acids. The deletion of the amino acid sequence from the amino acid at position 53 up to and including the amino acid at position 302 is the minimal deletion in the HA domain (FIG. 1A, second design). According to the invention, also a larger part of the HA domain may be deleted, e.g. the amino acid sequence starting with the amino acid at position 46 up to and including the amino acid at position 308, as shown in Figure A, third design.

In certain embodiments, the deletion in the HAT domain comprises the amino acid sequence from the amino acid at position 46 up to and including the amino acid at position 306.

In certain embodiments, the deletion in the HA domain comprises the amino acid sequence from the amino acid at position 47 up to and including the amino acid at position 306.

In certain embodiments, the deletion in the HA1 domain comprises the amino acid sequence from the amino acid at position 48 up to and including the amino acid at position 306.

In certain embodiments, the deletion in the HA1 domain comprises the amino acid sequence from the amino acid at position 49 up to and including the amino acid at position 306.

In certain embodiments, the deletion in the HA1 domain comprises the amino acid sequence from the amino acid at position 50 up to and including the amino acid at position 306.

In certain embodiments, the deletion in the HA1 domain comprises the amino acid sequence from the amino acid at position 51 up to and including the amino acid at position 306.

In certain embodiments, the deletion in the HA1 domain comprises the amino acid sequence from the amino acid at position 52 up to and including the amino acid at position 306.

In certain embodiments, the deletion in the HA1 domain comprises the amino acid sequence from the amino acid at position 53 up to and including the amino acid at position 306.

In certain embodiments, the deletion in the HA1 domain comprises the amino acid sequence from the amino acid at position 53 up to and including the amino acid at position 305.

In certain embodiments, the deletion in the HA1 domain comprises the amino acid sequence from the amino acid at position 48 up to and including the amino acid at position 304.

In certain embodiments, the deletion in the HA1 domain comprises the amino acid sequence from the amino acid at position 48 up to and including the amino acid at position 305.

In certain embodiments, the deletion in the HA1 domain comprises the amino acid sequence from the amino acid at position 46 up to and including the amino acid at position 302.

In certain embodiments, the deletion in the HA1 domain comprises the amino acid sequence from the amino acid at position 46 up to and including the amino acid at position 308.

In certain embodiments, the deletion in the HA1 domain comprises the amino acid sequence from the amino acid at position 47 up to and including the amino acid at position 308.

In certain embodiments, the deletion in the HA1 domain comprises the amino acid sequence from the amino acid at position 48 up to and including the amino acid at position 308.

In certain embodiments, the deletion in the HA1 domain comprises the amino acid sequence from the amino acid at position 49 up to and including the amino acid at position 308.

In certain embodiments, the deletion in the HA1 domain comprises the amino acid sequence from the amino acid at position 50 up to and including the amino acid at position 308.

In certain embodiments, the deletion in the HA1 domain comprises the amino acid sequence from the amino acid at position 51 up to and including the amino acid at position 308.

In certain embodiments, the deletion in the HA1 domain comprises the amino acid sequence from the amino acid at position 52 up to and including the amino acid at position 308.

In certain embodiments, the deletion in the HA1 domain comprises the amino acid sequence from the amino acid at position 53 up to and including the amino acid at position 308.

In a preferred embodiment, the deletion in the HA1 domain comprises at least the amino acid sequence from the amino acid at position 47 up to and including the amino acid at position 306.

In a preferred embodiment, the deletion in the HA1 domain consists of the amino acid sequence from the amino acid at position 47 up to and including the amino acid at position 306.

In some embodiments, the deletion in the HA1 domain has been replaced by a linking sequence of 1 to 10 amino acids.

In addition, the HA stem polypeptides of the invention comprise a modification of the trimerization region in the HA2 domain, preferably a modification in the C-helix, in order to improve trimerization of the HA stem polypeptides after deletion of the head region. According to the invention, said modification in the HA2 domain is a modification that enhances trimerization of the HA stem polypeptide.

In certain embodiments, said modification comprises the introduction of a heterologous trimerization domain in the C-helix. It is generally understood that the C-helix comprises the amino acid sequence from the amino acid at position 405 up to and including the amino acid at position 434 (H3 numbering). In a preferred embodiment, said heterologous trimerization domain has been introduced at a position corresponding to the amino acid sequence from the amino acid at position 405 up to and including the amino acid at position 419 (FIG. 1A). Thus, in certain embodiments, the original (wt) amino acid sequence in the HA2 domain from position 405 up to position 419 has been replaced by a heterologous trimerization sequence of the same length, i.e. with an identical number of amino acids.

In certain embodiments, the heterologous trimerization domain is a GCN4 sequence.

In certain preferred embodiments, the heterologous trimerization sequence comprises an amino acid sequence selected from the group consisting of:

```
                        (SEQ ID NO: 18)
RMKQIEDKIEEIESK;

                        (SEQ ID NO: 19)
RIKQIEDKIEEIESK;

                        (SEQ ID NO: 20)
RMEALEKKVDDIEKK;

                        (SEQ ID NO: 21)
RIEALEKKVDDIEKK;

                        (SEQ ID NO: 22)
RMENLEKKVDDIEEK;
and

                        (SEQ ID NO: 23)
RIENLEKKVDDIEEK.
```

In some embodiments, at least one of the amino acids of the heterologous trimerization sequence has been mutated into C, enabling the formation of an intermonomeric cysteine bridge.

In certain preferred embodiments, the heterologous trimerization sequence thus comprises an amino acid sequence selected from the group consisting of:

(SEQ ID NO: 24)
CMKQIEDKIEEIESK;

(SEQ ID NO: 25)
CIKQIEDKIEEIESK;

(SEQ ID NO: 26)
CMEALEKKVDDIEKK;

(SEQ ID NO: 27)
CIEALEKKVDDIEKK;

(SEQ ID NO: 28)
RMECLEKKVDDIEKK;
and (SEQ ID NO: 29)
RIECLEKKVDDIEKK.

In a preferred embodiment, the heterologous trimerization sequence comprises the amino acid sequence CMKQIEDKIEEIESK (SEQ ID NO: 24).

In certain embodiments, the modification comprises an optimization of the heptad repeat sequence in the C-helix, preferably in the trimerization region comprising the amino acid sequence from the amino acid at position 405 up to and including the amino acid at position 419. A heptad repeat, denoted $[abcdefg]_n$, typically has hydrophobic residues at a and d, and polar/charged residues at e and g. These motifs are the basis for most coiled coil structures, which are a structural motif in proteins in which alpha-helices are coiled together like the strands of a rope (dimers and trimers are the most common types) (Ciani et al., 2010).

As a further modification, the HA stem polypeptides according to the invention comprise at least two cysteine residues (capable of) forming an intramoneric cysteine (or disulphide) bridge. An engineered cysteine bridge can be introduced by mutating at least one (if the other is already a cysteine), but usually by mutating two residues that are spatially close into cysteine, which will spontaneously or by active oxidation form a covalent bond between the sulfur atoms of these residues. In a preferred embodiment, the polypeptides comprise a cysteine at position 310 and a cysteine at position 422, enabling the formation of an intramonomeric cysteine bridge. In certain embodiments, the polypeptides comprise a mutation of the amino acid at positions 310 and 422 into C, creating said intramonomeric cysteine bridge. These cysteine residues thus form an intramonomeric cysteine (or disulphide) bridge which stabilizes the protein (see FIG. 4).

Furthermore, in order to obtain stable trimeric HA stem polypeptides, the polypeptides of the invention comprise at least two cysteine residues forming an intermonomeric (interprotomeric) cysteine bridge. Thus, in certain embodiments, the polypeptides comprise a cysteine at position 397 in combination with a cysteine at position 405; or a cysteine at position 396 in combination with a cysteine at position 408; or a cysteine at position 399 in combination with a cysteine at position 405.

In certain embodiments, the polypeptides comprise a mutation of the amino acid at position 397 into C and a mutation of the amino acid at position 405 into C; or a mutation of the amino acid at position 396 into C and a mutation of the amino acid at position 408 into C; or a mutation of the amino acid at position 399 into C and a mutation of the amino acid at position 405 into C, creating an intermonomeric cysteine bridge between the cysteine at position 397 of a first monomer and the cysteine at position 405 of a second monomer; or between the cysteine at position 396 of a first monomer and the cysteine at position 408 of a second monomer; or between the cysteine at position 399 of a first monomer and the cysteine at position 405 of a second monomer. It is noted that, in some embodiments, the amino acids at position 405 and 408 are within the heterologous trimerization sequence.

In a preferred embodiment, the polypeptides comprise a cysteine at position 397 and a cysteine at position 405, creating an intermonomeric cysteine bridge between the cysteine at position 397 of a first monomer and the amino acid at position 405 of a second monomer.

In certain preferred embodiments, the polypeptides comprise a mutation of the amino acid at position 397 into cysteine and a mutation of the amino acid at position 405 into cysteine, creating an intermonomeric cysteine bridge between the cysteine at position 397 of a first monomer and the amino acid at position 405 of a second monomer.

Furthermore, in certain embodiments, at least one mutation has been introduced in the so-called B-loop, which B-loop comprises the amino acid sequence starting from the amino acid at position 385 up to and including the amino acid at position 404 (see FIG. 1C). According to the invention, the at least one mutation is a mutation of the amino acid at position 392 into P, R or Y, preferably into R or P. The mutation into R (a charged amino acid) eliminates the original exposed hydrophobic amino acid (F in most influenza HAs) after the head domain removal, and increases solubility and expression of the expressed stem polypeptides. The mutation into a P amino acid reduces the helix propensity of the B-loop. In certain embodiments, the at least one mutation in the B-loop is a mutation of the amino acid at position 392 into R. In certain embodiments, the at least one mutation in the B-loop is a mutation of the amino acid at position 392 into P.

Furthermore, in certain embodiments of the polypeptides of the invention, the amino acid corresponding to the amino acid at position 395 is I, the amino acid corresponding to the amino acid at position 399 is Y or C, preferably Y, the amino acid corresponding to the amino acid at position 400 is P, the amino acid corresponding to the amino acid at position 401 is K, the amino acid corresponding to the amino acid at position 402 is S, and/or the amino acid corresponding to the amino acid at position 404 is R or Q (again numbering according to H3 numbering). In certain embodiments, the amino acid at position 392 is P or R, the amino acid at position 395 is I; the amino acid at position 399 is Y; the amino acid at position 402 is S; and the amino acid at position 404 is R or Q.

In preferred embodiments, the polypeptides, as compared to a wild-type HA polypeptide, thus comprise at least one additional mutation in the B-loop selected from the group consisting of:

- a mutation of the amino acid corresponding to the amino acid at position 395 into I;
- a mutation of the amino acid corresponding to the amino acid at position 399 into Y or C, preferably Y;
- a mutation of the amino acid corresponding to the amino acid at position 400 into P;
- a mutation of the amino acid corresponding to the amino acid at position 401 into K;

a mutation of the amino acid corresponding to the amino acid at position 402 into S; and a mutation of the amino acid corresponding to the amino acid at position 404 into Q or R.

In certain embodiment, the polypeptides, as compared to a wild-type HA polypeptide, comprise a mutation of the amino acid at position 392 into P or R, a mutation of the amino acid at position 395 into I; a mutation of the amino acid at position 399 into Y; a mutation of the amino acid at position 402 into S; and optionally a mutation of the amino acid at position 404 into Q or R.

In certain embodiments, the amino acid at position 392 is P or R, the amino acid at position 395 is I; the amino acid at position 399 is Y; the amino acid at position 401 is K; the amino acid at position 402 is S; and optionally the amino acid at position 404 is R or Q.

In another preferred embodiment, the polypeptides, as compared to a wild-type HA polypeptide, comprise a mutation of the amino acid at position 392 into P or R, a mutation of the amino acid at position 395 into I; a mutation of the amino acid at position 399 into Y; a mutation of the amino acid at position 401 into K; a mutation of the amino acid at position 402 into S; and optionally a mutation of the amino acid at position 404 into R or Q.

In certain embodiments, the polypeptides of the invention comprise a B-loop comprising an amino acid sequence selected from the group consisting of:

```
                                    (SEQ ID NO: 126)
IEKMNTQYTAIGKEYNKSER;

                                    (SEQ ID NO: 127)
IEKMNTQYTAIGCEYNKSER;

                                    (SEQ ID NO: 128)
IEKMNTQPTAIGCEYNKSEQ;

                                    (SEQ ID NO: 129)
IEKMNTQRTAIGCEFNKSEQ;

                                    (SEQ ID NO: 130)
IEKMNTQPTAIGCEYNKSER;

                                    (SEQ ID NO: 131)
IEKMNTQPTAIGCEFNKSEQ;

                                    (SEQ ID NO: 132)
IEKMNTQRTAIGCEYNKSER;

                                    (SEQ ID NO: 133)
IEKMNTQRTAICKEYPKSEQ;
and

                                    (SEQ ID NO: 134)
IEKMNTQRTAIGKECNKSER.
```

Furthermore, according to the invention, the amino acid at position 434 is Q. In certain embodiments, the HA stem polypeptides thus comprise a mutation of the amino acid at position 434 into Q which improves its hydrogen bond interactions. In certain embodiments, the amino acid at position 434 is Q and the amino acid at position 442 is A. In certain embodiments, the polypeptides comprise a mutation of the amino acid at position 434 into Q, and a mutation at position 442 into A. These mutations improve the trimer interface interactions in the D and E helices and the nearby fusionpeptide and $B_2B_3$-loop.

It is again noted that as used herein the numbering of the amino acid positions is based on H3 numbering according to Winter et al. (1981). It is also again noted that the numbering of the amino acid positions as used herein is based on the numbering of the positions in a full length H3 HA polypeptide (HA0). Thus, as used herein, "an amino acid at position 434" refers to the amino acid at position 434 in H3 HA0. The numbering thus does not refer to the actual positions of the amino acids in the HA stem polypeptides of the invention, due to deletion of the head region (see FIG. 14).

Furthermore, in certain embodiments, the amino acid corresponding to the amino acid at position 323 is K and/or the amino acid corresponding to the amino acid at position 326 is K. In a preferred embodiment, the amino acid at position 323 is K and the amino acid at position 326 is K.

In certain embodiments, the amino acid corresponding to the amino acid at position 339 is T.

In certain embodiments, the amino acid corresponding to the amino acid at position 438 is E and/or the amino acid corresponding to the amino acid at position 442 is I.

In certain embodiments, the HA stem polypeptides thus further comprise one or more additional mutations in the HA1 and/or HA2 domain, as compared to a wild-type HA polypeptide.

In certain embodiments, the polypeptides comprise a mutation of the amino acid corresponding to the amino acid at position 323 into K and/or a mutation of the amino acid corresponding to the amino acid at position 326 into K. These mutations increase the solubility and expression of the molecule. In another embodiment, the stem polypeptides of the invention comprise a mutation of the amino acid at position 323 into K and mutation of the amino acid at position 326 into K.

In certain embodiments, the polypeptides comprise a mutation of the amino acid corresponding to the amino acid at position 339 into T. This mutation removes a solvent exposed hydrophobic amino acid in the fusion peptide loop (FP loop) and thereby increases the solubility of the molecule.

In certain preferred embodiments, the amino acid at position 323 is K, the amino acid at position 326 is K, the amino acid at position 339 is T, the amino acid at position 392 is Y, P or R, preferably P or R, the amino acid at position 395 is I, the amino acid at position 399 is Y, the amino acid at position 402 is S, the amino acid at position 404 is Q or R, the amino acid at position 434 is Q.

In certain preferred embodiments, the polypeptides comprise a mutation of the amino acid at position 323 into K, a mutation of the amino acid at position 326 into K, a mutation of the amino acid at position 339 into T, a mutation of the amino acid at position 392 into P or R, a mutation of the amino acid at position 395 into I, a mutation of the amino acid at position 399 into Y,a mutation of the amino acid at position 402 into S, a mutation of the amino acid at position 404 into Q or R, and a mutation of the amino acid at position 434 into Q.

In certain preferred embodiments, the amino acid at position 323 is K, the amino acid at position 326 is K, the amino acid at position 339 is T, the amino acid at position 392 is P or R, the amino acid at position 395 is I, the amino acid at position 399 is Y, the amino acid at position 402 is S, the amino acid at position 404 is Q or R, the amino acid at position 434 is Q, and the amino acid at position 442 is A.

In certain preferred embodiments, the polypeptides comprise a mutation of the amino acid at position 323 into K, a mutation of the amino acid at position 326 into K, a mutation of the amino acid at position 339 into T, a mutation of the amino acid at position 392 into P or R, a mutation of the amino acid at position 395 into I, a mutation of the amino acid at position 399 into Y,a mutation of the amino acid at position 402 into S, a mutation of the amino acid at position 404 into Q or R, and a mutation of the amino acid at position 434 into Q, and a mutation of the amino acid at position 442 into A.

In certain embodiments, the polypeptides comprise at least one further mutation selected from the group consisting of a mutation of the amino acid corresponding to the amino acid at position 438 into E as a possible alternative negatively charged amino acid and a mutation of the amino acid corresponding to the amino acid at position 442 into I to increase hydrophobicity in the trimer interface.

According to the invention, the HA stem polypeptide is a group 1 HA polypeptide. Thus, according to the invention, the modifications described herein have been introduced in HA of an influenza virus from phylogenetic group 1, such as an influenza virus comprising HA of the H1, H2 or H5 subtype, resulting in the HA stem polypeptides of the invention. In certain embodiments, the HA stem polypeptide is an H1 HA polypeptide. Thus, in certain embodiments, the HA stem polypeptide is derived from HA of an influenza A virus comprising HA of a H1 subtype, such as from the influenza virus A/Brisbane/59/2007 (H1N1), with the amino acid sequence SEQ ID NO:1, or A/California/07/09 (H1N1), with the amino acid sequence of SEQ ID NO: 2. It will be understood by the skilled person that the polypeptides of the invention may also be derived from HA of other influenza A virus strains from group 1, including but not limited to A/Texas/UR06-0526/2007 (H1N1) (SEQ ID NO: 3), A/NewYork/629/1995 (H1N1) (SEQ ID NO: 4), A/AA_Marton/1943 (H1N1) (SEQ ID NO: 5), A/Puerto Rico/8/1934 (H1), A/Michigan/45/2015 (H1), A/Adachi/2/57 (H2N2) (SEQ ID NO: 6), A/Singapore/1/57 (H2N2) (SEQ ID NO: 7), or influenza viruses comprising HA of the H5 subtype, including but not limited to A/Vietnam/1203/2004 (H5N1) (SEQ ID NO: 8) or A/Hong Kong/156/97 (H5).

As described above, the stem polypeptides may or may not comprise a linking sequence of 1-10 amino acid residues replacing the deleted HA1 sequence and thereby linking the two remaining HA1 parts. In certain embodiments, the linking sequence comprises from 1 to 5 amino acids. In certain embodiments, the linking sequence comprises 2, 3 or 4 amino acids. The linking sequence may be a heterologous linking sequence, i.e. an amino acid sequence that does not occur in naturally occurring, or wild-type, HA, such as, but not limited to G, GS, GGG, GSG, GSA, GSGS, GSAG, GGGG, GSAGS, GSGSG, GSAGSA, GSAGSAG, and GSGSGSG.

In preferred embodiments, the linking sequence is a homologous linking sequence, i.e. an amino acid sequence derived from the deleted corresponding head region such as, but not limited to AGSG, AGS, GSG, HAGA, DQEG, DTPV, FPKT, EPGD, EPG, TGNL. TPSS, TPS, ATGN, YPGD.

In preferred embodiments, the polypeptides do not comprise a linking sequence.

As described above, cleavage of the influenza HA0 protein (in HA1 and HA2) is required for its activity, facilitating the entry of the viral genome into the target cells by causing the fusion of the host endosomal membrane with the viral membrane.

In certain embodiments, the polypeptides of the invention comprise the natural protease cleavage site. Thus, it is known that the Arg (R)-Gly (G) sequence spanning HA1 and HA2 (i.e. amino acid positions 329 and 330) is a recognition site for trypsin and trypsin-like proteases and is typically cleaved for hemagglutinin activation (FIG. 1A).

In certain embodiments, the polypeptides do not comprise a protease cleavage site. Thus, in certain preferred embodiments, the protease cleavage site has been removed by mutation of the amino acid residue at position 329 into any amino acid other than arginine (R) or lysine (K). In certain embodiments, the amino acid residue at position 329 is not arginine (R). In a preferred embodiment, the polypeptides comprise a mutation of the amino acid at position 329 into glutamine (Q). Thus, in certain embodiments, the polypeptides of the invention comprise the cleavage site knock-out mutation R329Q to prevent putative cleavage of the molecule during production in vitro or in vivo after administration.

In other embodiments, the polypeptides comprise a polybasic cleavage site, e.g. a Furin cleavage site (as described in Example 6). Thus, the polypeptides can be cleaved by furin-like proteases within the cell to produce a cleaved mini-HA, similar to a natively folded and processed HA.

In certain embodiments, the polypeptides do not comprise a signal sequence. The signal sequence (sometimes referred to as signal peptide, targeting signal, localization signal, localization sequence, transit peptide, leader sequence or leader peptide) is a short peptide (usually 16-30 amino acids long) that is present at the N-terminus of the majority of newly synthesized proteins that are destined towards the secretory pathway. Signal sequences function to prompt a cell to translocate the protein, usually to the cellular membrane. In many instances the amino acids comprising the signal peptide are cleaved off the protein once its final destination has been reached. In influenza HA, the signal sequences typically comprise the first 16 amino acids of the amino acid sequence of the full-length HA0 (corresponding to the amino acids from position −6 to position 10 according to H3 numbering).

In certain embodiments, the polypeptides comprise (part of) a signal sequence. The polypeptides may comprise (part of) the wild-type signal sequence or may comprise (part of) alternative signal sequences, such as, but not limited to a signal sequence selected from the group of:

```
                                  (SEQ ID NO: 136)
MGSTAILGLLLAVLQGVCA
and

                                  (SEQ ID NO: 137)
MGMTSALLALLALALKPGAWA.
```

In certain embodiments, the polypeptides comprise an HA2 domain including the transmembrane and cytoplasmic domain (corresponding to the amino acid sequence starting with the amino acid corresponding to the amino acid at position 515 up to and including the amino acid corresponding to the amino acid at position 550 (H3 numbering)).

To produce secreted (soluble) stem polypeptides, in certain embodiments the polypeptides do not comprise the transmembrane and cytoplasmic domain. Thus, in certain embodiments, the polypeptides comprise a truncated HA2 domain, in particular an HA2 domain that is truncated at the C-terminal end. A truncated HA2 domain according to the invention thus is shorter than the full length HA2 sequence, by deletion of one or more amino acid residues at the C-terminal end of the HA2 domain.

In certain embodiments, the C-terminal part of the HA2 domain starting with the amino acid corresponding to the amino acid at position 516 has been deleted, thus removing substantially the full transmembrane and cytoplasmic domain.

Figure 12:
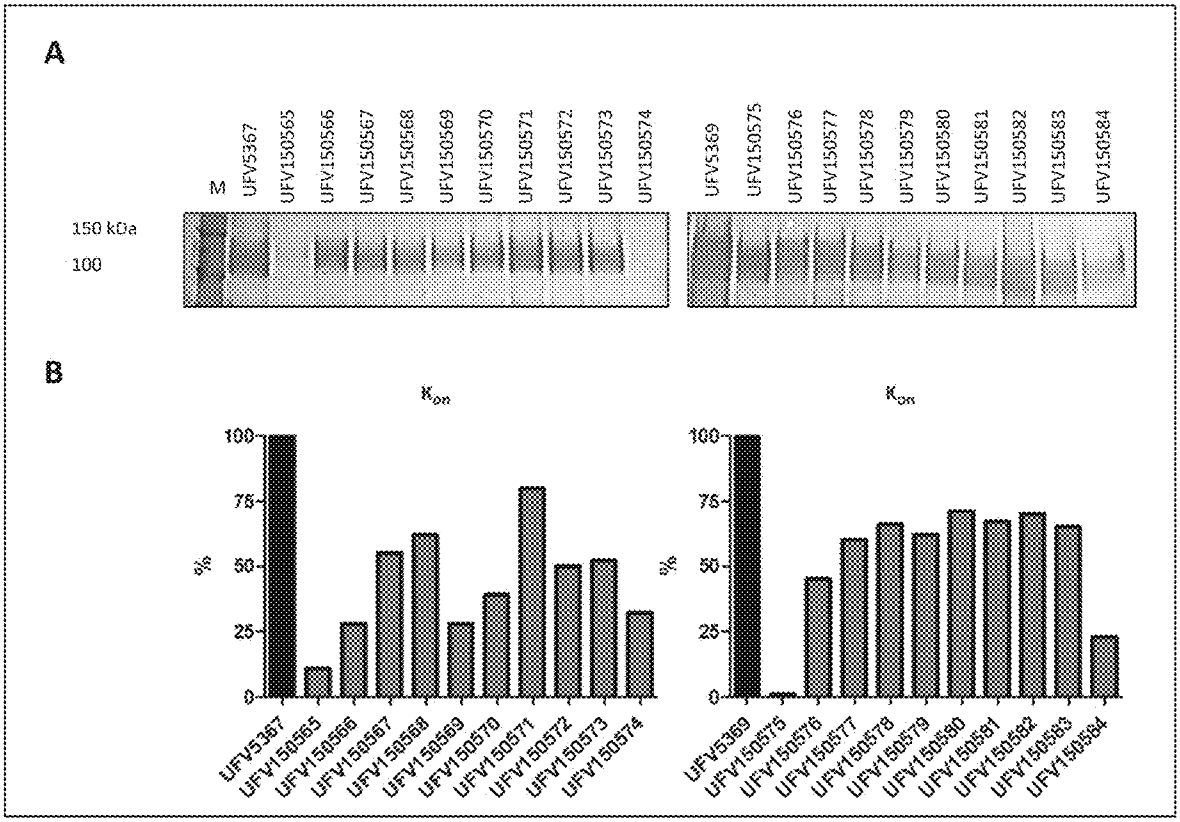
FIG. 12. Expression and antibody binding to polypeptide variants with alternative C-terminal truncations. A: Westernblot using an HA-specific single domain antibody. Almost all samples display a clear band on trimeric height that is similar to both reference polypeptides (UFV5367 and UFV5369). B: Binding of polypeptides to broadly neutralizing antibody CR9114 as determined by OCTET, shown are relative $K_{on}$ values of the polypeptides compared to reference design UFV5367 and UFV5369.

In certain embodiments, also a part of the C-terminal helix has been deleted. According to the present invention it has been found that even when a larger part of the HA2 domain is deleted, stable soluble HA stem polypeptides can be provided. Thus, in certain embodiments, the C-terminal part of the HA2 domain starting at the amino acid sequence at position 500, 501, 502, 503, 504, 505, 506, 507, 508, 509, 510, 511, 512, 513, 514 or 515 has been deleted (again numbering according to H3 numbering as described by Winter et al., supra) to produce a soluble polypeptide following expression in cells (FIG. 12).

In a preferred embodiment, the C-terminal part of the HA2 domain from the position corresponding to 516 has been deleted.

Optionally, a heterologous amino acid sequence (i.e. an amino acid sequence that does not naturally occur in influenza HA) has been linked to the (truncated) HA2 domain.

Thus, in certain embodiments, His-tag sequences, e.g. HHHHHH (SEQ ID NO: 113) or HHHHHHH (SEQ ID NO: 114.), or a FLAG tag (DYKDDDDK) (SEQ ID NO: 115) or a combination of these have been linked to the C-terminal amino acid of the (optionally truncated) HA2 domain for detection and/or purification purposes. In certain embodiments, the heterologous amino acid sequence, such as the His-tag sequence, may be connected to the (truncated) HA2 domain through a linker. In certain embodiments, the linker may contain (part of) a proteolytic cleavage site, e.g. the amino acid sequence IEGR (SEQ ID NO: 116) or LVPRGS (SEQ ID NO: 117) to enzymatically remove the His-tag sequence after purification.

In certain embodiments, the heterologous amino acid sequence that is linked to the C-terminal amino acid of the (truncated) HA2 domain comprises an amino acid sequence selected from the group consisting of:

(SEQ ID NO: 118)
GYIPEAPRDGQAYVRKDGEWVLLSTFL (foldon),, (SEQ ID NO: 119)
SGRDYKDDDDKLVPRGSPGSGYIPEAPRDGQAYVRKDGEWVLLSTFLGHH
HHHH (Flag-Foldon-His tag),, (SEQ ID NO: 120)
SGRDYKDDDDKPGGGGSGGGGSGGGGSGGGGSGGGGSGGGGSGGGGSHHH
HHH (FLAG-GS linker-His tag),, (SEQ ID NO: 121)
EGRAAAGGSGGGGSMVFTLEDFVGDWRQTAGYNLDQVLEQGGVSSLFQNL
GVSVTPIQRIVLSGENGLKIDIHVIIPYEGLSGDQMGQIEKIFKVVYPVD
DHHFKVILHYGTLVIDGVTPNMIDYFGRPYEGIAVFDGKKITVTGTLWNG
NKIIDERLINPDGSLLFRVTINGVTGWRLCERILAAAAWSHPQFEKGAAW
SHPQFEKGAAWSHPQFEK (Nanoluc-Strep tag),, (SEQ ID NO: 122)
EGRAAAGGSGGGGSMVFTLEDFVGDWRQTAGYNLDQVLEQGGVSSLFQNL
GVSVTPIQRIVLSGENGLKIDIHVIIPYEGLSGDQMGQIEKIFKVVYPVD
DHHFKVILHYGTLVIDGVTPNMIDYFGRPYEGIAVFDGKKITVTGTLWNG
NKIIDERLINPDGSLLFRVTINGVTGWRLCERILAGAAEPEA
(Nanoluc-C tag),, (Strep tag, SEQ ID NO: 154)
EGRAAAWSHPQFEKGAAWSHPQFEKGAAWSHPQFEK, -continued (SEQ ID NO: 123)
EGRAAALPETGGGAAEPEA (Sortase-C tag),, (SEQ ID NO: 124)
SGRDYKDDDDKPGGGGSGGGGSGGGGSGGGGSGGGGSGGGGSGGGGSWSH
PQFEKGAAWSHPQFEKGAAWSHPQFEK (FLAG-GS linker-Strep
tag),,
and (SEQ ID NO: 125)
EGRAAAEQKLISEEDLGGGGSGGGGSGGGGSGGGGSGGGGSGGGGSGGGGS
WSHPQFEKGAAWSHPQFEKGAAWSHPQFEK (Myc tag-GS linker-
Strep tag),.

In certain embodiments, a heterologous trimerization domain has been linked to the C-terminal amino acid of the (optionally truncated) HA2 domain, such as, but not limited to a "Foldon" trimerization domain (as described by Letarov et al. (1993); S-Guthe et al. (2004)), In certain embodiments, the HA stem polypeptides comprise an amino acid sequence comprising at least the amino acids 1-234 of SEQ ID NO: 30; an amino acid sequence comprising at least the amino acids 1-234 of SEQ ID NO: 31; an amino acid sequence comprising at least the amino acids 1-234 of SEQ ID NO: 52; an amino acid sequence comprising at least the amino acids 1-234 of SEQ ID NO: 53; an amino acid sequence comprising at least the amino acids 1-234 of SEQ ID NO: 54; an amino acid sequence comprising at least the amino acids 1-234 of SEQ ID NO: 55; an amino acid sequence comprising at least the amino acids 1-234 of SEQ ID NO: 56; an amino acid sequence comprising at least the amino acids 1-234 of SEQ ID NO: 57; an amino acid sequence comprising at least the amino acids 1-234 of SEQ ID NO: 58; an amino acid sequence comprising at least the amino acids 1-237 of SEQ ID NO: 59; an amino acid sequence comprising at least the amino acids 1-234 of SEQ ID NO: 60; an amino acid sequence comprising at least the amino acids 1-234 of SEQ ID NO: 61; an amino acid sequence comprising at least the amino acids 1-234 of SEQ ID NO: 62; an amino acid sequence comprising at least the amino acids 1-234 of SEQ ID NO: 63; an amino acid sequence comprising at least the amino acids 1-230 of SEQ ID NO: 64; an amino acid sequence comprising at least the amino acids 1-231 of SEQ ID NO: 65; an amino acid sequence comprising at least the amino acids 1-232 of SEQ ID NO: 66; an amino acid sequence comprising at least the amino acids 1-233 of SEQ ID NO: 67; an amino acid sequence comprising at least the amino acids 1-234 of SEQ ID NO: 68; an amino acid sequence comprising at least the amino acids 1-235 of SEQ ID NO: 69; an amino acid sequence comprising at least the amino acids 1-236 of SEQ ID NO: 70; an amino acid sequence comprising at least the amino acids 1-237 of SEQ ID NO: 71; an amino acid sequence comprising at least the amino acids 1-238 of SEQ ID NO: 72; an amino acid sequence comprising at least the amino acids 1-234 of SEQ ID NO: 73; an amino acid sequence comprising at least the amino acids 1-234 of SEQ ID NO: 74; an amino acid sequence comprising at least the amino acids 1-228 of SEQ ID NO: 75; an amino acid sequence comprising at least the amino acids 1-229 of SEQ ID NO: 76; an amino acid sequence comprising at least the amino acids 1-230 of SEQ ID NO: 77; an amino acid sequence comprising at least the amino acids 1-231 of SEQ ID NO: 78; an amino acid sequence comprising at least the amino acids 1-232 of SEQ ID NO: 79; an amino acid sequence comprising at least the amino acids 1-233 of SEQ ID NO: 80; an amino acid sequence comprising at least the amino acids 1-234 of SEQ ID NO: 81; an amino acid sequence comprising at least the amino acids 1-235 of SEQ ID NO: 82; an amino acid sequence comprising at least the amino acids 1-234 of SEQ ID NO: 83; an amino acid sequence comprising at least the amino acids 1-233 of SEQ ID NO: 84; an amino acid sequence comprising at least the amino acids 1-235 of SEQ ID NO: 85; an amino acid sequence comprising at least the amino acids 1-233 of SEQ ID NO: 86; an amino acid sequence comprising at least the amino acids 1-234 of SEQ ID NO: 87; an amino acid sequence comprising at least the amino acids 1-233 of SEQ ID NO: 88; an amino acid sequence comprising at least the amino acids 1-234 of SEQ ID NO: 89; an amino acid sequence comprising at least the amino acids 1-234 of SEQ ID NO: 90; an amino acid sequence comprising at least the amino acids 1-234 of SEQ ID NO: 91; an amino acid sequence comprising at least the amino acids 1-234 of SEQ ID NO: 92; an amino acid sequence comprising at least the amino acids 1-234 of SEQ ID NO: 93; an amino acid sequence comprising at least the amino acids 1-234 of SEQ ID NO: 94; an amino acid sequence comprising at least the amino acids 1-234 of SEQ ID NO: 95; an amino acid sequence comprising at least the amino acids 1-234 of SEQ ID NO: 96; an amino acid sequence comprising at least the amino acids 1-233 of SEQ ID NO: 97; an amino acid sequence comprising at least the amino acids 1-234 of SEQ ID NO: 98; an amino acid sequence comprising at least the amino acids 1-234 of SEQ ID NO: 99; an amino acid sequence comprising at least the amino acids 1-232 of SEQ ID NO: 100; an amino acid sequence comprising at least the amino acids 1-237 of SEQ ID NO: 101; an amino acid sequence comprising at least the amino acids 1-238 of SEQ ID NO: 102; an amino acid sequence comprising at least the amino acids 1-231 of SEQ ID NO: 103; an amino acid sequence comprising at least the amino acids 1-231 of SEQ ID NO: 104; an amino acid sequence comprising at least the amino acids 1-237 of SEQ ID NO: 105; an amino acid sequence comprising at least the amino acids 1-231 of SEQ ID NO: 106; an amino acid sequence comprising at least the amino acids 1-237 of SEQ ID NO: 107; an amino acid sequence comprising at least the amino acids 1-234 of SEQ ID NO: 108; an amino acid sequence comprising at least the amino acids 1-231 of SEQ ID NO: 109; an amino acid sequence comprising at least the amino acids 1-231 of SEQ ID NO: 110; an amino acid sequence comprising at least the amino acids 1-237 of SEQ ID NO: 111; an amino acid sequence comprising at least the amino acids 1-237 of SEQ ID NO: 112; an amino acid sequence comprising at least the amino acids 1-234 of SEQ ID NO: 135; an amino acid sequence comprising at least the amino acids 18-248 of SEQ ID NO: 147; an amino acid sequence comprising at least the amino acids 18-248 of SEQ ID NO: 148; an amino acid sequence comprising at least the amino acids 18-248 of SEQ ID NO: 149; an amino acid sequence comprising at least the amino acids 17-247 of SEQ ID NO: 150; an amino acid sequence comprising at least the amino acids 17-247 of SEQ ID NO: 151; an amino acid sequence comprising at least the amino acids 16-246 of SEQ ID NO: 152; or an amino acid sequence comprising at least the amino acids 18-248 of SEQ ID NO: 153.

In a preferred embodiment, the polypeptide comprises an amino acid sequence comprising at least the amino acids 1-231 of SEQ ID NO: 103, 104, 109 or 110.

In certain embodiments, the polypeptides comprise an amino acid sequence selected from the group consisting of SEQ ID NOs: 31, 31, 52-112 and 135.

In a preferred embodiment, the polypeptide comprises an amino acid sequence selected from the group consisting of SEQ ID NOs: 103, 104, 109 and 110.

In certain embodiments, the polypeptides are glycosylated when expressed in suitable cells (e.g. mammalian cells). The polypeptides may contain one or more native glycosylation motifs. In certain embodiments, the polypeptides comprise at least one additional/introduced glycosylation motif. In certain embodiments, the at least one glycosylation motif has been introduced by a mutation of the amino acid at position 402 into S. This mutation will introduce a n-linked glucosylation motif at position 400.

The polypeptides may also be administered in combination with or conjugated to nanoparticles, such as e.g. polymers, liposomes, virosomes, virus-like particles. The polypeptides may be combined with, encapsidated in or conjugated (e.g. covalently linked or adsorbed) to the nanoparticles The invention further provides nucleic acid molecules encoding the influenza HA stem polypeptides of the invention. It is understood by a skilled person that numerous different nucleic acid molecules can encode the same polypeptide as a result of the degeneracy of the genetic code. It is also understood that skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleic acid molecule encoding an amino acid sequence" includes all nucleotide sequences that are degenerate versions of each other and that encode the same amino acid sequence.

In certain embodiments, the nucleic acid molecules encoding the influenza HA stem polypeptides are codon optimized for expression in mammalian cells, such as human cells. Methods of codon-optimization are known and have been described previously (e.g. WO 96/09378).

In certain embodiments, the nucleic acid molecules encoding the influenza HA stem polypeptide comprise a nucleic acid sequence selected from SEQ ID NO: 138-145.

The influenza hemagglutinin stem domain polypeptides can be prepared according to any technique deemed suitable to one of skill, including techniques described below. Thus, the polypeptides of the invention may be synthesized as DNA sequences by standard methods known in the art and cloned and subsequently expressed, in vitro or in vivo, using suitable restriction enzymes and methods known in the art.

The invention further relates to vectors comprising a nucleic acid molecule encoding a polypeptide of the invention. In certain embodiments, a nucleic acid molecule according to the invention thus is part of a vector, e.g. a plasmid. Such vectors can easily be manipulated by methods well known to the person skilled in the art, and are for instance designed to be capable of replication in prokaryotic and/or eukaryotic cells. The vector used can be any vector that is suitable for cloning DNA and can be used for transcription of the nucleic acid of interest. When host cells are used, it is preferred that the vector is an integrating vector. Alternatively, the vector may be an episomally replicating vector. The person skilled in the art is capable of choosing suitable expression vectors, and inserting the nucleic acid sequences of the invention in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. According to the present invention, strong promoters that give high transcription levels in the eukaryotic cells of choice are preferred.

The constructs may be transfected into eukaryotic cells (e.g. plant, fungal, yeast or animal cells) or suitable prokaryotic expression systems like *E. coli* using methods that are well known to persons skilled in the art. In some cases, a suitable 'tag' sequence (such as for example, but not limited to, a his-, myc-, strep-, sortase, or flag-tag) or complete protein (such as for example, but not limited to, maltose binding protein or glutathione S transferase) may be added to the sequences of the invention, as described above, to allow for purification and/or identification of the polypeptides from the cells or supernatant. Optionally a sequence containing a specific proteolytic site can be included to afterwards remove the tag by proteolytic digestion.

In preferred embodiments, the polypeptides are produced in mammalian cells.

Purified polypeptides can be analyzed by spectroscopic methods known in the art (e.g. circular dichroism spectroscopy, Fourier Transform Infrared spectroscopy and NMR spectroscopy or X-ray crystallography) to investigate the presence of desired structures like helices and beta sheets. ELISA, AlphaLISA, biolayer interferometry (Octet) and FACS and the like can be used to investigate binding of the polypeptides of the invention to the broadly neutralizing antibodies, such as CR6261 and/or CR9114. Thus, polypeptides according to the invention having the correct conformation can be selected. Trimeric content can be analyzed for example by using SDS gel electrophoresis under non-reducing conditions, size exclusion chromatography in the presence of antibody Fab fragments of broadly neutralizing antibodies, such as CR6261 and/or CR9114, as well as AlphaLISA using differently labeled antibodies. Stability of the polypeptides can be assessed as described above after temperature stress, freeze-thaw cycles, increased protein concentration, or agitation. The melting temperature of the polypeptide can further be assed by Differential Scanning Fluorimetry (DSF) and/or Differential Scanning Calorimetry (DSC).

In certain embodiments, the vector is a human recombinant adenovirus. The present invention thus also provides recombinant adenoviral vectors comprising a nucleic acid molecule encoding a HA stem polypeptide according to the invention. In a preferred embodiment, the nucleic acid molecule encoding the stem polypeptide comprises a nucleic acid sequence selected from the group consisting of SEQ ID NO: 142, SEQ ID NO: 143, SEQ ID NO: 144 and SEQ ID NO: 145.

The preparation of recombinant adenoviral vectors is well known in the art. The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus. In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

In certain embodiments, the adenovirus is a human adenovirus of the serotype 26 or 35.

The invention further provides pharmaceutical composition comprising a polypeptide, a nucleic acid, and/or a vector according to the invention, and pharmaceutically acceptable carrier. The invention in particular relates to pharmaceutical compositions comprising a therapeutically effective amount of the polypeptides, nucleic acids, and/or vectors of the invention. The pharmaceutical compositions further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, excipient, or vehicle with which the polypeptides, nucleic acids, and/or vectors are administered. Saline solutions and aqueous dextrose and glycerol solutions can e.g. be employed as liquid carriers, particularly for injectable solutions.

The invention further relates to polypeptides, nucleic acids, and/or vectors as described herein for use as a medicament.

The invention in particular relates to polypeptides, nucleic acids, and/or vectors as described herein for use in inducing an immune response against an influenza virus.

The invention also relates to methods for inducing an immune response against an influenza A virus in a subject in need thereof, the method comprising administering to said subject, a polypeptide, nucleic acid molecule and/or vector as described above. A subject according to the invention preferably is a mammal that is capable of being infected with an influenza virus, or otherwise can benefit from the induction of an immune response, such subject for instance being a rodent, e.g. a mouse, a ferret, or a domestic or farm animal, or a non-human-primate, or a human. Preferably, the subject is a human subject.

In certain embodiments, the invention provides methods for inducing an immune response against a group 1 influenza A virus. The immune response may comprise a humoral (i.e. the induction of influenza virus neutralizing antibodies) and/or a cellular immune response. In certain embodiments, the invention provides methods for inducing an immune response against at least two, three, four, five or six subtypes of influenza A viruses. In certain embodiments, the invention provides methods for inducing an immune response against an influenza virus comprising HA of the H1 subtype.

In certain embodiments, the immune response induced is effective to prevent and/or treat an influenza virus infection caused by a group 1 influenza A virus, such as an influenza A virus comprising HA of the H1 subtype, and/or an influenza A virus comprising HA of the H2 subtype, and/or an influenza A virus comprising HA of the H5 subtype. In certain embodiments, the immune response induced is effective to prevent and/or treat an influenza virus infection caused by an influenza A virus comprising HA of the H1 subtype.

The invention further relates to polypeptides, nucleic acids, and/or vectors as described herein for use as an influenza vaccine.

In certain embodiments, the polypeptides, nucleic acid molecules and/or vectors of the invention are administered in combination with an adjuvant. The adjuvant for may be administered before, concomitantly with, or after administration of the polypeptides, nucleic acid molecules and/or vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Matrix M, or combinations thereof. In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof.

Administration of the polypeptides, nucleic acid molecules, and/or vectors according to the invention can be performed using standard routes of administration. Non-limiting examples include parenteral administration, such as intravenous, intradermal, transdermal, intramuscular, subcutaneous, etc, or mucosal administration, e.g. intranasal, oral, and the like. The skilled person will be capable to determine the various possibilities to administer the polypeptides, nucleic acid molecules, and/or vectors according to the invention, in order to induce an immune response.

In certain embodiments, the polypeptide, nucleic acid molecule, and/or vector is administered more than one time, i.e. in a so-called homologous prime-boost regimen. The administration of the second dose can be performed, for example, one week after the administration of the first dose, two weeks after the administration of the first dose, three weeks after the administration of the first dose, one month after the administration of the first dose, six weeks after the administration of the first dose, two months after the administration of the first dose, 3 months after the administration of the first dose, or 4 months or more after the administration of the first dose, etc, up to several years after the administration of the first dose of the polypeptide, nucleic acid molecule, and/or vector of the invention. It is also possible to administer the polypeptides, nucleic aid molecules and/or vectors more than twice, e.g. three times, four times, etc, so that the first priming administration is followed by more than one boosting administration.

The polypeptides, nucleic acid molecules, and/or vectors may also be administered, either as prime, or as boost, in a heterologous prime-boost regimen.

The invention further provides methods for preventing and/or treating, preferably preventing, an influenza virus disease in a subject in need thereof, comprising administering to said subject a polypeptide, a nucleic acid molecule and/or a vector as described herein. A therapeutically effective amount refers to an amount of the polypeptide, nucleic acid, and/or vector that is effective for preventing, ameliorating and/or treating a disease or condition resulting from infection by an influenza virus. Prevention encompasses inhibiting or reducing the spread of influenza virus or inhibiting or reducing the onset, development or progression of one or more of the symptoms associated with infection by an influenza virus. Ameloriation as used in herein may refer to the reduction of visible or perceptible disease symptoms, viremia, or any other measurable manifestation of influenza infection.

A subject in need of treatment includes subjects that are already inflicted with a condition resulting from infection with an influenza virus, as well as those in which infection with influenza virus is to be prevented. The polypeptides, nucleic acids and/or vectors of the invention thus may be administered to a naive subject, i.e., a subject that does not have a disease caused by an influenza virus infection or has not been and is not currently infected with an influenza virus infection, or to subjects that already have been infected with an influenza virus.

In an embodiment, prevention and/or treatment may be targeted at patient groups that are susceptible to influenza virus infection. Such patient groups include, but are not limited to e.g., the elderly (e.g. $\geq 50$ years old, $\geq 60$ years old, and preferably $\geq 65$ years old), the young (e.g. $\leq 5$ years old, $\leq 1$ year old), hospitalized patients, immunocompromised subjects, and patients who have been treated with an antiviral compound but have shown an inadequate antiviral response.

The polypeptides, nucleic acid molecules and/or vectors of the invention may be administered to a subject in combination with one or more other active agents, such as alternative influenza vaccines, monoclonal antibodies, antiviral agents, antibacterial agents, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

The invention is further illustrated in the following examples and figures. The examples are not intended to limit the scope of the invention in any way.

EXAMPLES

Example 1: Preparation of Stem-Based Polypeptides of the Invention

In WO2013/079473, a first series of influenza hemagglutinin stem polypeptides, compositions and vaccines and methods of their use in the prevention and/or treatment of influenza, were described, including the polypeptides H1-mini2-cluster 1+5+6-GCN, both as membrane-bound form (with natural transmembrane domain, SEQ ID NO: 45 in WO2013/079473) and as soluble form thereof, s-H1-mini2-cluster1+5+6-GCN4 (without natural transmembrane domain, SEQ ID NO: 145 in WO2013/079473).

In WO2014/191435, additional stem polypeptides derived from the full-length HA of H1N1 A/Brisbane/59/2007 were described, which comprised additional mutations as compared to H1-mini2-cluster1+5+6-GCN4, and also stably presented the broadly neutralizing epitope of CR6261 and/or CR9114.

These stem polypeptides were all created by deleting the head domain from HA1, in particular the region comprising the amino acids starting from position 46 up to and including the amino acid at position 306, and replacing the deleted region with a linker, as described in WO2013/079473. It is noted that in WO2013/079473, the numbering of the amino acid positions was based on the numbering of full length HA of influenza A/Brisbane/59/2007 (i.e. SEQ ID NO: 1 in WO2013/079473), whereas in the current invention the H3 numbering by Winter et al. is used.

The removal of the head domain leaves part of the molecule that was previously shielded from the aqueous solvent exposed, thereby destabilizing the structure of the polypeptides of the invention. For this reason, one or more amino acid residues in the B-loop, i.e. the region comprising the amino acids 385-404 (FIG. 1C) were mutated to stabilize the polypeptides. Similarly, in the area around the fusion peptide a number of hydrophobic residues are exposed to the solvent, caused by the fact that, unlike the native full-length HA, the polypeptides cannot be cleaved and undergo the associated conformational change that buries the hydrophobic fusion peptide in the interior of the protein. To address this issue some or all of the hydrophobic amino acid residues at position 323, 326, and 339 were mutated to hydrophilic residues as compared to the wild-type full-length HA from A/Brisbale/59/2007.

Furthermore, the polypeptides were resistant to protease cleavage by a mutation of the natural cleavage site, e.g. by mutation of the amino acid at position 329 into Q.

In WO2016/005480 a further series of stem polypeptides was described, wherein the GCN4 derived sequence RMKQIEDKIEEIESK (SEQ ID NO: 18) was introduced at position 405 to 419, such as e.g. the polypeptides designated 127H1-t2, s127H1-t2, and s127H1-t2long, derived from A/Brisbane/59/2007. In addition, stem polypeptides with the same modifications were made using HA from different influenza strains, for example polypeptides based on HA described from the H1N1 A/California/07/09 strain, such as smH1Cali3964-127H1-t2, and mH1 Cali3964-127H1-t2.

In WO2016/005482 the introduction of an intermonomeric cysteine bridge was described, resulting in increased amounts of trimeric stem polypeptides, including the polypeptides designated 127H1-t2-cl18 (also referred to as 5367), and the soluble version 127H-t2-cl18long, which were based on HA of influenza A/Brisbane/59/2007. Similar polypeptides were designed based on e.g. HA of the influenza virus A/California/07/09, e.g. the polypeptides designated mH1 Cali3964-127H1-t2-cl18 (also referred to as 5369) and smH1 Cali3964-127H1-t2-cl18long. These stem polypeptides comprised inter alia a deletion of the head region comprising the amino acids starting from position 46 up to and including the amino acid at position 306, wherein the resulting HA1 domains were linked through a 4-amino acid linker (GGGG); the GCN4 derived sequence RMKQIEDKIEEIESK (SEQ ID NO: 18) introduced in the HA2 domain at position 405-419; and a mutation of the amino acid at position 329 into Q to make the polypeptide resistant to protease cleavage. The polypeptides further comprised a mutation of the amino acid at position 397 into C and a mutation of the amino acid at position 405 into C (i.e. the first amino acid of the GCN4 sequence), thus forming an intermonomeric cysteine bridge between the cysteine at position 397 of a first monomer and the amino acid at position 405 of a second monomer.

Figure 3:
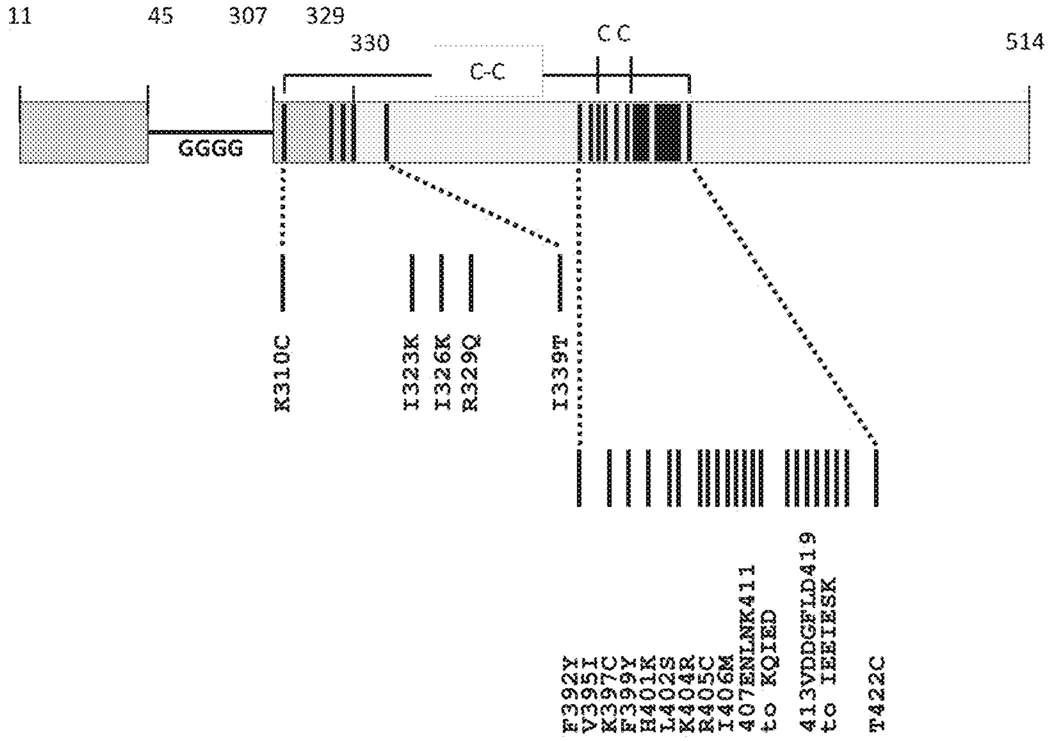
FIG. 3. Schematic drawing of the A/Brisbane based parental construct 5369.

In the research that led to the present invention, the previously described stem polypeptides have been optimized. The amino acid sequences of the wild-type HA derived from A/Brisbane/59/2007 and or A/California/07/09 are the sequences of SEQ ID NO: 1 and 2, respectively. The polypeptides UFV5367 (SEQ ID NO: 16) and UFV5369 (SEQ ID NO: 17) are herein referred to as the "parental strains/constructs" (schematically shown in FIGS. 2 and 3, respectively).

Novel HA stem polypeptides, including e.g. UFV150558 (SEQ ID NO: 30) and UFV150850 (SEQ ID NO: 53) thus were designed, which comprise additional modifications as compared to the previously described stem polypeptides UFV5367 (SEQ ID NO: 16) and UFV5369 (SEQ ID NO: 17). In particular, the polypeptides UFV150558 and UFV150850 comprise a mutation of the amino acid at position 392 in the B-loop into P or R, in combination with a mutation of the amino acid at position 434 into Q, or a mutation of the amino acid at position 392 in the B-loop into P or R, in combination with a mutation of the amino acid at position 434 into Q and a mutation at position 442 into A.

Figure 4:
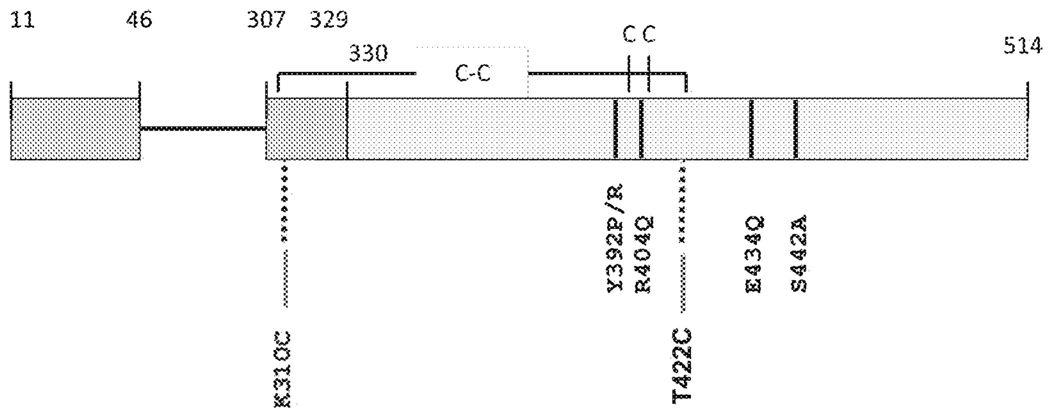
FIG. 4. Schematic drawing of an embodiment of a polypeptide of the invention, showing the new mutation of the amino acid at position 392 in the B-loop into P or R, a mutation of the amino acid at position 434 into Q and a mutation at position 442 into A, and further comprising a mutation of the amino acid at position 404 into Q.

In addition, further stem polypeptides were designed wherein no artificial linker was used to replace the deteled head region. The stem polypeptides UFV160655 (SEQ ID NO: 103), UFV160656 (SEQ ID NO: 104), UFV160664 (SEQ ID NO: 109) and UFV160665 (SEQ ID NO: 110) comprised a deletion of the head region from the amino acid at position 47 up to and including the amino acid at position 306, thus leaving a first part of the HA1 domain comprising the amino acids up to and including the amino acid 46, and a second part of the HA1 domain comprising the amino acids starting from the amino acid at position 307 up to the C-terminal amino acid of the HA1 domain (i.e. the amino acid at position 329). The first HA1 part was directly linked to the second HA1 part after deletion of the head, i.e. the remaining amino acid at position 46 (the C-terminal amino acid of the first part of the HA1 domain) was connected directly to the remaining amino acid at position 307 (the N-terminal amino acid of the second part of the HA1 domain). No artificial linker was introduced (see FIG. 1A, lower construct). The peptides also comprised the additional mutations of the amino acid at position 392 in the B-loop into P or R, in combination with a mutation of the amino acid at position 434 into Q, or in combination with a mutation of the amino acid at position 434 into Q and a mutation at position 442 into A (as schematically shown in FIG. 4).

Example 2: Expression of the Polypeptides According to the Invention

Protein expression in mammalian cells DNA fragments encoding the polypeptides of the invention UFV150558, UFV150850, UFV160655, UFV160656, UFV160664 and UFV160665) were synthesized (Genscript) and cloned in the pcDNA2004 plasmid (in-house modified pcDNA3 vector with an enhanced CMV promotor). The polypeptides were produced in HEK293F cells cultured in Freestyle™ medium by transient transfection using 293fectin™ transfection reagent (Invitrogen) of the prepared expression plasmids. The polypeptides were produced in Expi-CHO cells cultures in ExpiCHO™ Expression medium by transient transfection using the ExpiFectamine™ transfection reagent (Gibco, ThermoFisher Scientific). For the Expi-CHO cells culture the ExpiFectamine CHO enhancer and ExpiCHO feed (Gibco, ThermoFisher Scientific) were added 1 day post transfection. Culture supernatants containing the secreted polypeptides were harvested between day 7-11 (for ExpiCHO cells) by centrifugation, followed by filtration over a 0.2 m bottle top filter (Corning).

Culture Supernatant Analysis

The level of expressed polypeptide in the harvested culture supernatant was assessed through Bio-Layer Interferometry using the OCTET platform. In short, biotinylated mAb CR9114 was immobilized on Streptavidin (SA) biosensors (Pall FortéBio) after which a standard curve was established by assessing the binding shift of a dilution series of a well-defined purified homologous polypeptide. Subsequently, the binding shift of pre-diluted harvested culture supernatants containing the polypeptides of the invention (5-15 μg/mL diluted in kinetics buffer) was measured and the concentration of the polypeptides was calculated using the established standard curve.

The trimer content of the polypeptides in the culture supernatants was assessed in AlphaLISA by simultaneous binding of 1.5 nM of CR9114 and 1.5 nM of a Streptactin tagged single domain antibody (SD15016) having the sequence of SEQ ID NO: 13. Chemiluminescent emission at 615 nm was measured following 2 hours incubation at room temperature of the polypeptides with the antibody and single domain antibody in the presence of anti-human-IgG Acceptor and Streptactin Donor beads (Perkin Elmer). Only trimeric molecules that displayed more than one correctly folded epitope were bound by both antibodies simultaneously and thus gave a signal in this assay (in contrast to monomers and potential aggregates). The polypeptides were titrated based on protein concentration, as assessed by OCTET.

Results and Conclusion

Figure 5:
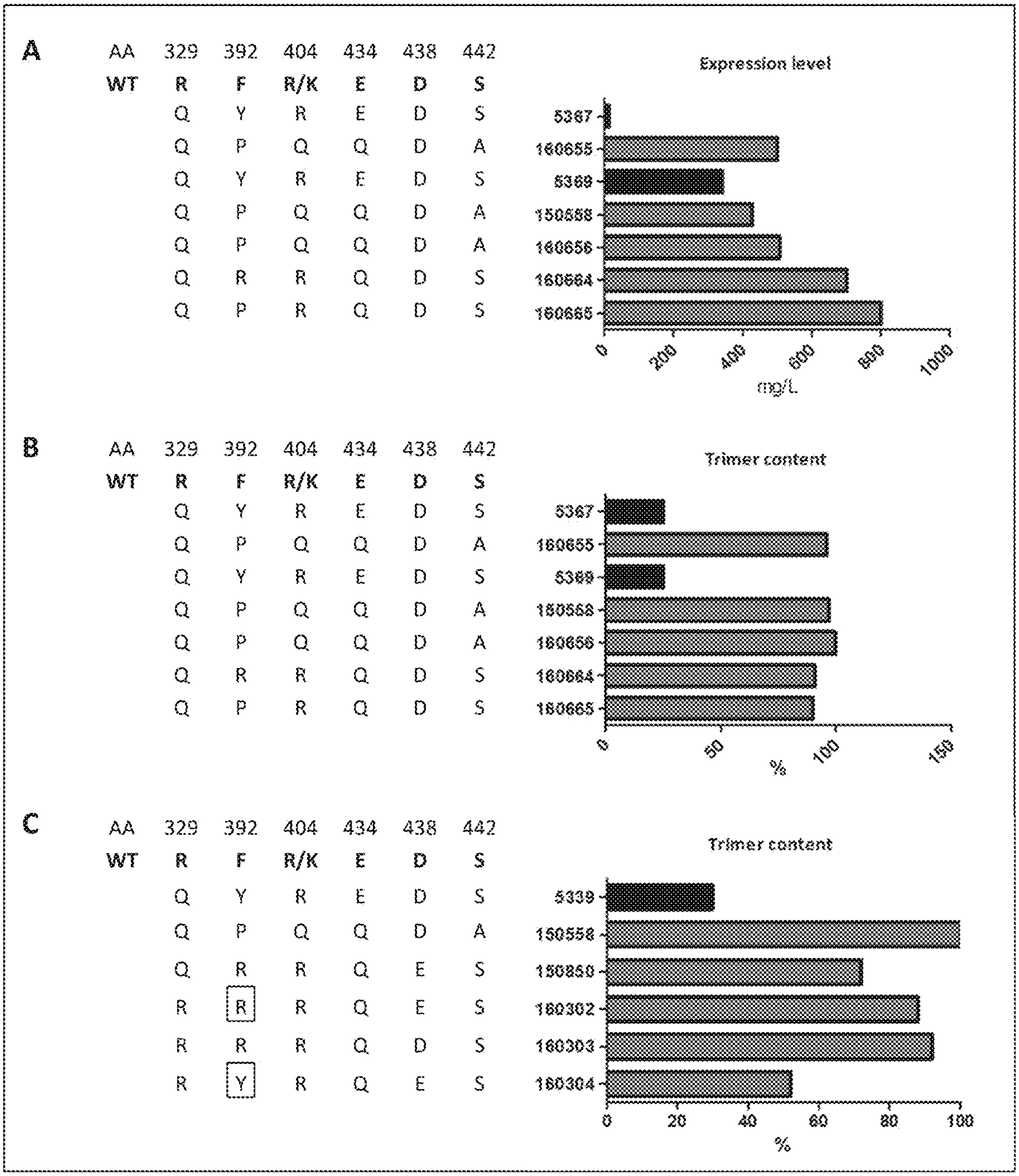
FIG. 5. Levels of expression and trimer content of several polypeptides of the invention (grey) and the parental designs (black). A: Protein expression levels as determined by OCTET (CR9114); B and C: Trimer content as determined by AlphaLISA (values are expressed in % relative to polypeptide UFV160656 that is set to 100%; value for polypeptide 5367 is an estimate based on Western blot). The experiment was performed multiple times and these data are representative for the values observed. The stabilizing mutations are shown in the left panels.

The polypeptide expression levels and trimer content were determined for three independent 70 mL ExpiCHO transfections at day 9 post transfection. The results are shown in FIG. 5. Compared to the previously described construct 5367 (SEQ ID NO: 16) (which comprises a deletion in the HA1 domain of amino acids starting from position 46 up to and including the amino acid at position 306, and comprises a 4G linker replacing the deleted portion in the HA1 domain), also referred to as the parental design/construct, the H1N1 A/Brisbane/07/59 based polypeptide UFV160655 (which comprises a deletion in the HA1 domain of amino acids starting from position 47 up to and including the amino acid at position 306, and does not comprise a 4G linker replacing the deleted portion in the HA1 domain, and includes the point mutations Y392P, R404Q, E434Q, and S442A) (SEQ ID NO: 103), clearly showed increased levels of expression (up to 40-fold), reaching ~500 mg/L culture supernatant (FIG. 5A).

The H1N1 A/California/07/09 derived parental polypeptide UFV5369 (SEQ ID NO: 17) was expressed at a level of ~350 mg/L culture supernatant. Polypeptide UFV150558, similar in design to polypeptide UFV5369, and further including the point mutations Y392P, R404Q, E434Q, and S442A (SEQ ID NO: 30) was expressed at a level of ~427 mg/L. The polypeptides UFV160656 (SEQ ID NO: 104) (comprising a deletion comprising the amino acids from position 47 up to and including the amino acid at position 306 and not comprising a 4G linker replacing the deleted portion in the HA1 domain, and comprising the point mutations Y392P, R404Q, E434Q, and S442A), UFV160664 (comprising the same deletion but only comprising the point mutations Y392R and E434Q) (SEQ ID NO: 109) and UFV160665 (comprising the same deletion and comprising the point mutations Y392P and E434Q) (SEQ ID NO: 110) were expressed at a higher level compared to 5369, up to ~800 mg/L culture supernatant (FIG. 5A).

With respect to the trimer content, all polypeptides comprising one or more of the additional new mutations, independent of both their strain backbone, the size of the deletion of the head and presence or absence of the 4G linker replacing the deleted portion of the HA1 domain, reached levels above 90% which were significantly higher than was obtained for the parental designs for which only ~25% of the expressed protein successfully formed trimers (FIG. 5B).

Additional polypeptides comprising a mutation of the amino acid at position 392 into Y, P or R in combination with a mutation of the amino acid at position 434 into Q were made, including UFV160302 (SEQ ID NO: 60) and UFV160303 (SEQ ID NO: 61). Polypeptide UFV160304 (SEQ ID NO: 62) that comprises a similar design as polypeptide UFV160302 but does not comprise the point mutation Y392R showed a lower trimer content (~1,7 fold) (FIG. 5C).

Taken together the polypeptides of the invention described in this Example, comprising a Y, P or R at position 392, in combination with a Q at position 434, displayed significantly increased levels of protein expression and trimer content (percentage of successfully formed trimers) compared to the parental designs. The presence of these amino acid at the positions 392 and 434 led to a significant improvement in expression, trimerization and stability.

Example 3: Purification of Trimeric Polypeptides of the Invention

Purification

The polypeptides were purified by means of a two-step protocol. First, the harvested and clarified culture supernatant was loaded on a HiScale 16/20 column (GE Healthcare) packed with an affinity resin (Capture Select) that consists of a HA specific single domain antibody, immobilized on Poros beads (obtained from ThermoFisher Scientific). This resin is highly specific for H1 strain derived hemagglutinin proteins. The column was intentionally overloaded by ~15% to improve isolation of the trimer. Following binding and equilibration in 50 mM Tris, 0.5 M NaCl, pH 7.4 the polypeptides were eluted by applying a step gradient to 0.1 M Tris, 2 M $MgCl_2$, 40% propylene glycol, pH 7.4. Based on the UV signal (A280) the elution fractions were pooled and filtrated through a Millex-GV 0.22 μm filter membrane (Merck Millipore). Subsequently, the collected elution peak was applied to a Superdex 200 pg 26/60 column (GE Healthcare) equilibrated in running buffer (20 mM Tris, 150 mM NaCl, pH 7.8) for polishing purpose, i.e. remove the minimal amount of multimeric and monomeric protein. The trimer fractions were pooled and purity was assessed by analytical SEC-MALS in a High Performance Liquid Chromatography (HPLC) Infinity 1260 series setup (Agilent). Of each purified polypeptide 40 μg was run (1 mL/min.) over a TSK gel G3000SWxl column (Sigma-Aldrich) and the molar mass of the eluted material was measured by a miniDAWN Treos Multi Angle Light Scattering detector and Optilab T-rex differential refractometer (Wyatt Technology). The data were analyzed by the Astra 6 software package and molecular weight calculations were derived from the refractive index signal.

Results and Conclusion

Figure 6:
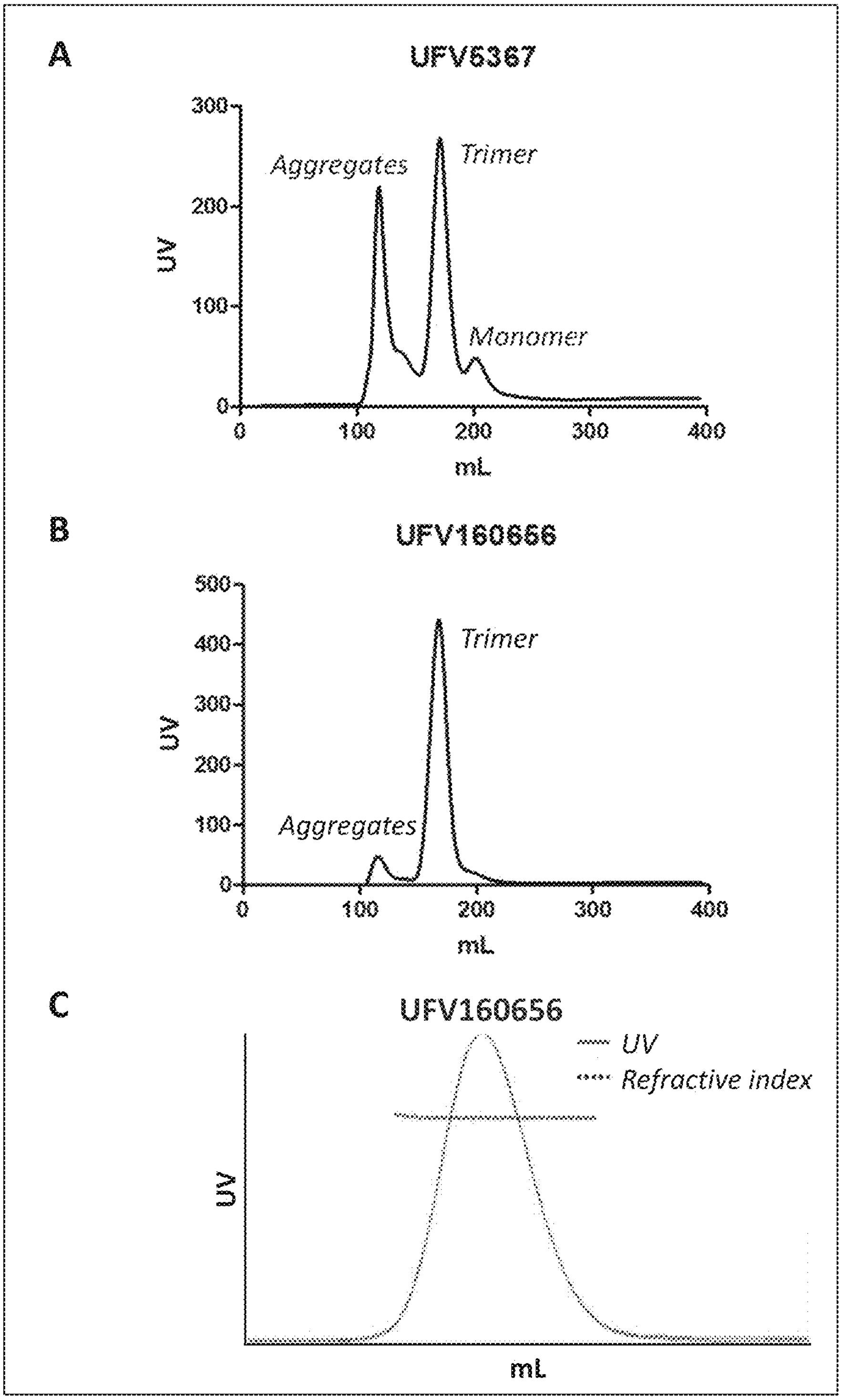
FIG. 6. The pooled Affinity Chromatography elution fractions separated by Size Exclusion Chromatography; aggregates, trimers and monomers are indicated (Panel A and B). SEC-MALS analysis of the pooled trimer fraction indicates that the polypeptide of the invention is very pure and homogeneous in molar mass (Panel C).

The elution profile of the second purification step (Size Exclusion Chromatography) indicated that a large amount of non-trimeric (aggregates and monomer) polypeptide 5367 was present in the pooled elution fractions of the affinity column. In contrast, the chromatogram of UFV160656 showed only a small amount of aggregates whereas the major species present was the trimeric polypeptide (FIGS. 6A and B).

The yield of the parental constructs UFV5367 and UFV5369 was 5 and 70 mg/L, respectively, whereas the yields for the polypeptides of the invention varied from 120-240 mg/L. The recovery percentage, calculated by comparison of the amount of protein present in the culture supernatant and the trimeric end product, was roughly 40-60%. Analysis of the pooled trimer fractions by analytical SEC-MALS showed that the purified material is pure; no other peaks in the UV signal were observed (FIG. 6B). Furthermore, the calculated molecular weight, ~96-106 kDa, corresponded with the expected molecular weight of the glycosylated trimeric polypeptide (FIG. 6C).

The above data indicated that purification of the polypeptides was achieved by a straightforward 2 step protocol resulting in very pure trimeric protein with high efficiency and yields well above 100 mg/L culture supernatant.

Example 4: Characterization of Trimerization of Polypeptides of the Invention by Size Exclusion Chromatography in the Presence of Binding Fab Fragments Characterization The folding and temperature stability of the purified polypeptides was assessed by (i) SEC-MALS analysis in presence of Fab-fragments, (ii) by Enzyme-Linked Immuno Sorbent Assay (ELISA), and (iii) by Differential Scanning Fluorimetry (DSF).

In-solution binding of Fab fragments to the polypeptides of the invention (also referred to as "mini-HA proteins") was monitored by Size Exclusion Chromatography (SEC) and multi-angle light scattering (MALS) analysis using a high-performance liquid chromatography system (Agilent) and miniDAWN TREOS instrument coupled to a Optilab T-rEX Refractive Index detector (Wyatt Technology). In total, 40 μg of the polypeptide or Fab fragments of mAbs CR6261, CR9114 and a negative control antibody were applied to a TSK-Gel G3000SWxl column (Sigma Aldrich) equilibrated in running buffer (150 mM NaPi, 50 mM NaCl, pH 7.0). Complex formation was verified by analysis of the polypeptides incubated in the presence of a 1.2-fold molar excess of Fab fragments. The data were analyzed by the Astra 6 software package and molecular weight calculations were derived from the refractive index signal.

The avidity of CR6261 and CR9114 binding to the polypeptides was assessed by biolayer interferometry measurements using an Octet RED384 (ForteBio). Biotinylated antibodies were immobilized on Streptavidin (SA) Dip and Read biosensors for kinetics (ForteBio). Real-time binding curves were measured by applying the sensor in a two-fold dilution series of the polypeptide in PBS diluted 10× concentrated kinetics buffer (ForteBio). The starting concentrations of the polypeptides were in the range of 0.15-10 nM. Dissociation constants (KD) were determined using steady state analysis, assuming a 1:1 binding model for bnAb to the polypeptides.

In addition, binding of antibodies and single domain antibodies (SDs) to the stem polypeptides of the invention was assessed by ELISA. First 50 μg per well of the protein was coated to the surface of OptiPlate-96 high bind plates (Perkin Elmer) in Phosphate Buffered Saline (PBS). Following overnight incubation at 4° C., washing (three times with PBS+0.05% Tween-20), blocking (1.5 hour at Room Temperature with PBS+0.05% Tween-20+1% Bovine Serum Albumin), and washing (three times with PBS+0.05% Tween-20), the plates were incubated for 1 hour at RT with the mAb and SDs in a three-fold dilution series with a starting concentration of 70 nM or 100 nM respectively. After another wash (three times with PBS+0.05% Tween-20) the Horse Radish Peroxidase conjugated to Mouse anti-human IgG (Jackson) was added in a 1:1000 dilution in block buffer (PBS+0.05% Tween-20+1% Bovine Serum Albumin). After another 1 hour incubation at RT and subsequent wash (three times with PBS+0.05% Tween-20), BM Chemiluminescence ELISA Substrate (Roche) was added and following a 15-minute incubation the luminescent signal was measured using a Synergy Neo plate reader (Perkin Elmer). The half maximum effective concentration ($EC_{50}$) values were calculated by the Spotfire suite (Tibco Software Inc.). The $EC_{50}$ is directly correlated to the binding strength of the respective antibody and thereby a measure for the quality of the antigen, i.e. its proper folding and stability.

The protein temperature stability was determined by DSF through monitoring the fluorescent emission of the polypeptide solution (6 μg) in the presence of 5× Sypro Orange Dye (ThermoFisher Scientific). Upon gradual increase of the temperature, from 25° C. to 95° C. (60° C. per hour), the polypeptides unfold and the fluorescent dye binds to the exposed hydrophobic residues. The melt curves were measured using a ViiA7 real time PCR machine (Applied BioSystems) and the $Tm_{50}$ values were calculated by the Spotfire suite (Tibco Software Inc.). The $Tm_{50}$ values represent the temperature at which 50% of the protein is unfolded and thus are a measure for the temperature stability of the polypeptides. Additionally, heat-induced denaturation was also determined by DSC in which the thermal transition midpoint (Tm) was determined by monitoring the difference in energy input between the sample and the reference cell using a MacriCal DSC system (Malvern). At a concentration of 1 mg/mL the samples were gradually heated, from 20° C. to 90° C. (100° C. per hour), and the runs were analyzed by the Origin software (Malvern). Based on the temperature (° C.) vs heat capacity (kcal/mol/° C.) plots the Tm values were calculated.

Results and Conclusion

The theoretical molecular weight of the trimeric polypeptides based on amino acids only is ~90 kDa, however, as each protein contains 5 N-linked glycosylation motifs (NxT/S) the molecular weight will be higher when produced in a mammalian expression system. The molecular weights as determined by SEC-MALS analysis were calculated to be in the range of 96-106 kDa indicating that the proteins are, as expected, significantly glycosylated (Table 1).

TABLE 1

Molecular weight of polypeptides of the invention (second column) and of the polypeptides in complex with the Fab fragments of bnAb CR6261 and CR9114 (third and fourth column) as determined by SEC-MALS using the signal for the refractive index. The molecular weight (MW) of Fab6261 and Fab9114 was determined at ~44 kDa.

| Polypeptide ID | MW polypeptide (kDa) | MW polypeptide + Fab6261 (kDa) | MW polypeptide + Fab9114 (kDa) |
|---|---|---|---|
| UFV5367 | 98 | 204 | 228 |
| UFV160655 | 96 | 204 | 225 |
| UFV5369 | 97 | 212 | 225 |
| UFV160656 | 103 | 217 | 235 |
| UFV160664 | 98 | 211 | 226 |
| UFV160665 | 106 | 235 | 254 |

Figure 7:
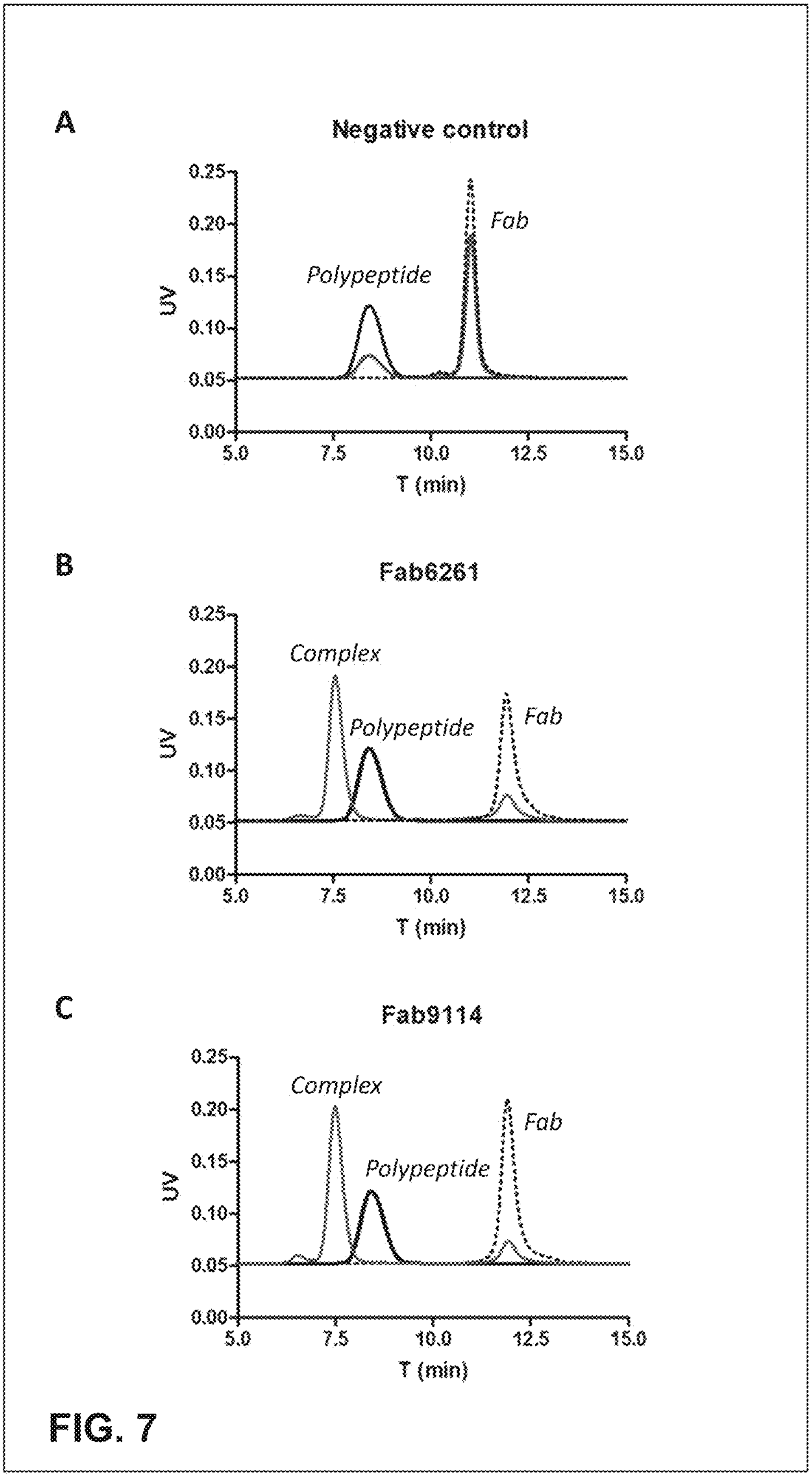
FIG. 7. SEC profiles of the trimeric stem polypeptide of the invention and Fab fragments. The overlay shows the chromatograms of the polypeptide (black), the Fab-fragment (dashed) and of the sample containing both (grey). The results for polypeptide 160656 are displayed. The overlapping peaks in panel A indicate that the Fab used as negative control does not bind to the polypeptide, whereas the polypeptides pre-incubated with Fab6261 (Panel B) and Fab9114 (Panel C) display a peak shift (reduced retention time) indicating complex formation (one trimer bound by three Fab fragments).

Antibody binding to the polypeptides indicates the correct folding of the polypeptides, and the presence of correctly folded epitopes of the broadly neutralizing antibodies (bnAbs). In solution binding of Fab-fragments CR9114, CR6261 and a non-binding Fab (negative control) was assessed by SEC-MALS analysis, as described above. Upon binding of the Fab-fragment to the polypeptide the molecular weight increase will result in a visible peak shift (shortened retention time) in the SEC. Furthermore, monitoring the MALS signal enables a molecular weight calculation of the complex formed. As anticipated, the Fab-fragment used as negative control did not bind; i.e. no peak shift of the polypeptide was observed upon addition of the Fab-fragment (FIG. 7A). In contrast, a clear peak shift to a shorter retention time was observed upon incubation with the other two Fab-fragments (FIGS. 7B and C). Furthermore, the molecular weight determination of the complex indicated that the polypeptide binds 3 Fab-fragments (Table 1), confirming that all three monomers within the trimeric polypeptide are properly folded and accessible for the antibodies.

To further assess the quality and folding of the polypeptides the dissociation constant ($K_D$) of the bnAbs CR6261 and CR9114 binding was determined by biolayer interferometry (Table 2). For all polypeptides, the binding avidity was below 1 nM indicating that the trimeric polypeptides represent the native HA stem surface.

TABLE 2

Binding of CR6261 and CR9114 to stem polypeptides of the invention. $K_D$ values of CR6261 and CR9114 binding as determined by biolayer interferometry and steady state analysis. Full length HA H1N1 A/Brisbane/59/07 was taken along for comparison.

| | $K_D$ (nM) | |
|---|---|---|
| Polypeptide ID | CR6261 | CR9114 |
| HA Brisbane | 1.1 | 0.71 |
| UFV5367 | 0.48 | 0.45 |
| UFV160655 | 0.55 | 0.49 |
| UFV5369 | 0.97 | 0.56 |
| UFV160656 | 0.60 | 0.54 |
| UFV160664 | 0.57 | 0.46 |
| UFV160665 | 0.56 | 0.39 |

Furthermore, the binding of antibodies was assessed by ELISA. Based on the S-curves $EC_{50}$ values were calculated that confirmed proper folding of the polypeptides. Both antibodies bound very strongly with $EC_{50}$ values below 1 nM (Table 3).

TABLE 3

Binding strength of antibodies to the purified polypeptides as determined by ELISA (Average EC50 values in nM of the S-curves of 3 independent assays).

| Polypeptide ID | CR6261 | CR9114 |
|---|---|---|
| UFV5367 | 0.417 | 0.410 |
| UFV160655 | 0.396 | 0.400 |
| UFV5369 | 0.391 | 0.389 |
| UFV160656 | 0.432 | 0.410 |
| UFV160664 | 0.395 | 0.379 |
| UFV160665 | 0.425 | 0.409 |

The thermal stability is a measure for the resilience of the polypeptides when exposed to stress, and thus for stability of the polypeptides. The polypeptides of the invention were gradually heated in the presence of a fluorescent dye that, over the course of the experiment, binds to the unfolding protein and the resulting change in fluorescence intensity was used to calculate the $Tm_{50}$ values (Table 4). Whereas the parental designs (UFV5367 and UFV5369) displayed a $Tm_{50}$ value of ~52 and ~57° C., respectively, strikingly, the polypeptides of the invention displayed values that are significantly higher (up to ~7° C.), indicating a significantly improved stability. A similar difference between the parental designs and the polypeptides of the invention was observed for the Tm values as determined by DSC. Overall the Tm-values (DSC) were ~2° C. higher than the Tm50 values (DSF) which was due to the difference in the way these values are determined; for DSC, the temperature at the peak max was determined, whereas for DSF the temperature was determined at ½ peak heights.

TABLE 4

Overview of Tm50 values of the purified polypeptides as determined by DSF and DSC.

| | $Tm_{50}$ (° C.) | |
|---|---|---|
| Polypeptide ID | DSF | DSC |
| UFV5367 | 51.8 ± 0.09 | — |
| UFV160655 | 58.5 ± 0.21 | — |
| UFV5369 | 57.2 ± 0.08 | 59.1 ± 0.01 |
| UFV160656 | 64.1 ± 0.14 | 66.2 ± 0.07 |

TABLE 4-continued

| Overview of Tm50 values of the purified polypeptides as determined by DSF and DSC. | | |
|---|---|---|
| | $Tm_{50}$ (° C.) | |
| Polypeptide ID | DSF | DSC |
| UFV160664 | 63.3 ± −0.12 | 65.3 ± 0.01 |
| UFV160665 | 62.5 ± 0.16 | 65.2 ± 0.16 |

The molecular weight of the polypeptides, the observed Fab-fragment binding in solution and the strong binding of Abs indicated that the parental designs and the polypeptides of the inventions are trimeric and well folded. Furthermore, as indicated by the calculated Tm50/Tm values, the polypeptides of the invention were considerably more resistant to thermal stress compared to the parental designs. Taken together the binding data and thermostability data indicate that the polypeptides of the invention are trimeric in solution, are properly folded (3 epitopes) and display significantly improved thermal stability compared to their parental designs.

Example 5: Alternative Deletions, Linkers and Head Domain Sequences According to the Invention

Designs

Figure 8:
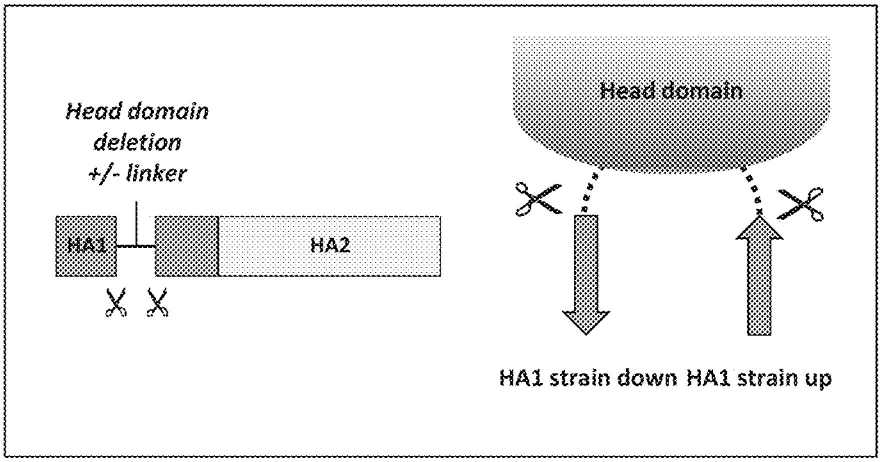
FIG. 8. Schematic representation of the HA head domain (HA1) removal. In the parental design, the head domain is removed and the two HA1 ends are connected by an artificial "GGGG-linker" (left panel). In the polypeptides of the invention the ends are directly connected (alternative cutting position) or by means of a homologous linker sequence originating from the head domain.

The influenza hemagglutinin (HA) stem polypeptides of the invention described above were derived from full length HA by deleting a part of the HA1 domain comprising the amino acids from position 47 up to and including the amino acid at position 306. No linking sequence was introduced. In the parental designs the deletion comprised the amino acids 46-306 and the two HA1 ends after deletion were connected by an artificial "GGGG-linker" (FIG. 8).

In this Example, further alternative cutting positions of the head and alternative homologous linkers were explored. Table 5 shows alternative cutting positions for removal of the HA1 head domain. The HA1 ends in the parental design are indicated in grey. The construct UFV160360 (SEQ ID NO: 63) comprises a deletion from the amino acid at position 46 up to and including the amino acid at position 306 and a 4G linker replacing the deleted portion in the HA1 domain, and further comprises the point mutations Y392P, R404Q, E434Q, and S442A. New constructs were made wherein up to 7 additional amino acid residues of the HA1 domain (HA1 up), the first (N-terminal) HA1 domain, and up to 4 additional amino acid residues of the HA1 down strand (the second, or C-terminal HA1 domain) were included, or up to 2 amino acid residues deleted, thus varying the size of the head deletion. These constructs also all comprised the point mutations Y392P, R404Q, E434Q, and S442A.

TABLE 5

Alternative head domain deletions, see also FIG. 5). The * indicates the mutation of a free cysteine (C) to a G. The numbers of the amino acid positions indicate amino acid position according to H3 numbering convention.

| | UVF# | HA1 up | | | | | Head domain deletions | | | | | | | | |
|---|---|---|---|---|---|---|---|---|---|---|---|---|---|---|---|
| A/Brisbane/59/07 | | N | L | L | E | N | S | H | N | G | K | | | | . . . |
| A/California/07/09 | | N | L | L | E | D | K | H | N | G | K | L | C | K | . . . |
| UFV160360 | | N | L | L | E | D | G | G | G | G | | | | | |
| AA position # | | 41 | 42 | 43 | 44 | 45 | 46 | 47 | 48 | 48 | 50 | 51 | 52 | 53 | |
| | UFV160361 | N | L | L | E | D | | | | | | | | | |
| | UFV160362 | N | L | L | E | D | K | | | | | | | | |
| | UFV160363 | N | L | L | E | D | K | H | | | | | | | |
| | UFV160364 | N | L | L | E | D | K | H | N | | | | | | |
| | UFV160365 | N | L | L | E | D | K | H | N | G | | | | | |
| | UFV160366 | N | L | L | E | D | K | H | N | G | K | | | | |
| | UFV160367 | N | L | L | E | D | K | H | N | G | K | L | | | |
| | UFV160368 | N | L | L | E | D | K | H | N | G | K | L | G* | | |
| | UFV160369 | N | L | L | E | D | K | H | N | G | K | L | G* | | |
| | UFV160370 | N | L | L | E | D | K | H | | | | | | | |
| | UFV160371 | N | L | L | E | D | | | | | | | | | |
| | UFV160372 | N | L | L | E | D | | | | | | | | | |
| | UFV160373 | N | L | L | E | D | K | | | | | | | | |
| | UFV160374 | N | L | L | E | D | K | H | | | | | | | |
| | UFV160375 | N | L | L | E | D | K | H | N | | | | | | |
| | UFV160376 | N | L | L | E | D | K | H | N | G | | | | | |
| | UFV160377 | N | L | L | E | D | K | H | N | G | K | | | | |
| | UFV160378 | N | L | L | E | D | K | H | N | G | K | L | | | |
| | UFV160379 | N | L | L | E | D | K | H | N | G | K | L | G* | | |

| | UVF# | Head domain deletions | | | | | HA1 down | | | |
|---|---|---|---|---|---|---|---|---|---|---|
| A/Brisbane/59/07 | | I | G | K | C | P | K | Y | V | K |
| A/California/07/09 | | I | G | E | C | P | K | Y | V | R |
| UFV160360 | | | | | | | K | Y | V | C |
| AA position # | | 302 | 303 | 304 | 305 | 306 | 307 | 308 | | |
| | UFV160361 | | | | | | K | Y | V | C |
| | UFV160362 | | | | | | K | Y | V | C |
| | UFV160363 | | | | | | K | Y | V | C |
| | UFV160364 | | | | | | K | Y | V | C |
| | UFV160365 | | | | | | K | Y | V | C |
| | UFV160366 | | | | | | K | Y | V | C |
| | UFV160367 | | | | | | K | Y | V | C |
| | UFV160368 | | | | | | K | Y | V | C |
| | UFV160369 | | | | | P | K | Y | V | C |

TABLE 5-continued

Alternative head domain deletions, see also FIG. 5). The * indicates the mutation of a free cysteine (C) to a G. The numbers of the amino acid positions indicate amino acid position according to H3 numbering convention.

| | | | | | | | | |
|---|---|---|---|---|---|---|---|---|
| UFV160370 | | | G* | P | K | Y | V | C |
| UFV160371 | G | E | G* | P | K | Y | V | C |
| UFV160372 | | | | | | | V | C |
| UFV160373 | | | | | | | V | C |
| UFV160374 | | | | | | | V | C |
| UFV160375 | | | | | | | V | C |
| UFV160376 | | | | | | | V | C |
| UFV160377 | | | | | | | V | C |
| UFV160378 | | | | | | | V | C |
| UFV160379 | | | | | | | V | C |

Table 6 below shows alternative homologous linkers. The HAT ends in the parental design are indicated in dark grey. Up to 5 residue long homologous linkers, i.e. originating from the HAT domain were introduced to connect the HAT ends. Again, the other constructs also all comprised the point mutations Y392P, R404Q, E434Q, and S442A.

TABLE 6

Alternative linkers derived from the deleted homologous head domain. The amino acid positions indicate amino acid position according to H3 numbering convention.

| | # | HA1 up | | | | | Introduced Linkers | | | | | | | | |
|---|---|---|---|---|---|---|---|---|---|---|---|---|---|---|---|
| A/Brisbane/59/07 | | N | L | L | E | N | S | H | N | G | K | | | | . . . |
| A/California/07/09 | | N | L | L | E | D | K | H | N | G | K | L | C | K | . . . |
| AA position # | | 41 | 42 | 43 | 44 | 45 | 46 | 47 | 48 | 49 | 50 | 51 | 52 | 53 | |
| UFV160360 | | N | L | L | E | D | G | G | G | G | | | | | |
| | UFV160380 | N | L | L | E | D | A | G | S | G | | | | | |
| | UFV160381 | N | L | L | E | D | A | G | S | | | | | | |
| | UFV160382 | N | L | L | E | D | A | G | S | G | I | | | | |
| | UFV160383 | N | L | L | E | D | A | G | S | G | I | | | | |
| | UFV160384 | N | L | L | E | D | G | S | G | I | | | | | |
| | UFV160385 | N | L | L | E | D | G | S | G | | | | | | |
| | UFV160386 | N | L | L | E | D | H | A | G | A | | | | | |
| | UFV160387 | N | L | L | E | D | D | Q | E | G | | | | | |
| | UFV160388 | N | L | L | E | D | D | T | P | V | | | | | |
| | UFV160389 | N | L | L | E | D | F | P | K | T | | | | | |
| | UFV160390 | N | L | L | E | D | E | P | G | D | | | | | |
| | UFV160391 | N | L | L | E | D | E | P | G | | | | | | |
| | UFV160392 | N | L | L | E | D | T | G | N | L | | | | | |
| | UFV160393 | N | L | L | E | D | T | P | S | S | | | | | |
| | UFV160394 | N | L | L | E | D | T | P | S | | | | | | |
| | UFV160395 | N | L | L | E | D | A | T | G | N | | | | | |
| | UFV160396 | N | L | L | E | D | Y | P | G | D | | | | | |
| | UFV160397 | N | L | L | E | D | Y | P | G | D | | | | | |

| | # | Introduced Linkers | | | | | HA1 down | | | |
|---|---|---|---|---|---|---|---|---|---|---|
| A/Brisbane/59/07 | | I | G | K | C | P | K | Y | V | K |
| A/California/07/09 | | I | G | E | C | P | K | Y | V | R |
| AA position # | | | | | 305 | 306 | 307 | 308 | 309 | 310 |
| UFV160360 | | | | | | | K | Y | V | C |
| | UFV160380 | | | | | | K | Y | V | C |
| | UFV160381 | | | | | | K | Y | V | C |
| | UFV160382 | | | | | | K | Y | V | C |
| | UFV160383 | | | | | | | | V | C |
| | UFV160384 | | | | | | K | Y | V | C |
| | UFV160385 | | | | | | K | Y | V | C |
| | UFV160386 | | | | | | K | Y | V | C |
| | UFV160387 | | | | | | K | Y | V | C |
| | UFV160388 | | | | | | K | Y | V | C |
| | UFV160389 | | | | | | K | Y | V | C |
| | UFV160390 | | | | | | K | Y | V | C |
| | UFV160391 | | | | | | K | Y | V | C |
| | UFV160392 | | | | | | K | Y | V | C |
| | UFV160393 | | | | | | K | Y | V | C |
| | UFV160394 | | | | | | K | Y | V | C |
| | UFV160395 | | | | | | K | Y | V | C |
| | UFV160396 | | | | | | K | Y | V | C |
| | UFV160397 | | | | | | | | V | C |

Characterization

DNA fragments encoding the polypeptides listed in table 5 and 6 were synthesized (Genscript) and cloned in the pcDNA2004 plasmid (in-house modified pcDNA3 vector with an enhanced CMV promotor). The polypeptides, including a C-terminal FLAG-linker-His tag for screening purpose, were produced in eukaryotic cell line Expi293F cells at microscale (200 μL). In short, cells were seeded in a 96-well microplate format (Greiner) at a cell density of 2.5 E+06 viable cells (vc)/mL in Opti-MEM (Gibco). Cells were transiently transfected using the ExpiFectamine 293 transfection kit (Gibco) and incubation for 3 days at 37° C., 250 rpm, 8% CO2 and 75% humidity. The culture supernatants were harvested by centrifugation (10 min. at 400×g) using a white 96-well Filter plates (0.22 μm PVDF membrane) to remove aggregates and cell debris.

The amount of polypeptides present in the culture supernatant, protein folding and trimer content were all assessed by Amplified Homogeneous Assay (AlphaLISA). Appropriate polypeptide dilutions in the linear range of the curve were used for analysis and all data was normalized to construct UFV160360 (SEQ ID NO: 63) that was set to 100%.

The relative polypeptide quantity in the harvested culture supernatant was determined by using Nickel donor beads (Perkin Elmer) and Anti-Flag Acceptor beads (Perkin Elmer). Appropriate dilutions of the culture supernatant in the linear range of the curve were used to avoid the hook-effect.

Similarly, the folding of the expressed polypeptides was verified by assessment of binding of antibodies CR9114 (2 nM) and single domain SD15004 (2 nM). For detection of the antibody binding Anti-human IgG Acceptor beads (Perkin Elmer) and Nickel Donor beads (Perkin Elmer) was used, for detecting binding of the Streptactin-tagged single domain Anti-His Acceptor beads (Perkin Elmer) and Streptactin Donor beads (Perkin Elmer) were used.

The multimer content was measured by simultaneous binding of CR9114 (2 nM) and Streptactin tagged SD15016 (2 nM) using a protocol similar to as described in example 2. The polypeptide was titrated based on protein concentration, as determined by OCTET. Only trimeric molecules offering both antibodies to bind give a signal in this assay (in contrast to monomers, dimers and potential aggregates).

Results and Conclusion

Figure 9:
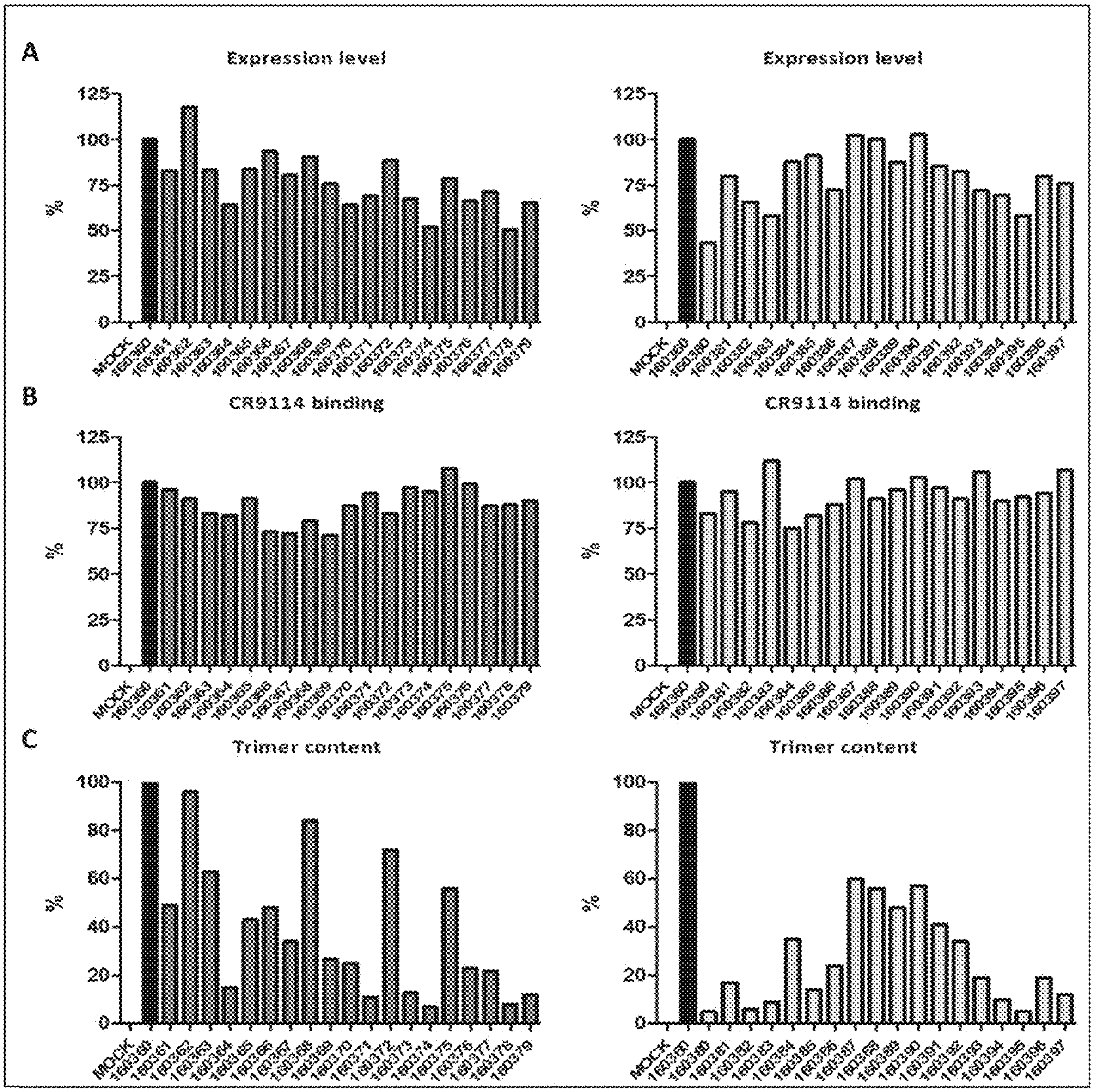
FIG. 9. Expression levels, antibody binding and trimer content of the polypeptides of the invention, as determined by AlphaLISA. A: expression levels, B: CR9114 binding and C: Trimer content. Designs including the alternative cuts are colored grey (left panel), designs including alternative linkers are colored light grey. All data are normalized to reference design UFV160360 (black).

Overall the polypeptides were expressed at a similar level to the reference protein (UFV160360) and no significant differences were observed between the designs with the alternative cutting positions (i.e. alternative head domain deletions) and the designs in which the HA1 ends were connected with a linker originating from the head domain (FIG. 9A). Similarly, no significant differences were observed for binding of bnAb CR9114 (FIG. 9B).

In contrast, some differences in relative trimer content were observed (FIG. 9C); the designs were less prone to forming trimeric mini-HA. On average, a ~2-fold decrease was observed for the designs in which an alternative cut was introduced whereas a ~3-fold decrease was observed across the designs in which the "GGGG-linker" is replaced by a sequence from the head domain.

These results show that although the trimeric content is somewhat decreased, well expressing and stable stem polypeptides were obtained which were correctly folded to present the epitope of the broadly neutralizing antibody CR9114.

Example 6: HA1/HA2 Cleavage Site Variations: Knock Out, Monobasic and Polybasic Cleavage Site Cleavage of the influenza HA0 protein (in HA1 and HA2) is required for its activity, facilitating the entry of the viral genome into the target cells by causing the fusion of host membrane with the viral membrane. The polypeptides of the invention described above were all expressed with the cleavage site knock-out mutation R329Q to prevent putative cleavage of the molecule during production in vitro and/or in vivo.

In this Example, several stem polypeptides were expressed with the natural monobasic cleavage site or including a polybasic cleavage site, e.g. a Furin cleavage site (Table 7). The polypeptides also comprised the mutations at position 392 and 434.

TABLE 7

Cleavage site variants.

| Polypeptide ID | Cleavage site | Sequence |
|---|---|---|
| UFV150850 | Knocked out | R329Q |
| UFV160302 | Monobasic | R329 (wildtype) |
| UFV160301 | Polybasic | RRRKK |
| UFV160503 | Polybasic | RKRR |

Culture Supernatant Analysis

DNA fragments encoding the polypeptides listed in table 7 were synthesized as described in Example 5.

The level of expressed polypeptide in the harvested culture supernatant was assessed through Bio-Layer Interferometry using the OCTET platform. In short biotinylated mAb CR9114 was immobilized on Streptavidin (SA) biosensors (Pall ForteBio) following which a standard curve was established by assessing the binding shift of a dilution series of a well-defined purified homologous polypeptide. Subsequently the binding shift of pre-diluted harvested culture supernatant containing the polypeptide (5-15 μg/mL diluted in kinetics buffer) was measured and the concentration was calculated using the established reference curve.

Results and Conclusion

Figure 10:
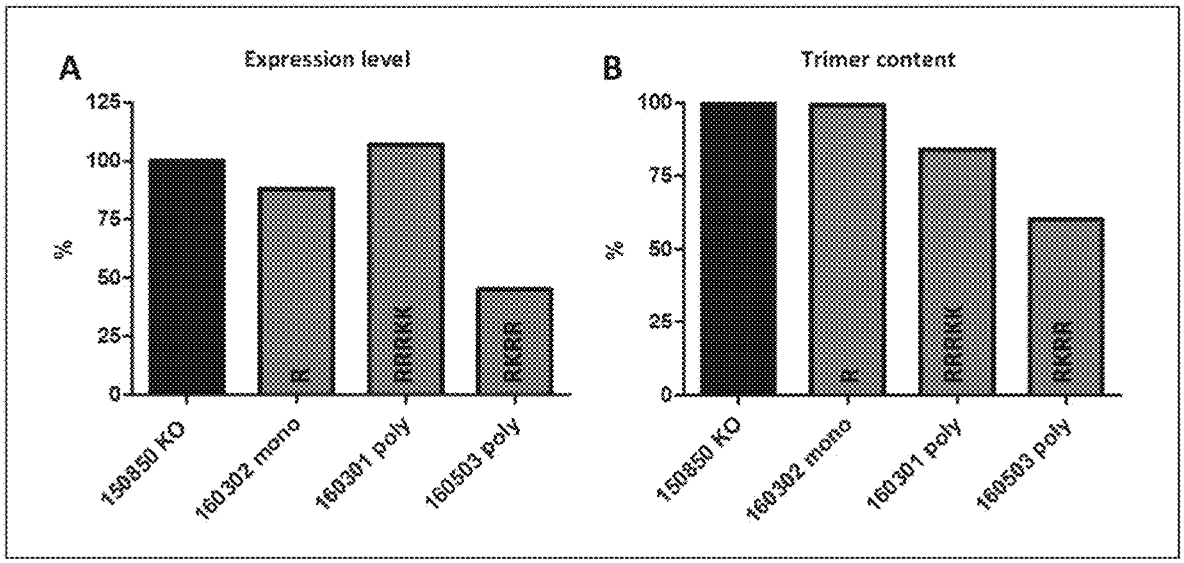
FIG. 10. Expression levels and trimerization of polypeptides of the invention. Expression levels were determined by OCTET (panel A) and trimer content by AlphaLISA (panel B). Data are normalized to reference polypeptide UFV150850.

No effect on the expression level was observed for the polypeptides in which a monobasic (R)- or polybasic cleavage site (RRRKK) was inserted, i.e. UFV160302 and UFV160301 respectively (FIG. 10). Both polypeptides were expressed at similar levels and showed similar levels of trimer content compared to the reference polypeptide UFV150850, which is resistant to protease cleavage through mutation of the amino acid at position 329 into Q.

For the second introduced polybasic cleavage site introduced (RKRR) a ~2-fold decrease in expression level and trimer content was observed (UFV160503).

Example 7: Example Sequences of GCN4 or Alternative Heptad Repeat Trimerization Domains Designs In the polypeptides of the invention as described above, the N-terminal end of the C-helix (top part of the molecule, see FIG. 1C), in particular the amino acid sequence starting from the amino acid at position 405 up to and including the amino acid at position 419 of the HA2 domain, was replaced by the GCN4 trimerization domain of SEQ ID NO: 113 in order to improve the trimerization tendency of the molecule. In this Example, optimizations of the coiled-coil interface were successfully explored by optimization of the heptad repeat sequence of the C-helix. Table 8 shows an alternative trimerization sequence in the polypeptide UFV160090 (SEQ ID NO: 56). The mutations in the N-terminal region of the C-helix are highlighted in light grey. The trimerization sequence of UFV160097 (SEQ ID NO: 58) is identical to the polypeptides as described in Example 1. The differences of the heptad repeat sequence in the N-terminal part of the C-helix with the Wild type HA are highlighted in grey.

TABLE 8

Sequences of GCN4 or alternative hepta repeat trimerization domains (for A/California/07/09 HA derived polypeptides). Numbers at the top indicate amino acid position according to H3 numbering convention.

| C-helix trimerization domain | UFV# | C-helix (amino acid postion of N-terminal region) 405 | 406 | 407 | 408 | 409 | 410 | 411 | 412 | 413 | 414 | 415 | 416 | 417 | 418 | 419 |
|---|---|---|---|---|---|---|---|---|---|---|---|---|---|---|---|---|
| wt A/Califomia/07/09 | wt | R | I | E | N | L | N | K | K | V | D | D | G | F | L | D |
| GCN4 | 160097 | C | M | K | Q | I | E | D | K | I | E | E | I | E | S | K |
| alternative heptad repeat | 160090 | C | I | E | A | K | E | K | K | V | D | D | I | E | K | K |

Culture Supernatant Analysis

DNA fragments encoding the polypeptides listed in Table 8 were synthesized as described above in Example 5.

All assessments on the harvested culture supernatants were performed by AlphaLISA similar as described for example 5. The CR9114 binding data was normalized on expression level.

Results and Conclusion

Figure 11:
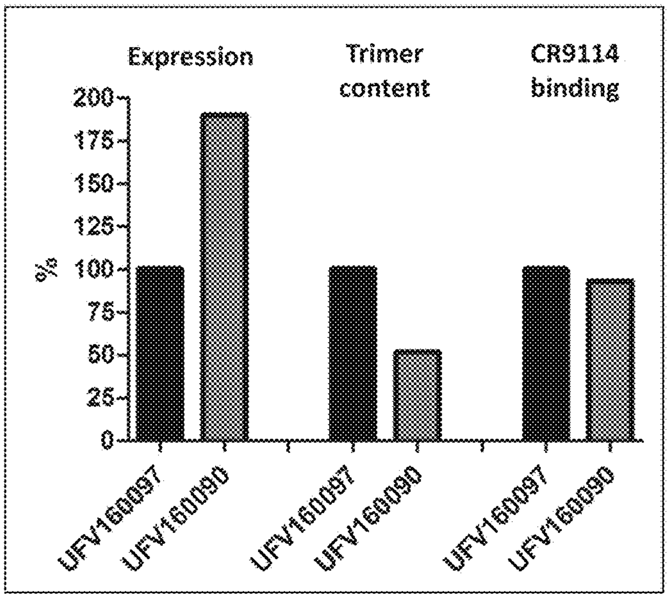
FIG. 11. Normalized expression levels, trimer content and CR9114 binding. Culture supernatants were analyzed by AlphaLISA. Reference construct UFV160097 contains the GCN4 like heptad repeat and is indicated in black whereas the polypeptide containing the alternative heptad repeat is colored grey. The CR9114 binding levels were normalized by the determined expression level.

AlphaLISA assessment of the harvested culture supernatants on polypeptide expression level, trimer content and CR9114 binding indicated that an alternative optimization of the C-helix trimer interface (i.e. other than the GCN4-like repeat, as present in the polypeptides described above) was tolerated. An improved protein expression level was observed (~2 fold), although a reduction in trimer content was observed (~2 fold). Binding of CR9114 was not affected (FIG. 11).

Example 8: Alternative Truncations at the C-Terminus of the Stem Polypeptides of the Invention Designs Hemagglutinin is a membrane protein that is located on the surface of the viral particle with the C-terminal part of the protein embedded in the viral membrane. For the soluble versions of the polypeptides of the invention the transmembrane domain was deleted by a truncation at the start of the transmembrane domain (TM). Additionally, alternative truncation positions were evaluated as well (Table 9 and 10).

TABLE 9

Alternative truncations of the C-terminus of the HA2 domain (for A/Brisbane/59/07 HA derived polypeptides). Numbers at the top indicate amino acid position according to H3 numbering convention.

| UVF# | Amino acid position and sequence of C-terminus of soluble mini-HA designs compared to wt 496 | 497 | 498 | 499 | 500 | 501 | 502 | 503 | 504 | 505 | 506 | 507 | 508 |
|---|---|---|---|---|---|---|---|---|---|---|---|---|---|
| A/Brisbane/59/07 | K | L | N | R | E | K | I | D | G | V | K | L | E |
| UFV5367 | K | L | N | R | E | K | I | D | G | V | K | L | E |
| UFV150565 | K | L | N | R | E | K | I | D | G | V | K | L | E |
| UFV150566 | K | L | N | R | E | K | I | D | G | V | K | L | E |
| UFV150567 | K | L | N | R | E | K | I | D | G | V | K | L | E |
| UFV150568 | K | L | N | R | E | K | I | D | G | V | K | L | E |
| UFV150569 | K | L | N | R | E | K | I | D | G | V | K | L | E |
| UFV150570 | K | L | N | R | E | K | I | D | G | V | K | L | |
| UFV150571 | K | L | N | R | E | K | I | D | G | V | | | |
| UFV150572 | K | L | N | R | E | K | I | D | | | | | |
| UFV150573 | K | L | N | R | E | K | | | | | | | |
| UFV150574 | K | L | N | R | | | | | | | | | |

| UVF# | Amino acid position and sequence of C-terminus of soluble mini-HA designs compared to wt 509 | 510 | 511 | 512 | 513 | 514 | 515 | TM domain 516 | 517 | 518 | 519 |
|---|---|---|---|---|---|---|---|---|---|---|---|
| A/Brisbane/59/07 | S | M | G | V | Y | Q | I | L | A | I | Y |
| UFV5367 | S | M | G | V | Y | Q | I | | | | |
| UFV150565 | S | M | G | V | Y | Q | I | L | A | I | Y |
| UFV150566 | S | M | G | V | Y | Q | I | L | A | | |
| UFV150567 | S | M | G | V | Y | | | | | | |
| UFV150568 | S | M | G | | | | | | | | |
| UFV150569 | S | | | | | | | | | | |
| UFV150570 | | | | | | | | | | | |
| UFV150571 | | | | | | | | | | | |
| UFV150572 | | | | | | | | | | | |
| UFV150573 | | | | | | | | | | | |
| UFV150574 | | | | | | | | | | | |

TABLE 10

Truncation of the C-terminus of the HA2 domain (for A/Califrnia/07/09 HA derived polypeptides). Numbers at the top indicate amino acid position according to H3 numbering convention.

| | Amino acid position and sequence of C-terminus of soluble mini-HA designs compared to wt | | | | | | | | | | | | |
|---|---|---|---|---|---|---|---|---|---|---|---|---|---|
| UVF# | 496 | 497 | 498 | 499 | 500 | 501 | 502 | 503 | 504 | 505 | 506 | 507 | 508 |
| A/California/07/09 | K | L | N | R | E | E | I | D | G | V | K | L | E |
| UFV5369 | K | L | N | R | E | E | I | D | G | V | K | L | E |
| UFV150575 | K | L | N | R | E | E | I | D | G | V | K | L | E |
| UFV150576 | K | L | N | R | E | E | I | D | G | V | K | L | E |
| UFV150577 | K | L | N | R | E | E | I | D | G | V | K | L | E |
| UFV150578 | K | L | N | R | E | E | I | D | G | V | K | L | E |
| UFV150579 | K | L | N | R | E | E | I | D | G | V | K | L | E |
| UFV150580 | K | L | N | R | E | E | I | D | G | V | K | L | |
| UFV150581 | K | L | N | R | E | E | I | D | G | V | | | |
| UFV150582 | K | L | N | R | E | E | I | D | | | | | |
| UFV150583 | K | L | N | R | E | E | | | | | | | |
| UFV150584 | K | L | N | R | | | | | | | | | |

| | Amino acid position and sequence of C-terminus of soluble mini-HA designs compared to wt | | | | | | | TM Domain | | |
|---|---|---|---|---|---|---|---|---|---|---|
| UVF# | 509 | 510 | 511 | 512 | 513 | 514 | 515 | 516 | 517 | 518 | 519 |
| A/California/07/09 | S | T | R | I | Y | Q | I | L | A | I | Y |
| UFV5369 | S | T | R | I | Y | Q | I | | | | |
| UFV150575 | S | T | R | I | Y | Q | I | L | A | I | Y |
| UFV150576 | S | T | R | I | Y | Q | I | L | A | | |
| UFV150577 | S | T | R | I | Y | | | | | | |
| UFV150578 | S | T | R | | | | | | | | |
| UFV150579 | S | | | | | | | | | | |
| UFV150580 | | | | | | | | | | | |
| UFV150581 | | | | | | | | | | | |
| UFV150582 | | | | | | | | | | | |
| UFV150583 | | | | | | | | | | | |
| UFV150584 | | | | | | | | | | | |

Culture Supernatant Analysis

DNA fragments encoding the polypeptides listed in Table 9 and Table 10 were synthesized as described in Example 5.

The harvested culture supernatants were analyzed for the presence of expressed polypeptide by Western Blotting. Samples were run on an SDS-PAGE gel, 4-12% Bis-Tris (ThermoFisher Scientific) under non-reducing conditions and transferred to a PVDF membrane using the iBlot id 2.0 system (ThermoFisher Scientific). For visualization of the bands corresponding with the polypeptides the membrane was blocked with 0.2% blocking agent (Milk powder—BioRad) in TBST prior to incubation with the H1 strain specific derived Hemagglutinin proteins and biotinylated single domain antibody (Influenza 6) sufficiently dilution in block buffer. Following washing (TBST) the membrane was incubated with HRP-labelled Streptavidin (Becton Dickinson 1:250 dilution in block buffer). Subsequently, following another wash step (TBST) the protein bands were visualized by incubation with Trueblue peroxidase substrate (KPL).

Binding of broadly neutralizing monoclonal antibody CR9114 to the expressed polypeptides of the invention was assessed in the harvested culture supernatant through Bio-Layer Interferometry using the OCTET platform. In short, two-fold diluted supernatants in kinetics buffer (Pall ForteBio) were assessed by Streptavidin (SA) biosensors (Pall ForteBio) loaded with biotinylated CR9114. Curve fitting over the initial 20 seconds of the association step is performed to calculate $K_{on}$ values; the concentration of the polypeptides in the culture supernatants was set to 50 mM and the curves were fitted in a 1:1 model. A MOCK sample was included as negative control.

Results and Conclusion

Minimal effect of the alternative C-terminal truncations was observed on the expression level of the polypeptides. All variants, except UFV150565 and UFV150574, displayed a clear band at trimeric height in the Western blot analysis of harvested culture supernatants (FIG. 12A).

The Octet analysis indicated that almost all designs (except UFV150575) did bind to the immobilized CR9114 (FIG. 12B), although overall lower $K_{on}$ values were observed for the C-terminal variants compared to the reference designs 5367 and 5369. This likely was partially due to the basic curve fitting procedure assuming identical protein concentration for all designs; however, binding of the polypeptide to the antibody is evident.

The results clearly show that truncations up to position 502 are possible.

Example 9: Interprotomeric Disulfide Bridges; Alternative Positions

Designs

The polypeptides of the invention are purified from the culture supernatant as covalent trimeric proteins. In the polypeptides as described earlier the covalent link has been established by the introduction of two cysteine residues, in the B-loop (position 397) and C-helix (position 405), that form a disulfide bridge by pairing with the cysteine residue in the adjacent monomer (intermonomeric disulphide bridge). In this Example, two alternative positions for these interprotomeric disulfide bridges were explored (Table 11).

TABLE 11

| Alternative positions for the cysteine residues that form inter-protomeric disulfide bridges. | | |
|---|---|---|
| Polypeptide ID | Cysteine introduction at amino acid postion | Parental Influenza Virus Strain |
| UFV160090 | 397 + 405 | H1N1 A/California/07/09 |
| UFV160093 | 398 + 405 | H1N1 A/California/07/09 |
| UFV160088* | 396 + 408 | H1N1 A/Brisbane/59/07 |

*Knocked out N-linked glycan motif (NxS) at position 400.

Culture Supernatant Analysis

DNA fragments encoding the polypeptides were synthesized as described above.

All assessments on the harvested culture supernatants were performed by AlphaLISA as described in Example 7.

Results and Conclusion

Figure 13:
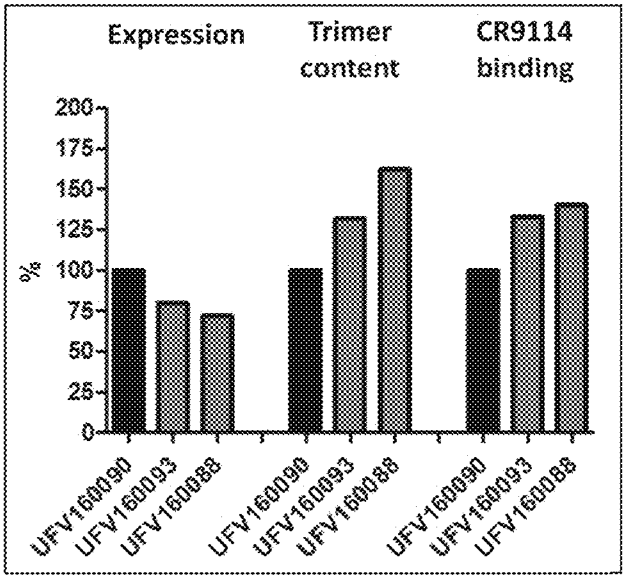
FIG. 13. Normalized expression level, trimer content and CR9114 binding. Culture supernatants were analyzed by AlphaLISA. Reference construct UFV160090 is indicated in black whereas the polypeptide containing introduced cysteines at alternative positions are colored grey. Trimer content and CR9114 binding levels were normalized based on the determined expression level.

AlphaLISA assessment of the harvested culture supernatants on polypeptide expression level, trimer content and CR9114 binding indicated that the alternative inter-protomeric disulfide bridges displayed similar or better than the reference polypeptide UFV160090 (FIG. 13). These data indicated introduction of cysteine residues at positions 398 and 405 (UFV160093) and 396 and 408 (UFV160088) provided an alternative to the inter-protomeric disulfide bridge formed by the introduced cysteines at the positions 397 and 405 (UFV160090).

Example 10: Protection Against Lethal Challenge with H1N1 A/Brisbane/59/07 after Immunization of Naïve Mice with Polypeptides of the Invention In this example, the protective efficacy (based on survival proportion at the end of the follow-up period) of a dose range of $AlOH_3$-adjuvanted UFV160664 in comparison to mock-immunized (PBS) animals and to a fixed dose of UFV4900 (exploratory) was evaluated.

Groups of 8-11 female BALB/c mice (age 6-8 weeks) were intramuscularly immunized 2 times at a 3-week interval with a dose range of soluble trimeric UFV160664 adjuvanted with 50 μg $AlOH_3$ (formulated as 2% Alyhydrogel). The dose range consisted of 4 10-fold dilutions starting at 30 μg up till 0.03 μg. As a positive control for the challenge model mice were immunized twice with 30 μg soluble trimeric UFV4900 (n=10), while 2 immunizations with PBS served as a negative control (n=11). Four weeks after the last immunization mice were bled to analyze the immune response (H1N1 A/Brisbane/59/07 full-length (FL) HA ELISA), and one day later the mice were challenged with 25×LD50 mouse-adapted H1N1 A/Brisbane/59/07 challenge virus and monitored (survival, weight, clinical scores) for 3 weeks. Survival proportion at end of follow-up was the primary outcome parameter.

Results

It was shown that $AlOH_3$-adjuvanted UFV160664 was immunogenic as H1N1 A/Brisbane/59/07 FL HA ELISA titers were significantly increased ($P<0.001$; Mann-Whitney-U test with stepwise, starting at highest dose and Bonferroni adjustment for multiple comparisons) compared to the PBS group for all doses tested. Titers of the 30 μg UFV160664 dose immunized animals were comparable to the 30 μg UFV4900 group (FIG. 15).

In addition, $AlOH_3$-adjuvanted UFV160664 provided significant protection ($P\leq0.003$; Fisher's exact test, Bonferroni correction over constructs, and step-wise testing, starting at highest dose) for all doses, except 0.03 μg, compared to the PBS group. Survival proportion of the 30 μg UFV160664 group (87.5%) was comparable to the 30 μg UFV4900 group (90%) (FIG. 16; upper panel). The bodyweight loss (defined by area under the curve) was significantly reduced ($P\leq0.012$; ANOVA, 2-fold Bonferroni correction over constructs, and step-wise testing, starting at highest dose) for all doses, except 0.03 μg, compared to the PBS group. Bodyweight loss of the 30 μg UFV160664 group was comparable to the 30 μg UFV4900 group (FIG. 16; lower panel).

Conclusion

According to the present invention, it has been shown that $AlOH_3$-adjuvanted UFV160664 is immunogenic and provides protection in a lethal H1N1 A/Brisbane/59/07 mouse challenge model. The immunogenicity and protective efficacy is comparable to $AlOH_3$-adjuvanted UFV4900.

Example 11: Protection Against Lethal Challenge with H1N1 A/Puerto Rico/8/34 after Immunization of Naïve Mice with Polypeptides of the Invention In this example, the protective efficacy (based on survival proportion at the end of the follow-up period) of a dose range of 2% Adjuplex-adjuvanted UFV160664 in comparison to mock-immunized (PBS) animals and to a fixed dose of UFV4900 (exploratory) was evaluated.

Again, groups of 8-11 female BALB/c mice (age 6-8 weeks) were intramuscularly immunized 2 times at a 3-week interval with a dose range of soluble trimeric UFV160664 adjuvanted with 2% (v/v) Adjuplex. The dose range consisted of 4 10-fold dilutions starting at 30 mcg up till 0.03 μg. As a positive control for the challenge model mice were immunized twice with 30 μg soluble trimeric UFV4900 (n=10), while 2 immunizations with PBS served as a negative control (n=11). Four weeks after the last immunization mice were challenged with 12.5×LD50 mouse-adapted H1N1 A/Puerto Rico/8/34 challenge virus and monitored (survival, weight, clinical scores) for 3 weeks. Survival proportion at end of follow-up was the primary outcome parameter.

Results

Figure 17:
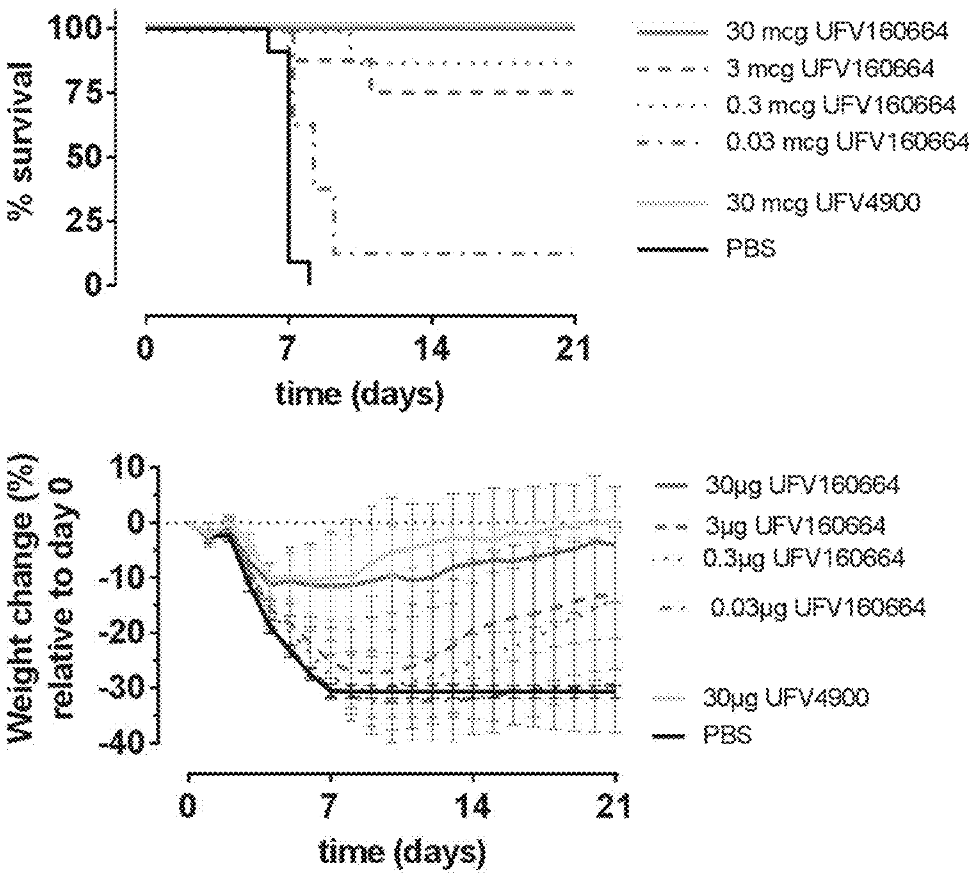
FIG. 17: Upper panel: Survival proportion during the follow-up period after H1N1 A/Puerto Rico/8/34 challenge of mice immunized with polypeptides of the invention. Bottom panel: Relative bodyweight during the follow-up period after H1N1 A/Puerto Rico/8/34 challenge of mice immunized with polypeptides of the invention. Relative bodyweight change was expressed relative to Day 0. Cumulative bodyweight loss during the follow-up period was determined by calculating the Area Under the Curve (AUC). Error bars denote 95% confidence interval.

It was shown that 2% Adjuplex-adjuvanted UFV160664 provided significant protection ($P\leq0.003$; Fisher's exact test, Bonferroni correction over constructs, and step-wise testing, starting at highest dose) for all doses, except 0.03 μg, compared to the PBS group. Survival proportion of the 30 μg UFV160664 group (100%) was identical to the 30 μg UFV4900 group (100%) (FIG. 17; upper panel).

The bodyweight loss (defined by area under the curve) was significantly reduced ($P\leq0.026$; ANOVA, 2-fold Bonferroni correction over constructs, and step-wise testing, starting at highest dose) for all doses, compared to the PBS group. Bodyweight loss of the 30 mcg UFV160664 group was comparable to the 30 mg UFV4900 group (FIG. 17, lower panel).

Conclusion

According to the present invention, it has been shown that 2% Adjuplex-adjuvanted UFV160664 provides protection in a lethal H1N1 A/Puerto Rico/8/34 mouse challenge model. Protective efficacy is comparable to 2% Adjuplex-adjuvanted UFV4900.

Example 12: Polypeptides of the Invention are Immunogenic and Shows Comparable Efficacy Relative to a Standard-of-Care Vaccine in a H1N1 A/Netherlands/602/09 Naïve Ferret Challenge Model In this example, the in vivo immunogenicity and protective efficacy (based on lung viral load at end of follow-up)

of two doses of UFV160664 in comparison to adjuvant-only immunized animals and to a standard-of-care seasonal influenza vaccine in a H1N1 A/Netherlands/602/09 naïve ferret challenge model was evaluated.

Groups (n=6) of naïve female ferrets were immunized intramuscularly three times, 3 weeks apart, with 50 or 5 μg UFV160664 adjuvanted with 5% Adjuplex. A negative control group was immunized with adjuvant only. A reference group representing standard of care was immunized with a commercially available standard-of-care (SoC) seasonal influenza vaccine. Four weeks after the final immunization animals were challenged intratracheally with $10^6$ TCID50 H1N1 A/Netherlands/602/09 at day 0. During the 4-day follow-up period several virological and clinical parameters were recorded.

Results

Figure 18:
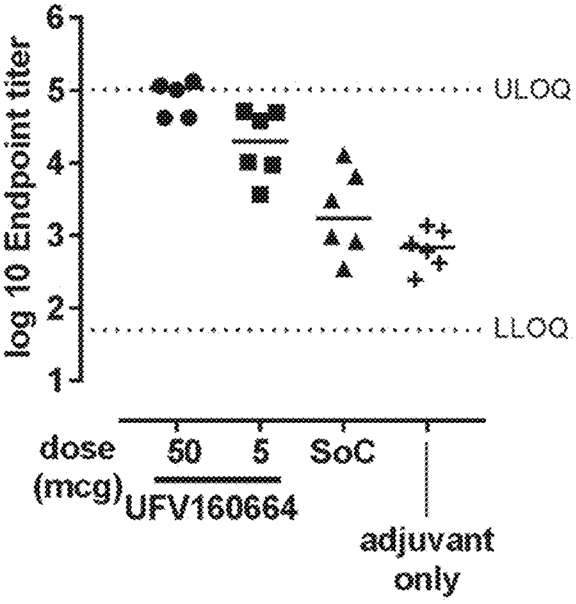
FIG. 18: H1 A/California/07/09 FL HA-specific antibody titers after immunization of ferrets with polypeptides of the invention. Statistical comparison of different dosages of polypeptide of the invention and SOC to the adjuvant only group using censored ANOVA with post-hoc t-test, starting at highest dose and Bonferroni adjustment for multiple comparisons. Dashed lines indicate ULLOQ (Uper Limit of Quantification) and LLOQ. Horizontal line per group denotes group median.

It was shown that both doses of 5% Adjuplex-adjuvanted UFV160664 induced significantly higher H1 A/California/07/09 HA-specific antibody titers compared to the adjuvant only group titers (P<0.001; censored ANOVA, with post-hoc t-test. Bonferroni correction for multiple comparisons and stepwise testing, starting at the highest dose), while SoC did not (FIG. 18). Both doses of 5% Adjuplex-adjuvanted UFV160664 induced significant higher H1 A/California/07/09 HA-specific antibody titers compared to the adjuvant only group titers (P<0.001; censored ANOVA, with post-hoc t-test, Bonferroni correction for multiple comparisons and stepwise testing, starting at the highest dose), while SoC did not (FIG. 18).

Figure 19:
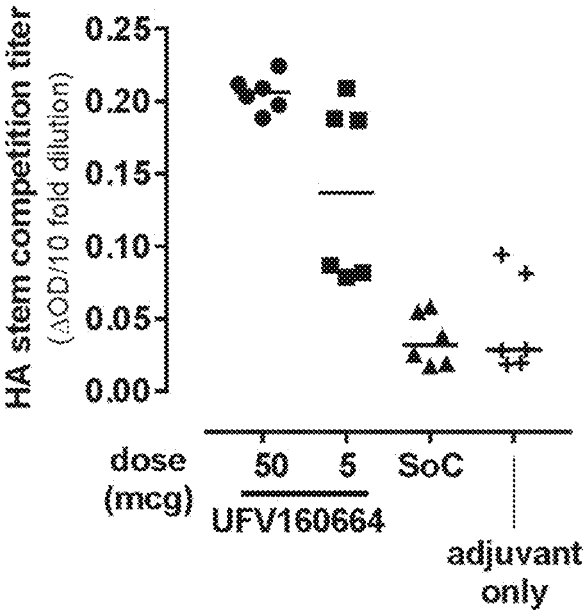
FIG. 19: H1 A/California/07/09 FL HA stem-specific antibody titers after immunization of ferrets with polypeptides of the invention. Statistical comparison of different dosages of polypeptide of the invention and SOC to the adjuvant only group using censored ANOVA with post-hoc t-test, starting at highest dose and Bonferroni adjustment for multiple comparisons. Horizontal line per group denotes group median.

In addition, both doses of 5% Adjuplex-adjuvanted UFV160664 induced significantly higher H1 A/California/07/09 HA stem-specific antibody titers (measured with a CR9114 competition assay) compared to the adjuvant only group titers (P<0.001; censored ANOVA, with post-hoc t-test, Bonferroni correction for multiple comparisons and stepwise testing, starting at the highest dose), while SoC did not (FIG. 19).

Figure 20:
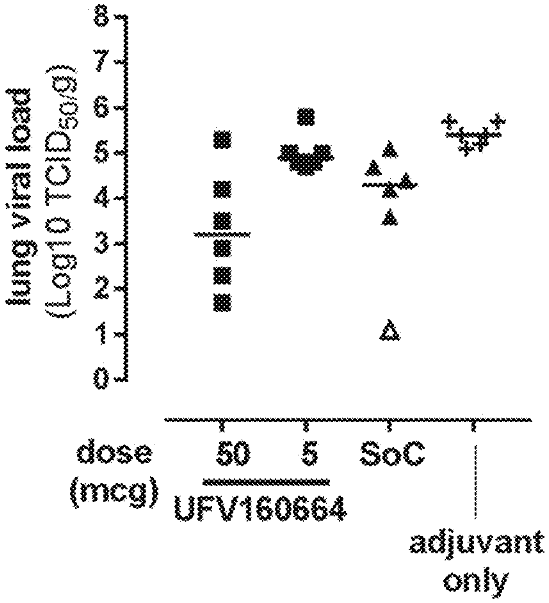
FIG. 20: Lung viral load titers at the end of the follow-up period (day 4 after challenge) after immunization of ferrets with polypeptides of the invention followed by challenge with H1N1 A/NL/602/09. Horizontal line per group denotes group median, open symbols denote samples at the Limit Of Detection (LOD).

The 50 μg 5% Adjuplex-adjuvanted UFV160664 dose and SoC significantly reduced lung viral load compared to the adjuvant only group titers (50 μg UFV160664: P<0.001, SoC: P<0.05; censored ANOVA, with post-hoc t-test, Bonferroni correction for multiple comparisons and stepwise testing, starting at the highest dose) (FIG. 20).

Conclusion

According to the present invention it has been shown that both doses of 5% Adjuplex-adjuvanted UFV160664 are immunogenic and that the 50 μg dose provides protection comparable to SoC vaccine reference group.

Example 13: Polypeptides of the Invention Shows Comparable Efficacy Relative to a Positive Control in a H5N1 A/Indonesia/05/05 Naïve Ferret Challenge Model In this example, the in vivo immunogenicity and protective efficacy (based on lung viral load at end of follow-up) of two doses of UFV160664 was evaluated in comparison to adjuvant-only immunized animals and to a positive control group, immunized with H5 FL HA homologous to the challenge strain (exploratory) in a heterosubtypic H5N1 A/Indonesia/05/05 naïve ferret challenge model.

Groups (n=6) of naïve female ferrets were immunized intramuscularly three times, 3 weeks apart, with 50 or 5 μg UFV160664 adjuvanted with 5% Adjuplex. A negative control group was immunized with adjuvant only. A positive control group was immunized 5% Adjuplex adjuvanted H5 A/Indonesia/05/05 HA, homologous to the challenge strain. Four weeks after the final immunization animals were challenged intratracheally with $10^5$ TCID50 H5N1 A/Indonesia/05/05 at day 0. During the 5 day follow-up period several virological and clinical parameters were recorded.

Results

Figure 21:
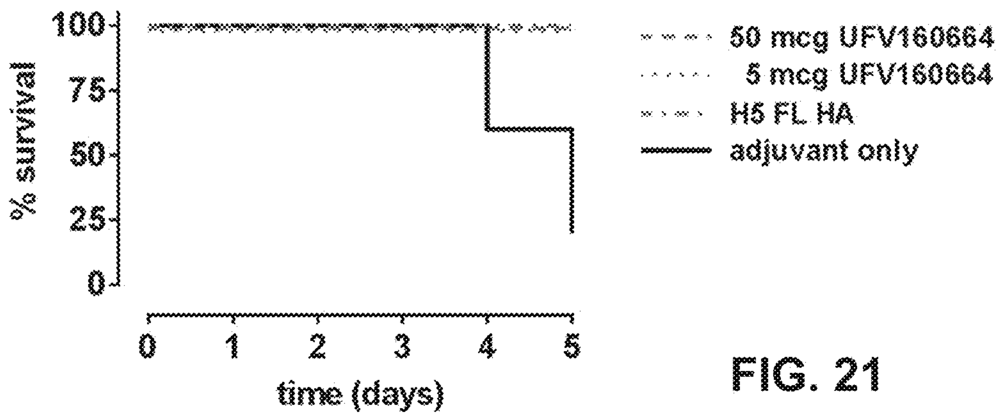
FIG. 21: Survival during the 5 day follow-up period of ferrets immunized with polypeptides of the inventions, H5 FL HA (positive challenge control) and adjuvant only (negative challenge control), followed by challenge with H5N1 A/Indonesia/05/05.
Figure 22:
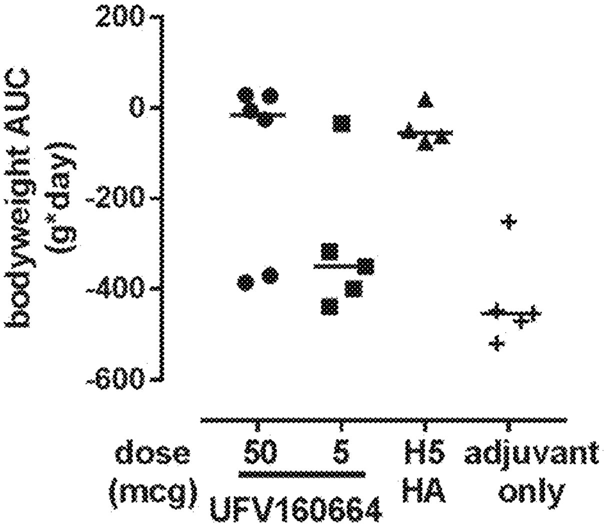
FIG. 22: Cumulative (AUC) bodyweight loss of individual animals, obtained from consecutive daily bodyweight measurements during the follow-up period (day 0 to 5), relative to the bodyweight ay day 0 after immunization of ferrets with polypeptides of the invention followed by challenge with H5N1 A/Indonesia/05/05. Horizontal line per group denotes group median.

It was shown that animals immunized with both doses of 5% Adjuplex-adjuvanted UFV160664 and the positive control group survived the follow-up period, while the survival proportion of the adjuvant-only group was 25% (FIG. 21). The cumulative bodyweight loss during follow up was reduced for four out of 6 animals immunized with 5% Adjuplex-adjuvanted 50 μg UFV160664 compared to the adjuvant only group. The positive control group had comparable reduction in body weight loss to the four animals of the 50 μg UFV160664 group, and reduction in bodyweight loss was significantly less compared to the adjuvant only group (P<0.001; ANOVA, with post-hoc t-test, Bonferroni correction for multiple comparisons and stepwise testing, starting at the highest dose) (FIG. 22).

Figure 23:
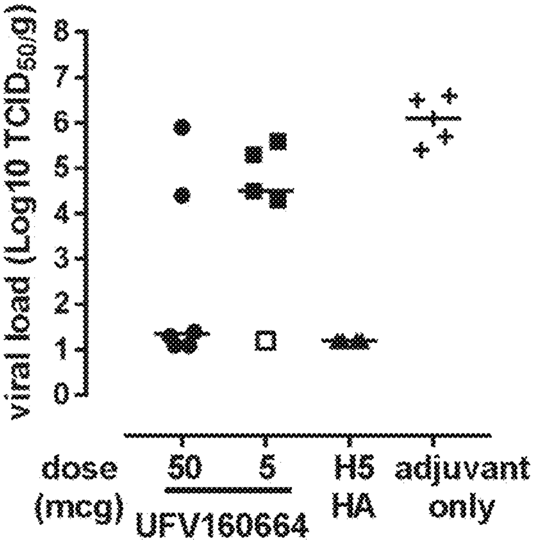
FIG. 23: Lung viral load titers at day of death or the end of the follow-up period (day 5 after challenge) after immunization of ferrets with polypeptides of the invention followed by challenge with H5N1 A/Indonesia/05/05. Horizontal line per group denotes group median, open symbols denote samples at the Limit Of Detection (LOD).

Both the 5% Adjuplex-adjuvanted 50 mcg UFV160664 and the positive control group significantly reduced lung viral load compared to the adjuvant only group (50 μg UFV160664: P<0.01, positive control: P<0.05; censored ANOVA, with post-hoc t-test, Bonferroni correction for multiple comparisons and stepwise testing, starting at the highest dose) (FIG. 23).

Figure 24:
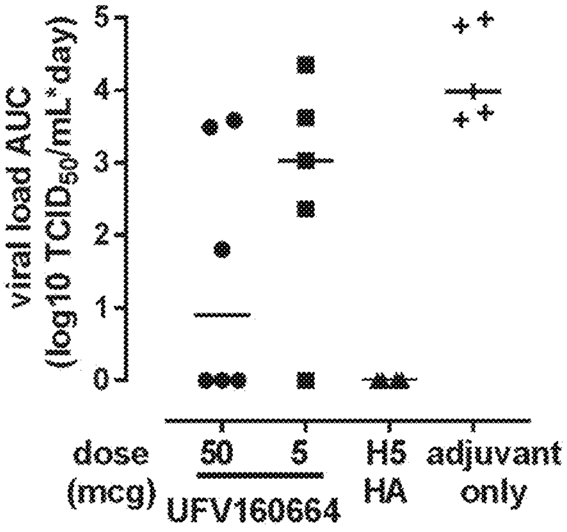
FIG. 24: Cumulative (AUC) throat viral load, obtained from consecutive daily throat swabs during the follow-up period (day 0 to 5), relative to the bodyweight ay day 0 after immunization of ferrets with polypeptides of the invention followed by challenge with H5N1 A/Indonesia/05/05. Horizontal line per group denotes group median.

Both the 5% Adjuplex-adjuvanted 50 μg UFV160664 and the positive control group significantly reduced cumulative (daily swabs) throat viral load compared to the adjuvant only group (50 mcg UFV160664: P<0.05, positive control: P<0.001; ANOVA, with post-hoc t-test, Bonferroni correction for multiple comparisons and stepwise testing, starting at the highest dose) (FIG. 24).

Conclusion

According to the present invention, it was show that both the 5 μg and 50 μg UFV160664 doses prevented mortality. In addition, the 50 μg UFV160664 dose reduced bodyweight loss and significantly reduced lung and throat viral load, comparable to the positive control group.

Example 14: Humoral and Cellular Immunogenicity after Immunization of Naïve Mice with Adenoviral Vector Expressing Polypeptide of the Invention In this example, the humoral and cellular immunogenicity of a dose range of an adenovector 26 (Ad26) containing nucleic acid expressing a polypeptide of the invention (in particular polypeptide UFV 171590), was evaluated. For comparison, control mice were immunized with the empty adenovector, a fixed dose of 2% Adjuplex adjuvanted UFV160664 protein, or a heterologous immunization regimen of UFV171590 prime, adjuvanted UFV160664 boost, was evaluated.

Groups of female BALB/c mice received two intramuscular immunizations, four weeks apart. Three groups of eight mice were immunized with either $10^8$, $10^9$ or $10^{10}$ virus particles (vp) of UFV171590. As negative control, four mice received two immunizations with $10^{10}$ vp of the empty adenovector (Ad26_empty). A group of five mice received two protein immunizations with 30 μg of soluble trimeric UFV160664 adjuvanted with 2% Adjuplex. A group of five mice received a prime immunization with $10^{10}$ vp UFV171590, followed by a boost immunization with 30 μg UFV160664 adjuvanted with 2% Adjuplex. Three weeks after the boost immunization mice were sacrificed and blood and spleen samples were isolated to analyze the humoral immune response to H1 A/California/07/09 (full-length (FL)

ELISA and stem-competition ELISA) and the cellular immune response to UFV160664 peptides (T-cell ELISpot), respectively.

Results

Figure 25:
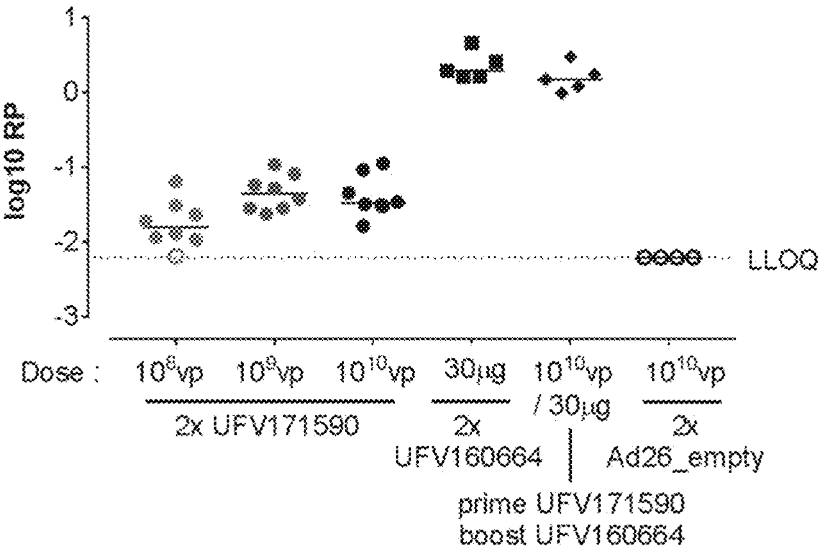
FIG. 25: H1 A/California/07/09 FL HA-specific antibody titers after immunization of mice with polypeptides of the invention. The dashed line indicates the LLOQ (Lower Limit of Quantification), open symbols represent samples on LLOQ, the horizontal line per group denotes the group median.
Figure 26:
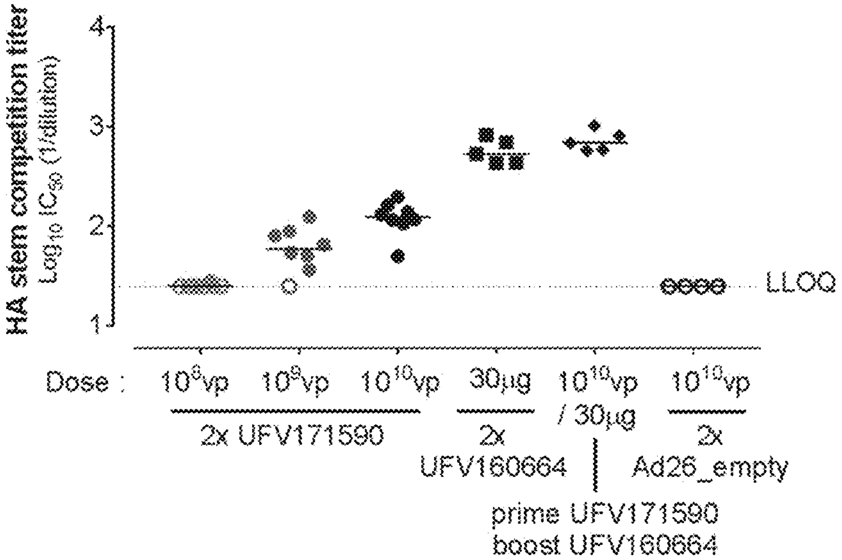
FIG. 26: H1 A/California/07/09 FL HA stem-specific antibody titers after immunization of mice with polypeptides of the invention. The dashed line indicates the LLOQ (Lower Limit of Quantification), open symbols represent samples on LLOQ, the horizontal line per group denotes the group median.

It was shown that all doses of the adenovector containing nucleic acid expressing the polypeptide of this invention induced significant H1 A/California FL HA ELISA binding titers compared to immunization with the empty vector ($10^8$ vp, $10^9$ vp and $10^{10}$ vp: p<0.001, likelihood ratio test-based Tobit regression model). (FIG. 25). In addition, significant HA stem-specific antibody titers (measured with a CR9114 competition assay) were induced by $10^9$ and $10^{10}$ vp of UFV171590 compared to the empty vector (p<0.001; likelihood ratio test-based Tobit regression model) (FIG. 26). Both prime-boost with adjuvanted UFV160664 as well as UFV171590 prime, adjuvanted UFV160664 boost, induced significant H1 A/California/07/09 FL HA binding titers (FIG. 25) and HA stem-specific antibody titers (p<0.001 likelihood ratio test-based Tobit regression model) (FIG. 26).

Figure 27:
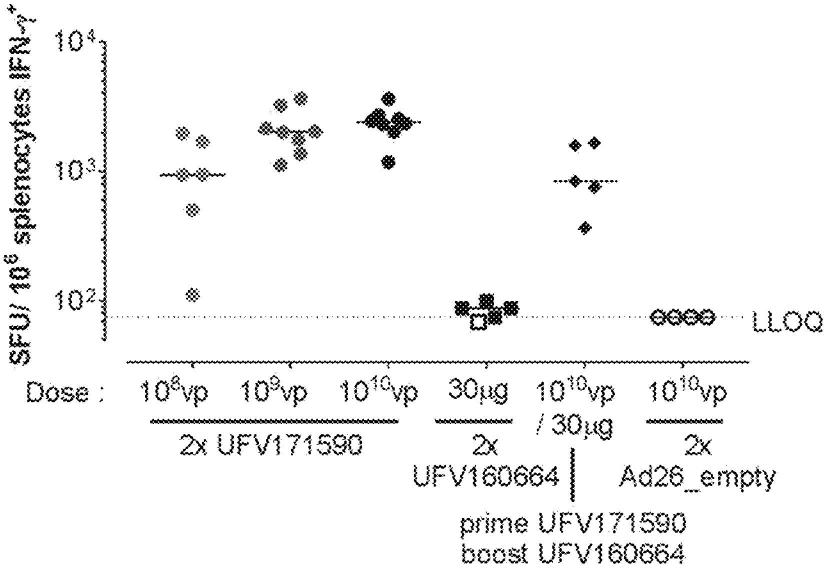
FIG. 27: IFN-γ producing T-cells per million splenocytes of immunized mice, after in vitro stimulation with UFV160664 peptides. The dashed line indicates the LLOQ (Lower Limit of Quantification), open symbols represent samples on LLOQ, the horizontal line per group denotes the group median.

In addition to a significant humoral response, UFV171590 induced a significant IFN-γ T-cell response compared to the empty vector as measured after stimulation by UFV160664 peptides by T-cell ELISpot (FIG. 27). All doses of UFV171590 induced significant T-cell responses (p<0.001; likelihood ratio test-based Tobit regression model), as well as the group of mice which received UFV171590-prime followed by UFV160664-boost immunization (p<0.001). Two immunizations with adjuvanted UFV160664 did not induce a detectable IFN-γ T-cell response (FIG. 27).

Conclusion

It has been shown that an adenovector 26 expressing a polypeptide of the invention (UFV171590) induces significant humoral and cellular responses to H1 A/California/07/09 FL HA in a mouse model, either in a homologous immunization regimen or in combination with adjuvanted UFV160664 boost. Adjuvanted UFV160664 also induced a significant humoral immune response but did not induce a detectable T-cell response in absence of a prime with UFV171590.

Example 15: Transfer of Mutations from Polypeptide 160664 to Different Group 1 Backbones Protein Expression in Mammalian Cells DNA fragments encoding additional polypeptides of the invention (i.e. based on different HA backbones, see FIG. 28A) were synthesized (Genscript) and cloned in the pcDNA2004 plasmid (in-house modified pcDNA3 vector with an enhanced CMV promotor). The polypeptides were produced in Expi-CHO cell cultures in ExpiCHO™ Expression medium by transient transfection using the Expi-Fectamine™ (Gibco, ThermoFisher Scientific). To the Expi-CHO cells cultures, ExpiFectamine CHO enhancer and ExpiCHO feed (Gibco, ThermoFisher Scientific) was added one day post transfection. Culture supernatants containing secreted polypeptides were harvested at day 7 by centrifugation followed by 0.2 μm filtration.

Culture Supernatant Analysis

The level of expressed polypeptide in the harvested culture supernatant was assessed through Bio-Layer Interferometry using the OCTET platform. In short, biotinylated mAb CR9114 was immobilized on Streptavidin (SA) biosensors (Pall FortéBio) following which a standard curve was established by assessing the binding shift of a dilution series of a well-defined purified homologous polypeptide. Subsequently the binding shift of pre-diluted harvested culture supernatant containing the polypeptide (~5-15 μg/mL diluted in kinetics buffer) was measured and the concentration was calculated using the established calibration curve.

Secondly, the content of polypeptides of the invention in the Expi-CHO culture harvests was assessed by analytical SEC in a High-Performance Liquid Chromatography (HPLC) Infinity 1260 series setup (Agilent). Culture supernatant containing the polypeptide ~3 μg protein injection, except for UFV180500 (0.8 μg), was run (1 mL/min.) over a TSK gel G3000SWxl column (Sigma-Aldrich) and the eluate was monitored by UV detection (OD280, mAU). The SEC profiles were analyzed by the Astra 6 software package (Wyatt Technology). Folding of the polypeptide was assessed by Amplified Homogeneous Assay (AlphaLISA). This in-solution and in-binding equilibrium assay is based on successful binding of both a donor and acceptor bead to the polypeptide. When in close proximity, laser irradiation of the donor bead at 680 nm generates a flow of singlet oxygen, triggering chemical events in nearby acceptor bead, resulting in a chemiluminescent emission at 615 nm. AlphaLISA assay was performed by simultaneous addition of Nickel donor beads (10 μg/mL) and anti-human IgG acceptor beads (10 μg/mL, both PerkinElmer) to culture supernatant in presence of either CR9114 (2 nM) or MD3606 (2 nM). The polypeptide-containing culture supernatants were titrated in a 3-fold dilution range starting at 1667 ng/mL. Read out was performed after 2 hours of incubation (room temperature) using the EnSight™ multimode plate reader (PerkinElmer).

Results and Conclusion

Figure 28:
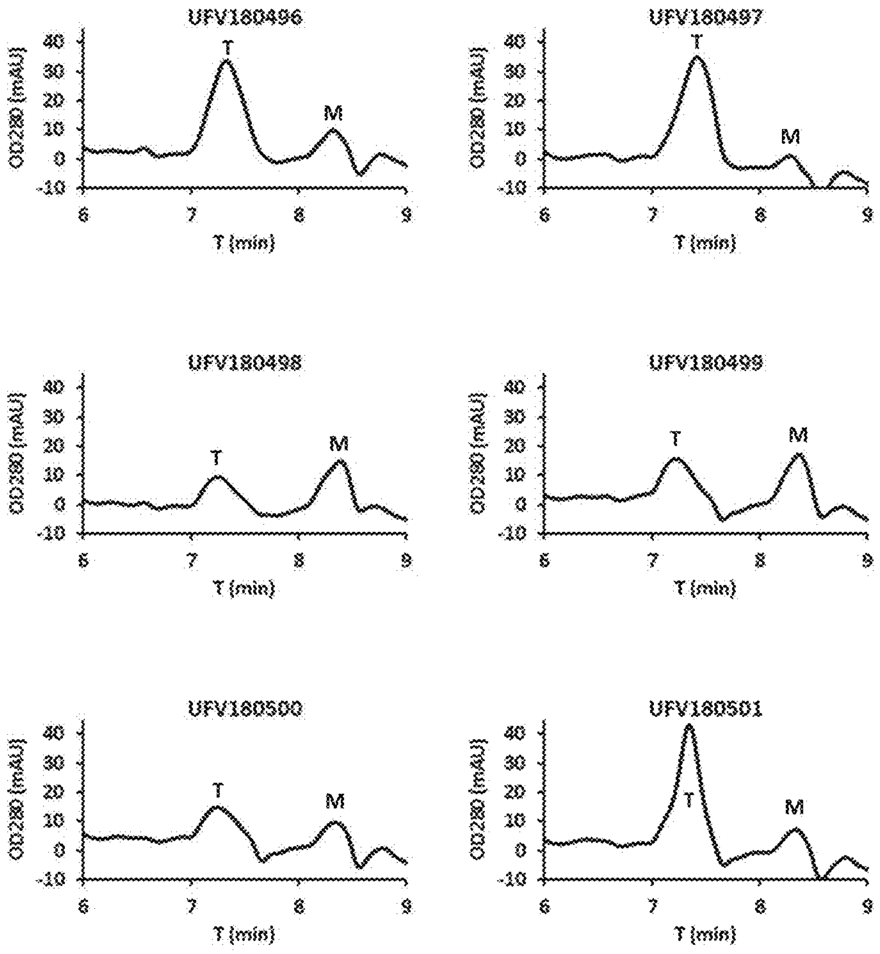
FIG. 28: In vitro characterization of culture supernatants of EXPI-CHO expressed trimeric stem polypeptides derived from different Group 1 influenza strains wherein the mutations of the UFV160664 construct were transferred. A. Protein expression levels as determined by OCTET (anti-His2); B. SEC profiles, trimer and monomer peak indicated with respectively ‘T’ and ‘M’; C. Binding curves of the polypeptides to mAb CR9114 and MD3606 as determined by AlphaLISA. The mutations of the trimeric stem polypeptide of the invention in strain A/California/07/09) are transferable to other Group 1 backbones; trimeric mini-HA is expressed and binding of stem specific antibody CR9114 and multidomain MD3606 is observed.

Analysis of the 35 mL ExpiCHO transfections shows the His-tagged polypeptides are expressed (FIG. 28A). The expression levels varied from 42 mg/L (backbone H5 A/Vietnam/1203/04) up to 375 mg/L (backbone H1 A/California/07/09) and indicate that all polypeptides express well. Furthermore, the SEC profiles (FIG. 28B) show that for each expressed polypeptide a significant trimeric (T) and a monomeric (M) fraction is detectable. Differences in relative trimer and monomer content were observed depending on the utilized backbone strain. To further assess the correct folding of the polypeptide, binding of a relevant antibody (CR9114) and multidomain (MD3606) was assessed by AlphaLISA. For all polypeptide a specific binding signal for both CR9114 and MD3606 was observed (FIG. 28C). The expression, SEC profiles and binding data indicate that the mutations according to the present invention (e.g. the mutations of UFV160664, which is based on strain A/California/07/09) are transferable to other Group 1 backbones. Thus, the polypeptides UFV180496, UFV180497, UFV190498, UFV180499, UFV180500 and UFV180501, were all correctly folded and trimeric and secreted into the culture supernatant.

TABLE 12

Standard amino acids, abbreviations and properties

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |

TABLE 12-continued

| Standard amino acids, abbreviations and properties | | | | |
|---|---|---|---|---|
| Amino Acid | 3-Letter | 1-Letter | Side chain polarity | Side chain charge (pH 7.4) |
| glutamine | Gln | Q | polar | Neutral |
| glycine | Gly | G | nonpolar | Neutral |
| histidine | His | H | polar | positive (10%) neutral (90%) |
| isoleucine | Ile | I | nonpolar | Neutral |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

REFERENCES

Bommakanti et al. (2010), Proc. Natl. Acad. Sci. USA 107(31): 13701-13706.

Bommakanti et al. (2012), J Virol 86: 13434.

Ciani et al. (2010), Proc. Natl. Acad. Sci. USA 107(46): 19850-19855.

Ekiert et al. (2009), Science 324:246.

Ekiert et al. (2011), Science 333: 844.

Das et al. (1985), Prog Nucleic Acid Res Mol Biol 32: 217-236.

Gill et al. (2001), Gene Therapy 8: 1539-1546.

Kaufmann (2000), Mol Biotechnol 16: 151-160.

Letarov et al. (1993), Biochemistry Moscow 64: 817-823.

Lorieau et al. (2010), Proc. Natl. Acad. Sci. USA, 107: 11341.

Lu et al. (2014), Proc. Natl. Acad. Sci. USA, 111: 125-130.

Mallajosyula et al. (2014), PNAS, published online Jun. 9, 2014: E2514-E2523.

S-Guthe et al. (2004), J. Mol. Biol. 337: 905-915.

Steel et al. (2010), mBio 1(1): 1-9.

Throsby et al. (2008), Plos One 12(3): 1-15.

Winter et al. (1981) Nature 292: 72-75.

SEQUENCES

SEQ ID NO 1: H1 Full length (A/Brisbane/59/2007)

```
MKVKLLVLLC TFTATYADTI CIGYHANNST DTVDTVLEKN VTVTHSVNLL    50
ENSHNGKLCL LKGIAPLQLG NCSVAGWILG NPECELLISK ESWSYIVEKP   100
NPENGTCYPG HFADYEELRE QLSSVSSFER FEIFPKESSW PNHTVTGVSA   150
SCSHNGESSF YRNLLWLTGK NGLYPNLSKS YANNKEKEVL VLWGVHHPPN   200
IGDQKALYHT ENAYVSVVSS HYSRKFTPEI AKRPKVRDQE GRINYYWTLL   250
EPGDTIIFEA NGNLIAPRYA FALSRGFGSG IINSNAPMDK CDAKCQTPQG   300
AINSSLPFQN VHPVTIGECP KYVRSAKLRM VTGLRNIPSI QSRGLFGAIA   350
GFIEGGWTGM VDGWYGYHHQ NEQGSGYAAD QKSTQNAING ITNKVNSVIE   400
KMNTQFTAVG KEFNKLERRM ENLNKKVDDG FIDIWTYNAE LLVLLENERT   450
LDFHDSNVKN LYEKVKSQLK NNAKEIGNGC FEFYHKCNDE CMESVKNGTY   500
DYPKYSEESK LNREKIDGVK LESMGVYQIL AIYSTVASSL VLLVSLGAIS   550
FWMCSNGSLQ CRICI                                         565
```

SEQ ID NO 2: H1 Full length (A/California/07/2009)

```
MKAILVVLLYTFATANADTLCIGYHANNSTDTVDTVLEKNVTVTHSVNLLEDKHNGK
LCKLRGVAPLHLGKCNIAGWILGNPECESLSTASSWSYIVETPSSDNGTCYPGDFID
YEELREQLSSVSSFERFEIFPKTSSWPNHDSNKGVTAACPHAGAKSFYKNLIWLVKK
GNSYPKLSKSYINDKGKEVLVLWGIHHPSTSADQQSLYQNADAYVFVGSSRYSKKFK
PEIAIRPKVRDQEGRMNYYWTLVEPGDKITFEATGNLVVPRYAFAMERNAGSGIIIS
DTPVHDCNTTCQTPKGAINTSLPFQNIHPITIGKCPKYVKSTKLRLATGLRNIPSIQ
SRGLFGAIAGFIEGGWTGMVDGWYGYHHQNEQGSGYAADLKSTQNAIDEITNKVNSV
IEKMNTQFTAVGKEFNHLEKRIENLNKKVDDGFLDIWTYNAELLVLLENERTLDYHD
SNVKNLYEKVRSQLKNNAKEIGNGCFEFYHKCDNTCMESVKNGTYDYPKYSEEAKLN
REEIDGVKLESTRIYQILAIYSTVASSLVLVVSLGAISFWMCSNGSLQCRICI
```

SEQ ID NO 3: A/Texas/UR06-0526/2007 (H1N1)

```
MKVKLLVLLCTFTATYADTICIGYHANNSTDTVDTVLEKNVTVTHSVNLLEDSHNGK
LCLLKGTAPLQLGNCSVAGWILGNPECELLISKESWSYIVETPNPENGTCYPGYFAD
YEELREQLSSVSSFERFEIFPKESSWPNHTVTGVSASCSHNGKSSFYRNLLWLTGKN
GLYPNLSKSYANNKEKEVLVLWGVHHPPNIGDQRALYHTENAYVSVVSSHYSRRFTP
EIAKRPKVRDQEGRINYYWILLEPGDTIIFEANGNLIAPRFAFALSRGFGSGIITSN
APMGECDAKCQTPQGAINSSLPFQNVHPVTIGECPKYVRSAKLRMVTGLRNIPSIQS
RGLFGAIAGFIEGGWTGMVDGWYGYHHQNEQGSGYAADQKSTQNAINGITNKVNSVI
EKMNTQFTAVGKEFNKLERRMENLNKKVDDGFLDIWTYNAELLVLLENERTLDFHDS
NVKNLYEKVKNQLKNNAKEIGNGCFEFYHKCNDECMESVKNGTYDYPKYSEESKLNR
EKIDGVKLESMGVYQILAIYSTVASSLVLLISLGAISFWMCSNGSLQCRICI
```

SEQ ID NO 4: A/NewYork/629/1995 (H1N1)

```
MKVKLLVLLCAFTATYADTICIGYHANNSTDTVDTVLEKNVTVTHSVNLLEDSHNGK
LCRLKGTAPLQLGNCSVAGWILGNPECESLFSKESWSYIAETPNPENGTCYPGYFAD
YEELREQLSSVSSFERFEIFPKESSWPNHTVTKGVTASCSHNGKSSFYKNLLWLTEK
NGLYPNLSKSYVNNKEKEVLVLWGVHHPSNIGDQRAIYHTENAYVSVVSSHYSRRFT
PEIAKRPKVRDQEGRINYYWILLEPGDTIIFEANGNLIAPWYAFALSRGFGSGIITS
NASMSECDAKCQTPQGAINSSLPFQNVHPVTIGECPKYVRSTKLRMVTGLRNIPSIQ
SRGLFGAIAGFIEGGWIGMIDGWYGYHHQNEQGSGYAADQKSTQNAIDGITNKVNSV
IEKMNTQFTAVGKEFNKLERRMENLNKKVDDGFLDIWTYNAELLVLLENERILDFHD
SNVKNLYEKVKNQLKNNAKEIGNGCFEFYHKCNNECMESVKNGTYDYPKYSEESKLN
REKIDGVKLESMGVYQILAIYSTVASSLVLLVSLGAISFWMCSNGSLQCRICI
```

-continued

SEQUENCES

SEQ ID NO 5: A/AA_Marton/1943 (H1N1)
MKARLLVLLCALAATDADTICIGYHANNSIDTVDTVLEKNVIVIHSVNLLEDSHNGK
LCRLKGIAPLQLGKCNIAGWILGNPECESLLSERSWSYIVETPNSENGTCYPGDFID
YEELREQLSSVSSFERFEIFSKESSWPKHNTIRGVTAACSHAGKSSFYRNLLWLTEK
DGSYPNLNNSYVNKKGKEVLVLWGVHHPSNIKDQQTLYQKENAYVSVVSSNYNRRFT
PEIAERPKVRGQAGRMNYYWILLKPGDTIMFEANGNLIAPWYAFALSRGFGSGIITS
NASMHECDTKCQTPQGAINSSLPFQNIHPVTIGECPKYVRSTKLRMVTGLRNIPSIQ
SRGLFGAIAGFIEGGWIGMIDGWYGYHHQNEQGSGYAADQKSTQNAINGITNKVNSV
IEKMNTQFTAVGKEFNNLEKRMENLNKKVDDGFLDIWTYNAELLVLLENERILDFHD
SNVKNLYEKVKNQLRNNAKEIGNGCFEFYHKCNNECMESVKNGTYDYPKYSEESKLN
REKIDGVKLESMGVYQILAIYSTVASSLVLLVSLGAISFWMCSNGSLQCRICI SEQ ID NO 6: A/Adachi/2/57 (H2N2)
MAIIYLILLFTAVRGDQICIGYHANNSTEKVDTILERNVIVTHAKDILEKTHNGKLC
KLNGIPPLELGDCSIAGWLLGNPECDRLLSVPEWSYIMEKENPRNGLCYPGSFNDYE
ELKHLLSSVKHFEKVKILPKDRWTQHTTIGGSQACAVSGNPSFFRNMVWLIKKGSDY
PVAKGSYNNTSGEQMLIIWGVHHPIDETEQRTLYQNVGTYVSVGISTLNKRSTPEIA
TRPKVNGLGSRMEFSWILLDMWDTINFESIGNLIAPEYGFKISKRGSSGIMKTEGIL
ENCETKCQTPLGAINTTLPFHNVHPLTIGECPKYVKSEKLVLATGLRNVPQIESRGL
FGAIAGFIEGGWQGMVDGWYGYHHSNDQGSGYAADKESTQKAFDGITNKVNSVIEKM
NTQFEAVGKEFGNLERRLENLNKKMEDGFLDVWTYNAELLVLMENERILDFHDSNVK
NLYDKVRMQLRDNVKELGNGCFEFYHKCDDECMNSVKNGTYDYPKYEEESKLNRNEI
KGVKLSSMGVYQILAIYATVAGSLSLAIMMAGISFWMCSNGSLQCRICI SEQ ID NO 7: A/Singapore/1/57 (H2N2)
MAIIYLILLFTAVRGDQICIGYHANNSTEKVDTILERNVIVTHAKDILEKTHNGKLC
KLNGIPPLELGDCSIAGWLLGNPECDRLLSVPEWSYIMEKENPRDGLCYPGSFNDYE
ELKHLLSSVKHFEKVKILPKDRWTQHTTIGGSRACAVSGNPSFFRNMVWLTEKGSNY
PVAKGSYNNTSGEQMLIIWGVHHPNDEKEQRTLYQNVGTYVSVGISTLNKRSTPDIA
TRPKVNGLGSRMEFSWILLDMWDTINFESIGNLIAPEYGFKISKRGSSGIMKTEGIL
ENCETKCQTPLGAINTTLPFHNVHPLTIGECPKYVKSEKLVLATGLRNVPQIESRGL
FGAIAGFIEGGWQGMIDGWYGYHHSNDQGSGYAADKESTQKAFDGITNKVNSVIEKM
NTQFEAVGKEFSNLERRLENLNKKMEDGFLDVWTYNAELLVLMENERILDFHDSNVK
NLYDKVRMQLRDNVKELGNGCFEFYHKCDDECMNSVKNGTYDYPKYEEESKLNRNEI
KGVKLSSMGVYQILAIYATVAGSLSLAIMMAGISFWMCSNGSLQCRICI SEQ ID NO 8: A/Viet Nam/1203/2004 H5N1)
MEKIVLLFAIVSLVKSDQICIGYHANNSTEQVDTIMEKNVTVTHAQDILEKKHNGKL
CDLDGVKPLILRDCSVAGWLLGNPMCDEFINVPEWSYIVEKANPVNDLCYPGDFNDY
EELKHLLSRINHFEKIQIIPKSSWSSHEASLGVSSACPYQGKSSFFRNVVWLIKKNS
TYPTIKRSYNNTNQEDLLVLWGIHHPNDAAEQTKLYQNPTTYISVGTSTLNQRLVPR
IATRSKVNGQSGRMEFFWTILKPNDAINFESNGNFIAPEYAYKIVKKGDSTIMKSEL
EYGNCNTKCQTPMGAINSSMPFHNIHPLTIGECPKYVKSNRLVLATGLRNSPQRERR
RKKRGLFGAIAGFIEGGWQGMVDGWYGYHHSNEQGSGYAADKESTQKAIDGVINKVN
SIIDKMNTQFEAVGREFNNLERRIENLNKKMEDGFLDVWTYNAELLVLMENERTLDF
HDSNVKNLYDKVRLQLRDNAKELGNGCFEFYHKCDNECMESVRNGTYDYPQYSEEAR
LKREEISGVKLESIGIYQILSIYSTVASSLALAIMVAGLSLWMCSNGSLQCRICI >CR9114 VH PROTEIN (SEQ ID NO: 9)
QVQLVQSGAEVKKPGSSVKVSCKSSGGISNNYAISWVRQAPGQGLDWMGGISPIFGS
TAYAQKFQGRVTISADIFSNTAYMELNSLTSEDTAVYFCARHGNYYYYSGMDVWGQG
TTVTVSS >CR9114 VL PROTEIN (SEQ ID NO: 10)
SYVLTQPPAVSGTPGQRVTISCSGSDSNIGRRSVNWYQQFPGTAPKLLIYSNDQRPS
VVPDRFSGSKSGTSASLAISGLQSEDEAEYYCAAWDDSLKGAVFGGGTQLTVL >CR6261 VH PROTEIN (SEQ ID NO: 11)
E V Q L V E S G A E V K K P G S S V K V S C K A S G G P F
R S Y A I S W V R Q A P G Q G P E W M G G I I P I F G T T
K Y A P K F Q G R V T I T A D D F A G T V Y M E L S S L R
S E D T A M Y Y C A K H M G Y Q V R E T M D V W G K G T T
VTVSS >CR6261 VL PROTEIN (SEQ ID NO: 12)
Q S V L T Q P P S V S A A P G Q K V T I S C S G S S S N I
G N D Y V S W Y Q Q L P G T A P K L L I Y D N N K R P S G
I P D R F S G S K S G T S A T L G I T G L Q T G D E A N Y
Y C A T W D R R P T A Y V V F G G G T K L T V L G SEQ ID NO 13: SD15016
EVQLVESGGGLVQAGGSLRLSCVASGMFFGIAAMGWYRQAPGKQRELVANITSDFST
NYADSVKDRFTISRDNAENTVYLQMNSLKPEDTAVYYCAADSLGTGWRHYYYWGQGT
QVTVSSAAAWSHPQFEKGAAWSHPQFEKGAAWSHPQFEK -continued

| SEQUENCES |
| --- |

SEQ ID NO: 14: SD15004
EVQLVESGGGLVQPGGSLRLSCAVSISIFDIYAMDWYRQAPGKQRDLVATSFRDGST
NYADSVKGRFTISRDNAKNTLYLQMNSLKPEDTAVYLCHVSLYRDPLGVAGGMGVYW
GKGALVTVSSAAAWSHPQFEKGAAWSHPQFEKGAAWSHPQFEK

SEQ ID NO: 15 CAA24269.1 haemagglutinin (Influenza A virus (A/Aichi/2/1968 (H3N2) (excluding signal sequence)
QDLPGNDNST ATLCLGHHAV PNGTLVKTIT DDQIEVTNAT ELVQSSSTGK 50
ICNNPHRILD GIDCTLIDAL LGDPHCDVFQ NETWDLFVER SKAFSNCYPY 100
DVPDYASLRS LVASSGTLEF ITEGFTWTGV TQNGGSNACK RGPGSGFFSR 150
LNWLTKSGST YPVLNVTMPN NDNFDKLYIW GIHHPSTNQE QTSLYVQASG 200
RVTVSTRRSQ QTIIPNIGSR PWVRGLSSRI SIYWTIVKPG DVLVINSNGN 250
LIAPRGYFKM RTGKSSIMRS DAPIDTCISE CITPNGSIPN DKPFQNVNKI 300
TYGACPKYVK QNTLKLATGM RNVPEKQTRG LFGAIAGFIE NGWEGMIDGW 350
YGFRHQNSEG TGQAADLKST QAAIDQINGK LNRVIEKTNE KFHQIEKEFS 400
EVEGRIQDLE KYVEDTKIDL WSYNAELLVA LENQHTIDLT DSEMNKLFEK 450
TRRQLRENAE EMGNGCFKIY HKCDNACIES IRNGTYDHDV YRDEALNNRF 500
QIKGVELKSG YKDWILWISF AISCFLLCVV LLGFIMWACQ RGNIRCNICI 550

SEQ ID NO 16: UFV5367
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLESMGVYQI

SEQ ID NO 17: UFV5369
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNIQYTAIGCEYNKSERCMKQIEDKIEEIESKIWCYNAELLVLLENERTLD
YHDSNVKNLYEKVRSQLKNNAKEIGNGCFEFYHKCDNICMESVKNGTYDYPKYSEEA
KLNREEIDGVKLESTRIYQI

SEQ ID NO 135: UFV150553
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQRTAIGCEFNKSEQCMKQIEDKIEEIESKIWCYNAELLVLLENQRTLD
FHDSNVKNLYEKVKSQLKNNAKEIGNGCFEFYHKCNDECMESVKNGTYDYPKYSEES
KLNREKIDGVKLESMGVYQI

SEQ ID NO 30: UFV150558
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNIQPTAIGCEYNKSEQCMKQIEDKIEEIESKIWCYNAELLVLLENQRTLD
YHDANVKNLYEKVRSQLKNNAKEIGNGCFEFYHKCDNICMESVKNGTYDYPKYSEEA
KLNREEIDGVKLESTRIYQI

SEQ ID NO 31: UFV150559
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNIQRTAIGCEFNKSEQCMKQIEDKIEEIESKIWCYNAELLVLLENQRTLD
YHDSNVKNLYEKVRSQLKNNAKEIGNGCFEFYHKCDNICMESVKNGTYDYPKYSEEA
KLNREEIDGVKLESTRIYQI

SEQ ID NO 32: UFV150565
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLESMGVYQILAIY

SEQ ID NO 33: UFV150566
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLESMGVYQILA

SEQ ID NO 34: UFV150567
DTICIGYHANNSIDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLESMGVY

-continued

| SEQUENCES |
| --- |

SEQ ID NO 35: UFV150568
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLESMG

SEQ ID NO 36: UFV150569
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKLES

SEQ ID NO 37: UFV150570
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGVKL

SEQ ID NO 38: UFV150571
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNIQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKIDGV

SEQ ID NO 39: UFV150572
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNTQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREKID

SEQ ID NO 40: UFV150573
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNTQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNREK

SEQ ID NO 41: UFV150574
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNTQYTAIGCEYNKSERCMKQIEDKIEEIESKIWCYNAELLVLLENERTLD
FHDSNVKNLYEKVKSQLKNNAKEIGNGCFEFYHKCNDECMESVKNGTYDYPKYSEES
KLNR

SEQ ID NO 42: UFV150575
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKLESTRIYQILAIY

SEQ ID NO 43: UFV150576
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKLESTRIYQILA

SEQ ID NO 44: UFV150577
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKLESTRIY

SEQ ID NO 45: UFV150578
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKLESTR

-continued

| SEQUENCES |
| --- |

SEQ ID NO 46: UFV150579
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKLES

SEQ ID NO 47: UFV150580
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGVKL

SEQ ID NO 48: UFV150581
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEIDGV

SEQ ID NO 49: UFV150582
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREEID

SEQ ID NO 50: UFV150583
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNREE

SEQ ID NO 51: UFV150584
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQYTAIGCEYNKSERCMKQIEDKIEEIESKIWCYNAELLVLLENERTLD
YHDSNVKNLYEKVRSQLKNNAKEIGNGCFEFYHKCDNTCMESVKNGTYDYPKYSEEA
KLNR

SEQ ID NO 52: UFV150849
DTICIGYHANNSTDTVDTVLEKNVTVTHSVNLLENGGGGKYVCSAKLRMVTGLRNKP
SKQSQGLFGAIAGFTEGGWIGMVDGWYGYHHQNEQGSGYAADQKSTQNAINGITNKV
NSVIEKMNTQRTAIGCEYNKSERCMKQIEDKIEEIESKIWCYNAELLVLLENQRTLE
FHDSNVKNLYEKVKSQLKNNAKEIGNGCFEFYHKCNDECMESVKNGTYDYPKYSEES
KLNREKIDGVKLESMGVYQI

SEQ ID NO 53: UFV150850
DTLCIGYHANNSTDTVDTVLEKNVTVTHSVNLLEDGGGGKYVCSTKLRLATGLRNKP
SKQSQGLFGAIAGFTEGGWIGMVDGWYGYHHQNEQGSGYAADLKSTQNAIDEITNKV
NSVIEKMNTQRTAIGCEYNKSERCMKQIEDKIEEIESKIWCYNAELLVLLENQRTLE
YHDSNVKNLYEKVRSQLKNNAKEIGNGCFEFYHKCDNTCMESVKNGTYDYPKYSEEA
KLNREEIDGVKLESTRIYQI

SEQ ID NO 54: UFV150552
DTICIGYHANNSTDTVDTVLEKNVTVTHSVNLLENGGGGKYVCSAKLRMVTGLRNKP
SKQSQGLFGAIAGFTEGGWTGMVDGWYGYHHQNEQGSGYAADQKSTQNAINGITNKV
NSVIEKMNTQPTAIGCEYNKSEQCMKQIEDKIEEIESKIWCYNAELLVLLENQRTLD
FHDANVKNLYEKVKSQLKNNAKEIGNGCFEFYHKCNDECMESVKNGTYDYPKYSEES
KLNREKIDGVKLESMGVYQI

SEQ ID NO 55: UFV160088
DTICIGYHANNSTDTVDTVLEKNVTVTHSVNLLENGGGGKYVCSAKLRMVTGLRNKP
SKQSRGLFGAIAGFIEGGWTGMVDGWYGYHHQNEQGSGYAADQKSTQNAINGITNKV
NSVIEKMNIQRTAICKEYPKSEQRMECLEKKVDDIEKKIWCYNAELLVLLENQRTLE
FHDINVKNLYEKVKSQLKNNAKEIGNGCFEFYHKCNDECMESVKNGTYDYPKYSEES
KLNREKIDGVKLESMGVYQI

SEQ ID NO 56: UFV160090
DTLCIGYHANNSTDTVDTVLEKNVTVTHSVNLLEDGGGGKYVCSTKLRLATGLRNKP
SKQSQGLFGAIAGFTEGGWTGMVDGWYGYHHQNEQGSGYAADLKSTQNAIDEITNKV
NSVIEKMNTQRTAIGCEYNKSERCIEALEKKVDDIEKKIWCYNAELLVLLENQRTLE
YHDSNVKNLYEKVRSQLKNNAKEIGNGCFEFYHKCDNTCMESVKNGTYDYPKYSEEA
KLNREEIDGVKLESTRIYQI

-continued

| SEQUENCES |
|---|
| SEQ ID NO 57: UFV160093<br>DTLCIGYHANNSTDTVDTVLEKNVTVTHSVNLLEDGGGGKYVCSTKLRLATGLRNKP<br>SKQSQGLFGAIAGFTEGGWTGMVDGWYGYHHQNEQGSGYAADLKSTQNAIDEITNKV<br>NSVIEKMNTQRTAIGKECNKSERCIEALEKKVDDIEKKIWCYNAELLVLLENQRTLE<br>YHDSNVKNLYEKVRSQLKNNAKEIGNGCFEFYHKCDNTCMESVKNGTYDYPKYSEEA<br>KLNREEIDGVKLESTRIYQI |
| SEQ ID NO 58: UFV160097<br>DTLCIGYHANNSTDTVDTVLEKNVTVTHSVNLLEDGGGGKYVCSTKLRLATGLRNKP<br>SKQSQGLFGAIAGFTEGGWTGMVDGWYGYHHQNEQGSGYAADLKSTQNAIDEITNKV<br>NSVIEKMNTQRTAIGCEYNKSERCMKQIEDKIEEIESKIWCYNAELLVLLENQRTLE<br>YHDSNVKNLYEKVRSQLKNNAKEIGNGCFEFYHKCDNTCMESVKNGTYDYPKYSEEA<br>KLNREEIDGVKLESTRIYQI |
| SEQ ID NO 59: UFV160301<br>DTLCIGYHANNSTDTVDTVLEKNVTVTHSVNLLEDGGGGKYVCSTKLRLATGLRNKP<br>SKQRRRKKGLFGAIAGFTEGGWTGMVDGWYGYHHQNEQGSGYAADLKSTQNAIDEIT<br>NKVNSVIEKMNTQRTAIGCEYNKSERCMKQIEDKIEEIESKIWCYNAELLVLLENQR<br>TLEYHDSNVKNLYEKVRSQLKNNAKEIGNGCFEFYHKCDNTCMESVKNGTYDYPKYS<br>EEAKLNREEIDGVKLESTRIYQI |
| SEQ ID NO 60: UFV160302<br>DTLCIGYHANNSTDTVDTVLEKNVTVTHSVNLLEDGGGGKYVCSTKLRLATGLRNKP<br>SKQSRGLFGAIAGFTEGGWTGMVDGWYGYHHQNEQGSGYAADLKSTQNAIDEITNKV<br>NSVIEKMNTQRTAIGCEYNKSERCMKQIEDKIEEIESKIWCYNAELLVLLENQRTLE<br>YHDSNVKNLYEKVRSQLKNNAKEIGNGCFEFYHKCDNTCMESVKNGTYDYPKYSEEA<br>KLNREEIDGVKLESTRIYQI |
| SEQ ID NO 61: UFV160303<br>DTLCIGYHANNSTDTVDTVLEKNVTVTHSVNLLEDGGGGKYVCSTKLRLATGLRNKP<br>SKQSRGLFGAIAGFTEGGWTGMVDGWYGYHHQNEQGSGYAADLKSTQNAIDEITNKV<br>NSVIEKMNTQRTAIGCEYNKSERCMKQIEDKIEEIESKIWCYNAELLVLLENQRTLD<br>YHDSNVKNLYEKVRSQLKNNAKEIGNGCFEFYHKCDNTCMESVKNGTYDYPKYSEEA<br>KLNREEIDGVKLESTRIYQI |
| SEQ ID NO 62: UFV160304<br>DTLCIGYHANNSTDTVDTVLEKNVTVTHSVNLLEDGGGGKYVCSTKLRLATGLRNKP<br>SKQSRGLFGAIAGFTEGGWTGMVDGWYGYHHQNEQGSGYAADLKSTQNAIDEITNKV<br>NSVIEKMNTQYTAIGCEYNKSERCMKQIEDKIEEIESKIWCYNAELLVLLENQRTLE<br>YHDSNVKNLYEKVRSQLKNNAKEIGNGCFEFYHKCDNTCMESVKNGTYDYPKYSEEA<br>KLNREEIDGVKLESTRIYQI |
| SEQ ID NO: 63: UFV160360<br>DTLCIGYHANNSTDTVDTVLEKNVTVTHSVNLLEDGGGGKYVCSTKLRLATGLRNKP<br>SKQSQGLFGAIAGFTEGGWTGMVDGWYGYHHQNEQGSGYAADLKSTQNAIDEITNKV<br>NSVIEKMNTQPTAIGCEYNKSEQCMKQIEDKIEEIESKIWCYNAELLVLLENQRTLD<br>YHDANVKNLYEKVRSQLKNNAKEIGNGCFEFYHKCDNTCMESVKNGTYDYPKYSEEA<br>KLNREEIDGVKLESTRIYQI |
| SEQ ID NO 64: UFV160361<br>DTLCIGYHANNSTDTVDTVLEKNVTVTHSVNLLEDKYVCSTKLRLATGLRNKPSKQS<br>QGLFGAIAGFTEGGWTGMVDGWYGYHHQNEQGSGYAADLKSTQNAIDEITNKVNSVI<br>EKMNTQPTAIGCEYNKSEQCMKQIEDKIEEIESKIWCYNAELLVLLENQRTLDYHDA<br>NVKNLYEKVRSQLKNNAKEIGNGCFEFYHKCDNTCMESVKNGTYDYPKYSEEAKLNR<br>EEIDGVKLESTRIYQI |
| SEQ ID NO 65: UFV160362<br>DTLCIGYHANNSTDTVDTVLEKNVTVTHSVNLLEDKKYVCSTKLRLATGLRNKPSKQ<br>SQGLFGAIAGFTEGGWTGMVDGWYGYHHQNEQGSGYAADLKSTQNAIDEITNKVNSV<br>IEKMNTQPTAIGCEYNKSEQCMKQIEDKIEEIESKIWCYNAELLVLLENQRTLDYHD<br>ANVKNLYEKVRSQLKNNAKEIGNGCFEFYHKCDNTCMESVKNGTYDYPKYSEEAKLN<br>REEIDGVKLESTRIYQI |
| SEQ ID NO 66: UFV160363<br>DTLCIGYHANNSTDTVDTVLEKNVTVTHSVNLLEDKHKYVCSTKLRLATGLRNKPSK<br>QSQGLFGAIAGFTEGGWTGMVDGWYGYHHQNEQGSGYAADLKSTQNAIDEITNKVNS<br>VIEKMNIQPTAIGCEYNKSEQCMKQIEDKIEEIESKIWCYNAELLVLLENQRTLDYH<br>DANVKNLYEKVRSQLKNNAKEIGNGCFEFYHKCDNTCMESVKNGTYDYPKYSEEAKL<br>NREEIDGVKLESTRIYQI |
| SEQ ID NO 67: UFV160364<br>DTLCIGYHANNSTDTVDTVLEKNVTVTHSVNLLEDKHNKYVCSTKLRLATGLRNKPS<br>KQSQGLFGAIAGFTEGGWTGMVDGWYGYHHQNEQGSGYAADLKSTQNAIDEITNKVN<br>SVIEKMNTQPTAIGCEYNKSEQCMKQIEDKIEEIESKIWCYNAELLVLLENQRTLDY<br>HDANVKNLYEKVRSQLKNNAKEIGNGCFEFYHKCDNTCMESVKNGTYDYPKYSEEAK<br>LNREEIDGVKLESTRIYQI |

-continued

| SEQUENCES |
|---|

SEQ ID NO 68: UFV160365
DTLCIGYHANNSTDTVDTVLEKNVTVTHSVNLLEDKHNGKYVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 69: UFV160366
DTLCIGYHANNSTDTVDTVLEKNVTVTHSVNLLEDKHNGKKYVCSTKLRLATGLRNK
PSKQSQGLFGAIAGFTEGGWTGMVDGWYGYHHQNEQGSGYAADLKSTQNAIDEITNK
VNSVIEKMNTQPTAIGCEYNKSEQCMKQIEDKIEEIESKIWCYNAELLVLLENQRTL
DYHDANVKNLYEKVRSQLKNNAKEIGNGCFEFYHKCDNTCMESVKNGTYDYPKYSEE
AKLNREEIDGVKLESTRIYQI

SEQ ID NO 70: UFV160367
DTLCIGYHANNSTDTVDTVLEKNVTVTHSVNLLEDKHNGKLKYVCSTKLRLATGLRN
KPSKQSQGLFGAIAGFTEGGWTGMVDGWYGYHHQNEQGSGYAADLKSTQNAIDEITN
KVNSVIEKMNIQPTAIGCEYNKSEQCMKQIEDKIEEIESKIWCYNAELLVLLENQRT
LDYHDANVKNLYEKVRSQLKNNAKEIGNGCFEFYHKCDNTCMESVKNGTYDYPKYSE
EAKLNREEIDGVKLESTRIYQI

SEQ ID NO 71: UFV160368
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQPTAIGCEYNKSEQCMKQIEDKIEEIESKIWCYNAELLVLLENQR
TLDYHDANVKNLYEKVRSQLKNNAKEIGNGCFEFYHKCDNTCMESVKNGTYDYPKYS
EEAKLNREEIDGVKLESTRIYQI

SEQ ID NO 72: UFV160369
DTLCIGYHANNSTDTVDTVLEKNVTVTHSVNLLEDKHNGKLGPKYVCSTKLRLATGL
RNKPSKQSQGLFGAIAGFTEGGWTGMVDGWYGYHHQNEQGSGYAADLKSTQNAIDEI
TNKVNSVIEKMNTQPTAIGCEYNKSEQCMKQIEDKIEEIESKIWCYNAELLVLLENQ
RTLDYHDANVKNLYEKVRSQLKNNAKEIGNGCFEFYHKCDNTCMESVKNGTYDYPKY
SEEAKLNREEIDGVKLESTRIYQI

SEQ ID NO: 73: UFV160370
DTLCIGYHANNSTDTVDTVLEKNVTVTHSVNLLEDKHGPKYVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 74: UFV160371
DTLCIGYHANNSTDTVDTVLEKNVTVTHSVNLLEDGEGPKYVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 75: UFV160372
DTLCIGYHANNSTDTVDTVLEKNVTVTHSVNLLEDVCSTKLRLATGLRNKPSKQSQG
LFGAIAGFTEGGWTGMVDGWYGYHHQNEQGSGYAADLKSTQNAIDEITNKVNSVIEK
MNTQPTAIGCEYNKSEQCMKQIEDKIEEIESKIWCYNAELLVLLENQRTLDYHDANV
KNLYEKVRSQLKNNAKEIGNGCFEFYHKCDNTCMESVKNGTYDYPKYSEEAKLNREE
IDGVKLESTRIYQI

SEQ ID NO 76: UFV160373
DTLCIGYHANNSTDTVDTVLEKNVTVTHSVNLLEDKVCSTKLRLATGLRNKPSKQSQ
GLFGAIAGFTEGGWTGMVDGWYGYHHQNEQGSGYAADLKSTQNAIDEITNKVNSVIE
KMNIQPTAIGCEYNKSEQCMKQIEDKIEEIESKIWCYNAELLVLLENQRTLDYHDAN
VKNLYEKVRSQLKNNAKEIGNGCFEFYHKCDNTCMESVKNGTYDYPKYSEEAKLNRE
EIDGVKLESTRIYQI

SEQ ID NO 77: UFV160374
DTLCIGYHANNSTDTVDTVLEKNVTVTHSVNLLEDKHVCSTKLRLATGLRNKPSKQS
QGLFGAIAGFTEGGWTGMVDGWYGYHHQNEQGSGYAADLKSTQNAIDEITNKVNSVI
EKMNTQPTAIGCEYNKSEQCMKQIEDKIEEIESKIWCYNAELLVLLENQRTLDYHDA
NVKNLYEKVRSQLKNNAKEIGNGCFEFYHKCDNTCMESVKNGTYDYPKYSEEAKLNR
EEIDGVKLESTRIYQI

SEQ ID NO 78: UFV160375
DTLCIGYHANNSTDTVDTVLEKNVTVTHSVNLLEDKHNVCSTKLRLATGLRNKPSKQ
SQGLFGAIAGFTEGGWTGMVDGWYGYHHQNEQGSGYAADLKSTQNAIDEITNKVNSV
IEKMNTQPTAIGCEYNKSEQCMKQIEDKIEEIESKIWCYNAELLVLLENQRTLDYHD
ANVKNLYEKVRSQLKNNAKEIGNGCFEFYHKCDNTCMESVKNGTYDYPKYSEEAKLN
REEIDGVKLESTRIYQI

-continued

| SEQUENCES |
| --- |

SEQ ID NO 79: UFV160376
DTLCIGYHANNSTDTVDTVLEKNVTVTHSVNLLEDKHNGVCSTKLRLATGLRNKPSK
QSQGLFGAIAGFTEGGWTGMVDGWYGYHHQNEQGSGYAADLKSTQNAIDEITNKVNS
VIEKMNTQPTAIGCEYNKSEQCMKQIEDKIEEIESKIWCYNAELLVLLENQRTLDYH
DANVKNLYEKVRSQLKNNAKEIGNGCFEFYHKCDNTCMESVKNGTYDYPKYSEEAKL
NREEIDGVKLESTRIYQI

SEQ ID NO 80: UFV160377
DTLCIGYHANNSTDTVDTVLEKNVTVTHSVNLLEDKHNGKVCSTKLRLATGLRNKPS
KQSQGLFGAIAGFTEGGWTGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNTCMESVKNGTYDYPKYSEEAK
LNREEIDGVKLESTRIYQI

SEQ ID NO 81: UFV160378
DTLCIGYHANNSTDTVDTVLEKNVTVTHSVNLLEDKHNGKLVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 82: UFV160379
DTLCIGYHANNSTDTVDTVLEKNVTVTHSVNLLEDKHNGKLGVCSTKLRLATGLRNK
PSKQSQGLFGAIAGFTEGGWTGMVDGWYGYHHQNEQGSGYAADLKSTQNAIDEITNK
VNSVIEKMNIQPTAIGCEYNKSEQCMKQIEDKIEEIESKIWCYNAELLVLLENQRTL
DYHDANVKNLYEKVRSQLKNNAKEIGNGCFEFYHKCDNICMESVKNGTYDYPKYSEE
AKLNREEIDGVKLESTRIYQI

SEQ ID NO 83: UFV160380
DTLCIGYHANNSTDTVDTVLEKNVTVTHSVNLLEDAGSGKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 84: UFV160381
DTLCIGYHANNSTDTVDTVLEKNVTVTHSVNLLEDAGSKYVCSTKLRLATGLRNKPS
KQSQGLFGAIAGFTEGGWIGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNICMESVKNGTYDYPKYSEEAK
LNREEIDGVKLESTRIYQI

SEQ ID NO 85: UFV160382
DTLCIGYHANNSTDTVDTVLEKNVTVTHSVNLLEDAGSGIKYVCSTKLRLATGLRNK
PSKQSQGLFGAIAGFTEGGWTGMVDGWYGYHHQNEQGSGYAADLKSTQNAIDEITNK
VNSVIEKMNIQPTAIGCEYNKSEQCMKQIEDKIEEIESKIWCYNAELLVLLENQRTL
DYHDANVKNLYEKVRSQLKNNAKEIGNGCFEFYHKCDNICMESVKNGTYDYPKYSEE
AKLNREEIDGVKLESTRIYQI

SEQ ID NO 86: UFV160383
DTLCIGYHANNSTDTVDTVLEKNVTVTHSVNLLEDAGSGIVCSTKLRLATGLRNKPS
KQSQGLFGAIAGFTEGGWIGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNICMESVKNGTYDYPKYSEEAK
LNREEIDGVKLESTRIYQI

SEQ ID NO 87: UFV160384
DTLCIGYHANNSTDTVDTVLEKNVTVTHSVNLLEDGSGIKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 88: UFV160385
DTLCIGYHANNSTDTVDTVLEKNVTVTHSVNLLEDGSGKYVCSTKLRLATGLRNKPS
KQSQGLFGAIAGFTEGGWIGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNICMESVKNGTYDYPKYSEEAK
LNREEIDGVKLESTRIYQI

SEQ ID NO 89: UFV160386
DTLCIGYHANNSTDTVDTVLEKNVTVTHSVNLLEDHAGAKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

-continued

| SEQUENCES |
| --- |

SEQ ID NO 90: UFV160387
DTLCIGYHANNSTDTVDTVLEKNVTVTHSVNLLEDDQEGKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 91: UFV160388
DTLCIGYHANNSTDTVDTVLEKNVTVTHSVNLLEDDTPVKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 92: UFV160389
DTLCIGYHANNSTDTVDTVLEKNVTVTHSVNLLEDFPKTKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 93: UFV160390
DTLCIGYHANNSTDTVDTVLEKNVTVTHSVNLLEDEPGDKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 94: UFV160391
DTLCIGYHANNSTDTVDTVLEKNVTVTHSVNLLEDEPGKYVCSTKLRLATGLRNKPS
KQSQGLFGAIAGFTEGGWIGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNICMESVKNGTYDYPKYSEEAK
LNREEIDGVKLESTRIYQI

SEQ ID NO 95: UFV160392
DTLCIGYHANNSTDTVDTVLEKNVTVTHSVNLLEDTGNLKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO: 96: UFV160393
DTLCIGYHANNSTDTVDTVLEKNVTVTHSVNLLEDTPSSKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 97: UFV160394
DTLCIGYHANNSTDTVDTVLEKNVTVTHSVNLLEDTPSKYVCSTKLRLATGLRNKPS
KQSQGLFGAIAGFTEGGWIGMVDGWYGYHHQNEQGSGYAADLKSTQNAIDEITNKVN
SVIEKMNTQPTAIGCEYNKSEQCMKQIEDKIEEIESKIWCYNAELLVLLENQRTLDY
HDANVKNLYEKVRSQLKNNAKEIGNGCFEFYHKCDNICMESVKNGTYDYPKYSEEAK
LNREEIDGVKLESTRIYQI

SEQ ID NO 98: UFV160395
DTLCIGYHANNSTDTVDTVLEKNVTVTHSVNLLEDATGNKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 99: UFV160396
DTLCIGYHANNSTDTVDTVLEKNVTVTHSVNLLEDYPGDKYVCSTKLRLATGLRNKP
SKQSQGLFGAIAGFTEGGWIGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 100: UFV160397
DTLCIGYHANNSTDTVDTVLEKNVTVTHSVNLLEDYPGDVCSTKLRLATGLRNKPSK
QSQGLFGAIAGFTEGGWTGMVDGWYGYHHQNEQGSGYAADLKSTQNAIDEITNKVNS
VIEKMNIQPTAIGCEYNKSEQCMKQIEDKIEEIESKIWCYNAELLVLLENQRTLDYH
DANVKNLYEKVRSQLKNNAKEIGNGCFEFYHKCDNICMESVKNGTYDYPKYSEEAKL
NREEIDGVKLESTRIYQI

-continued

| SEQUENCES |
|---|

SEQ ID NO 101: UFV160503
DTLCIGYHANNSTDTVDTVLEKNVTVTHSVNLLEDGGGGKYVCSTKLRLATGLRNKP
SKQSRKRRGLFGAIAGFTEGGWTGMVDGWYGYHHQNEQGSGYAADLKSTQNAIDEIT
NKVNSVIEKMNIQRTAIGCEYNKSERCMKQIEDKIEEIESKIWCYNAELLVLLENQR
TLEYHDSNVKNLYEKVRSQLKNNAKEIGNGCFEFYHKCDNICMESVKNGTYDYPKYS
EEAKLNREEIDGVKLESTRIYQI

SEQ ID NO 102: UFV160504
DTLCIGYHANNSTDTVDTVLEKNVTVTHSVNLLEDGGGGKYVCSTKLRLATGLRNKP
QRERRRKKRGLFGAIAGFTEGGWTGMVDGWYGYHHQNEQGSGYAADLKSTQNAIDEI
TNKVNSVIEKMNTQRTAIGCEYNKSERCMKQIEDKIEEIESKIWCYNAELLVLLENQ
RTLEYHDSNVKNLYEKVRSQLKNNAKEIGNGCFEFYHKCDNICMESVKNGTYDYPKY
SEEAKLNREEIDGVKLESTRIYQI

SEQ ID NO 103: UFV160655
DTICIGYHANNSTDTVDTVLEKNVTVTHSVNLLENSKYVCSAKLRMVTGLRNKPSKQ
SQGLFGAIAGFTEGGWTGMVDGWYGYHHQNEQGSGYAADQKSTQNAINGITNKVNSV
IEKMNTQPTAIGCEYNKSEQCMKQIEDKIEEIESKIWCYNAELLVLLENQRTLDFHD
ANVKNLYEKVKSQLKNNAKEIGNGCFEFYHKCNDECMESVKNGTYDYPKYSEESKLN
REKIDGVKLESMGVYQI

SEQ ID NO 104: UFV160656
DTLCIGYHANNSTDTVDTVLEKNVTVTHSVNLLEDKKYVCSTKLRLATGLRNKPSKQ
SQGLFGAIAGFTEGGWTGMVDGWYGYHHQNEQGSGYAADLKSTQNAIDEITNKVNSV
IEKMNTQPTAIGCEYNKSEQCMKQIEDKIEEIESKIWCYNAELLVLLENQRTLDYHD
ANVKNLYEKVRSQLKNNAKEIGNGCFEFYHKCDNTCMESVKNGTYDYPKYSEEAKLN
REEIDGVKLESTRIYQI

SEQ ID NO 105: UFV160657
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQPTAIGCEYNKSEQCMKQIEDKIEEIESKIWCYNAELLVLLENQR
TLDYHDANVKNLYEKVRSQLKNNAKEIGNGCFEFYHKCDNTCMESVKNGTYDYPKYS
EEAKLNREEIDGVKLESTRIYQI

SEQ ID NO 106: UFV160658
DTLCIGYHANNSTDTVDTVLEKNVTVTHSVNLLEDKKYVCSTKLRLATGLRNKPSKQ
SQGLFGAIAGFTEGGWTGMVDGWYGYHHQNEQGSGYAADLKSTQNAIDEITNKVNSV
IEKMNTQRTAIGCEYNKSERCMKQIEDKIEEIESKIWCYNAELLVLLENQRTLEYHD
SNVKNLYEKVRSQLKNNAKEIGNGCFEFYHKCDNTCMESVKNGTYDYPKYSEEAKLN
REEIDGVKLESTRIYQI

SEQ ID NO 107: UFV160659
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQRTAIGCEYNKSERCMKQIEDKIEEIESKIWCYNAELLVLLENQR
TLEYHDSNVKNLYEKVRSQLKNNAKEIGNGCFEFYHKCDNTCMESVKNGTYDYPKYS
EEAKLNREEIDGVKLESTRIYQI

SEQ ID NO: 108: UFV160663
DTLCIGYHANNSTDTVDTVLEKNVTVTHSVNLLEDGGGGKYVCSTKLRLATGLRNKP
SKQSQGLFGAIAGFTEGGWTGMVDGWYGYHHQNEQGSGYAADLKSTQNAIDEITNKV
NSVIEKMNTQRTAIGCEYNKSERCMKQIEDKIEEIESKIWCYNAELLVLLENQRTLD
YHDSNVKNLYEKVRSQLKNNAKEIGNGCFEFYHKCDNTCMESVKNGTYDYPKYSEEA
KLNREEIDGVKLESTRIYQI

SEQ ID NO 109: UFV160664
DTLCIGYHANNSTDTVDTVLEKNVTVTHSVNLLEDKKYVCSTKLRLATGLRNKPSKQ
SQGLFGAIAGFTEGGWTGMVDGWYGYHHQNEQGSGYAADLKSTQNAIDEITNKVNSV
IEKMNTQRTAIGCEYNKSERCMKQIEDKIEEIESKIWCYNAELLVLLENQRTLDYHD
SNVKNLYEKVRSQLKNNAKEIGNGCFEFYHKCDNTCMESVKNGTYDYPKYSEEAKLN
REEIDGVKLESTRIYQI

SEQ ID NO 110: UFV160665
DTLCIGYHANNSTDTVDTVLEKNVTVTHSVNLLEDKKYVCSTKLRLATGLRNKPSKQ
SQGLFGAIAGFTEGGWTGMVDGWYGYHHQNEQGSGYAADLKSTQNAIDEITNKVNSV
IEKMNTQPTAIGCEYNKSERCMKQIEDKIEEIESKIWCYNAELLVLLENQRTLDYHD
SNVKNLYEKVRSQLKNNAKEIGNGCFEFYHKCDNTCMESVKNGTYDYPKYSEEAKLN
REEIDGVKLESTRIYQI

SEQ ID NO 11: UFV160666
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQRTAIGCEYNKSERCMKQIEDKIEEIESKIWCYNAELLVLLENQR
TLDYHDSNVKNLYEKVRSQLKNNAKEIGNGCFEFYHKCDNTCMESVKNGTYDYPKYS
EEAKLNREEIDGVKLESTRIYQI

-continued

| SEQUENCES |
|---|

SEQ ID NO 112: UFV160667
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQPTAIGCEYNKSERCMKQIEDKIEEIESKIWCYNAELLVLLENQR
TLDYHDSNVKNLYEKVRSQLKNNAKEIGNGCFEFYHKCDNTCMESVKNGTYDYPKYS
EEAKLNREEIDGVKLESTRIYQI

SEQ ID NO 138: UFV160655
ATGAAAGTCAAACTGCTGGTCCTGCTGTGCACCTTCACCGCCACTTACGCCGACACC
ATCTGTATTGGGTACCACGCTAACAACTCCACCGACACAGTGGATACCGTGCTGGAG
AAGAACGTGACCGTGACACACTCTGTGAACCTGCTGGAGAATTCCAAGTACGTCTGC
AGCGCCAAGCTGAGGATGGTGACAGGCCTGAGAAATAAGCCCAGCAAGCAGTCCCAG
GGCCTGTTCGGAGCAATCGCAGGCTTTACCGAGGGAGGATGGACAGGAATGGTGGAC
GGATGGTACGGCTATCACCACCAGAACGAGCAGGGCTCCGGCTATGCCGCCGATCAG
AAGTCTACCCAGAACGCCATCAATGGCATCACAAACAAGGTCAATAGCGTGATCGAG
AAGATGAACACCCAGCCTACAGCCATCGGCTGCGAGTACAATAAGTCCGAGCAGTGC
ATGAAGCAGATCGAGGACAAGATCGAGGAGATCGAGTCTAAGATCTGGTGCTATAAC
GCCGAGCTGCTGGTGCTGCTCGAGAATCAGAGGACCCTGGACTTCCACGATGCCAAC
GTGAAGAATCTGTACGAGAAGGTGAAGTCCCAGCTGAAGAACAATGCCAAGGAGATC
GGCAACGGCTGTTTCGAGTTTTACCACAAGTGCAACGACGAGTGTATGGAGTCCGTG
AAGAATGGCACATACGATTATCCTAAGTATTCTGAGGAGAGCAAACTGAATCGGGAA
AAAATCGATGGCGTGAAACTGGAATCAATGGGGGTGTATCAGATCTAATAA

SEQ ID NO 139: UFV160656
ATGAAGGCCATCCTGGTGGTGCTGCTGTACACCTTCGCCACAGCCAACGCCGACACC
CTGTGCATCGGGTACCACGCCAACAATTCCACCGACACAGTGGATACAGTGCTGGAG
AAGAATGTGACCGTGACACACTCCGTGAACCTGCTGGAGGATAAGAAGTACGTCTGC
AGCACCAAGCTGAGGCTGGCCACAGGCCTGAGAAACAAGCCAAGCAAGCAGTCCCAG
GGCCTGTTCGGAGCCATCGCCGGCTTTACCGAGGGAGGATGGACAGGAATGGTGGAC
GGATGGTACGGCTATCACCACCAGAACGAGCAGGGCAGCGGATACGCCGCCGACCTG
AAGTCCACCCAGAATGCCATCGACGAGATTACCAACAAGGTCAATAGCGTGATTGAG
AAGATGAACACCCAGCCCACAGCCATCGGCTGCGAGTACAATAAGAGCGAGCAGTGT
ATGAAGCAGATTGAGGATAAGATTGAGGAGATTGAGTCCAAGATTTGGTGCTATAAC
GCCGAGCTGCTGGTGCTGCTCGAGAATCAGAGGACCCTGGACTACCACGATGCCAAC
GTGAAGAATCTGTATGAGAAGGTGAGGAGCCAGCTGAAGAACAATGCCAAGGAGATT
GGCAACGGCTGTTTCGAGTTTTACCACAAGTGCGACAACACCTGTATGGAGTCTGTG
AAGAATGGCACATACGATTATCCCAAGTATAGCGAGGAGGCCAAGCTGAATCGGGAG
GAAATCGATGGCGTGAAGCTGGAGAGCACCCGCATCTACCAGATCTAATAA

SEQ ID NO 140: UFV160664
ATGAAGGCCATCCTGGTCGTCCTGCTGTACACTTTCGCCACCGCCAACGCTGATACC
CTGTGCATCGGGTACCACGCTAACAACTCTACCGACACAGTGGATACCGTGCTGGAG
AAGAACGTGACCGTGACACACTCTGTGAATCTGCTGGAGGATAAGAAGTACGTCTGC
AGCACCAAGCTGAGGCTGGCCACAGGCCTGAGAAACAAGCCCAGCAAGCAGAGCCAG
GGCCTGTTTGGAGCAATTGCAGGCTTTACCGAGGGCGGCTGGACAGGCATGGTGGAT
GGCTGGTACGGCTATCACCACCAGAATGAGCAGGGATCTGGATATGCTGCTGACCTG
AAGTCTACCCAGAATGCCATTGATGAGATCACAAACAAGGTCAATAGCGTGATCGAG
AAGATGAACACCCAGCGGACAGCCATCGGCTGCGAGTACAATAAGTCCGAGAGGTGC
ATGAAGCAGATCGAGGACAAGATCGAGGAGATCGAGTCTAAGATCTGGTGCTATAAC
GCCGAGCTGCTGGTGCTGCTCGAGAATCAGCGGACCCTGGACTACCACGACAGCAAC
GTGAAGAATCTGTATGAGAAGGTGCGCTCCCAGCTGAAGAACAATGCCAAGGAGATC
GGCAACGGCTGTTTCGAGTTTTACCACAAGTGCGACAACACCTGTATGGAGTCTGTG
AAGAATGGCACATACGATTATCCCAAGTATAGCGAGGAGGCCAAGCTGAATAGGGAG
GAAATCGATGGCGTGAAGCTGGAGTCTACAAGAATCTACCAGATCTAATAA

SEQ ID NO 141: UFV160665
ATGAAGGCCATCCTGGTCGTCCTGCTGTACACTTTCGCCACCGCCAACGCTGATACC
CTGTGCATCGGGTACCACGCTAACAACTCTACCGACACAGTGGATACCGTGCTGGAG
AAGAACGTGACCGTGACACACTCTGTGAATCTGCTGGAGGATAAGAAGTACGTCTGC
AGCACCAAGCTGAGGCTGGCCACAGGCCTGAGAAACAAGCCCAGCAAGCAGAGCCAG
GGCCTGTTTGGAGCAATTGCAGGCTTTACCGAGGGCGGCTGGACAGGCATGGTGGAT
GGCTGGTACGGCTATCACCACCAGAATGAGCAGGGATCTGGATATGCTGCTGACCTG
AAGTCTACCCAGAATGCCATTGATGAGATCACAAACAAGGTCAATAGCGTGATCGAG
AAGATGAACACCCAGCCTACAGCCATCGGCTGCGAGTACAATAAGTCCGAGAGGTGC
ATGAAGCAGATCGAGGACAAGATCGAGGAGATCGAGTCTAAGATCTGGTGCTATAAC
GCCGAGCTGCTGGTGCTGCTCGAGAATCAGCGGACCCTGGACTACCACGACAGCAAC
GTGAAGAATCTGTATGAGAAGGTGCGCTCCCAGCTGAAGAACAATGCCAAGGAGATC
GGCAACGGCTGTTTCGAGTTTTACCACAAGTGCGACAACACCTGTATGGAGTCTGTG
AAGAATGGCACATACGATTATCCCAAGTATAGCGAGGAGGCCAAGCTGAATAGGGAG
GAAATCGATGGCGTGAAGCTGGAGTCTACAAGAATCTACCAGATCTAATAA

SEQ ID NO 142: UFV171588 (UFV160655 + TM))
ATGAAGGTCAAACTGCTGGTCCTGCTGTGCACTTTTACTGCCACCTACGCTGACACT
ATCTGTATCGGGTACCACGCAAACAACTCAACCGACACAGTGGATACCGTGCTGGAG
AAGAACGTGACCGTGACACACTCCGTGAACCTGCTGGAGAATAGCAAGTACGTCTGC
AGCGCCAAGCTGCGGATGGTGACAGGCCTGAGAAATAAGCCCTCTAAGCAGAGCCAG
GGACTGTTCGGAGCAATCGCAGGCTTTACCGAGGGAGGATGGACAGGAATGGTGGAC

-continued

| SEQUENCES |
| --- |

GGATGGTACGGCTATCACCACCAGAACGAGCAGGGCAGCGGCTATGCCGCCGATCAG
AAGTCCACCCAGAACGCCATCAATGGCATCACAAACAAGGTGAACAGCGTGATCGAG
AAGATGAACACCCAGCCTACAGCCATCGGCTGCGAGTATAATAAGAGCGAGCAGTGT
ATGAAGCAGATCGAGGACAAGATCGAGGAGATCGAGTCCAAGATCTGGTGCTACAAC
GCCGAGCTGCTGGTGCTGCTGGAGAATCAGCGCACCCTGGACTTCCACGATGCCAAC
GTGAAGAATCTGTATGAGAAGGTGAAGAGCCAGCTGAAGAACAATGCCAAGGAGATC
GGCAACGGCTGTTTCGAGTTTTACCACAAGTGCAACGACGAGTGTATGGAGAGCGTG
AAGAATGGCACCTACGATTATCCTAAGTATTCCGAGGAGTCTAAGCTGAATCGGGAG
AAAATCGATGGCGTGAAGCTGGAGTCCATGGGCGTGTACCAGATCCTGGCCATCTAT
TCTACAGTGGCCAGCTCCCTGGTGCTGCTGGTGAGCCTGGGGGCTATTTCATTCTGG
ATGTGCTCTAACGGCTCTCTCCAGTGTCGCATTTGTATCTGATAA

SEQ ID NO 143: UFV171589 (UFV160656 + TM)
ATGAAGGCCATTCTGGTCGTGCTGCTGTACACTTTCGCCACCGCTAACGCTGACACC
CTGTGCATCGGGTACCACGCCAATAACTCCACCGACACAGTGGATACCGTGCTGGAG
AAGAACGTGACCGTGACACACTCTGTGAATCTGCTGGAGGACAAGAAGTACGTCTGC
AGCACCAAGCTGAGGCTGGCCACAGGCCTGAGAAACAAGCCCTCTAAGCAGAGCCAG
GGCCTGTTCGGAGCAATCGCAGGCTTTACCGAGGGAGGATGGACAGGCATGGTGGAT
GGCTGGTACGGCTATCACCACCAGAACGAGCAGGGATCCGGATATGCCGCCGACCTG
AAGTCTACCCAGAATGCCATCGACGAGATCACAAACAAGGTCAATTCTGTGATCGAG
AAGATGAACACCCAGCCTACAGCCATCGGCTGCGAGTACAATAAGAGCGAGCAGTGT
ATGAAGCAGATCGAGGACAAGATCGAGGAGATCGAGTCCAAGATCTGGTGCTATAAC
GCCGAGCTGCTGGTGCTGCTGGAGAATCAGAGGACCCTGGACTACCACGATGCCAAC
GTGAAGAATCTGTATGAGAAGGTGCGGTCCCAGCTGAAGAACAATGCCAAGGAGATC
GGCAACGGCTGTTTCGAGTTTTACCACAAGTGCGACAACACCTGTATGGAGTCCGTG
AAGAATGGCACATACGATTATCCCAAGTATTCTGAGGAGGCCAAGCTGAATCGGGAG
GAAATCGATGGCGTGAAGCTGGAGTCTACCCGCATCTACCAGATCCTGGCCATCTAT
AGCACAGTGGCCAGCTCCCTGGTGCTGGTGGTGTCCCTGGGGGCTATCTCTTTCTGG
ATGTGCTCAAATGGGTCCCTCCAGTGTCGCATCTGTATCTGATAA

SEQ ID NO 144: UFV171590 (UFV160664 + TM)
ATGAAGGCCATTCTGGTCGTGCTGCTGTACACTTTCGCCACCGCTAACGCTGACACC
CTGTGCATCGGGTACCACGCCAATAACTCCACCGACACAGTGGATACCGTGCTGGAG
AAGAACGTGACCGTGACACACTCTGTGAATCTGCTGGAGGACAAGAAGTACGTCTGC
AGCACCAAGCTGAGGCTGGCCACAGGCCTGAGAAACAAGCCCTCTAAGCAGAGCCAG
GGCCTGTTCGGAGCAATCGCAGGCTTTACCGAGGGAGGATGGACAGGCATGGTGGAT
GGCTGGTACGGCTATCACCACCAGAACGAGCAGGGATCCGGATATGCCGCCGACCTG
AAGTCTACCCAGAATGCCATCGACGAGATCACAAACAAGGTCAATTCTGTGATCGAG
AAGATGAACACCCAGAGGACAGCCATCGGCTGCGAGTACAATAAGAGCGAGAGGTGT
ATGAAGCAGATCGAGGACAAGATCGAGGAGATCGAGTCCAAGATCTGGTGCTATAAC
GCCGAGCTGCTGGTGCTGCTGGAGAATCAGAGGACCCTGGACTACCACGATAGCAAC
GTGAAGAATCTGTATGAGAAGGTGCGGTCCCAGCTGAAGAACAATGCCAAGGAGATC
GGCAACGGCTGTTTCGAGTTTTACCACAAGTGCGACAACACCTGTATGGAGTCCGTG
AAGAATGGCACATACGATTATCCCAAGTATTCTGAGGAGGCCAAGCTGAATCGGGAG
GAAATCGATGGCGTGAAGCTGGAGTCTACCCGCATCTACCAGATCCTGGCCATCTAT
AGCACAGTGGCCAGCTCCCTGGTGCTGGTGGTGTCCCTGGGGGCTATCTCTTTCTGG
ATGTGCTCAAATGGGTCCCTCCAGTGTCGCATCTGTATCTGATAA

SEQ ID NO 145: UFV171591 (UFV160665 + TM)
ATGAAGGCCATTCTGGTCGTGCTGCTGTACACTTTCGCCACCGCTAACGCTGACACC
CTGTGCATCGGGTACCACGCCAATAACTCCACCGACACAGTGGATACCGTGCTGGAG
AAGAACGTGACCGTGACACACTCTGTGAATCTGCTGGAGGACAAGAAGTACGTCTGC
AGCACCAAGCTGAGGCTGGCCACAGGCCTGAGAAACAAGCCCTCTAAGCAGAGCCAG
GGCCTGTTCGGAGCAATCGCAGGCTTTACCGAGGGAGGATGGACAGGCATGGTGGAT
GGCTGGTACGGCTATCACCACCAGAACGAGCAGGGATCCGGATATGCCGCCGACCTG
AAGTCTACCCAGAATGCCATCGACGAGATCACAAACAAGGTCAATTCTGTGATCGAG
AAGATGAACACCCAGCCTACAGCCATCGGCTGCGAGTACAATAAGAGCGAGAGGTGT
ATGAAGCAGATCGAGGACAAGATCGAGGAGATCGAGTCCAAGATCTGGTGCTATAAC
GCCGAGCTGCTGGTGCTGCTGGAGAATCAGAGGACCCTGGACTACCACGATAGCAAC
GTGAAGAATCTGTATGAGAAGGTGCGGTCCCAGCTGAAGAACAATGCCAAGGAGATC
GGCAACGGCTGTTTCGAGTTTTACCACAAGTGCGACAACACCTGTATGGAGTCCGTG
AAGAATGGCACATACGATTATCCCAAGTATTCTGAGGAGGCCAAGCTGAATCGGGAG
GAAATCGATGGCGTGAAGCTGGAGTCTACCCGCATCTACCAGATCCTGGCCATCTAT
AGCACAGTGGCCAGCTCCCTGGTGCTGGTGGTGTCCCTGGGGGCTATCTCTTTCTGG
ATGTGCTCAAATGGGTCCCTCCAGTGTCGCATCTGTATCTGATAA

SEQ ID NO: 146: MD3606 PROTEIN
EVQLVESGGGLVQPGGSLRLSCAVSISIFDIYAMDWYRQAPGKQRDLVATSFRDGST
NYADSVKGRFTISRDNAKNTLYLQMNSLKPEDTAVYLCHVSLYRDPLGVAGGMGVYW
GKGALVTVSSGGGGSGGGGSEVQLVESGGGLVQAGGSLKLSCAASGRTYAMGWFRQA
PGKEREFVAHINALGTRTYYSDSVKGRFTISRDNAKNTEYLEMNNLKPEDTAVYYCT
AQGQWRAAPVAVAAEYEFWGQGTQVIVSSGGGGSGGGGSEVQLVESGGGLVQPGGSL
RLSCAATGFTLENKAIGWFRQTPGSEREGVLCISKSGSWTYYTDSMRGRFTISRDNA
ENTVYLQMDSLKPEDTAVYYCATTTAGGGLCWDGTTFSRLASSWGQGTQVTVSSGGG
GSGGGGSEVQLVESGGGLVQPGGSLKLSCAASGFTFSTSWMYWLRQAPGKGLEWVSV
INTDGGTYYADSVKDRFTISRDNAKDTLYLQMSSLKSEDTAVYYCAKDWGGPEPTRG
QGTQVTVSSDKTHTCPPCPAPELLGGPSVFLFPPKPKDTLMISRTPEVTCVVVDVSH

-continued

| SEQUENCES |
|---|
| EDPEVKFNWYVDGVEVHNAKTKPREEQYNSTYRVVSVLTVLHQDWLNGKEYKCKVSN<br>KALPAPIEKTISKAKGQPREPQVYTLPPSREEMTKNQVSLICLVKGFYPSDIAVEWE<br>SNGQPENNYKTTPPVLDSDGSFFLYSKLTVDKSRWQQGNVFSCSVMHEALHNHYTQK<br>SLSLSPGK |
| SEQ ID NO: 147: UFV180496 H1 A/California/07/09<br>MKAILVVLLYTFATANADTLCIGYHANNSTDTVDTVLEKNVTVTHSVNLLEDKKYVC<br>STKLRLATGLRNKPSKQSQGLFGAIAGFTEGGWTGMVDGWYGYHHQNEQGSGYAADL<br>KSTQNAIDEITNKVNSVIEKMNTQRTAIGCEYNKSERCMKQIEDKIEEIESKIWCYN<br>AELLVLLENQRTLDYHDSNVKNLYEKVRSQLKNNAKEIGNGCFEFYHKCDNTCMESV<br>KNGTYDYPKYSEEAKLNREEIDGVKLESTRIYQIHHHHHH |
| SEQ ID NO: 148: UFV180497 H1 A/Michigan/45/2015<br>MKAILVVLLYTFTTANADTLCIGYHANNSTDTVDTVLEKNVTVTHSVNLLEDKKYVC<br>STKLRLATGLRNKPSKQSQGLFGAIAGFTEGGWTGMVDGWYGYHHQNEQGSGYAADL<br>KSTQNAIDKITNKVNSVIEKMNTQRTAIGCEYNKSEKCMKQIEDKIEEIESKIWCYN<br>AELLVLLENQRTLDYHDSNVKNLYEKVRNQLKNNAKEIGNGCFEFYHKCDNTCMESV<br>KNGTYDYPKYSEEAKLNREKIDGVKLESTRIYQIHHHHHH |
| SEQ ID NO: 149: UFV180498 H1 A/Puerto Rico/8/1934<br>MKANLLVLLCALAAADADTICIGYHANNSTDTVDTVLEKNVTVTHSVNLLEDSKYVC<br>SAKLRMVTGLRNKPSKQSQGLFGAIAGFTEGGWIGMIDGWYGYHHQNEQGSGYAADQ<br>KSTQNAINGITNKVNSVIEKMNIQRTAIGCEYNKSEKCMKQIEDKIEEIESKIWCYN<br>AELLVLLENQRILDFHDSNVKNLYEKVKSQLKNNAKEIGNGCFEFYHKCDNECMESV<br>RNGTYDYPKYSEESKLNREKVDGVKLESMGIYQIHHHHHH |
| SEQ ID NO: 150: UFV180499 H5 A/Hong Kong/156/97<br>MEKTVLLLATVSLVKSDQICIGYHANNSTEQVDTIMEKNVIVTHAQDILERTKYVCS<br>NRLVLATGLRNKPQKESQGLFGAIAGFTEGGWQGMVDGWYGYHHSNEQGSGYAADKE<br>STQKAIDGVINKVNSIINKMNIQREAIGCEYNKSERCMKQIEDKIEEIESKVWCYNA<br>ELLVLMENQRILDFHDSNVKNLYDKVRLQLRDNAKELGNGCFEFYHKCDNECMESVK<br>NGTYDYPQYSEEARLNREEISGVKLESMGTYQIHHHHHH |
| SEQ ID NO: 151: UFV180500 H5 A/Vietnam/1203/04<br>MEKIVLLFAIVSLVKSDQICIGYHANNSTEQVDTIMEKNVIVTHAQDILEKKKYVCS<br>NRLVLATGLRNKPQKESQGLFGAIAGFTEGGWQGMVDGWYGYHHSNEQGSGYAADKE<br>STQKAIDGVINKVNSIIDKMNIQREAIGCEYNKSERCMKQIEDKIEEIESKVWCYNA<br>ELLVLMENQRILDFHDSNVKNLYDKVRLQLRDNAKELGNGCFEFYHKCDNECMESVR<br>NGTYDYPQYSEEARLKREEISGVKLESIGIYQIHHHHHH |
| SEQ ID NO: 152: UFV180501 H2 A/Singapore/1/57<br>MAIIYLILLFTAVRGDQICIGYHANNSTEKVDTILERNVIVTHAKDILEKTKYVCSE<br>KLVLATGLRNKPQKESQGLFGAIAGFTEGGWQGMVDGWYGYHHSNDQGSGYAADKES<br>TQKAFDGITNKVNSVIEKMNIQREAIGCEYSKSERCMKQIEDKIEEIESKVWCYNAE<br>LLVLMENQRILDFHDSNVKNLYDKVRMQLRDNVKELGNGCFEFYHKCDDECMNSVKN<br>GTYDYPKYEEESKLNRNEIKGVKLSSMGVYQIHHHHHH |
| SEQ ID NO: 153: UFV171590 (UFV160664 + TM)<br>MKAILVVLLYTFATANADTLCIGYHANNSIDTVDTVLEKNVIVIHSVNLLEDKKYVC<br>STKLRLATGLRNKPSKQSQGLFGAIAGFTEGGWIGMVDGWYGYHHQNEQGSGYAADL<br>KSTQNAIDEITNKVNSVIEKMNIQRTAIGCEYNKSERCMKQIEDKIEEIESKIWCYN<br>AELLVLLENQRILDYHDSNVKNLYEKVRSQLKNNAKEIGNGCFEFYHKCDNICMESV<br>KNGTYDYPKYSEEAKLNREEIDGVKLESTRIYQILAIYSTVASSLVLVVSLGAISFW<br>MCSNGSLQCRICI |

The invention claimed is:

1. A group 1 influenza A hemagglutinin (HA) stem polypeptide, comprising an HA1 and a HA2 domain, said HA stem polypeptide comprising an amino acid sequence which comprises:

a deletion of the head region in the HA1 domain;

(ii) a modification of the trimerization region in the HA2 domain;

(iii) at least 2 cysteine residues forming an intramonomeric disulphide bridge;

(iv) at least 2 cysteine residues forming an intermonomeric disulphide bridge;

wherein the amino acid corresponding to the amino acid at position 392 is P, R or Y, and the amino acid corresponding to the amino acid at position 434 is Q, and wherein the numbering of the amino acid positions is based on H3 numbering as used in SEQ ID NO: 15.

2. Polypeptide according to claim 1, wherein said stem polypeptides comprise an amino acid sequence which comprises:

a deletion of the head region in the HA1 domain, said deletion comprising at least the amino acid sequence from the amino acid corresponding to the amino acid at position 53 up to and including the amino acid corresponding to the amino acid at position 302;

(ii) a modification of the trimerization region in the C-helix, said trimerization region comprising the amino acid sequence from the amino acid corresponding to the amino acid at position 405 up to and including the amino acid corresponding to the amino acid at position 419;

(iii) a cysteine at the amino acid position corresponding to position 310 and a cysteine at the position corresponding to position 422;

(iv) a cysteine at the position corresponding to position 397 in combination with a cysteine at the position corresponding to position 405; or a cysteine at the position corresponding to position 396 in combination with a cysteine at the position corresponding to position 408; or a cysteine at the position corresponding to position 399 in combination with a cysteine at position 405;

wherein the amino acid at the position corresponding to position 392 is P, R or Y, and wherein the amino acid at the position corresponding to position 434 is Q.

3. Polypeptide according to claim 1, wherein the deletion in the HA1 domain comprises at least the amino acid sequence from the amino acid at position 47 up to and including the amino acid at position 306.

4. Polypeptide according to claim 1, wherein the modification of the trimerization domain comprises the introduction of a heterologous trimerization domain in the C-helix.

5. Polypeptide according to claim 4, wherein the heterologous trimerization domain is a GCN4 sequence.

6. Polypeptide according to claim 1, wherein the modification of the trimerization domain comprises an optimization of the heptad repeat sequence in the C-helix.

7. Polypeptide according to claim 1, wherein the amino acid corresponding to the amino acid 392 is Y, P or R and the amino acid corresponding to the amino acid at position 434 is Q and the amino acid at the position corresponding to position 442 is A.

8. Polypeptide according to claim 1, comprising a cysteine at the position corresponding to position 397 in combination with a cysteine at the position corresponding to position 405.

9. Polypeptide according to claim 1, wherein:

the amino acid at the position corresponding to position 395 is I;

the amino acid at the position corresponding to position 399 is Y or C;

the amino acid at the position corresponding to position 400 is P;

the amino acid at the position corresponding to position 401 is K;

the amino acid at the position corresponding to position 402 is S; and/or the amino acid at the position corresponding to position 404 is R or Q.

10. Polypeptide according to claim 1, wherein the amino acid corresponding to the amino acid at position 323 is K and/or the amino acid corresponding to the amino acid at position 326 is K.

11. Polypeptide according to claim 1, wherein the amino acid corresponding to the amino acid at position 339 is T.

12. Polypeptide according to anyone of the preceding claim 1, wherein the polypeptide does not comprise a protease cleavage site.

13. Polypeptide according to claim 12, wherein the amino acid at position 329 is not arginine (R).

14. Polypeptide according to claim 1, wherein the polypeptide comprises a natural cleavage site or a polybasic cleavage site.

15. Polypeptide according to claim 1, wherein the polypeptide comprises (part) of a signal sequence.

16. Polypeptide according to claim 1, comprising a truncated HA2 domain.

17. Polypeptide according to claim 16, wherein the polypeptide does not comprise a transmembrane and cytoplasmic domain.

18. Polypeptide according to claim 1, wherein at least the C-terminal part of the HA2 domain starting with the amino acid corresponding to the amino acid at position 516 has been deleted.

19. Polypeptide according to claim 1, wherein the deletion in the HA1 domain has been replaced by a linking sequence of 1-10 amino acids.

20. Nucleic acid encoding a polypeptide according to claim 1.

21. Vector comprising a nucleic acid molecule encoding a group 1 HA stem polypeptide according to claim 1.

22. Vector according to claim 21, wherein the vector is a recombinant adenoviral vector.

23. Pharmaceutical composition comprising a polypeptide according to claim 1 and a pharmaceutically acceptable carrier.

24. A method for inducing an immune response against an influenza virus in a subject in need thereof comprising administering the polypeptide according to claim 1.

25. A vaccine comprising the polypeptide according to claim 1.

26. The peptide of claim 1, wherein, the amino acid corresponding to the amino acid at position 392 is P or R.

27. The peptide of claim 9, wherein, the amino acid at the position corresponding to position 399 is Y.

28. The peptide of claim 13, wherein, the amino acid at position 329 is glutamine (Q).

29. Pharmaceutical composition comprising a nucleic acid according to claim 20 and a pharmaceutically acceptable carrier.

30. Pharmaceutical composition comprising a vector according to claim 21 and a pharmaceutically acceptable carrier.

31. A method for inducing an immune response against an influenza virus in a subject in need thereof comprising administering the nucleic acid according to claim 20 to the subject.

32. A method for inducing an immune response against an influenza virus in a subject in need thereof comprising administering the vector according to claim 21 to the subject.

33. A vaccine comprising the nucleic acid according to claim 20.

34. A vaccine comprising the vector according to claim 21.

* * * * *